(12) United States Patent
Dombroski et al.

(10) Patent No.: US 7,056,918 B2
(45) Date of Patent: Jun. 6, 2006

(54) BENZIMIDAZOLE ANTI-INFLAMMATORY COMPOUNDS

(75) Inventors: Mark A. Dombroski, Waterford, CT (US); Michael A. Letavic, Mystic, CT (US); Kim F. McClure, Mystic, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/094,717

(22) Filed: Mar. 11, 2002

(65) Prior Publication Data

US 2003/0092749 A1   May 15, 2003

Related U.S. Application Data

(60) Provisional application No. 60/274,791, filed on Mar. 9, 2001.

(51) Int. Cl.
*A61K 31/4184* (2006.01)
*C07D 403/04* (2006.01)
*C07D 403/14* (2006.01)

(52) U.S. Cl. .............................. 514/234.5; 514/254.06; 514/255; 514/256; 514/314; 514/322; 514/338; 514/387; 544/139; 544/333; 544/370; 544/405; 546/167; 546/199; 546/273.7; 548/305.1; 548/306.1

(58) Field of Classification Search ............ 548/306.1, 548/305.1; 546/273.7, 167, 199; 544/370, 544/405, 333, 139; 514/387, 234.5, 254.06, 514/255.05, 256, 322, 338, 314, 255
See application file for complete search history.

(56) References Cited

U.S. PATENT DOCUMENTS

| | | | |
|---|---|---|---|
| 5,716,955 A | 2/1998 | Adams et al. | 514/235.8 |
| 5,716,972 A | 2/1998 | Adams et al. | 514/341 |
| 5,717,100 A | 2/1998 | Selnick et al. | 546/194 |
| 5,756,499 A | 5/1998 | Adams et al. | 514/235.8 |
| 5,777,097 A | 7/1998 | Lee et al. | 536/24.31 |

FOREIGN PATENT DOCUMENTS

| | | | |
|---|---|---|---|
| SU | 667560 | * | 6/1979 |
| WO | 9901449 | | 1/1999 |
| WO | 9961440 | | 12/1999 |
| WO | 0006563 | | 2/2000 |
| WO | 0031065 | | 6/2000 |
| WO | 0035911 | | 6/2000 |
| WO | 0040243 | | 7/2000 |
| WO | 0041698 | | 7/2000 |
| WO | 0063204 | | 10/2000 |

OTHER PUBLICATIONS

Blokhin et al., CA 102:113371, 1985.*
Blokhin et al., CA 91:75094, 1979..*
Surovtsev et al., CA 91:21212, 1979.*
Blokhin et al., CA 90:187811, 1979.*
Blokhin et al., CA 90:137048, 1979.*
Blokhin et al., CA 89:43246, 1978.*
Rozin et al., CA 83:9900, 1975.*
Golub et al., Science, vol. 286, Oct. 15, 1999, pp. 531-537.*
Lee et al., Immunopharmacology, 47 (2000), pp. 185-201.*
The Journal of Biological Chemistry, vol. 271, No. 40, pp. 24313-24316 (1996).
Bioorganic & Medicinal Chemistry Letters, 10, pp. 2047-2050 (2000); and.
Bioorganic & Medicinal Chemistry Letters, 11, pp. 9-12 (2001).

* cited by examiner

*Primary Examiner*—Laura L. Stockton
(74) *Attorney, Agent, or Firm*—Julie M. Lappin; Charles Ashbrook

(57) ABSTRACT

The present invention relates to novel triazolo-pyridines of the formula I

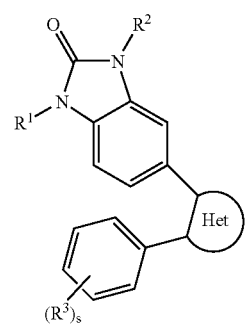

wherein Het is an optionally substituted 5-membered heterocycle containing one to two heteroatoms selected from nitrogen, sulfur and oxygen wherein at least one of said heteroatoms atoms must be nitrogen;

$R^2$ is selected from the group consisting of hydrogen, $(C_1-C_6)$alkyl or other suitable substituents;

$R^3$ is selected from the group consisting of hydrogen, $(C_1-C_6)$alkyl or other suitable substituents;

s is an integer from 0–5;

to intermediates for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, repurfusion or ischemia in stroke or heart attack, autoimmune diseases and other disorders.

32 Claims, No Drawings

BENZIMIDAZOLE ANTI-INFLAMMATORY COMPOUNDS

This application claims the benefit U.S. Provisional Application 60/274,791, filed Mar. 9, 2001.

The present invention relates to novel benzimidazoles, to intermediates for their preparation, to pharmaceutical compositions containing them and to their medicinal use. The compounds of the present invention are potent inhibitors of MAP kinases, preferably p38 kinase. They are useful in the treatment of inflammation, osteoarthritis, rhematoid arthritis, cancer, reperfusion or ischemia in stroke or heart attack, autoimmune diseases and other disorders.

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T. Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling pathway. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726735 (1995)].

While many signaling pathways are part of normal cell homeostasis, numerous cytokines (e.g., IL-1 and TNF) and certain other mediators of inflammation (e.g., COX-2, and iNOS) are produced only as a response to stress signals such as bacterial lippopolysaccharide (LPS). Early evidence suggesting that the signal transduction pathway leading to LPS-induced cytokine biosynthesis involved protein kinases came from studies of Weinstein [Weinstein, et al., J. Immunol 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Additional evidence of the involvement of the p38 kinase in LPS-stimulated signal transduction pathway leading to the initiation of proinflammatory cytokine biosynthesis was provided by the discovery of p38 kinase (CSBP 1 and 2) by Lee [Lee; et al,. Nature, 372, 739(1994)] as the molecular target for a novel class of anti-inflammatory agents. Thus, compounds which inhibit p38 will inhibit IL-1 and TNF synthesis in human monocytes. Such results have been reported by [Lee, et al., Int. J. Immunopharmac. 10(7), 835(1988)] and [Lee; et al., Annals N.Y. Acad. Sci., 696, 149(1993)].

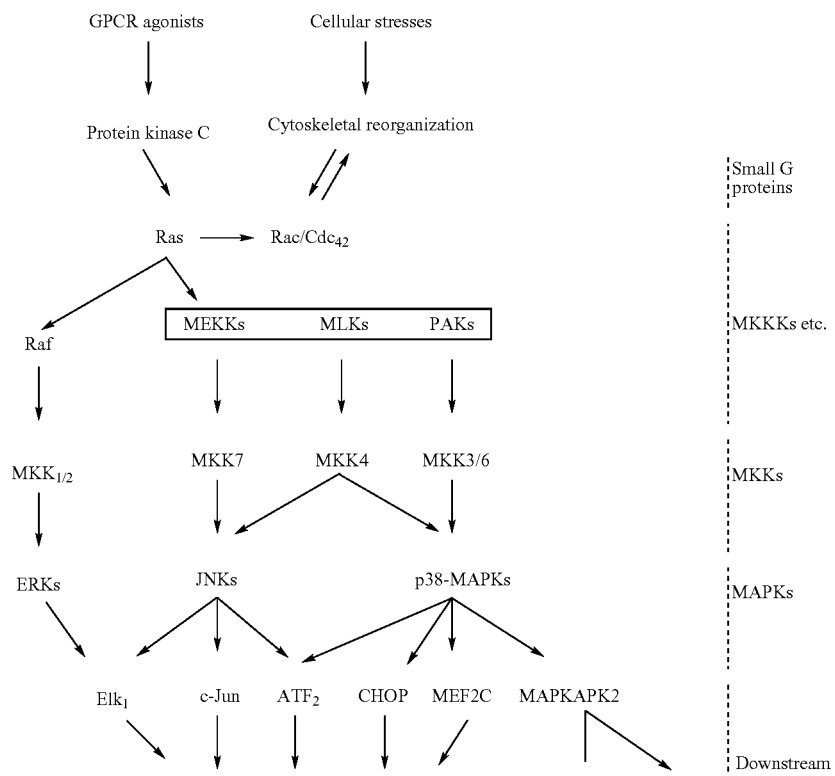

FIG. 1
MAP Kinase Family: General Feature

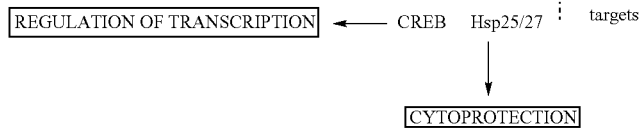

It is now accepted that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27. It is now known that MAPKAP-2 is essential for LPS induced TNFα biosynthesis [Kotlyarov et al. *Nature Cell Biol.*, 1, 94 (1999), see also Cohen, P. *Trends Cell Biol.*, 353–361(1997)].

In addition to inhibiting IL-1 and TNF, CSBP/p38 kinase inhibitors also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1 stimulated synthesis of collagenase and stromelysin. These and additional data demonstrate that CSBP/p38 is involved not only cytokine synthesis, but also in cytokine signaling [CSBP/p38 kinase reviewed in Cohen, P. *Trends Cell Biol.*, 353–361 (1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g,. Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chonic inflammatory disease states such as the inflammatory reaction induced by endotoxin or inflammatory bowel disease, tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells, Dinarello, *J. Clinical Immunology*, 5 (5), 287–297 (1985).

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid information, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysach-haride (LPS). IL-8 stimulates a number of functions in vitro. It has been shown to have chemoattractant properties for neutrophils, T-lymphocytes, and basophils. In addition it induces histamine release from basophils from both normal and atopic individuals as well lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increase in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3); 1453–1461. (1996); Griswold, et al., *Pharmacol. Comm.*, 7, 323–229 (1996)].

There remains a need for treatment, in this field, for compounds which are cytokine suppressive anti-inflammatory drugs, i.e., compounds which are capable of inhibiting the CSBP/p38/RK kinase.

CSBP/p38/RK kinase inhibitors are well known to those skilled in the art. International Patent Publication WO 00/40243, published Jul. 13, 2000, refers to pyridine substituted pyridine compounds and states that these compounds are p38 inhibitors. International Patent Publication WO 00163204, published Oct. 26, 2000, refers to substituted azole compounds and states that these compounds are p38 inhibitors. International Patent Publication WO 00/31065, published Jun. 2, 2000, refers to certain heterocyclic compounds and states that these compounds are p38 inhibitors. International Patent Publication WO 00/06563, published Feb. 10, 2000, refers to substituted imidazole compounds and states that these compounds are p38 inhibitors. International Patent Publication WO 00/41698, published Jul. 20, 2000, refers to certain w-carboxy aryl substituted diphenyl urea compounds and states that these compounds are p38 inhibitors. U.S. Pat. No. 5,716,955 refers to certain substituted imidazole compounds and states that these compounds are p38 inhibitors. U.S. Pat. No. 5,716,972 refers to certain pyridinyl substituted imidazole compounds and states that these compounds are p38 inhibitors. U.S. Pat. No. 5,717,100 refers to certain pyridinyl substituted imidazole compounds and states that these compounds are p38 inhibitors. U.S. Pat. No. 5,756,499 refers to certain substituted imidazole compounds and states that these compounds are p38 inhibitors.

Benzimidazolone containing compounds are also know. Blokhin et al., Synthesis and properties of 2-(2-α-furylvinyl)-45-diarylimidazole, *Khim. Khim. Tekhnol*, 27 (10), 1148–50 (1984) refers to certain 2-vinyl-4-aryl-5-benzimidazolone-imidazoles. Blokhin et al., "Study of the kinetics of the radical polymerization of methyl methacrylate in the presence of heteroanalogs of triarylimidazoles," *Khim. Khim. Tekhnol*, 22(3) 358–9 (1979) refers to other benzimidazolone derivatives.

SUMMARY OF THE INVENTION

The present invention relates to a compound of the formula

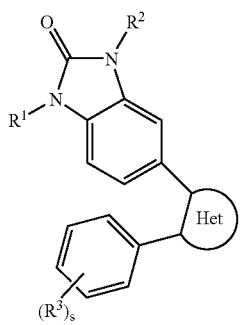

I wherein Het is an optionally substituted 5-membered heteroaryl containing one to two heteroatoms selected from nitrogen, sulfur and oxygen wherein at least one of said heteroatoms atoms must be nitrogen;

$R^1$ and $R^2$ are each independently selected from the group consisting of hydrogen, $(C_1-C_6)$alkyl or other suitable substituents;

$R^3$ is selected from the group consisting of hydrogen, $(C_1-C_6)$alkyl or other suitable substituents; and s is an integer from zero to five;

and pharmaceutically acceptable salts and prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, aryl carbonyl groups, aryloxycarbonyl groups, alkylsulfonyl groups, arylsulfonyl groups and the like. Those skilled in the art will appreciate that many substituents can be substituted by additional substituents.

More specifically, the present invention also relates to a compound of the formula

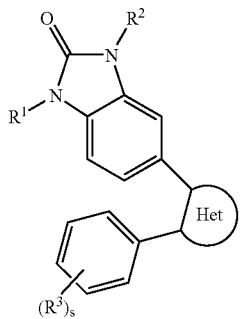

I wherein Het is an optionally substituted 5-membered heteroaryl which taken together with $(R^3-)_s$ phenyl is selected from the group consisting of

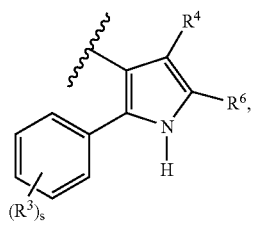

(a)

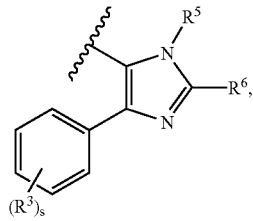

(b)

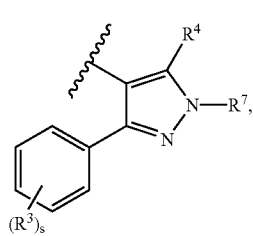

(c)

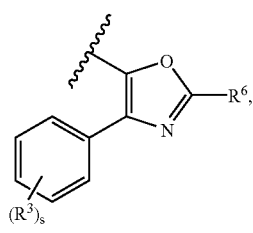

(d)

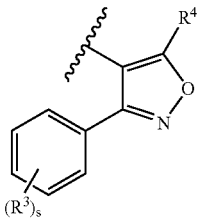

(e)

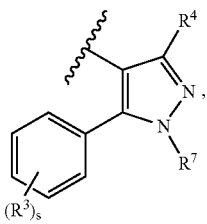

(f)

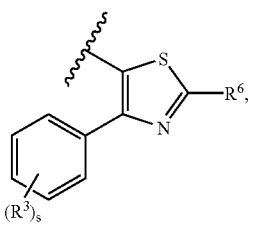

(g)

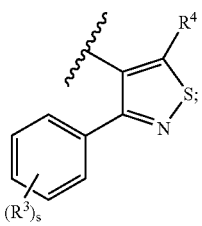

(h)

$R^1$ and $R^2$ are each independently selected from the group consisting of hydrogen, $(C_1-C_6)$alkyl, $(C_3-C_{10})$cycloalkyl, phenyl, $(C_1-C_{10})$heteroaryl and $(C_1-C_{10})$heterocyclic; wherein each of the aforesaid $(C_1-C_6)$alkyl, $(C_3-C_{10})$cycloalkyl, phenyl, $(C_1-C_{10})$heteroaryl and $(C_1-C_{10})$heterocyclic substituents may optionally be independently substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_1-C_{10})$heteroaryl, $(C_1-C_{10})$heterocyclic, formyl, —CN, $(C_1-C_6)$alkyl-(C=O)—, phenyl-(C=O)—, HO—(C=O)—, $(C_1-C_6)$alkyl-O—(C=O)—, $(C_1-C_6)$alkyl-NH—(C=O)—, [$(C_1-C_6)$alkyl]$_2$-N—(C=O)—, phenyl-NH—(C=O)—, phenyl-[(($C_1-C_6$)alkyl)-N]—(C=O)—, —NO$_2$, amino, $(C_1-C_6)$alkylamino, [$(C_1-C_6)$alkyl]$_2$-amino, $(C_1-C_6)$alkyl-(C=O)—NH—, $(C_1-C_6)$alkyl-(C=O)—[(($C_1-C_6$)alkyl)-N]—, phenyl-(C=O)—NH—, phenyl-(C=O)—[(($C_1-C_6$)alkyl)-N]—, H$_2$N—(C=O)—NH—, $(C_1-C_6)$alkyl-HN—(C=O)—NH—, [$(C_1-C_6)$alkyl-]$_2$N—(C=O)—NH—, $(C_1-C_6)$alkyl-HN—(C=O)—[(($C_1-C_6$)alkyl)-N]—, [$(C_1-C_6)$alkyl-]$_2$N—(C=O)—[(($C_1-C_6$)alkyl)-N]—, phenyl-HN—(C=O)—NH—, (phenyl-)$_2$N—(C=O)—NH—, phenyl-HN—(C=O)—[(($C_1-C_6$)alkyl)-N]—, (phenyl-)$_2$N—(C=O)—[(($C_1-C_6$)alkyl)-N]—, $(C_1-C_6)$alkyl-O—(C=O)—NH—, $(C_1-C_6)$alkyl-O—(C=O)—[(($C_1-C_6$)alkyl)-N]—, phenyl-O—(C=O)—NH—, phenyl-O—(C=O)—[(($C_1-C_6$)alkyl)-N]—, $(C_1-C_6)$alkyl-SO$_2$NH—, phenyl-SO$_2$NH—, $(C_1-C_6)$alkyl-SO$_2$—, phenyl-SO$_2$—, hydroxy, $(C_1-C_6)$alkoxy, perhalo$(C_1-C_6)$alkoxy, phenoxy, $(C_1-C_6)$alkyl-(C=O)—O—, phenyl-(C=O)—O—, H$_2$N—(C=O)—O—, $(C_1-C_6)$alkyl-HN—(C=O)—O—, [$(C_1-C_6)$alkyl-]$_2$N—(C=O)—O—, phenyl-HN—(C=O)—O—, and (phenyl-)$_2$N—(C=O)—O—; wherein two adjacent substituents on said R$^1$ or R$^2$ $(C_3-C_{10})$cycloalkyl, phenyl. $(C_1-C_{10})$heteroaryl or $(C_1-C_{10})$heterocyclic may be taken together with the carbon or heteroatom to which they are attached to form a five to six membered carbocyclic or heterocyclic ring; wherein each of said moieties containing a phenyl alternative may optionally be substituted by one or two radicals independently selected from the group consisting of $(C_1-C_6)$alkyl, halo, $(C_1-C_6)$alkoxy, $(C_1-C_6)$alkyl and perhalo$(C_1-C_6)$alkoxy;

each R$^3$ is independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O), $(C_1-C_6)$alkyl-O—(C=O)—, H$_2$N(C=O)—, $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)— and $(C_1-C_6)$alkyl-(C=O)—O—; wherein two adjacent R$^3$ substituents may optionally be taken together to form a three to six membered carbocyclic or heterocyclic ring;

s is an integer from zero to five;

R$^4$ and R$^6$ are each independently selected from the group consisting of hydrogen, halo and R$^9$—B—(CH$_2$)$_n$—;

n is an integer from zero to six;

each B is independently a bond, —(CHR$^{10}$)—, —O—, —S—, —(SO$_2$)—, —(C=O)—, —O(C=O)—, —(C=O)—O—, —(C=O)—NR$^{10}$—, —(R$^{10}$—N)—, —(R$^{10}$—N)—SO$_2$—, —(R$^{10}$—N)—(C=O)—, —SO$_2$—(NR$^{10}$)—, —(R$^{10}$—N)—(C=O)—(NR$^{11}$)—, —(O)—(C=O)—(NR$^{10}$)— or —(R$^{10}$—N)—(C=O)—O—;

R$^5$ and R$^7$ are each independently selected from the group consisting of hydrogen, R$^{14}$—(CR$^{15}$H)$_p$—, phenyl, $(C_1-C_{10})$heteroaryl, $(C_1-C_{10})$heterocyclic, $(C_3-C_{10})$cycloalkyl, $(C_1-C_6)$alkyl-(SO$_2$)—, phenyl-(SO$_2$)—, H$_2$N—(SO$_2$)—, $(C_1-C_6)$alkyl-NH—(SO$_2$)—, [$(C_1-C_6)$alkyl-]$_2$N—(SO$_2$)—, phenyl-NH—(SO$_2$)—, (phenyl-)$_2$N—(SO$_2$)—, R$^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $(C_1-C_{10})$heterocyclic-O—(C=O)—, $(C_3-C_{10})$cycloalkyl-O—(C=O)—, H$_2$N—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, [$(C_1-C_6)$alkyl-]$_2$N—(C=O)—, (phenyl-)$_2$N—(C=O)—, phenyl-[$((C_1-C_6)$alkyl)-N]—(C=O)—, $(C_1-C_{10})$heteroaryl-[$((C_1-C_6)$alkyl)-N]—(C=O)—, $(C_1-C_{10})$heterocyclic-[$((C_1-C_6)$alkyl)-N]—(C=O)—, and $(C_3-C_{10})$cycloalkyl-[$((C_1-C_6)$alkyl)-N]—(C=O)—, wherein each of the aforesaid phenyl, heterocyclic, heteroaryl or cycloalkyl R$^5$ and R$^7$ alternatives may optionally be independently substituted by one to four moieties independently selected from the group consisting of halo, R$^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-SO$_2$—, formyl, —CN, $(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, [$(C_1-C_6)$alkyl]$_2$-N—(C=O)—, phenyl-[$((C_1-C_6)$alkyl)-N]—(C=O)—, hydroxy, $(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —NO$_2$, amino, $(C_1-C_6)$alkylamino, [$(C_1-C_6)$alkyl]$_2$-amino, formamidyl, $(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $(C_1-C_6)$alkyl-(C=O)—[$((C_1-C_6)$alkyl)-N]—, phenyl-(C=O)—[$((C_1-C_6)$alkyl-N]—, $(C_1-C_6)$alkyl-SO$_2$NH—, $(C_3-C_{10})$cycloalkyl-SO$_2$NH—, phenyl-SO$_2$NH—, $(C_1-C_{10})$heterocyclic-SO$_2$NH— and $(C_1-C_{10})$heteroaryl-SO$_2$NH—; wherein each of said phenyl and heteroaryl moiety alternatives may optionally be substituted by one or two radicals independently selected from halo, $(C_1-C_6)$alkyl, $(C_1-C_6)$alkoxy, perfluoro$(C_1-C_6)$alkyl and perfluoro$(C_1-C_6)$alkoxy;

p is an integer from one to six;

R$^9$ is selected from the group consisting of hydrogen, —CF$_3$, —C≡N, R$^{13}$—(R$^{12}$CH)$_m$—, phenyl, $(C_1-C_{10})$heteroaryl, $(C_1-C_{10})$heterocyclic and $(C_3-C_{10})$cycloalkyl; wherein each of the aforesaid R$^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N—(C=O)—, $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two adjacent substituents on said R$^9$ phenyl, $(C_1-C_{10})$heterocyclic or $(C_3-C_{10})$cycloalkyl may be taken together with the carbon or heteroatom to which they are attached to form a five to six membered heterocyclic or carbocyclic ring;

m is an integer from one to six;

$R^{10}$ is hydrogen, $(C_1-C_6)$alkyl-$SO_2$— or $(C_1-C_6)$alkyl;

$R^{11}$ is hydrogen or $(C_1-C_6)$alkyl;

each $R^{12}$ is independently selected from the group consisting of hydrogen, amino, $(C_1-C_6)$alkoxy or $(C_1-C_6)$alkyl;

$R^{13}$ is selected from the group consisting of hydrogen, $(C_1-C_6)$alkyl, $(C_2-C_6)$alkenyl, $(C_2-C_6)$alkynyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, phenyl-$SO_2$—NH—, $(C_1-C_6)$alkyl-$SO_2$-$[((C_1-C_6)$alkyl)-N]$—, phenyl-$SO_2$—$[((C_1-C_6)$alkyl)-N]$—, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $H_2$N(C=O)—, $(C_1-C_6)$alkyl-NH—(C=O)—, $[(C_1-C_6)$alkyl$]_2$-N—(C=O)—, phenyl-NH—(C=O)—, phenyl-$[((C_1-C_6)$alkyl)-N]$—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—;

$R^{14}$ is selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, $(C_1-C_{10})$heterocyclic, $(C_1-C_{10})$heteroaryl, phenyl-(S=O)—, $(C_1-C_6)$alkyl-$SO_2$—, phenyl-$SO_2$—, $H_2$N—$SO_2$—, $(C_1-C_6)$alkyl-NH—$SO_2$—, phenyl-NH—$SO_2$—, $[(C_1-C_6)$alkyl-$]_2$N—$SO_2$—, (phenyl-$)_2$N—$SO_2$—, formyl, —CN, $(C_1-C_6)$alkyl-(C=O)—, phenyl-(C=O)—, $(C_1-C_{10})$heteroaryl-(C=O), $(C_1-C_{10})$heterocyclic-(C=O)—, $(C_3-C_{10})$cycloalkyl-(C=O)—, HO—(C=O)—, $R^{16}$—$(C_1-C_6)$alkyl-O—(C=O), $(C_3-C_{10})$cycloalkyl-O—(C=O)—, $(C_1-C_{10})$heterocyclic-O—(C=O)—, $H_2$N—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, $(C_1-C_{10})$heteroaryl-$[((C_1-C_6)$alkyl)-N]$—(C=O)—, $(C_1-C_{10})$heterocyclic-$[((C_1-C_6)$alkyl)-N]$—(C=O)—, $(C_3-C_{10})$cycloalkyl-$[((C_1-C_6)$alkyl)-N]$—(C=O)—, hydroxy, $R^6$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^6$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—$[((C_1-C_6)$alkyl)-N]$—, phenyl-(C=O)—$[((C_1-C_6)$alkyl)-N]$—, $R^{16}$—$(C_1-C_6)$alkyl-$SO_2$NH—, $(C_3-C_{10})$cycloalkyl-$SO_2$NH—, phenyl-$SO_2$NH—, $(C_1-C_{10})$heterocyclic-$SO_2$NH— and $(C_1-C_{10})$heteroaryl-$SO_2$NH—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2$N—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—$[((C_1-C_6)$alkyl)-N]$—, phenyl-(C=O)—$[((C_1-C_6)$alkyl)-N]$—, $R^{16}$—$(C_1-C_6)$alkyl-$SO_2$NH—, $(C_3-C_{10})$cycloalkyl-$SO_2$NH—, phenyl-$SO_2$NH—, $(C_1-C_{10})$heterocyclic-$SO_2$NH— and $(C_1-C_{10})$heteroaryl-$SO_2$NH—; wherein each of said phenyl and heteroaryl moiety alternatives may optionally be substituted by one or two radicals independently selected from the group consisting of halo, $(C_1-C_6)$alkyl, $(C_1-C_6)$alkoxy, perfluoro$(C_1-C_6)$alkyl and perfluoro$(C_1-C_6)$alkoxy;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2$N—(C=O)—, $(C_1-C_6)$alkyl-NH—(C=O)—, $[(C_1-C_6)$alkyl$]_2$-N—(C=O)—, hydroxy, $(C_1-C_6)$alkoxy, $(C_1-C_6)$alkyl-(C=O)—O—, amino, $(C_1-C_6)$alkylamino, $[(C_1-C_6)$alkyl$]_2$-amino, formamidyl and $(C_1-C_6)$alkyl-(C=O)—NH—;

each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_1-C_{10})$heterocyclic, HO—(C=O)—, $(C_1-C_6)$alkyl-O—(C=O)—, $H_2$N—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, $(C_1-C_6)$alkyl-(C=O)—O—, —$NO_2$, amino, $(C_1-C_6)$alkylamino, $[(C_1-C_6)$alkyl$]_2$-amino, formamidyl and $(C_1-C_6)$alkyl-(C=O)—NH—; wherein said $(C_1-C_{10})$ heterocyclic may optionally be substituted by one to three substituents independently selected from the group consisting of halo, $(C_1-C_6)$alkyl, $(C_1-C_6)$alkoxy, amino, $(C_1-C_6)$alkylamino and $[(C_1-C_6)$alkyl$]_2$-amino;

or $R^4$ and $R^6$ or $R^4$ and $R^7$ or $R^5$ and $R^6$ may be taken together with the atoms to which they are attached to form an optionally substituted five to ten membered saturated, unsaturated or aromatic ring optionally containing two to three heteroatoms independently selected from NH, N, O, S, SO or $SO_2$; wherein said ring may be optionally substituted by one to three substituents independently selected from the group consisting of oxo, halo, $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, phenyl-S—, phenyl-(S=O)—, phenyl-$SO_2$—, $(C_1-C_6)$alkyl-NH—$SO_2$—, $[(C_1-C_6)$alkyl$]_2$-N—$SO_2$—, phenyl-NH—$SO_2$—, (phenyl$)_2$-N—$SO_2$—, phenyl-$[N(C_1-C_6)$ alkyl]-SO$_2$—, formyl, (C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, HO—(C=O)—, (C$_1$–C$_6$)alkyl-O—(C=O)—, (C$_1$–C$_{10}$)heterocyclic-O—(C=O)—, (C$_3$–C$_{10}$)cycloalkyl-O—(C=O)—, H$_2$N—(C=O)—, (C$_1$–C$_6$)alkyl-NH—(C=O)—, [(C$_1$–C$_6$)alkyl]$_2$-N—(C=O)—, phenyl-NH—(C=O)—, phenyl-[(C$_1$–C$_6$)alkyl)-N]—(C=O)—, (C$_1$–C$_{10}$)heteroaryl-NH—(C=O)—, (C$_1$–C$_{10}$)heteroaryl-[(C$_1$–C$_6$)alkyl)-N]—(C=O)—, (C$_1$–C$_{10}$)heterocyclic-NH—(C=O)—, (C$_1$–C$_{10}$)heterocyclic-[((C$_1$–C$_6$)alkyl)-N]—(C=O)—, (C$_3$–C$_{10}$)cycloalkyl-NH—(C=O)—, (C$_3$–C$_{10}$)cycloalkyl-[((C$_1$–C$_6$)alkyl)-N]—(C=O)—, amino, (C$_1$–C$_6$)alkylamino, [(C$_1$–C$_6$)alkyl]$_2$amino, (C$_1$–C$_6$)alkyl-SO$_2$—NH—, phenyl-SO$_2$—NH—, (C$_1$–C$_6$)alkyl-SO$_2$—[((C$_1$–C$_6$)alkyl)-N]—, phenyl-SO$_2$—[((C$_1$–C$_6$)alkyl)-N]—, formamidyl, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$)alkyl)-N]—, (C$_1$–C$_{10}$)heteroaryl-(C=O)—NH—, (C$_1$–C$_{10}$)heteroaryl-(C=O)—[((C$_1$–C$_6$)alkyl)-N]—, (C$_1$–C$_{10}$)heterocyclic-(C=O)—NH—, (C$_1$–C$_{10}$)heterocyclic-(C=O)—[((C$_1$–C$_6$)alkyl)-N]—, (C$_3$–C$_{10}$)cycloalkyl-(C=O)—NH—, (C$_3$–C$_{10}$)cycloalkyl-(C=O)—[((C$_1$–C$_6$)alkyl)-N]—, H$_2$N(C=O)—NH—, (C$_1$–C$_6$)alkyl-HN—(C=O)—NH—, (C$_1$–C$_6$)alkyl-HN—(C=O)—[((C$_1$–C$_6$)alkyl)-N]—, [(C$_1$–C$_6$)alkyl]$_2$-N—(C=O)—NH—, [(C$_1$–C$_6$)alkyl]$_2$-N—(C=O)—[((C$_1$–C$_6$)alkyl)-N]—, phenyl-HN—(C=O)—NH—, phenyl-HN—(C=O)—[((C$_1$–C$_6$)alkyl)-N]—, (phenyl)$_2$-N—(C=O)—NH—, (phenyl)$_2$-N—(C=O)—[((C$_1$–C$_6$)alkyl)-N]—, (C$_1$–C$_{10}$)heteroaryl-HN—(C=O)—NH—, (C$_1$–C$_{10}$)heteroaryl-HN—(C=O)—[((C$_1$–C$_6$)alkyl)-N]—, [(C$_1$–C$_{10}$)heteroaryl]$_2$-N—(C=O)—[((C$_1$–C$_6$)alkyl)-N]—, [(C$_1$–C$_{10}$)heteroaryl]$_2$-N—(C=O)—NH—, (C$_1$–C$_{10}$)heterocyclic-HN—(C=O)—NH—, (C$_1$–C$_{10}$)heterocyclic-HN—(C=O)—[((C$_1$–C$_6$)alkyl)-N]—, [(C$_1$–C$_{10}$)heterocyclic]$_2$-N—(C=O)—[((C$_1$–C$_6$)alkyl)-N]—, [(C$_1$–C$_{10}$)heterocyclic]$_2$-N—(C=O)—NH—, (C$_3$–C$_{10}$)cycloalkyl-HN—(C=O)—NH—, (C$_3$–C$_{10}$)cycloalkyl-HN—(C=O)—[((C$_1$–C$_6$)alkyl)-N]—, [(C$_3$–C$_{10}$)cycloalkyl]$_2$-N—(C=O)—[((C$_1$–C$_6$)alkyl)-N]—, [(C$_3$–C$_{10}$)cycloalkyl]$_2$-N—(C=O)—NH—, (C$_1$–C$_6$)alkyl-(C=O)—O—, phenyl-(C=O)—O—, (C$_1$–C$_{10}$)heteroaryl-(C=O)—O—, (C$_1$–C$_{10}$)heterocyclic-(C=O)—O—, (C$_3$–C$_{10}$)cycloalkyl-(C=O)—O—, (C$_1$–C$_6$)alkyl-NH—(C=O)—O—, [(C$_1$–C$_6$)alkyl]$_2$-N—(C=O)—O—, phenyl-NH—(C=O)—O—, (C$_1$–C$_{10}$)heteroaryl-NH—(C=O)—O—, (C$_1$–C$_{10}$)heterocyclic-NH—(C=O)—O— and (C$_3$–C$_{10}$)cycloalkyl-NH—(C=O)—O—;

with the proviso that when (R$^3$)$_s$-phenyl-Het is (b), R$^6$ is R$^9$—B—(CH$_2$)$_n$—; n is zero and B is a bond; then R$^9$ must be other than phenyl;

or a pharmaceutically acceptable salt thereof.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl. The phrase "each of said alkyl" as used herein refers to any of the preceding alkyl moieties within a group such alkoxy, alkenyl or alkylamino. Preferred alkyls include (C$_1$–C$_4$)alkyl, most preferably methyl and ethyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1 ]octanyl and bicyclo[5.2.0]nonanyl, etc.); optionally containing 1–2 double bonds and optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

As used herein, the term "halogen" includes fluoro, chloro, bromo or iodo or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

As used herein, the term "(C$_2$–C$_6$)alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "phenyl-[(C$_1$–C$_6$)alkyl)-N]—(C=O)—," as used herein, refers to a disubstituted amide group of the formula

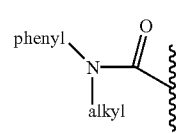

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^4$, $R^5$, $R^6$ and $R^7$ heteroaryls).

The term "heterocyclic" as used herein refers to a cyclic group containing 1–9 carbon atoms and 1–4 hetero atoms selected from N, O, S or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxcithiazinyl, indolinyl, isoindolinyl, quincuclidinyl, chromanyl, isochromanyl, benzocazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

Alternative, as used herein refers to a substituent, group or moiety which contains as any component of the substituent, group or moiety the designated alternative.

A preferred embodiment of the present invention is that group of compounds of formula I wherein $R^2$ is $(C_1-C_6)$ alkyl, more preferably $(C_1-C_5)$alkyl, more preferably $(C_1-C_4)$alkyl.

Another embodiment of the present invention is that group of compounds of formula I wherein $R^1$ is $(C_1-C_6)$ alkyl, more preferably $(C_1-C_5)$alkyl, more preferably $(C_1-C_4)$alkyl.

Another embodiment of the present invention is that group of compounds of formula I, wherein $R^1$ is optionally substituted $(C_3-C_6)$cycloalkyl, more preferably optionally substituted cyclobutyl or cyclopentyl; more preferably optionally substituted by 1 to 3 substituents selected from the group consiting of fluoro, chloro, trifluoromethyl, hydroxy, $(C_1-C_6)$alkoxy, amino, trifluoromethoxy, and $(C_1-C_6)$alkyl.

Another embodiment of the present invention is that group of compounds of formula I wherein $R^1$ is optionally substituted phenyl; more preferably optionally substituted by 1 to 3 substituents selected from the group consiting of fluoro, chloro, trifluoromethyl, hydroxy, $(C_1-C_6)$alkoxy, amino, trifluoromethoxy, and $(C_1-C_6)$alkyl.

Another embodiment of the present invention is that group of compounds of formula I wherein $R^1$ is optionally substituted $(C_1-C_{10})$heterocyclic, more preferably optionally substituted tetrahydrofuranyl, more preferably optionally substituted by 1 to 2 substituents independenty selected from the group consiting of fluoro, chloro, trifluoromethyl, hydroxy, $(C_1-C_6)$alkoxy, amino, trifluoromethoxy, and $(C_1-C_6)$alkyl.

Another embodiment of the present invention include that group of compounds of formula I wherein $R^1$ is optionally substituted $(C_1-C_{10})$heteroaryl, more preferably optionally substituted thiophenyl and pyridinyl, more preferably optionally substituted by 1 to 2 substituents independently selected from the group consiting of fluoro, chloro, trifluoromethyl, hydroxy, $(C_1-C_6)$alkoxy, amino, trifluoromethoxy, and $(C_1-C_6)$alkyl.

Another embodiment of the present invention is that group of compounds of formula I, wherein $R^1$ or $R^2$ is hydrogen.

An embodiment of the present invention includes compounds of formula I, referred to as the phenyl-pyrrolyl-benzoimidazoles, wherein the compounds have the formula

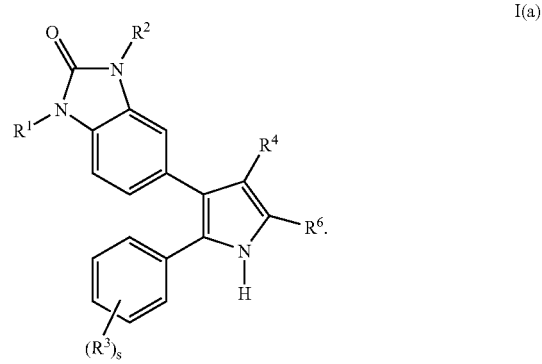

I(a)

Other embodiments of the present invention include that group of compounds of formula I(a) in combination with each of the aforementioned embodiments of $R^1$ and $R^2$.

Preferred compounds of the present invention include compounds of formula I, referred to as the phenyl-imidazolyl-benzoimidazolones, wherein the compounds have the formula

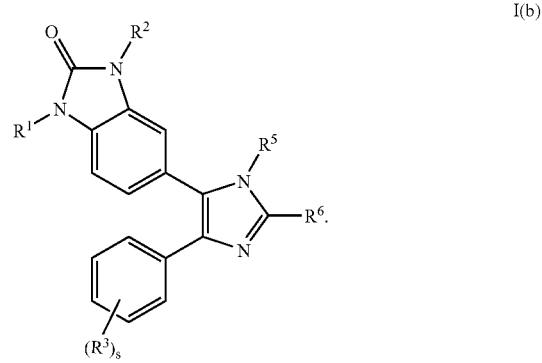

I(b)

Other embodiments of the present invention include that group of compounds of formula I(b) in combination with each of the aforementioned embodiments of $R^1$ and $R^2$.

Other preferred compounds of the present invention include compound of formula I, referred to as the phenyl-pyrazolyl-benzoimidazolones, wherein the compounds have the formula

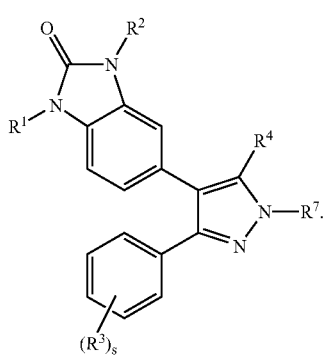

I(c)

Other embodiments of the present invention include that group of compounds of formula I(c) in combination with each of the aforementioned embodiments of $R^1$ and $R^2$.

Another embodiment of the present invention includes compounds of formula I, referred to as the phenyl-oxazolyl-benzoimidazolones, wherein the compounds have the formula

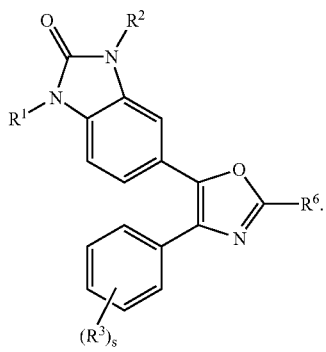

I(d)

Other embodiments of the present invention include that group of compounds of formula I(d) in combination with each of the aforementioned embodiments of $R^1$ and $R^2$.

Another embodiment of the present invention includes compounds of formula I, referred to as the phenyl-isoxazolyl-benzoimidazolones, wherein the compounds have the formula

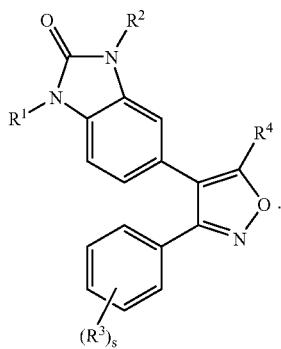

I(e)

Other embodiments of the present invention include that group of compounds of formula I(e) in combination with each of the aforementioned embodiments of $R^1$ and $R^2$.

Another embodiment of the present invention includes compounds of formula I, referred to as the phenyl-pyrazolyl-benzoimidazolones, wherein the compounds have the formula

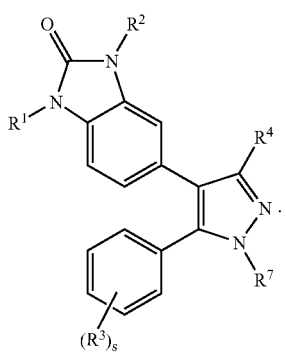

I(f)

Other embodiments of the present invention include that group of compounds of formula I(f) in combination with each of the aforementioned embodiments of $R^1$ and $R^2$.

Another embodiment of the present invention includes compounds of formula I, referred to as the phenyl-thiazolyl-benzoimidazolones, wherein the compounds have the formula

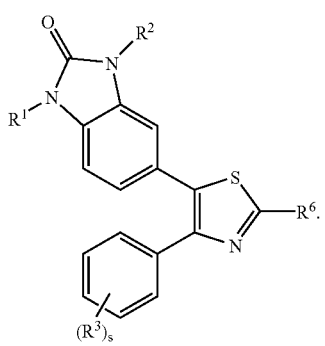

I(g)

Other embodiments of the present invention include that group of compounds of formula I(g) in combination with each of the aforementioned embodiments of $R^1$ and $R^2$.

Another embodiment of the present invention includes compounds of formula I, referred to as the phenyl-isothiazolyl-benzoimidazolones, wherein the compounds have the formula

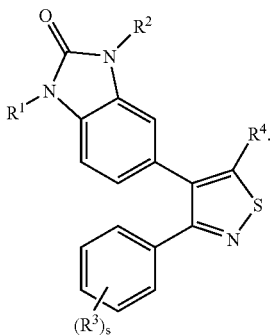

Other embodiments of the present invention include that group of compounds of formula I(h) in combination with each of the aforementioned embodiments of $R^1$ and $R^2$.

Another preferred embodiment of the present invention is that group of compounds of formula I (and I(a), I(c), I(e), I(f), and I(h)) wherein $R^4$ is hydrogen. Other embodiments of the present invention include those compounds of formula I (and I(a), I(c), I(e), I(f), and I(h)) wherein $R^4$ is hydrogen in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—$(CH_2)_n$— and n is zero. Other embodiments of the present invention include those compounds of formula I (and I(a), I(c), I(e), I(f), and I(h)) wherein $R^4$ is $R^9$—B—$(CH_2)_n$— and n is zero in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—$(CH_2)_n$— and n is an integer from one to six, more preferably one to five Other embodiments of the present invention include those compounds of formula I (and I(a), I(c), I(e), I(f), and I(h)) wherein $R^4$ is $R^9$—B—$(CH_2)_n$— and n is one to six, preferably one to five, in combination with the aforementioned embodiments of $R^1$ and $R^2$.

Another preferred embodiment of the present invention is that group of compounds of formula I (and I(a), I(c), I(e), I(f), and I(h)) wherein $R^4$ is $R^9$—B—$(CH_2)_n$—; n is zero; B is a bond and $R^9$ is $R^3$—$(R^{12}CH)_m$—. Other embodiments of the present invention include those compounds of formula I (and I(a), I(c), I(e), I(f), and I(h)) wherein $R^4$ is $R^9$—B—$(CH_2)_n$—, n is zero and $R^9$ is $R^{13}$—$(R^{12}CH)_m$— in combination with the aforementioned embodiments of $R^1$ and $R^2$. More preferred embodiments of the invention of formula I (and I(c), I(e) and I(f)) are those compounds wherein $R^4$ is $R^9$—B—$(CH_2)_n$—, n is zero, $R^9$ is $R^{13}$—$(R^{12}CH)_m$—, m is one to six and $R^{12}$ and $R^{13}$ are each hydrogen.

Another embodiment of the present invention is that group of compounds of formula I (and I(a), I(c), I(e), I(f), and I(h)) wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is selected from the group consisting of hydrogen and $R^{13}$—$(R^{12}CH)_m$—; more preferably wherein $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1$–$C_6)$alkyl, $(C_2$–$C_6)$alkenyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo$(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-$S$—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$alkyl]$_2$-amino, $(C_1$–$C_6)$alkyl-$SO_2$—NH—, $(C_1$–$C_6)$alkyl-(C=O)—NH—, $(C_1$–$C_6)$alkyl-(C=O)—[(($C_1$–$C_6)$alkyl)-N]—, phenyl-(C=O)—NH—, phenyl-(C=O)—[(($C_1$–$C_6)$alkyl)-N]—, $(C_1$–$C_6)$alkyl-$SO_2$—NH—, phenyl-$SO_2$—NH—, $(C_1$–$C_6)$alkyl-$SO_2$—[(($C_1$–$C_6)$alkyl)-N]—, phenyl-$SO_2$—[(($C_1$–$C_6)$alkyl)-N]—, —CN, $(C_1$–$C_8)$alkyl-(C=O)—, phenyl-(C=O)—, $(C_1$–$C_{10})$heteroaryl-(C=O)—, $(C_1$–$C_{10})$heterocyclic-(C=O)—, $(C_3$–$C_{10})$cycloalkyl-(C=O)—, $(C_1$–$C_{10})$heteroaryl-NH—(C=O)—, $(C_1$–$C_{10})$heterocyclic-NH—(C=O)—, $(C_3$–$C_{10})$cycloalkyl-NH—(C=O)—, HO—(C=O)—, $(C_1$–$C_6)$alkyl-O—(C=O)—, $H_2N(C=O)$—, $(C_1$–$C_6)$alkyl-NH—(C=O)—, [$(C_1$–$C_6)$alkyl]$_2$-N—(C=O)—, phenyl-NH—(C=O)—, phenyl-[(($C_1$–$C_6)$alkyl)-N]—(C=O)—, $(C_1$–$C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; $R^9$ is hydrogen or $R^{13}$—$(R^2CH)_m$—; more preferably wherein $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is as described above, in combination with the aforementioned embodiments of $R^1$ and $R^2$ Another more preferred embodiment of the present invention is that group of compounds of formula I (and I(a), I(c), I(e), I(f), and I(h)) wherein $R^4$ is $R^9$—B—$(CH_2)_n$—; n is zero; B is —$(R^{10}$—N)—; $R^9$ is hydrogen or $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1$–$C_6)$alkyl, hydroxy, $(C_1$–$C_6)$alkoxy, amino, $(C_1$–$C_6)$alkylamino, [$(C_1$–$C_6)$alkyl]$_2$amino, $(C_2$–$C_6)$alkenyl, $(C_2$–$C_6)$alkynyl, phenyl, $(C_1$–$C_{10})$heteroaryl, $(C_1$–$C_{10})$heterocyclic and $(C_3$–$C_{10})$cycloalkyl. Other embodiments of the present invention include those compounds of formula I (and I(a), I(c), I(e), I(f), and I(h)) wherein $R^4$ is $R^9$—B—$(CH_2)_n$—; n is zero; B is —$(R^{10}$—N)—; $R^9$ is hydrogen or $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1$–$C_6)$alkyl, hydroxy, $(C_1$–$C_6)$alkoxy, amino, $(C_1$–$C_6)$alkylamino, [$(C_1$–$C_6)$alkyl]$_2$amino, $(C_2$–$C_6)$alkenyl, $(C_2$–$C_6)$alkynyl, phenyl, $(C_1$–$C_{10})$heteroaryl, $(C_1$–$C_{10})$heterocyclic and $(C_3$–$C_{10})$cycloalkyl, in combination with the aforementioned embodiments of $R^1$ and $R^2$. More preferred embodiments of the invention is that group of compounds of formula I (and I(c), I(e) and I(f)) wherein $R^4$ is $R^9$—B—$(CH_2)_n$—, n is zero, B is —$(R^{10}$—N)—, $R^9$ is $R^{13}$—$(R^{12}CH)_m$—, m is 1–6, and $R^{10}$, $R^{12}$ and $R^{13}$ are each hydrogen.

Another embodiment of the present invention is that group of group of compounds of formula I (and I(a), I(c), I(e), I(f), and I(h)) wherein $R^4$ is $R^9$—B—$(CH_2)_n$—; n is zero; B is a bond, and $R^9$ is selected from the group consisting of optionally substituted phenyl, $(C_1$–$C_{10})$heterocyclic, $(C_1$–$C_{10})$heteroaryl and $(C_3$–$C_{10})$cycloalkyl; wherein each of the aforesaid $R^9$ phenyl, $(C_1$–$C_{10})$heteroaryl, $(C_1$–$C_{10})$heterocyclic and $(C_3$–$C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—(CH$_2$)$_n$—; n is zero; B is a bond, and $R^9$ is as described above, in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—(CH$_2$)$_n$—; n is zero; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and $R^9$ is selected from the group consisting of optionally substituted phenyl, $(C_1-C_{10})$heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-Cr)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—(CH$_2$)$_n$—; n is zero; B is —(C=O)—(R$^{10}$—N)—, —(R$^{10}$—N)—, —SO$_2$—(R$^{10}$—N)—, —(R$^{10}$—N)—(C=O)—(NR$^{11}$) or —(R$^{10}$—N)—(C=O)—O—; and $R^9$ is as described above, in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—(CH$_2$)$_n$—; n is an integer from one to six, more preferably one to five, more preferably one to three; B is a bond, and $R^9$ is selected from the group consisting of optionally substituted phenyl, $(C_1-C_{10})$heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—(CH$_2$)$_n$—; n is an integer from one to six, more preferably one to five, more preferably one to three; B is a bond, and $R^9$ is as described above, in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—(CH$_2$)$_n$—; n is an integer from one to six, more preferably one to five, more preferably one to three; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and $R^9$ is selected from the group consisting of optionally substituted phenyl, $(C_1-C_{10})$heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, [$(C_1-C_6)$alkyl]$_2$-N—(C=O)—, phenyl-NH—(C=O)—, phenyl-[$((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl- (C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is an integer from one to six, more preferably one to five, more preferably one to three; B is —(C=O)—$(R^{10}$—N)—, —$(R^{10}$—N)—, —$SO_2$—$(R^{10}$—N)—, —$(R^{11}$—N)—(C=O)—$(NR^{11})$— or —$(R^{10}$—N)—(C=O)—O—; and $R^9$ is as described above, in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—$(CH_2)_n$—; n is an integer from one to six, more preferably one to five, more preferably one to three; B is a bond, and $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, $(C_1-C_6)$alkyl-$SO_2$—NH—, phenyl-$SO_2$—NH—, $(C_1-C_6)$alkyl-$SO_2$—[$((C_1-C_6)$alkyl)-N]—, phenyl-$SO_2$—[$((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)—, $(C_1-C_6)$alkyl-NH—(C=O)—, $[(C_1-C_6)$alkyl$]_2$-N—(C=O)—, phenyl-NH—(C=O)—, phenyl-[$((C_1-C_6)$alkyl)-N]—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is an integer from one to six, more preferably one to five, more preferably one to three; B is a bond, and $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ as described above, in combination with the aforementioned embodiments of $R^1$ and $R^2$.

Another embodiment of the present invention is that group of compounds of formula I (and I(a), I(c), I(e), I(f), and I(h)) wherein $R^4$ is $R^9$—B—$(CH_2)_n$—; n is an integer from one to six, more preferably one to five, more preferably one to three; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_8)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, $(C_1-C_6)$alkyl-$SO_2$—NH—, phenyl-$SO_2$—NH—, $(C_1-C_6)$alkyl-$SO_2$—[$((C_1-C_6)$alkyl)-N]—, phenyl-$SO_2$—[$((C_1-C_8)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)—, $(C_1-C_6)$alkyl-NH—(C=O)—, $[(C_1-C_6)$alkyl$]_2$-N—(C=O)—, phenyl-NH—(C=O)—, phenyl-[$((C_1-C_6)$alkyl)-N]—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is an integer from one to six, more preferably one to five, more preferably one to three; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is as described above, in combination with the aforementioned embodiments of $R^1$ and $R^2$.

Another embodiment of the present invention is that group of compounds of formula I (and I(c) and I(f)) wherein $R^7$ is selected from the group consisting of hydrogen, phenyl, $(C_1-C_{10})$heteroaryl, $(C_1-C_{10})$heterocyclic, $(C_3-C_{10})$cycloalkyl, $R^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $H_2N$—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)— and $(C_3-C_{10})$cycloalkyl-NH—(C=O)—; wherein each of the aforesaid phenyl, heterocyclic, heteroaryl or cycloalkyl $R^7$ alternatives may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-[$((C_1-C_6)$alkyl)-N]—(C=O)—, hydroxy, $(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $(C_1-C_6)$alkylamino, $[(C_1-C_6)$alkyl$]_2$-amino, formamidyl, $(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $(C_1-C_6)$alkyl-(C=O)—[$((C_1-C_6)$alkyl)-N]—, phenyl-(C=O)—[$((C_1-C_6)$alkyl)-N]—, $(C_1-C_6)$alkyl-$SO_2$NH—, $(C_3-C_{10})$cycloalkyl-$SO_2$NH—, phenyl-$SO_2$NH—, $(C_1-C_{10})$heterocyclic-$SO_2$NH— and $(CO_1-C_{10})$heteroaryl-$SO_2$NH—; wherein each of said phenyl and heteroaryl moieties may optionally be substituted by one or two radicals independently selected from the group consisting of halo, $(C_1–C_6)$alkyl, $(C_1–C_6)$alkoxy, amino, $(C_1–C_6)$ alkylamino and $[(C_1–C_6)alkyl]_2$-amino. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^1$ and $R^2$ embodiments.

Another embodiment of the present invention is that group of compounds of formula I (and I(c) and I(f)) wherein $R^7$ is selected from the group consisting of $R^{16}$—$(C_1–C_6)$alkyl-(C=O)—, phenyl-(C=O)—, $(C_1–C_{10})$heteroaryl-(C=O)—, $(C_1–C_{10})$heterocyclic-(C=O)—, $(C_3–C_{10})$cycloalkyl-(C=O)—, $(C_1–C_6)$alkyl-O—(C=O)—, $H_2N$—(C=O)—, $(C_1–C_6)$alkyl-NH—(C=O)—, phenyl-NH—(C=O)—, $(C_1–C_{10})$heteroaryl-NH—(C=O)—, $(C_1–C_{10})$heterocyclic-NH—(C=O)— and $(C_3–C_{10})$cycloalkyl-NH—(C=O)—; wherein each of the aforesaid phenyl, heterocyclic, heteroaryl or cycloalkyl $R^7$ alternatives may optionally be independently substituted by one to four moieties independently selected from the group consisting of halo, $R^{16}$—$(C_1–C_6)$alkyl, $(C_2–C_6)$alkenyl, $(C_2–C_6)$alkynyl, perhalo$(C_1–C_6)$alkyl, $(C_3–C_{10})$cycloalkyl, phenyl, benzyl, $(C_1–C_{10})$heterocyclic, $(C_1–C_{10})$heteroaryl, $(C_1–C_6)$alkyl-$SO_2$—, formyl, —CN, $(C_1–C_6)$alkyl-(C=O)—, $(C_3–C_{10})$cycloalkyl-(C=O)—, phenyl-(C=O)—, $(C_1–C_{10})$heterocyclic-(C=O)—, $(C_1–C_{10})$heteroaryl-(C=O)—, HO—(C=O)—, $(C_1–C_6)$alkyl-O—(C=O)—, $(C_3–C_{10})$cycloalkyl-O—(C=O)—, $(C_1–C_{10})$heterocyclic-O—(C=O)—, $(C_1–C_{10})$heteroaryl-O—(C=O)—, $(C_1–C_6)$alkyl-NH—(C=O)—, $(C_3–C_{10})$cycloalkyl-NH—(C=O)—, phenyl-NH—(C=O)—, $(C_1–C_{10})$heterocyclic-NH—(C=O)—, $(C_1–C_{10})$heteroaryl-NH—(C=O)—, $[(C_1–C_6)alkyl]_2$-N—(C=O)—, phenyl-$[((C_1–C_6)alkyl)$-N]—(C=O)—, hydroxy, $(C_1–C_6)$alkoxy, perhalo$(C_1–C_6)$alkoxy, $(C_3–C_{10})$cycloalkyl-O—, phenoxy, $(C_1–C_{10})$heterocyclic-O—, $(C_1–C_{10})$heteroaryl-O—, $(C_1–C_6)$alkyl-(C=O)—O—, $(C_3–C_{10})$cycloalkyl-(C=O)—O—, phenyl-(C=O)—O—, $(C_1–C_{10})$heterocyclic-(C=O)—O—, $(C_1–C_{10})$heteroaryl-(C=O)—O—, —$NO_2$, amino, $(C_1–C_6)$alkylamino, $[(C_1–C_6)alkyl]_2$-amino, formamidyl, $(C_1–C_6)$alkyl-(C=O)—NH—, $(C_3–C_{10})$cycloalkyl-(C=O)—NH—, phenyl-(C=O)—NH—, $(C_1–C_{10})$heterocyclic-(C=O)—NH—, $(C_1–C_{10})$heteroaryl-(C=O)—NH—, $(C_1–C_6)$alkyl-(C=O)—$[((C_1–C_6)alkyl)$-N]—, phenyl-(C=O)—$[((C_1–C_6)alkyl)$-N]—, $(C_1–C_6)$alkyl-$SO_2NH$—, $(C_3–C_{10})$cycloalkyl-$SO_2NH$—, phenyl-$SO_2NH$—, $(C_1–C_{10})$heterocyclic-$SO_2NH$— and $(C_1–C_{10})$heteroaryl-$SO_2NH$—; wherein each of said phenyl and heteroaryl moiety alternatives may optionally be substituted by one or two radicals independently selected from the group consisting of halo, $(C_1–C_6)$alkyl, $(C_1–C_6)$alkoxy, amino, $(C_1–C_6)$alkylamino and $[(C_1–C_6)alkyl]_2$-amino. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^1$ and $R^2$ embodiments.

Another preferred embodiment of the present invention is that group of compounds of formula I (and I(c) and I(f)) wherein $R^7$ is selected from the group consisting of hydrogen, and optionally substituted phenyl, $(C_1–C_{10})$heteroaryl, $(C_1–C_{10})$heterocyclic and $(C_3–C_{10})$cycloalkyl. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^1$ and $R^2$ embodiments. A more preferred embodiment of the present invention is that group of compounds of formula I(c) wherein $R^7$ is hydrogen.

Another embodiment of the present invention is that group of compounds of formula I (and I(c) and I(f)) wherein $R^7$ is $R^{14}$—$(CR^{15}H)_p$—; p is one to six, preferably one to four; and $R^{14}$ is selected from the group consisting of hydrogen, halo, $(C_2–C_6)$alkenyl, $(C_2–C_6)$alkynyl, perhalo$(C_1–C_6)$alkyl, $(C_3–C_{10})$cycloalkyl, phenyl, $(C_1–C_{10})$heterocyclic, $(C_1–C_{10})$heteroaryl, formyl, —CN, $(C_1–C_6)$alkyl-(C=O)—, phenyl-(C=O)—, $(C_1–C_{10})$heteroaryl-(C=O)—, $(C_1–C_{10})$heterocyclic-(C=O)—, $(C_3–C_{10})$cycloalkyl-(C=O)—, HO—(C=O)—, $R^{16}$—$(C_1–C_6)$alkyl-O—(C=O)—, $(C_3–C_{10})$cycloalkyl-O—(C=O)—, $(C_1–C_{10})$heterocyclic-O—(C=O)—, $(C_1–C_{10})$heteroaryl-O—(C=O)—, $H_2N$—(C=O)—, $R^{16}$—$(C_1–C_6)$alkyl-NH—(C=O)—, $(C_3–C_{10})$cycloalkyl-NH—(C=O)—, phenyl-NH—(C=O)—, $(C_1–C_{10})$heterocyclic-NH—(C=O)—, $(C_1–C_{10})$heteroaryl-NH—(C=O)—, $[(C_1–C_6)alkyl]_2$-N—(C=O)—, phenyl-$[((C_1–C_6)alkyl)$-N]—(C=O)—, $(C_1–C_{10})$heteroaryl-$[((C_1–C_6)alkyl)$-N]—(C=O)—, $(C_1–C_{10})$heterocyclic-$[((C_1–C_6)alkyl)$-N]—(C=O)—, $(C_3–C_{10})$cycloalkyl-$[((C_1–C_6)alkyl)$-N]—(C=O)—, hydroxy, $R^{16}$—$(C_1–C_6)$alkoxy, perhalo$(C_1–C_6)$alkoxy, $(C_3–C_{10})$cycloalkyl-O—, phenoxy, $(C_1–C_{10})$heterocyclic-O—, $(C_1–C_{10})$heteroaryl-O—, $R^{16}$—$(C_1–C_6)$alkyl-(C=O)—O—, $(C_3–C_{10})$cycloalkyl-(C=O)—O—, phenyl-(C=O)—O—, $(C_1–C_{10})$heterocyclic-(C=O)—O—, $(C_1–C_{10})$heteroaryl-(C=O)—O—, amino, $R^{16}$—$(C_1–C_6)$alkylamino, $[(C_1–C_6)alkyl]_2$-amino, formamidyl, $R^{16}$—$(C_1–C_6)$alkyl-(C=O)—NH—, $(C_3–C_{10})$cycloalkyl-(C=O)—NH—, phenyl-(C=O)—NH—, $(C_1–C_{10})$heterocyclic-(C=O)—NH—, $(C_1–C_{10})$heteroaryl-(C=O)—NH—, $R^{16}$—$(C_1–C_6)$alkyl-(C=O)—$[((C_1–C_6)alkyl)$-N]—, phenyl-(C=O)—$[((C_1–C_6)alkyl)$-N]—, $R^{16}$—$(C_1–C_6)$alkyl-$SO_2NH$—, $(C_3–C_{10})$cycloalkyl-$SO_2NH$—, phenyl-$SO_2NH$—, $(C_1–C_{10})$heterocyclic-$SO_2NH$— and $(C_1–C_{10})$heteroaryl-$SO_2NH$—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—$(C_1–C_6)$alkyl, $(C_2–C_6)$alkenyl, $(C_2–C_6)$alkynyl, perhalo$(C_1–C_6)$alkyl, $(C_3–C_{10})$cycloalkyl, phenyl, benzyl, $(C_1–C_{10})$heterocyclic, $(C_1–C_{10})$heteroaryl, $(C_1–C_8)$alkyl-$SO_2$—, formyl, —CN, $R^{16}$—$(C–C_6)$alkyl-(C=O)—, $(C_3–C_{10})$cycloalkyl-(C=O)—, phenyl-(C=O)—, $(C_1–C_{10})$heterocyclic-(C=O)—, $(C_1–C_{10})$heteroaryl-(C=O)—, HO—(C=O)—, $(C_1–C_6)$alkyl-O—(C=O)—, $(C_3–C_{10})$cycloalkyl-O—(C=O)—, $(C_1–C_{10})$heterocyclic-O—(C=O)—, $(C_1–C_{10})$heteroaryl-O—(C=O)—, $H_2N$—(C=O)—, $R^{16}$—$(C_1–C_6)$alkyl-NH—(C=O)—, $(C_3–C_{10})$cycloalkyl-NH—(C=O)—, phenyl-NH—(C=O)—, $(C_1–C_{10})$heterocyclic-NH—(C=O)—, $(C_1–C_{10})$heteroaryl-NH—(C=O)—, $[(C_1–C_6)alkyl]_2$-N—(C=O)—, phenyl-$[((C_1–C_6)alkyl)$-N]—(C=O)—, hydroxy, $R^{16}$—$(C_1–C_6)$alkoxy, perhalo$(C_1–C_6)$alkoxy, $(C_3–C_{10})$cycloalkyl-O—, phenoxy, $(C_1–C_{10})$heterocyclic-O—, $(C_1–C_{10})$heteroaryl-O—, $R^{16}$—$(C_1–C_6)$alkyl-(C=O)—O—, $(C_3–C_{10})$cycloalkyl-(C=O)—O—, phenyl-(C=O)—O—, $(C_1–C_{10})$heterocyclic-(C=O)—O—, $(C_1–C_{10})$heteroaryl-(C=O)—O—, —$NO_2$, amino, $R^{16}$—$(C_1–C_6)$alkylamino, $[(C_1–C_6)alkyl]_2$-amino, formamidyl, $R^{16}$—$(C_1–C_6)$alkyl-(C=O)—NH—, $(C_3–C_{10})$cycloalkyl-(C=O)—NH—, phenyl-(C=O)—NH—, $(C_1–C_{10})$heterocyclic-(C=O)—NH—, $(C_1–C_{10})$heteroaryl-(C=O)—NH—, $R^{16}$—$(C_1–C_6)$alkyl-(C=O)—$[((C_1–C_6)alkyl)$-N]—, phenyl-(C=O)—$[((C_1–C_6)alkyl)$-N]—, $R^{16}$—$(C_1–C_6)$alkyl-$SO_2NH$—, $(C_3–C_{10})$cycloalkyl-$SO_2NH$—, phenyl-$SO_2NH$—, ($C_1$–$C_{10}$)heterocyclic-$SO_2NH$— and ($C_1$–$C_{10}$)heteroaryl-$SO_2NH$—; wherein each of said phenyl and heteroaryl moiety alternatives may optionally be substituted by one or two radicals independently selected from the group consisting of halo, ($C_1$–$C_6$)alkyl, ($C_1$–$C_6$)alkoxy, amino, ($C_1$–$C_6$) alkylamino or [($C_1$–$C_6$)alkyl]$_2$-amino;

each $R^{15}$ is independently selected from the group consisting of hydrogen, halo, ($C_1$–$C_6$)alkyl, ($C_2$–$C_6$)alkenyl, perhalo($C_1$–$C_6$)alkyl, HO—(C=O)—, ($C_1$–$C_6$)alkyl-O—(C=O)—, $H_2N$—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, amino, ($C_1$–$C_6$) alkylamino, [($C_1$–$C_6$)alkyl]$_2$-amino, formamidyl and ($C_1$–$C_6$)alkyl-(C=O)—NH—; and each $R^{16}$ is independently selected from the group consisting of hydrogen, halo, ($C_1$–$C_6$)alkyl, ($C_2$–$C_6$)alkenyl, ($C_2$–$C_6$)alkynyl, perhalo($C_1$–$C_6$)alkyl, HO—(C=O)—, ($C_1$–$C_6$)alkyl-O—(C=O)—, $H_2N$—(C=O)—, ($C_1$–$C_6$) alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, ($C_1$–$C_6$) alkyl-(C=O)—O—, —$NO_2$, amino, ($C_1$–$C_6$)alkylamino, [($C_1$–$C_6$)alkyl]$_2$-amino, formamidyl and ($C_1$–$C_6$)alkyl-(C=O)—NH—. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^1$ and $R^2$ embodiments.

Another preferred embodiment of the present invention is that group of compounds of formula I (and I(c) and I(f)) wherein $R^7$ is $R^{14}$—($CR^{15}H$)$_p$—; p is one to four; $R^{14}$ is selected from the group consisting of hydrogen, halo, ($C_1$–$C_6$)alkyl, ($C_2$–$C_6$)alkenyl, ($C_3$–$C_{10}$)cycloalkyl, phenyl, ($C_1$–$C_{10}$)heterocyclic, ($C_1$–$C_{10}$)heteroaryl, HO—(C=O)—, $R^{16}$—($C_1$–$C_6$)alkyl-O—(C=O)—, $H_2N$—(C=O)—, $R^{16}$—($C_1$–$C_6$)alkyl-NH—(C=O)—, phenyl-NH—(C=O)—, ($C_1$–$C_{10}$)heterocyclic-NH—(C=O)—, [($C_1$–$C_6$) alkyl]$_2$-N—(C=O)—, phenyl-[N—(($C_1$–$C_6$)alkyl)]-(C=O)—, hydroxy, $R^{16}$—($C_1$–$C_6$)alkoxy, phenoxy, amino, $R^{16}$—($C_1$–$C_6$)alkylamino, [($C_1$–$C_6$)alkyl]$_2$-amino and $R^{16}$—($C_1$–$C_6$)alkyl-(C=O)—NH—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—($C_1$–$C_6$)alkyl, ($C_2$–$C_6$)alkenyl, ($C_2$–$C_6$)alkynyl, perhalo($C_1$–$C_6$)alkyl, ($C_1$–$C_6$)alkyl-$SO_2$—, formyl, —CN, $R^{16}$—($C_1$–$C_6$)alkyl-(C=O)—, HO—(C=O)—, ($C_1$–$C_6$)alkyl-O—(C=O)—, $H_2N$—(C=O)—, $R^{16}$—($C_1$–$C_6$)alkyl-NH—(C=O)—, [($C_1$–$C_6$)alkyl]$_2$-N—(C=O)—, hydroxy, $R^{16}$—($C_1$–$C_6$)alkoxy, perhalo($C_1$–$C_6$) alkoxy, $R^{15}$—($C_1$–$C_6$)alkyl-(C=O)—O—, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, $R^{16}$—($C_1$–$C_6$)alkyl-(C=O)—[(($C_1$–$C_6$)alkyl)-N]— and $R^{16}$—($C_1$–$C_6$)alkyl-$SO_2NH$—;

each $R^{15}$ is independently selected from the group consisting of hydrogen, halo, ($C_1$–$C_6$)alkyl, ($C_2$–$C_6$)alkenyl, perhalo($C_1$–$C_6$)alkyl, HO—(C=O)—, ($C_1$–$C_6$)alkyl-O—(C=O)—, $H_2N$—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, amino, ($C_1$–$C_6$) alkylamino, [($C_1$–$C_6$)alkyl]$_2$-amino, formamidyl and ($C_1$–$C_6$)alkyl-(C=O)—NH—; wherein no more than two of said $R^{15}$ groups may be other than hydrogen; and each $R^{16}$ is independently selected from the group consisting of hydrogen, halo, ($C_1$–$C_6$)alkyl, ($C_2$–$C_6$)alkenyl, ($C_2$–$C_6$)alkynyl, perhalo($C_1$–$C_6$)alkyl, HO—(C=O)—, ($C_1$–$C_6$)alkyl-O—(C=O)—, $H_2N$—(C=O)—, ($C_1$–$C_6$) alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, ($C_1$–$C_6$) alkyl-(C=O)—O—, —$NO_2$, amino, ($C_1$–$C_6$)alkylamino, [($C_1$–$C_6$)alkyl]$_2$-amino, formamidyl and ($C_1$–$C_6$)alkyl-(C=O)—NH—. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^1$ and $R^2$ embodiments.

A more preferred embodiment of the present invention are those group of compounds of formula I(c) wherein $R^7$ is $R^{14}$—($CR^{15}H$)$_p$—; p is one to four; $R^{14}$ is selected from the group consisting of hydrogen, ($C_2$–$C_4$)alkenyl, HO—(C=O)—, ($C_1$–$C_3$)alkyl-O—(C=O)—, $H_2N$—(C=O)—, ($C_1$–$C_3$)alkyl-NH—(C=O)—, [($C_1$–$C_2$)alkyl]$_2$-N—(C=O)—, hydroxy, ($C_1$–$C_3$)alkoxy, amino, ($C_1$–$C_4$)alkylamino, [($C_1$–$C_4$)alkyl]$_2$-amino and ($C_1$–$C_3$)alkyl-(C=O)—NH—; and each $R^{15}$ is independently selected from the group consisting of hydrogen, ($C_1$–$C_2$)alkyl, hydroxy, and amino. More preferred compounds of formula I(c) are those compounds wherein the combined molecular weight of the $R^4$ and $R^7$ substituents is less than 200 AMU. More preferably, the combined molecular weight of the $R^4$ and $R^7$ substituents is less than 100 AMU.

Another embodiment of the present invention is that group of compounds of formula I (and I(b)) wherein $R^5$ is hydrogen. Other embodiments of the present invention include those compounds of formula I (and I(b)) wherein $R^5$ is hydrogen, in combination with each of the aforementioned $R^1$ and $R^2$ embodiments.

Another preferred embodiment of the present invention is that group of compounds of formula I (and I(b)) wherein $R^5$ is ($C_1$–$C_{10}$)heterocyclic or ($C_1$–$C_{10}$)heteroaryl; wherein each of the aforesaid heterocyclic and heteroaryl substituents may optionally be independently substituted by one to four moieties independently selected from the group consisting of halo, ($C_1$–$C_6$)alkyl, ($C_1$–$C_6$)alkoxy, HO—(C=O)—, ($C_1$–$C_6$)alkyl-O—(C=O)—, $H_2N$—(C=O)—, ($C_1$–$C_6$)alkyl-NH—(C=O)— and [($C_1$–$C_6$)alkyl]$_2$-N—(C=O)—. Other embodiments of the present invention include those compounds of formula I (and I(b)) wherein $R^5$ is said optionally substituted ($C_1$–$C_{10}$)heterocyclic or ($C_1$–$C_{10}$)heteroaryl, in combination with each of the aforementioned $R^1$ and $R^2$ embodiments. More preferred heterocyclic groups are pyrrolidinyl, piperidinyl and azetidinyl.

Another preferred embodiment of the present invention is that group of compounds of formula I (and I(b)) wherein $R^5$ is $R^4$-($CHR^{15}$)$_p$—, p is 1–6; and $R^{14}$ is selected from the group consisting of hydrogen, ($C_1$–$C_6$)alkyl, ($C_2$–$C_6$)alkenyl, perhalo($C_1$–$C_6$)alkyl, ($C_3$–$C_{10}$)cycloalkyl, phenyl, ($C_1$–$C_{10}$)heterocyclic, ($C_1$–$C_{10}$)heteroaryl, phenyl-(S=O)—, ($C_1$–$C_6$)alkyl-$SO_2$, phenyl-$SO_2$—, $H_2N$—$SO_2$—, ($C_1$–$C_6$)alkyl-NH—$SO_2$—, phenyl-NH—$SO_2$—, [($C_1$–$C_6$)alkyl-]$_2$N—$SO_2$—, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, HO—(C=O)—, ($C_1$–$C_6$)alkyl-O—(C=O)—, ($C_3$–$C_{10}$)cycloalkyl-O—(C=O)—, ($C_1$–$C_{10}$)heterocyclic-O—(C=O)—, ($C_1$–$C_{10}$)heteroaryl-O—(C=O)—, $H_2N$—(C=O)—, ($C_1$–$C_6$)alkyl-NH—(C=O)—, ($C_3$–$C_{10}$)cycloalkyl-NH—(C=O)—, phenyl-NH—(C=O)—, ($C_1$–$C_{10}$)heterocyclic-NH—(C=O)—, ($C_1$–$C_{10}$)heteroaryl-NH—(C=O)—, [($C_1$–$C_6$)alkyl]$_2$-N—(C=O)—, phenyl-[(($C_1$–$C_6$)alkyl)-N]—(C=O)—, ($C_1$–$C_{10}$)heteroaryl-[N—($C_1$–$C_6$)alkyl]-(C=O)—, ($C_1$–$C_{10}$)heterocyclic-[(($C_1$–$C_6$) alkyl)-N]—(C=O)—, ($C_3$–$C_{10}$)cycloalkyl[(($C_1$–$C_6$)alkyl)-N]—(C=O)—, hydroxy, $R^{16}$—($C_1$–$C_5$)alkoxy, perhalo ($C_1$–$C_5$)alkoxy, ($C_3$–$C_{10}$)cycloalkyl-O—, phenoxy, ($C_1$–$C_{10}$)heterocyclic-O—, ($C_1$–$C_{10}$)heteroaryl-O—, $R^{16}$—($C_1$–$C_6$)alkyl-(C=O)—O—, ($C_3$–$C_{10}$)cycloalkyl-(C=O)—O—, phenyl-(C=O)—O—, ($C_1$–$C_{10}$)heterocyclic-(C=O)—O—, ($C_1$–$C_{10}$)heteroaryl-(C=O)—O—, —NO$_2$, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, ($C_3$–$C_{10}$)cycloalkyl-(C=O)—NH—, phenyl-(C=O)—NH—, $R^{16}$—($C_1$–$C_6$)alkyl-SO$_2$NH—, ($C_3$–$C_{10}$)cycloalkyl-SO$_2$NH—, phenyl-SO$_2$NH—, ($C_1$–$C_{10}$)heterocyclic-SO$_2$NH— and ($C_1$–$C_{10}$)heteroaryl-SO$_2$NH—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—($C_1$–$C_6$)alkyl, ($C_2$–$C_6$)alkenyl, ($C_2$–$C_6$)alkynyl, perhalo($C_1$–$C_6$)alkyl, ($C_3$–$C_{10}$)cycloalkyl, phenyl, benzyl, ($C_1$–$C_{10}$)heterocyclic, ($C_1$–$C_{10}$)heteroaryl, ($C_1$–$C_6$)alkyl-SO$_2$—, formyl, —CN, $R^{16}$—($C_1$–$C_6$)alkyl-(C=O)—, ($C_3$–$C_{10}$)cycloalkyl-(C=O)—, phenyl-(C=O)—, ($C_1$–$C_{10}$)heterocyclic-(C=O)—, ($C_1$–$C_{10}$)heteroaryl-(C=O)—, HO—(C=O)—, ($C_1$–$C_6$)alkyl-O—(C=O)—, ($C_3$–$C_{10}$)cycloalkyl-O—(C=O)—, ($C_1$–$C_{10}$)heterocyclic-O—(C=O)—, ($C_1$–$C_{10}$)heteroaryl-O—(C=O)—, H$_2$N—(C=O)—, $R^{16}$—($C_1$–$C_6$)alkyl-NH—(C=O)—, ($C_3$–$C_{10}$)cycloalkyl-NH—(C=O)—, phenyl-NH—(C=O)—, ($C_1$–$C_{10}$)heterocyclic-NH—(C=O)—, ($C_1$–$C_{10}$)heteroaryl-NH—(C=O)—, [($C_1$–$C_6$)alkyl]$_2$-N—(C=O)—, phenyl-[(($C_1$–$C_6$)alkyl)-N]—(C=O)—, hydroxy, $R^{16}$—($C_1$–$C_6$)alkoxy, perhalo($C_1$–$C_6$)alkoxy, ($C_3$–$C_{10}$)cycloalkyl-O—, phenoxy, ($C_1$–$C_{10}$)heterocyclic-O—, ($C_1$–$C_{10}$)heteroaryl-O—, $R^{16}$—($C_1$–$C_6$)alkyl-(C=O)—O—, ($C_3$–$C_{10}$)cycloalkyl-(C=O)—O—, phenyl-(C=O)—O—, ($C_1$–$C_{10}$)heterocyclic-(C=O)—O—, ($C_1$–$C_{10}$)heteroaryl-(C=O)—O—, —NO$_2$, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, ($C_3$–$C_{10}$)cycloalkyl-(C=O)—NH—, phenyl-(C=O)—NH—, ($C_1$–$C_{10}$)heterocyclic-(C=O)—NH—, ($C_1$–$C_{10}$)heteroaryl-(C=O)—NH—, $R^{16}$—($C_1$–$C_6$)alkyl-(C=O)—[(($C_1$–$C_6$)alkyl)-N]—, phenyl-(C=O)—[($C_1$–$C_6$)alkyl-N]—, $R^6$—($C_1$–$C_6$)alkyl-SO$_2$NH—, ($C_3$–$C_{10}$)cycloalkyl-SO$_2$NH—, phenyl-SO$_2$NH—, ($C_1$–$C_{10}$)heterocyclic-SO$_2$NH— and ($C_1$–$C_{10}$)heteroaryl-SO$_2$NH—; and wherein each of said phenyl and heteroaryl moiety alternatives may optionally be substituted by one or two radicals independently selected from halo, ($C_1$–$C_6$)alkyl, ($C_1$–$C_6$)alkoxy, amino, ($C_1$–$C_6$)alkylamino and [($C_1$–$C_6$)alkyl]$_2$-amino. Other embodiments of the present invention include those compounds of formula I (and I(b)) wherein $R^5$ is said $R^{14}$—(CHR$^{15}$)$_p$—, p is 1–6; and $R^{14}$ is as defined above, in combination with each of the aforementioned $R^1$ and $R^2$ embodiments.

Another preferred embodiment of the present invention is that group of compounds of formula I (and I(b)) wherein $R^5$ is $R^{14}$—(CHR$^{15}$)$_p$—, p is 1–6; and $R^{14}$ is selected from the group consisting of hydrogen, ($C_1$–$C_6$)alkyl, ($C_2$–$C_6$)alkenyl, ($C_3$–$C_{10}$)cycloalkyl, phenyl, ($C_1$–$C_{10}$)heterocyclic, ($C_1$–$C_{10}$)heteroaryl, HO—(C=O)—, ($C_1$–$C_6$)alkyl-O—(C=O)—, H$_2$N—(C=O)—, ($C_1$–$C_6$)alkyl-NH—(C=O)—, phenyl-NH—(C=O)—, ($C_1$–$C_{10}$)heterocyclic-NH—(C=O)—, [($C_1$–$C_6$)alkyl]$_2$-N—(C=O)—, phenyl-[(($C_1$–$C_6$)alkyl)-N]—(C=O)—, hydroxy, $R^{16}$—($C_1$–$C_6$)alkoxy, phenoxy, amino, $R^{16}$—($C_1$–$C_6$)alkylamino, [($C_1$–$C_6$)alkyl]$_2$-amino, $R^{16}$—($C_1$–$C_6$)alkyl-(C=O)—NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—($C_1$–$C_6$)alkyl, ($C_2$–$C_6$)alkenyl, ($C_2$–$C_6$)alkynyl, perhalo($C_1$–$C_6$)alkyl, ($C_1$–$C_6$)alkyl-SO$_2$—, formyl, —CN, $R^{16}$—($C_1$–$C_6$)alkyl-(C=O)—, HO—(C=O)—, ($C_1$–$C_6$)alkyl-O—(C=O)—, H$_2$N—(C=O)—, $R^{16}$—($C_1$–$C_6$)alkyl-NH—(C=O)—, [($C_1$–$C_6$)alkyl]$_2$-N—(C=O)—, hydroxy, $R^{16}$—($C_1$–$C_6$)alkoxy, perhalo($C_1$–$C_6$)alkoxy, $R^{16}$—($C_1$–$C_6$)alkyl-(C=O)—O—, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, $R^{16}$—($C_1$–$C_6$)alkyl-(C=O)—[(($C_1$–$C_6$)alkyl)-N]— and $R^{16}$—($C_1$–$C_6$)alkyl-SO$_2$NH—;

each $R^{15}$ is independently selected from the group consisting of hydrogen, halo, ($C_1$–$C_6$)alkyl, ($C_2$–$C_6$)alkenyl, perhalo($C_1$–$C_6$)alkyl, HO—(C=O)—, ($C_1$–$C_6$)alkyl-O—(C=O)—, H$_2$N—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, amino, ($C_1$–$C_6$)alkylamino, [($C_1$–$C_6$)alkyl]$_2$-amino, formamidyl and ($C_1$–$C_6$)alkyl-(C=O)—NH—; wherein no more than two of said $R^{15}$ groups may be other than hydrogen; and each $R^{16}$ is independently selected from the group consisting of hydrogen, halo, ($C_1$–$C_6$)alkyl, ($C_2$–$C_6$)alkenyl, ($C_2$–$C_6$)alkynyl, perhalo($C_1$–$C_6$)alkyl, HO—(C=O)—, ($C_1$–$C_6$)alkyl-O—(C=O)—, H$_2$N—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, ($C_1$–$C_6$)alkyl-(C=O)—O—, —NO$_2$, amino, ($C_1$–$C_6$)alkylamino, [($C_1$–$C_6$)alkyl]$_2$-amino, formamidyl and ($C_1$–$C_6$)alkyl-(C=O)—NH—.

Other embodiments of the present invention include that group of compounds of formula I (and I(b)) wherein $R^5$ is said $R^{14}$—(CHR$^{15}$)$_p$—, p is 1–6; and $R^{14}$, $R^{15}$ and $R^{16}$ are as defined above, in combination with each of the aforementioned $R^1$ and $R^2$ embodiments.

A more preferred embodiment of the present invention are those group of compounds of formula I (and I(b)) wherein $R^5$ is $R^{14}$—(CHR$^{15}$)$_p$—, p is 1–6; and $R^{14}$ is selected from the group consisting of hydrogen, ($C_2$–$C_4$)alkenyl, ($C_1$–$C_{10}$)heterocyclic, HO—(C=O)—, ($C_1$–$C_3$)alkyl-O—(C=O)—, H$_2$N—(C=O)—, ($C_1$–$C_3$)alkyl-NH—(C=O)—, hydroxy, ($C_1$–$C_3$)alkoxy, amino, ($C_1$–$C_3$)alkylamino, and [($C_1$–$C_2$)alkyl]$_2$-amino; and each $R^{15}$ is independently selected from the group consisting of hydrogen, ($C_1$–$C_6$)alkyl, hydroxy, ($C_1$–$C_3$)alkoxy, perhalo($C_1$)alkoxy, amino, ($C_1$–$C_2$)alkylamino, [($C_1$–$C_2$)alkyl]$_2$-amino, formamidyl and ($C_1$–$C_6$)alkyl-(C=O)—NH—; wherein no more than two of said $R^{15}$ groups may be other than hydrogen.

Another embodiment of the present invention is that group of compounds of formula I (and I(a), I(b), I(d), I(g)) wherein $R^6$ is hydrogen. Other embodiments of the present invention include those compounds of formula I (and I(a), I(b), I(d), I(g)) wherein $R^6$ is hydrogen, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—(CH$_2$)$_n$— and n is zero. Other embodiments of the present invention include those compounds of formula I (and I(a), I(b), I(d), I(g)) wherein $R^6$ is $R^9$—B—(CH$_2$)$_n$— and n is zero, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—(CH$_2$)$_n$— and n is an integer from one to six, more preferably from one to five. Other embodiments of the present invention include those compounds of formula I (and I(a), I(b), I(d), I(g)) wherein $R^6$ is $R^9$—B—$(CH_2)_n$— and n is an integer from one to six, more preferably from one to five, in combination with each of the aforementioned I(a) $R^4$ embodiments, I(b) $R^5$ embodiments or with each of the aforementioned $R^1$ and $R^2$ embodiments.

Another preferred embodiment of the present invention is that group of compounds of formula I (and I(a), I(b), I(d), I(g)) wherein $R^6$ is $R^9$—B—$(CH_2)_n$—; n is zero; B is a bond and $R^9$ is selected from the group consisting of hydrogen, —$CF_3$, —C—N, $(C_1-C_{10})$heteroaryl, $(C_1-C_{10})$heterocyclic or $(C_3-C_{10})$cycloalkyl; wherein each of the aforesaid $(C_1-C_{10})$heteroaryl, $(C_1-C_{10})$heterocyclic and $(C_3-C_{10})$cycloalkyl may optionally be substituted by one to three moieties independently selected from the group consisting of halo, $(C_1-C_6)$alkyl, $(C_2-C_6)$alkenyl, $(C_1-C_6)$alkynyl, perhalo$(C_1-C_6)$alkyl, hydroxy, $(C_1-C_6)$alkoxy, perhalo$(C_1-C_8)$alkoxy, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, [$(C_1-C_6)$alkyl]$_2$-amino, $(C_1-C_6)$alkyl-$SO_2$—NH—, $(C_1-C_6)$alkyl-(C=O)—NH—, $(C_1-C_6)$alkyl-(C=O)—[$((C_1-C_6)$alkyl)-N]—, —CN, $(C_1-C_6)$alkyl-(C=O)—, HO—(C=O)—, $(C_1-C_6)$alkyl-O—(C=O)—, $H_2$N(C=O)—, $(C_1-C_6)$alkyl-NH—(C=O)—, [$(C_1-C_6)$alkyl]$_2$-N—(C=O)— and $(C_1-C_6)$alkyl-(C=O)—O—. Other embodiments of the present invention include those compounds of formula I (and I(a), I(b), I(d), I(g)) wherein $R^6$ is $R^9$—B—$(CH_2)_n$— and n is zero; B is a bond and $R^9$ is as defined above, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—$(CH_2)_n$—; n is zero; B is —(C=O)—$NR^{10}$—, —($R^{10}$—N)—, —($R^{10}$—N)—$SO_2$—, —($R^{10}$—N)—(C=O)—, >C=O, —O—(C=O)—, —$SO_2$—($NR^{10}$)—, —($R^{10}$—N)—(C=O)—($NR^{11}$)—; and $R^9$ is selected from the group consisting of hydrogen, $(C_3-C_{10})$cycloalkyl or phenyl; wherein the aforesaid phenyl and $(C_3-C_{10})$cycloalkyl may optionally be substituted by one to three moieties independently selected from the group consisting of halo, $(C_1-C_6)$alkyl, $(C_2-C_6)$alkenyl, $(C_2-C_6)$alkynyl, perhalo$(C_1-C_6)$alkyl, hydroxy, $(C_1-C_6)$alkoxy, perhalo$(C_1-C_6)$alkoxy, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, [$(C_1-C_6)$alkyl]$_2$-amino, $(C_1-C_6)$alkyl-$SO_2$—NH—, $(C_1-C_6)$alkyl-(C=O)—NH—, $(C_1-C_6)$alkyl-(C=O)—[N($C_1-C_6$)alkyl]-, —CN, $(C_1-C_6)$alkyl-(C=O)—, HO—(C=O)—, $(C_1-C_6)$alkyl-O—(C=O)—, $H_2$N(C=O)— $(C_1-C_6)$alkyl-NH—(C=O)—, [$(C_1-C_6)$alkyl]$_2$-N—(C=O)— and $(C_1-C_6)$alkyl-(C=O)—O—. Other embodiments of the present invention include those compounds of formula I (and I(a), I(b), I(d), I(g)) wherein $R^6$ is $R^9$—B—$(CH_2)_n$— and n is zero; B is —(C=O)—$NR^{10}$—, —($R^{10}$—N)—, —($R^{10}$—N)—$SO_2$—, —($R^{10}$—N)—(C=O)—, >C=O, —O—(C=O)—, —$SO_2$—($NR^{10}$)—, —($R^{10}$—N)—(C=O)—($NR^{11}$)—; and $R^9$ is as defined above, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—$(CH_2)_n$—; n is zero; B is a bond; $R^9$ is $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, amino, $(C_1-C_{10})$alkylamino, [$(C_1-C_6)$alkyl]$_2$amino, $(C_1-C_6)$alkyl-$SO_2$—NH—, phenyl-$SO_2$—NH—, $(C_1-C_6)$alkyl-$SO_2$—[N—$(C_1-C_6)$alkyl]-, phenyl-$SO_2$—[N—$(C_1-C_6)$alkyl]-, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, [$(C_1-C_6)$alkyl]$_2$-amino, $(C_1-C_6)$alkyl-$SO_2$—NH—, $(C_1-C_6)$alkyl-(C=O)—NH—, $(C_1-C_6)$alkyl-(C=O)—[N($C_1-C_8$)alkyl]-, phenyl-(C=O)—NH—, phenyl-(C=O)—[N—$(C_1-C_6)$alkyl]-, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2$N(C=O)—, $(C_1-C_6)$alkyl-NH—(C=O)—, [$(C_1-C_6)$alkyl]$_2$-N—(C=O)—, phenyl-NH—(C=O)—, phenyl-[N-(($C_1-C_6$)alkyl)]-(C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$— and n is zero; B is a bond; $R^9$ is $R^{13}$—$(R^{12}CH)_m$—; m is 1–6; $R^{10}$ is hydrogen or methyl; $R^{12}$ is hydrogen or methyl; and $R^{13}$ is as defined above, in combination with each of the aforementioned I(a) $R^4$ embodiments, I(b) $R^5$ embodiments or with each of the aforementioned $R^1$ and $R^2$ embodiments.

Another preferred embodiment of the present invention is that group of compounds of formula I (and I(a), I(b), I(d), I(g)) wherein $R^6$ is $R^9$—B—$(CH_2)_n$—; n is zero; B is —(C=O)—$NR^{10}$—, —($R^{10}$—N)—, >C=O, —O—(C=O)—, —($R^{10}$—N)—(C=O)— or —($R^{10}$—N)—(C=O)—($NR^{11}$)—; $R^9$ is $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, amino, $(C_1-C_6)$alkylamino, [$(C_1-C_6)$alkyl]$_2$amino, $(C_1-C_6)$alkyl-$SO_2$—NH—, phenyl-$SO_2$—NH—, $(C_1-C_6)$alkyl-$SO_2$—[N—$(C_1-C_6)$alkyl]-, phenyl-$SO_2$—[N—$(C_1-C_6)$alkyl]-, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, [$(C_1-C_6)$alkyl]$_2$-amino, $(C_1-C_6)$alkyl-$SO_2$—NH—, $(C_1-C_6)$alkyl-(C=O)—NH—, $(C_1-C_6)$alkyl-(C=O)—[N $(C_1-C_6)$alkyl]-, phenyl-(C=O)—NH—, phenyl-(C=O)—[N—$(C_1-C_6)$alkyl]-, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2$N(C=O)—, $(C_1-C_6)$alkyl-NH—(C=O)—, [$(C_1-C_6)$alkyl]$_2$-N—(C=O)—, phenyl-NH—(C=O)—, phenyl-[N—(($C_1-C_6$)alkyl)]-(C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$— and n is zero; B is —(C=O)—$NR^{10}$—, —($R^{10}$—N)—, —($R^{10}$—N)—$SO_2$—, —($R^{10}$—N)—(C=O)—, >C=O, —O—(C=O)—, —$SO_2$—($NR^{10}$)—, —($R^{10}$—N)—(C=O)—($NR^{11}$)—; and $R^9$ is $R^{13}$—$(R^{12}CH)_m$—; m is 1–6; $R^{10}$ is hydrogen or methyl; $R^{12}$ is hydrogen or methyl; and $R^{13}$ is as defined above, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—$(CH_2)_n$—; n is an integer from one to six, more preferably one to five, more preferably one to three; B is a bond, and $R^9$ is selected from the group consisting of optionally substituted phenyl, $(C_1-C_{10})$heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, $[(C_1-C_6)$alkyl]$_2$-N—(C=O)—, phenyl-NH—(C=O)—, phenyl-$[((C_1-C_6)$alkyl)-N]$—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(b), I(d), I(g))wherein $R^6$ is $R^9$—B—$(CH_2)_n$—; n is an integer from one to six, more preferably one to five, more preferably one to three; B is a bond, and $R^9$ is as described above, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—$(CH_2)_n$—; n is an integer from one to six, more preferably one to five, more preferably one to three; B is —(C=O)—($R^{10}$—N)—, —($R^{10}$—N)—, —SO$_2$—($R^{10}$—N)—, —($R^{10}$—N)—(C=O)—(NR$^{11}$)— or —($R^{10}$—N)—(C=O)—O—; and $R^9$ is selected from the group consisting of optionally substituted phenyl, $(C_1-C_{10})$ heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$ heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, $[(C_1-C_6)$alkyl]$_2$-N—(C=O)—, phenyl-NH—(C=O)—, phenyl-$[((C_1-C_6)$alkyl)-N]$—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$—; n is an integer from one to six, more preferably one to five, more preferably one to three; B is —(C=O)—($R^{10}$—N)—, —($R^{10}$—N)—, —SO$_2$—($R^{10}$—N)—, —($R^{10}$—N)—(C=O)—(NR$^{11}$)— or —($R^{10}$—N)—(C=O)—O—; and $R^9$ is as described above, in combination with each of the aforementioned I(a) $R^4$ embodiments, I(b) $R^5$ embodiments or with each of the aforementioned $R^1$ and $R^2$ embodiments.

Another embodiment of the present invention is that group of compounds of formula I (and I(a), I(b), I(d), I(g)) wherein $R^6$ is $R^9$—B—$(CH_2)_n$—; n is an integer from one to six, more preferably one to five, more preferably one to three; B is a bond, and $R^9$ is $R^{13}$—($R^{12}$CH)$_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$ heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, $(C_1-C_6)$alkyl-SO$_2$—NH—, phenyl-SO$_2$—NH—, $(C_1-C_6)$alkyl-SO$_2$—$[((C_1-C_6)$alkyl)-N]$—, phenyl-SO$_2$—$[((C_1-C_6)$alkyl)-N]$—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, H$_2$N(C=O)—, $(C_1-C_6)$alkyl-NH—(C=O)—, $[(C_1-C_8)$alkyl]$_2$-N—(C=O)—, phenyl-NH—(C=O)—, phenyl-$[((C_1-C_6)$alkyl)-N]$—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^6$ is $R^9$—B—$(CH_2)_n$—; n is an integer from one to six, more preferably one to five, more preferably one to three; B is —(C=O)—($R^{10}$—N)—, —($R^{10}$—N)—, —SO$_2$—($R^{10}$—N)—, —($R^{10}$—N)—(C=O)—(NR$^{11}$)— or —($R^{10}$—N)—(C=O)—O—; $R^9$ is $R^{13}$—($R^{12}$CH)$_m$—; m is 1–6; $R^{10}$ is hydrogen or methyl; each $R^{12}$ is independently selected from the groups consisting of hydrogen or methyl; and $R^{13}$ is as described above, in combination with each of the aforementioned I(a) $R^4$ embodiments, I(b) $R^5$ embodiments or with each of the aforementioned $R^1$ and $R^2$ embodiments.

Another preferred embodiment of the present invention is that group of compounds of formula I (and I(a), I(b), I(d), I(g)) wherein $R^6$ is $R^9$—B—$(CH_2)_n$—; n is an interger from one to six; B is —(C=O)—NR$^{10}$—, —($R^{10}$—N)—, >C=O, —O—(C=O)—, —($R^{10}$—N)—(C=O)— or —($R^{10}$—N)—(C=O)—(NR$^{11}$)—; $R^9$ is $R^{13}$—($R^{12}$CH)$_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, amino, $(C_1-C_6)$alkylamino, $[(C_1-C_6)alkyl]_2$amino, $(C_1-C_6)$alkyl-SO$_2$—NH—, phenyl-SO$_2$—NH—, $(C_1-C_6)$alkyl-SO$_2$—[N—$(C_1-C_6)$alkyl]-, phenyl-SO$_2$—[N—$(C_1-C_6)$alkyl]-, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)alkyl]_2$-amino, $(C_1-C_6)$alkyl-SO$_2$—NH—, $(C_1-C_6)$alkyl-(C=O)—NH—, $(C_1-C_6)$alkyl-(C=O)—[N(C_1-C_6)alkyl]-, phenyl-(C=O)—NH—, phenyl-(C=O)—[N—$(C_1-C_6)$alkyl]-, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, H$_2$N(C=O)—, $(C_1-C_6)$alkyl-NH—(C=O)—, $[(C_1-C_6)alkyl]_2$-N—(C=O)—, phenyl-NH—(C=O)—, phenyl-[N—$((C_1-C_6)$alkyl)]-(C=O)—, $(C_1-C_6)$alkyl-(C=O)—O— and phenyl-(C=O)—O—. Other embodiments of the present invention include those compounds of formula I (and I(a), I(b), I(d), I(g)) wherein R$^6$ is R$^9$—B—(CH$_2$)$_n$— and n is 1–6; B is —(C=O)—NR$^{10}$—, —(R$^{10}$—N)—, —(R$^{10}$—N)—SO$_2$—, —(R$^{10}$—N)—(C=O)—, >C=O, —O—(C=O)—, —SO$_2$—(NR$^{10}$)—, —(R$^{10}$—N)—(C=O)—(NR$^{11}$)—; and R$^9$ is R$^{13}$—(R$^{12}$CH)$_m$—; m is 1–6; R$^{10}$ is hydrogen or methyl; R$^{12}$ is hydrogen or methyl; and R$^{13}$ is as defined above, in combination with each of the aforementioned I(a) R$^4$ embodiments, I(b) R$^5$ embodiments or with each of the aforementioned R$^1$ and R$^2$ embodiments.

An embodiment of the present invention is that group of compounds of formula I wherein s is an integer from zero to four and each R$^3$ is independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)alkyl]_2$-amino, $(C_1-C_6)$alkyl-SO$_2$—NH—, $(C_1-C_6)$alkyl-(C=O)—NH—, $(C_1-C_6)$alkyl-(C=O)—[((C_1-C_6)alkyl)-N]—, phenyl-(C=O)—NH—, phenyl-(C=O)—[((C_1-C_6)alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)—, $(C_1-C_6)$alkyl-NH—(C=O)—, $[(C_1-C_6)alkyl]_2$-N—(C=O)—, phenyl-NH—(C=O)—, phenyl-[((C_1-C_6)alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)— and $(C_1-C_6)$alkyl-(C=O)—O—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and each R$^3$ is independently selected from the group consisting of halo, —CN, $(C_1-C_6)$alkyl, $(C_2-C_6)$alkenyl, $(C_2-C_6)$alkynyl and perhalo$(C_1-C_6)$alkyl. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and zero, one or two of R$^3$ are independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, amino, $(C_1-C_6)$alkylamino, $[(C_1-C_6)alkyl]_2$-amino, —CN, and H$_2$N(C=O)—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and one of R$^3$ is selected from the group consisting of optionally substituted phenyl, $(C_1-C_{10})$heteroaryl, $(C_1-C_{10})$heterocyclic and $(C_3-C_{10})$cycloalkyl. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and one of R$^3$ is selected from the group consisting of hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$— and $(C_1-C_6)$alkyl-NH—SO$_2$—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and one of R$^3$ is selected from the group consisting of amino, $(C_1-C_6)$alkylamino, $[(C_1-C_6)alkyl]_2$-amino, $(C_1-C_6)$alkyl-SO$_2$—NH—, $(C_1-C_6)$alkyl-(C=O)—NH—, $(C_1-C_6)$alkyl-(C=O)—[((C_1-C_6)alkyl)-N]—, phenyl-(C=O)—NH— and phenyl-(C=O)—[N—$(C_1-C_6)$alkyl]-. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^1$ and R$^2$ embodiments.

Another embodiment of the present invention is that group of compounds of formula I wherein s is an integer from zero to four and one of R$^3$ is selected from the group consisting of $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, H$_2$N(C=O)—, $(C_1-C_6)$alkyl-NH—(C=O)—, $[(C_1-C_6)alkyl]_2$-N—(C=O)—, phenyl-NH—(C=O)—, phenyl-[((C_1-C_6)alkyl)-N]—(C=O)— and $(C_1-C_6)$alkyl-(C=O)—O—.

Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^1$ and $R^2$ embodiments.

Another embodiment of the present invention is that group of compounds of formula I wherein s is an integer from zero to three and each $R^3$ is independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, —$NO_2$, amino, $(C_1-C_6)$alkylamino, $[(C_1-C_6)$alkyl$]_2$-amino, —CN, and $H_2N(C=O)$—. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^1$ and $R^2$ embodiments.

Preferred compounds of the present invention is that group of compounds of formula I wherein s is an integer from zero to two and each $R^3$ is independently selected from the group consisting of halo, $(C_1-C_6)$alkyl, perhalo$(C_1-C_6)$alkyl, $(C_1-C_6)$alkoxy, perhalo$(C_1-C_6)$alkoxy and —CN. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^1$ and $R^2$ embodiments.

More preferred compounds of the present invention is that group of compounds of formula I wherein s is an integer from zero to three and each $R^3$ is independently selected from the group consisting of fluoro, chloro and methyl. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^1$ and $R^2$ embodiments.

Examples of specific preferred compounds of the formula I are the following:

1,3-Dimethyl-5-(2-pyridin-3-yl-5-m-tolyl-1H-imidazol-4-yl)-1,3-dihydro-benzoimidazol-2-one;
1,3-Diethyl-5-(2-piperidin-4-yl-5-m-tolyl-3H-imidazol-4-yl)-1,3-dihydro-benzoimidazol-2-one;
1-Isobutyl-3-methyl-5-(2-piperidin-4-yl-5-m-tolyl-3H-imidazol-4-yl)-1,3-dihydro-benzoimidazol-2-one;
1-Isopropyl-3-methyl-5-(5-phenyl-2-pyrimidin-5-yl-1H-imidazol-4-yl)-1,3-dihydro-benzoimidazol-2-one;
N-[5-(1-Isobutyl-3-methyl-2-oxo-2,3-dihydro-1H-benzoimidazol-5-yl)-4-m-tolyl-1H-imidazol-2-yl]-acetamide;
N-{5-(4-Fluoro-phenyl)-4-[3-methyl-2-oxo-1-(tetrahydrofuran-3-yl)-2,3-dihydro-1H-benzoimidazol-5-yl]-1H-imidazol-2-yl}-acetamide;
[4-(1-Isopropyl-3-methyl-2-oxo-2,3-dihydro-1H-benzoimidazol-5-yl)-5-m-tolyl-1H-imidazol-2-yl]-urea;
1,3-Diethyl-5-(5-m-tolyl-1H-imidazol-4-yl)-1,3-dihydro-benzoimidazol-2-one;
1-Cyclopentyl-3-methyl-5-(5-m-tolyl-1H-imidazol-4-yl)-1,3-dihydro-benzoimidazol-2-one;
1-Methyl-5-(5-m-tolyl-1H-imidazol-4-yl)-1,3-dihydro-benzoimidazol-2-one;
4-(4-Fluoro-phenyl)-5-(3-methyl-2-oxo-1-phenyl-2,3-dihydro-1H-benzoimidazol-5-yl)-1H-imidazole-2-carboxylic acid;
5-(3-Methyl-2-oxo-1-phenyl-2,3-dihydro-1H-benzoimidazol-5-yl)-4-m-tolyl-1H-imidazole-2-carboxylic acid amide;
1-Ethyl-5-[5-(4-fluoro-phenyl)-2-pyridin-3-yl-1H-imidazol-4-yl]-3-methyl-1,3-dihydro-benzoimidazol-2-one;
1-Methyl-6-(2-pyrazin-2-yl-5-m-tolyl-1H-imidazol-4-yl)-1,3-dihydro-benzoimidazol-2-one;
3-Methyl-1-phenyl-5-(2-pyrazin-2-yl-5-m-tolyl-1H-imidazol-4-yl)-1,3-dihydro-benzoimidazol-2-one;
5-[5-(4-Fluoro-3-methyl-phenyl)-2-pyrazin-2-yl-1H-imidazol-4-yl]-3-methyl-1-phenyl-1,3-dihydro-benzoimidazol-2-one;
1-(2-Chloro-phenyl)-3-methyl-5-(5-m-tolyl-3H-imidazol-4-yl)-1,3-dihydro-benzoimidazol-2-one;
1-(3,4-Dimethoxy-phenyl)-3-methyl-5-(5-m-tolyl-1H-imidazol-4-yl)-1,3-dihydro-benzoimidazol-2-one;
1-Cyclopentyl-5-(2-furan-3-yl-5-m-tolyl-1H-imidazol-4-yl)-3-methyl-1,3-dihydro-benzoimidazol-2-one; and
3-Methyl-1-phenyl-5-(4-m-tolyl-oxazol-5-yl)-1,3-dihydro-benzoimidazol-2-one.

Other specific benzoimidazolone compounds of formula I include the following:

5-[5-(4-Fluoro-phenyl)-2-pyrazin-2-yl-1H-imidazol-4-yl]-1-isopropyl-3-methyl-1,3-dihydro-benzoimidazol-2-one;
1-Isopropyl-3-methyl-5-(2-pyrimidin-5-yl-5-m-tolyl-1H-imidazol-4-yl)-1,3-dihydro-benzoimidazol-2-one;
1-(2-Chloro-phenyl)-3-methyl-5-(2-pyrazin-2-yl-5-m-tolyl-3H-imidazol-4-yl)-1,3-dihydro-benzoimidazol-2-one;
5-(3-Methyl-2-oxo-1-phenyl-2,3-dihydro-1H-benzoimidazol-5-yl)-4-m-tolyl-1H-imidazole-2-carboxylic acid;
1-(2-Chloro-phenyl)-3-methyl-5-(4-m-tolyl-oxazol-5-yl)-1,3-dihydro-benzoimidazol-2-one;
5-[5-(4-Fluoro-3-methyl-phenyl)-2-pyrimidin-5-yl-1H-imidazol-4-yl]-3-methyl-1-phenyl-1,3-dihydro-benzoimidazol-2-one;
4-[1-(2-Chloro-phenyl)-3-methyl-2-oxo-2,3-dihydro-1H-benzoimidazol-5-yl]-5-(4-fluoro-3-methyl-phenyl)-1H-imidazole-2-carboxylic acid amide;
5-(4-Fluoro-3-methyl-phenyl)-4-[1-(2-fluoro-phenyl)-3-methyl-2-oxo-2,3-dihydro-1H-benzoimidazol-5-yl]-1H-imidazole-2-carboxylic acid amide;
(4-[1-(2-Chloro-phenyl)-3-methyl-2-oxo-2,3-dihydro-1H-benzoimidazol-5-yl]-5-m-tolyl-1H-imidazol-2-yl)-urea;
1-(2-Chloro-4-methoxy-phenyl)-3-methyl-5-(2-pyrazin-2-yl-5-m-tolyl-1H-imidazol-4-yl)-1,3-dihydro-benzoimidazol-2-one;
1-(2-Chloro-4-methoxy-phenyl)-5-[5-(4-fluoro-3-methyl-phenyl)-2-pyrazin-2-yl-1H-imidazol-4-yl]-3-methyl-1,3-dihydro-benzoimidazol-2-one;
5-[5-(4-Fluoro-3-methyl-phenyl)-2-pyrazin-2-yl-1H-imidazol-4-yl]-3-methyl-1-pyridin-3-yl-1,3-dihydro-benzoimidazol-2-one;
3-Methyl-5-(2-pyrazin-2-yl-5-m-tolyl-1H-imidazol-4-yl)-1-pyridin-3-yl-1,3-dihydro-benzoimidazol-2-one;
4-(3-Methyl-2-oxo-1-pyridin-3-yl-2,3-dihydro-1H-benzoimidazol-5-yl)-5-m-tolyl-1H-imidazole-2-carboxylic acid amide;
4-(3-Methyl-2-oxo-1-pyridin-4-yl-2,3-dihydro-1H-benzoimidazol-5-yl)-5-m-tolyl-1H-imidazole-2-carboxylic acid amide;
4-(3-Methyl-2-oxo-1-pyridin-2-yl-2,3-dihydro-1H-benzoimidazol-5-yl)-5-m-tolyl-1H-imidazole-2-carboxylic acid amide;
4-[1-(2-Chloro-4-methoxy-phenyl)-3-methyl-2-oxo-2,3-dihydro-1H-benzoimidazol-5-yl]-5-m-tolyl-1H-imidazole-2-carboxylic acid amide;

4-[1-(2-Chloro-4-methoxy-phenyl)-3-methyl-2-oxo-2,3-dihydro-1H-benzoimidazol-5-yl]-5-(4-fluoro-3-methyl-phenyl)-1H-imidazole-2-carboxylic acid amide;
5-(4-Fluoro-3-methyl-phenyl)-4-(3-methyl-2-oxo-1-o-tolyl-2,3-dihydro-1H-benzoimidazol-5-yl)-1H-imidazole-2-carboxylic acid amide;
4-[1-(2-Fluoro-4-methoxy-phenyl)-3-methyl-2-oxo-2,3-dihydro-1H-benzoimidazol-5-yl]-5-m-tolyl-1H-imidazote-2-carboxylic acid amide;
3-Methyl-1-phenyl-5-(4-m-tolyl-thiazol-5-yl)-1,3-dihydro-benzoimidazol-2-one;
5-(5-Amino-3-m-tolyl-1H-pyrazol-4-yl)-3-methyl-1-phenyl-1,3-dihydro-benzoimidazol-2-one;
5-(5-Amino-3-m-tolyl-1H-pyrazol-4-yl)-1-(2-chloro-phenyl)-3-methyl-1,3-dihydro-benzoimidazol-2-one;
5-(5-Amino-3-m-tolyl-1H-pyrazol-4-yl)-1-(3,4-dimethoxy-phenyl)-3-methyl-1,3-dihydro-benzoimidazol-2-one;
3-Methyl-5-(2-methyl-4-m-tolyl-oxazol-5-yl)-1-phenyl-1,3-dihydro-benzoimidazo(-2-one;
3-Methyl-5-(2-methyl-4-m-tolyl-thiazol-5-yl)-1-phenyl-1,3-dihydro-benzoimidazol-2-one;
1,3-Dimethyl-5-(5-methyl-3-phenyl-1H-pyrazol-4-yl)-1,3-dihydro-benzoimidazol-2-one;
1,3-Dimethyl-5-(5-methyl-3-m-tolyl-1H-pyrazol-4-yl)-1,3-dihydro-benzoimidazol-2-one;
5-[3-(4-Fluoro-phenyl)-5-methyl-1H-pyrazol-4-yl]-1,3-dimethyl-1,3-dihydro-benzoimidazol-2-one;
1,3-Diethyl-5-(5-methyl-3-phenyl-1H-pyrazol-4-yl)-1,3-dihydro-benzoimidazol-2-one;
1,3-Diethyl-5-(5-methyl-3-m-tolyl-1H-pyrazol-4-yl)-1,3-dihydro-benzoimidazol-2-one;
5-(5-Amino-3-m-tolyl-1H-pyrazol-4-yl)-1,3-diethyl-1,3-dihydro-benzoimidazol-2-one;
5-(1-Acetyl-5-methyl-3-m-tolyl-1H-pyrazol-4-yl)-1,3-dimethyl-1,3-dihydro-benzoimidazol-2-one;
5-(1-Benzoyl-5-methyl-3-m-tolyl-1H-pyrazol-4-yl)-1,3-dimethyl-1,3-dihydro-benzoimidazol-2-one;
5-(1-Acetyl-3-methyl-5-m-tolyl-1H-pyrazol-4-yl)-1,3-dimethyl-1,3-dihydro-benzoimidazol-2-one;
[4-(1,3-Dimethyl-2-oxo-2,3-dihydro-1H-benzoimidazol-5-yl)-5-methyl-3-m-tolyl-pyrazol-1-yl]-acetic acid tert-butyl ester;
[4-(1,3-Dimethyl-2-oxo-2,3-dihydro-1H-benzoimidazol-5-yl)-3-methyl-5-m-tolyl-pyrazol-1-yl]-acetic acid tert-butyl ester;
5-(1,5-Dimethyl-3-m-tolyl-1H-pyrazol-4-yl)-1,3-dimethyl-1,3-dihydro-benzoimidazol-2-one;
[4-(1,3-Dimethyl-2-oxo-2,3-dihydro-1H-benzoimidazol-5-yl)-5-methyl-3-m-tolyl-pyrazol-1-yl]-acetic acid;
[4-(1,3-Dimethyl-2-oxo-2,3-dihydro-1H-benzoimidazol-5-yl)-3-methyl-5-m-tolyl-pyrazol-1-yl]-acetic acid;
1,3-Dimethyl-5-(3-m-tolyl-1H-pyrazol-4-yl)-1,3-dihydro-benzoimidazol-2-one;
5-[2-(1-Benzyl-piperidin-4-yl)-3-m-tolyl-1H-pyrazol-4-yl]-1,3-diethyl-1,3-dihydro-benzoimidazol-2-one;
[4-(1,3-Diethyl-2-oxo-2,3-dihydro-1H-benzoimidazol-5-yl)-5-m-tolyl-2H-pyrazol-1-yl]-acetic acid ethyl ester;
5-[3-(3,4-Difluoro-phenyl)-5-methyl-1H-pyrazol-4-yl]-1,3-diethyl-1,3-dihydro-benzoimidazol-2-one;
5-[3-(2,4-Difluoro-phenyl)-5-methyl-1H-pyrazol-4-yl]-1,3-diethyl-1,3-dihydro-benzoimidazol-2-one;
5-[3-(3-Chloro-4-fluoro-phenyl)-5-methyl-1H-pyrazol-4-yl]-1,3-diethyl-1,3-dihydro-benzoimidazol-2-one;
1,3-Diethyl-5-[3-(4-fluoro-phenyl)-5-methyl-1H-pyrazol-4-yl]-1,3-dihydro-benzoimidazol-2-one;
1,3-Diethyl-5-(1-methyl-3-m-tolyl-1H-pyrazol-4-yl)-1,3-dihydro-benzoimidazol-2-one
1,3-Diethyl-5-(1-phenyl-5-m-tolyl-1H-pyrazol-4-yl)-1,3-dihydro-benzoimidazol-2-one;
1,3-Diethyl-5-[1-(4-methanesulfonyl-phenyl)-5-m-tolyl-1H-pyrazol-4-yl]-1,3-dihydro-benzoimidazol-2-one;
1,3-Diethyl-5-(3-m-tolyl-1H-pyrazol-4-yl)-1,3-dihydro-benzoimidazol2-one;
1,3-Diethyl-5-(2-pyridin-2-yl-3-m-tolyl-1H-pyrazol-4-yl)-1,3-dihydro-benzoimidazol-2-one;
3-Dimethyl-5-(3-phenyl-1H-pyrazol-4-yl)-1,3-dihydro-benzoimidazol-2-one;
3-Diethyl-5-(5-methylamino-3-m-tolyl-1H-pyrazol-4-yl)-1,3-dihydro-benzoimidazol-2-one;
3-Diethyl-5-(3-phenyl-1H-pyrazol-4-yl)-1,3-dihydro-benzoimidazol-2-one;
3-Diethyl-5-(1-pyridin-4-yl-5-m-tolyl-1H-pyrazol-4-yl)-1,3-dihydro-benzoimidazol-2-one;
3-Diethyl-5-(5-ethylamino-3-phenyl-1H-pyrazol-4-yl)-1,3-dihydro-benzoimidazol-2-one;
3-Diethyl-5-[5-(2-methoxy-ethylamino)-3-phenyl-1H-pyrazol-4-yl]-1,3-dihydro-benzoimidazol-2-one;
[2-(1-Benzyl-piperidin-4-yl)-3-phenyl-1H-pyrazol-4-yl]-1,3-dimethyl-1,3-dihydro-benzoimidazol-2-one;
3-Dimethyl-5-[3-(3-morpholin-4-yl-propylamino)-5-m-tolyl-1H-pyrazol-4-yl]-1,3-dihydro-benzoimidazol-2-one;
3-Dimethyl-5-[3-(2-morpholin-4-yl-ethylamino)-5-m-tolyl-1H-pyrazol-4-yl]-1,3-dihydro-benzoimidazol-2-one;
[3-(3-Dimethylamino-propylamino)-5-m-tolyl-1H-pyrazol-4-yl]-1,3-dimethyl-1,3-dihydro-benzoimidazol-2-one;
(5-Cyclohexylamino-3-phenyl-1H-pyrazol-4-yl)-1,3-diethyl-1,3-dihydro-benzoimidazol-2-one;
3-Dimethyl-5-(3-phenyl-2-piperidin-4-yl-1H-pyrazol-4-yl)-1,3-dihydro-benzoimidazol-2-one;
3-Diethyl-5-[5-(2-morpholin-4-yl-ethylamino)-3-phenyl-1H-pyrazol-4-yl]-1,3-dihydro-benzoimidazol-2-one;
(3-Allylamino-5-phenyl-1H-pyrazol-4-yl)-1,3-dimethyl-1,3-dihydro-benzoimidazol-2-one;
(5-Benzylamino-3-phenyl-1H-pyrazol-4-yl)-1,3-dimethyl-1,3-dihydro-benzoimidazol-2-one;
3-Dimethyl-5-[3-(3-morpholin-4-yl-propylamino)-5-m-tolyl-1H-pyrazol-4-yl]-1,3-dihydro-benzoimidazol-2-one;
3-Dimethyl-5-[3-(2-morpholin-4-yl-ethylamino)-5-m-tolyl-1H-pyrazol-4-yl]-1,3-dihydro-benzoimidazol-2-one;
3-Dimethyl-5-[3-(3-morpholin-4-yl-propylamino)-5-phenyl-1H-pyrazol-4-y]-1,3-dihydro-benzoimidazol-2-one;
3-Dimethyl-5-[3-(2-morpholin-4-yl-ethylamino)-5-phenyl-1H-pyrazol-4-yl]-1,3-dihydro-benzoimidazol-2-one
[4-(1,3-Diethyl-2-oxo-2,3-dihydro-1H-benzoimidazol-5-yl)-5-m-tolyl-2H-pyrazol-1-yl]-N-ethyl-acetamide;
3-Dimethyl-5-(3-methylamino-5-m-tolyl-1H-pyrazol-4-yl)-1,3-dihydro-benzoimidazol-2-one;
3-Dimethyl-5-(3-methylamino-5-m-tolyl-1H-pyrazol-4-yl)-1,3-dihydro-benzoimidazol-2-one;
3-Diethyl-5-[5-phenyl-3-(2-piperidin-1-yl-ethylamino)-1H-pyrazol-4-yl]-1,3-dihydro-benzoimidazol-2-one;
[3-(3-Dimethylamino-propylamino)-5-m-tolyl-1H-pyrazol-4-yl]-1,3-dimethyl-1,3-dihydro-benzoimidazol-2-one;
3-Diethyl-5-[1-(2-hydroxy-ethyl)-5-m-tolyl-1H-pyrazol-4-yl]-1,3-dihydro-benzoimidazol-2-one;
5-[3-(2,2-Dimethoxy-ethylamino)-5-m-tolyl-1H-pyrazol-4-yl]-1,3-dimethyl-1,3-dihydro-benzoimidazol-2-one;
5-[3-(3-Dimethylamino-propylamino)-5-m-tolyl-1H-pyrazol-4-yl]-1,3-diethyl-1,3-dihydro-benzoimidazol-2-one;
Diethyl-5-[2-(2-morpholin-4-yl-ethyl)-3-m-tolyl-1H-pyrazol-4-yl]-1,3-dihydro-benzoimidazol-2-one;

(5-Benzylamino-3-m-tolyl-1H-pyrazol-4-yl)-1,3-diethyl-1,3-dihydro-benzoimidazol-2-one;
1,3-Diethyl-5-[3-(2-morpholin-4-yl-ethylamino)-5-m-tolyl-1H-pyrazol-4-yl]-1,3-dihydro-benzoimidazol-2-one;
1,3-Diethyl-5-[3-(2-piperidin-1-yl-ethylamino)-5-m-tolyl-1H-pyrazol-4-yl]-1,3-dihydro-benzoimidazol-2-one;
[4-(1,3-Diethyl-2-oxo-2,3-dihydro-1H-benzoimidazol-5-yl)-3-m-tolyl-pyrazol-1-yl]-acetic acid tert-butyl ester;
[4-(1,3-Diethyl-2-oxo-2,3-dihydro-1H-benzoimidazol-5-yl)-3-m-tolyl-pyrazol-1-yl]-acetic acid;
[4-(1,3-Diethyl-2-oxo-2,3-dihydro-1H-benzoimidazol-5-yl)-5-m-tolyl-pyrazol-1-yl]-acetic acid tert-butyl ester;
[4-(1,3-Diethyl-2-oxo-2,3-dihydro-1H-benzoimidazol-5-yl)-5-m-tolyl-pyrazol-1-yl]-acetic acid;
1,3-Diethyl-5-[1-(2-oxo-2-pyrrolidin-1-yl-ethyl)-5-m-tolyl-1H-pyrazol-4-yl]-1,3-dihydro-benzoimidazol-2-one;
2-[4-(1,3-Diethyl-2-oxo-2,3-dihydro-1H-benzoimidazol-5-yl)-5-m-tolyl-pyrazol-1-yl]-N-propyl-acetamide;
2-[4-(1,3-Diethyl-2-oxo-2,3-dihydro-1H-benzoimidazol-5-yl)-5-m-tolyl-pyrazol-1-yl]-N-(2-ethoxy-ethyl)-acetamide;
1,3-Diethyl-5-[1-(2-oxo-2-piperidin-1-yl-ethyl)-5-m-tolyl-1H-pyrazol-4-yl]-1,3-dihydro-benzoimidazol-2-one;
2-[4-(1,3-Diethyl-2-oxo-2,3-dihydro-1H-benzoimidazol-5-yl)-3-m-tolyl-pyrazol-1-yl]-N-ethyl-acetamide;
2-[4-(1,3-Diethyl-2-oxo-2,3-dihydro-1H-benzoimidazol-5-yl)-5-m-tolyl-pyrazol-1-yl]-N-ethyl-acetamide;
2-[4-(1,3-Diethyl-2-oxo-2,3-dihydro-1H-benzoimidazol-5-yl)-5-m-tolyl-pyrazol-1-yl]-N-(2-methoxy-ethyl)-acetamide;
5-(3-Allylamino-5-m-tolyl-1H-pyrazol-4-yl)-1,3-diethyl-1,3-dihydro-benzoimidazol-2-one;
[4-(1,3-Dimethyl-2-oxo-2,3-dihydro-1H-benzoimidazol-5-yl)-3-m-tolyl-pyrazol-1-yl]-acetic acid tert-butyl ester;
[4-(1,3-Dimethyl-2-oxo-2,3-dihydro-1H-benzoimidazol-5-yl)-5-m-tolyl-pyrazol-1-yl]-acetic acid tert-butyl ester;
1,3-Diethyl-5-[1-(2-morpholin-4-yl-2-oxo-ethyl)-5-m-tolyl-1H-pyrazol-4-yl]-1,3-dihydro-benzoimidazol-2-one;
[4-(1,3-Dimethyl-2-oxo-2,3-dihydro-1H-benzoimidazol-5-yl)-3-m-tolyl-pyrazol-1-yl]-acetic acid;
[4-(1,3-Dimethyl-2-oxo-2,3-dihydro-1H-benzoimidazol-5-yl)-5-m-tolyl-pyrazol-1-yl]-acetic acid;
5-(1-Allyl-3-m-tolyl-1H-pyrazol-4-yl)-1,3-diethyl-1,3-dihydro-benzoimidazol-2-one;
1,3-Diethyl-5-[1-(2-pyrrolidin-1-yl-ethyl)-5-m-tolyl-1H-pyrazol-4-yl]-1,3-dihydro-benzoimidazol-2-one;
1,3-Diethyl-5-[l-(2-morpholin-4-yl-2-oxo-ethyl)-3-m-tolyl-1H-pyrazol-4-yl]-1,3-dihydro-benzoimidazol-2-one;
5-(1-Allyl-5-m-tolyl-1H-pyrazol-4-yl)-1,3-diethyl-1,3-dihydro-benzoimidazol-2-one
1,3-Diethyl-5-{1-[2-(2-methoxy-ethylamino)-ethyl]-5-m-tolyl-1H-pyrazol-4-yl}-1,3-dihydro-benzoimidazol-2-one;
2-[4-(1,3-Diethyl-2-oxo-2,3-dihydro-1H-benzoimidazol-5-yl)-3-m-tolyl-pyrazol-1-yl]-N-(2-methoxy-ethyl)-acetamide;
1,3-Diethyl-5-[-(2-ethylamino-ethyl)-5-m-tolyl-1H-pyrazol-4-yl]-1,3-dihydro-benzoimidazol-2-one;
5-[3-(3-Diethylamino-propylamino)-5-m-tolyl-1H-pyrazol-4-yl]-1,3-diethyl-1,3-dihydro-benzoimidazol-2-one;
5-[3-(3-Dimethylamino-propylamino)-5-phenyl-1H-pyrazol-4-yl]-1,3-dimethyl-1,3-dihydro-benzoimidazol-2-one;
1,3-Diethyl-5-{1-[2-(4-methyl-piperazin-1-yl)-2-oxo-ethyl]-3-m-tolyl-1H-pyrazol-4-yl}-1,3-dihydro-benzoimidazol-2-one;
1,3-Dimethyl-5-[1-(2-morpholin-4-yl-2-oxo-ethyl)-3-m-tolyl-1H-pyrazol-4-yl]-1,3-dihydro-benzoimidazol-2-one;
1,3-Dimethyl-5-[3-(2-pyrrolidin-1-yl-ethylamino)-5-m-tolyl-1H-pyrazol-4-yl]-1,3-dihydro-benzoimidazol-2-one;
5-[3-(3-Diethylamino-propylamino)-5-phenyl-1H-pyrazol-4-yl]-1,3-diethyl-1,3-dihydro-benzoimidazol-2-one;
5-[3-(2-Dimethylamino-ethylamino)-5-phenyl-1H-pyrazol-4-yl]-1,3-diethyl-1,3dihydro-benzoimidazol-2-one;
4-([4-(1,3-Diethyl-2-oxo-2,3-dihydro-1H-benzoimidazol-5-yl)-3-m-tolyl-pyrazol-1-yl]-acetyl)-piperazine-1-carboxylic acid tert-butyl ester;
2-[4-(1,3-Diethyl-2-oxo-2,3-dihydro-1H-benzoimidazol-5-yl)-3-m-tolyl-pyrazol-1-yl]-N-(3-dimethylamino-propyl)-acetamide;
2-[4-(1,3-Diethyl-2-oxo-2,3-dihydro-1H-benzoimidazol-5-yl)-3-m-tolyl-pyrazol-1-yl]-acetamide;
1,3-Diethyl-5-[1-(2-oxo-2-piperazin-1-yl-ethyl)-3-m-tolyl-1H-pyrazol-4-yl]-13-dihydro-benzoimidazol-2-one;
5-[3-(2-Diethylamino-ethylamino)-5-phenyl-1H-pyrazol-4-yl]-1,3-dimethyl-1,3-dihydro-benzoimidazol-2-one;
5-[3-(2-Diethylamino-ethylamino)-5-m-tolyl-1H-pyrazol-4-yl]-1,3-dimethyl-1,3-dihydro-benzoimidazol-2-one;
2-[4-(1,3-Diethyl-2-oxo-2,3-dihydro-1H-benzoimidazol-5-yl)-3-m-tolyl-pyrazol-1-yl]-N-(1-ethyl-pyrrolidin-2-ylmethyl)-acetamide;
[4-(1,3-Diethyl-2-oxo-2,3-dihydro-1H-benzoimidazol-5-yl)-3-phenyl-pyrazol-1-yl]-acetic acid;
2-[4-(1,3-Diethyl-2-oxo-2,3-dihydro-1H-benzoimidazol-5-yl)-3-m-tolyl-pyrazol-1-yl]-N-(2-dimethylamino-ethyl)-acetamide;
2-[4-(1,3-Diethyl-2-oxo-2,3-dihydro-1H-benzoimidazol-5-yl)-3-phenyl-pyrazol-1-yl]-N-(2-dimethylamino-ethyl)-acetamide;
1,3-Diethyl-5-(1-[2-(2-methoxy-ethylamino)-ethyl]-3-m-tolyl-1H-pyrazol-4-yl)-1,3-dihydro-benzoimidazol-2-one;
1,3-Diethyl-5-[5-phenyl-3-(2-pyrrolidin-1-yl-ethylamino)-1H-pyrazol-4-yl]1,3-dihydro-benzoimidazol-2-one;
5-[3-(2-Dimethylamino-ethylamino)-5-m-tolyl-1H-pyrazol-4-yl-1,3-diethyl-1,3-dihydro-benzoimidazol-2-one;
N-(1-Benzyl-pyrrolidin-3-yl)-2-[4-(1,3-diethyl-2-oxo-2,3-dihydro-1 Hbenzoimidazol-5-yl)-3-m-tolyl-pyrazol-1-yl]-acetamide;
1,3-Diethyl-5-[1-(2-oxo-2-piperazin-1-yl-ethyl)-3-phenyl-1H-pyrazol-4-yl]-1,3-dihydro-benzoimidazol-2-one;
N-(1-Benzyl-pyrrolidin-3-yl)-2-[4-(1,3-diethyl-2-oxo-2,3-dihydro-1 Hbenzoimidazol-5-yl)-3-phenyl-pyrazol-1-yl]-acetamide;
5-[3-(3-Diethylamino-propylamino)-5-phenyl-1H-pyrazol-4-yl]-1,3-dimethyl-1,3-dihydro-benzoimidazol-2-one;
5-[3-(3-Diethylamino-propylamino)-5-m-tolyl-1H-pyrazol-4-yl]-1,3-dimethyl-1,3-dihydro-benzoimidazol-2-one;
5-{1-[2-(3-Amino-pyrrolidin-1-yl)-2-oxo-ethyl]-3-m-tolyl-1H-pyrazol-4-yl}-1,3-diethyl-1,3-dihydro-benzoimidazol-2-one;
5-(1-Allyl-3-phenyl-1H-pyrazol-4-yl)-1,3-diethyl-1,3-dihydro-benzoimidazol-2-one;
1,3-Diethyl-5-[1-(2-morpholin-4-yl-ethyl)-3-phenyl-1H-pyrazol-4-yl]-1,3-dihydro-benzoimidazol-2-one;
2-[4-(1,3-Diethyl-2-oxo-2,3-dihydro-1H-benzoimidazol-5-yl)-3-phenyl-pyrazol-1-yl]-N-pyrrolidin-3-yl-acetamide;
1,3-Diethyl-5-[1-(2-morpholin-4-yl-ethyl)-3-m-tolyl-1H-pyrazol-4-yl]-1,3-dihydro-benzoimidazol-2-one; and
5-[1-(2-Dimethylamino-ethyl)-3-m-tolyl-1H-pyrazol-4-yl]-1,3-diethyl-1,3-dihydro-benzoimidazol-2-one.

The present invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine mediated disease which comprises administering an effective cytokine-interfering amount of a compound of Formula (I) or a pharmaceutically acceptable salt thereof.

Certain compounds of Formula (I) are capable of inhibiting inducible pro-inflammatory proteins, such as COX-2, also referred to by many other names such as prostaglandin endoperoxide synthase-2 (PGHS-2) and are therefore of use in therapy. These proinflammatory lipid mediators of the cyclooxygenase (COX) pathway are produced by the inducible COX-2 enzyme. Regulation, therefore of COX-2 which is responsible for these products derived from arachidonic acid, such as prostaglandins, affect a wide variety of cells and tissues. Expression of COX-1 is not effected by compounds of Formula (I). This selective inhibition of COX-2 is accepted as alleviating or sparing ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management, therefore, includes treatment of neuromuscular pain, headache, cancer pain, and arthritis pain. Compounds of Formula (I), or a pharmaceutically acceptable salt thereof, are of use in therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of treatment in a human, or other mammal, by inhibition of the synthesis of the COX-2 enzyme.

In particular, compounds of Formula (I) or a pharmaceutically acceptable salt thereof are of use in the therapy of any disease state in a human, or other mammal, which is exacerbated by or caused by excessive or unregulated IL-1, IL-8 or TNF production by such mammal's cells, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

Use of a p38 inhibitor for the treatment of p38 mediated disease states, can include, but is not limited to neurodegenerative diseases, such as Alzheimer's disease, Parkinson's disease and multiple sclerosis, etc. In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic obstructive pulmonary disease, chronic pulmonary inflammatory disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment of topical disease states mediated by or exacerbated by excessive cytokine production, such as by IL-1 or TNF respectively, such as inflamed joints, eczema, contact dermatitis psoriasis and other inflammatory skin conditions such as sunburn; inflammatory eye conditions including conjunctivitis; pyresis, pain and other conditions associated with inflammation. Periodontal disease has also been implicated in cytokine production, both topically and systemically. Hence, the use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering, to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit a cytokine, in particular IL-1, IL-6, IL-8 or TNF, production such that it is regulated down to normal levels, or in some cases to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1. IL-6, IL-8 and TNF is based upon the effects of the compounds of Formula (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event to normal or sub-normal levels; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease state mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the treatment of a disease state which is exacerbated by, or caused by, excessive or unregulated cytokine production.

As used herein, the cytokine referred to in the phrase "inhibition of a cytokine for use in the treatment of a HIV-infected human" is a cytokine which is implicated in (a)

the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A relatively new member of the MAP kinase family, alternatively termed CSBP, p38 or RK, has been identified by several laboratories [See Lee et al., *Nature,* Vol. 300, n(72), 739–746 (1994)]. Activation of this protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors of the present invention, compounds of Formula (I), have been detemined to be potent and selective inhibitors of CSBP/p38/RK kinase activity. These inhibitors are of aid in determining the signaling pathways involvement in inflammatory responses. In particular, a definitive signal transduction pathway can be prescribed to the action of lipopolysaccharide in cytokine production in macrophages. In addition to those diseases already noted herein, treatment of stroke, neurotrauma/CNS head injury, cardiac, brain and renal reperfusion injury, thrombosis, glomerulonephritis, diabetes and pancreatic p cells, multiple sclerosis, muscle degeneration, eczema, psoriasis, sunburn, and conjunctivitis are also included.

Cytokine inhibitors of the present invention were tested in a number of animal models for anti-inflammatory activity. Model systems were chosen that were relatively insensitive to cyclooxygenase inhibitors in order to reveal the unique activities of cytokine suppressive agents. Inhibitors of the present invention exhibited significant activity in many such in vivo studies. Specifically, compounds of the present invention demonstrated effectiveness in the collagen-induced arthritis model and inhibition of TNF production in the endotoxic shock model. In the latter study, the reduction in plasma level of TNF correlated with survival and protection from endotoxic shock related mortality. Compounds of the present invention also demonstrated effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61, Votta et al., (1994) in vitro. *Bone* 15, 533–538; Lee et al., (1993.). *B Ann. N.Y. Acad. Sci.* 696, 149–170.

It is also recognized that both IL-6 and IL-8 are produced during rhinovirus (HRV) infections and contribute to the pathogenesis of common cold and exacerbation of asthma associated with HRV infection (Turner et al., (1998), *Clin. Infec. Dis., Vol.* 26, p. 840; Teren et al. (1997), *Am. J. Respir. Crit. Care Med.,* Vol. 155, p. 1362; Grunberg et al. (1997), *Am. J. Respir. Crit. Care Med.,* Vol. 156, p. 609 and Zhu et al., *J. Clin. Invest.* (1996), Vol. 97, p 421). It has also been demonstrated in vitro that infection of pulmonary epithelial cells with HRV results in production of IL-6 and IL-8 (Subauste et al., *J. Clin. Invest.* (1995), Vol. 96, p. 549). Epithelial cells represent the primary site of infection of HRV. Therefore, another aspect of the present invention is a method of treatment to reduce inflammation associated with a rhinovirus infection, not necessarily a direct effect of the virus itself.

Another aspect of the present invention involve the novel use of these p38/cytokine inhibitors for the treatment of chronic inflammatory or proliferative or angiogenic diseases, which are caused by excessive, or inappropriate angiogenesis.

Chronic diseases which have an inappropriate angiogenic component are various ocular neovasualizations, such as diabetic retinopathy and macular degeneration. Other chronic diseases which have an excessive or increased proliferation of vasculature are tumor growth and metastasis, atherosclerosis and certain arthritic conditions. Therefore, cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating an ERK/MAP kinase, preferably a p38 kinase, mediated disease in a mammal in need thereof, preferably a human, which comprises administering to said mammal, an effective amount of a compound of Formula (I) or a pharmaceutically acceptable salt thereof.

Preferred p38 mediated diseases for treatment include, but are not limited to, arthritis, psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, ischemic and hemorrhagic stroke, neurotrauma/closed head injury, asthma, adult respiratory distress syndrome, chronic obstructive pulmonary disease, cerebral malaria, meningitis, chronic pulmonary inflammatory disease, silicosis, pulmonary sarcostosis, bone resorption disease, osteoporosis, restenosis, cardiac and renal reperfusion injury, brain and renal reperfusion injury, chronic renal failure, thrombosis, glomerularonephritis, diabetes, diabetic retinopathy, macular degeneration, graft vs. host reaction, allograft rejection, inflammatory bowel disease, Crohn's disease, ulcerative colitis, neurodegenerative disease, multiple sclerosis, muscle degeneration, diabetic retinopathy, macular degeneration, tumor growth and metastasis, angiogenic disease, rhinovirus infection, peroral disease, such as gingivitis and periodontitis, eczema, contact dermatitis, psoriasis, sunburn, and conjunctivitis.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions for the treatment of a condition selected from the group consisting of arthritis, psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, ischemic and hemorrhagic stroke, neurotrauma/closed head injury, asthma, adult respiratory distress syndrome, chronic obstructive pulmonary disease, cerebral malaria, chronic pulmonary inflammatory disease, cerebral malaria, meningitis, chronic pulmonary inflammatory disease, silicosis, pulmonary sarcostosis, bone resorption disease, osteoporosis, restenosis, cardiac and renal reperfusion injury, brain and renal reperfusion injury, chronic renal failure, thrombosis, glomerularonephritis, diabetes, diabetic retinopathy, macular degeneration, graft vs. host reaction, allograft rejection, inflammatory bowel disease, Crohn's disease, ulcerative colitis, neuro-degenerative disease, multiple sclerosis, muscle degeneration, diabetic retinopathy, macular degeneration, tumor growth and metastasis, angiogenic disease, rhinovirus infection, peroral disease, such as gingivitis and periodontitis, eczema, contact dermititis, psoriasis, sunburn, and conjunctivitis in a mammal, including a human, comprising an amount of a compound of formula I effective in such treatment and a pharmaceutically acceptable carrier.

This invention also encompasses pharmaceutical compositions for the treatment of a condition which can be treated by the inhibition of ERK/MAP kinase in a mammal, including a human, comprising an amount of a compound of formula I effective in such treatment and a pharmaceutically acceptable carrier.

This invention also encompasses pharmaceutical compositions for the treatment of a condition which can be treated by the inhibition of p38 kinase in a mammal, including a human, comprising an amount of a compound of formula I effective in such treatment and a pharmaceutically acceptable carrier.

This invention also encompasses pharmaceutical compositions containing prodrugs of compounds of the formula I. This invention also encompasses methods of treating or preventing disorders that can be treated or prevented by the inhibition of ERK/MAP comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The invention also encompasses sustained release compositions.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as celecoxib, rofecoxib, valdecoxib and etoricoxib) low dose methotrexate, lefunomide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

DETAILED DESCRIPTION OF THE INVENTION

Compounds of the formula I may be prepared according to the following reaction schemes and discussion. Unless otherwise indicated, m, n, p, s, B, $R^1$ through $R^{16}$ and Het and structural formula I in the reaction schemes and discussion that follow are as defined above.

Scheme 1
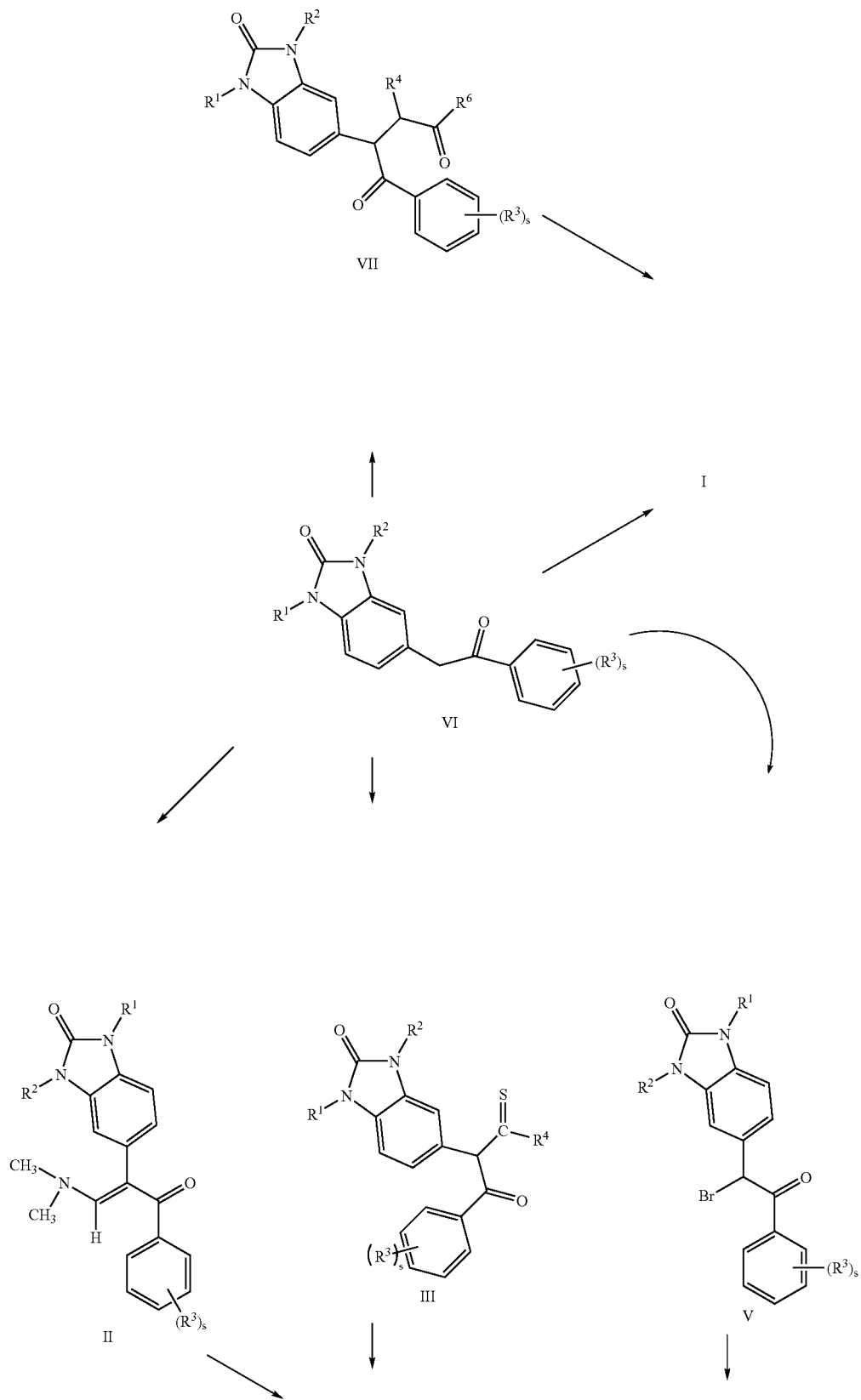

-continued
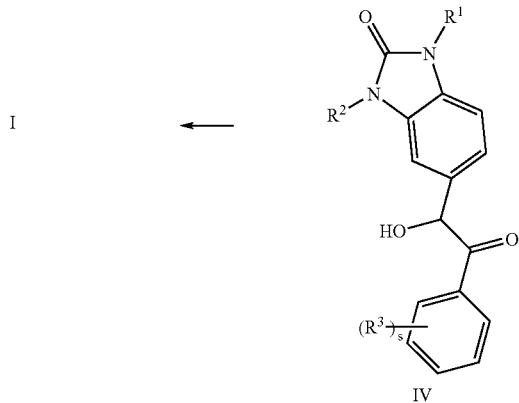
IV
Scheme 2
Scheme 3
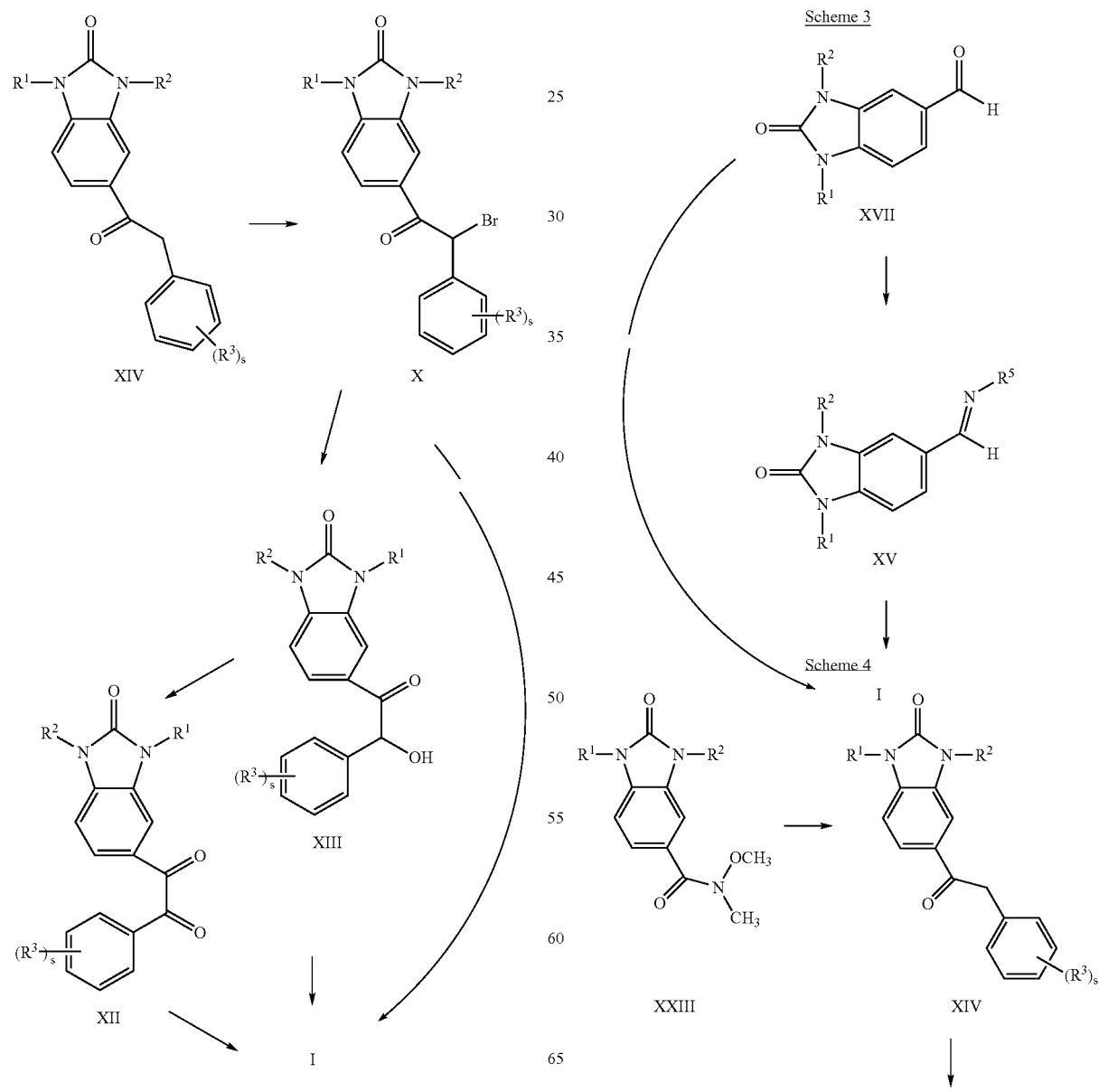

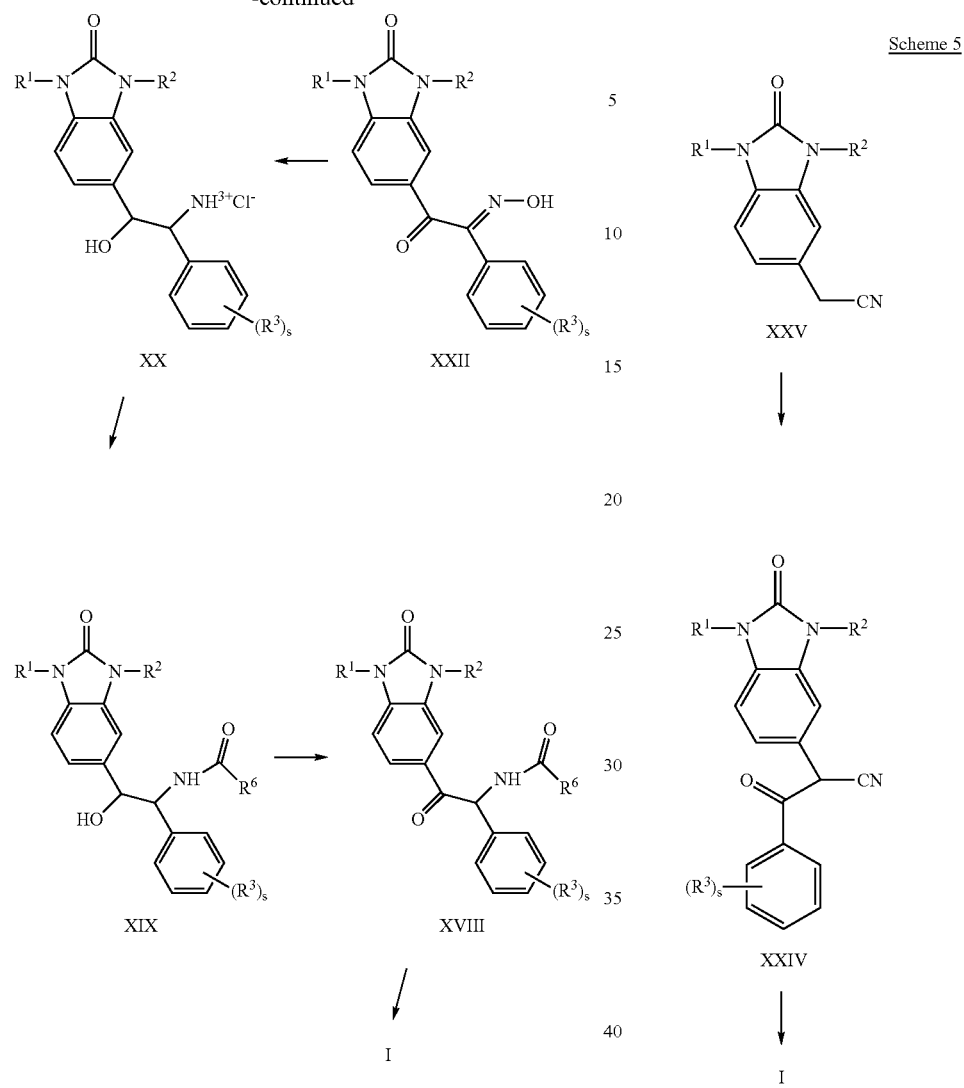
Scheme 5
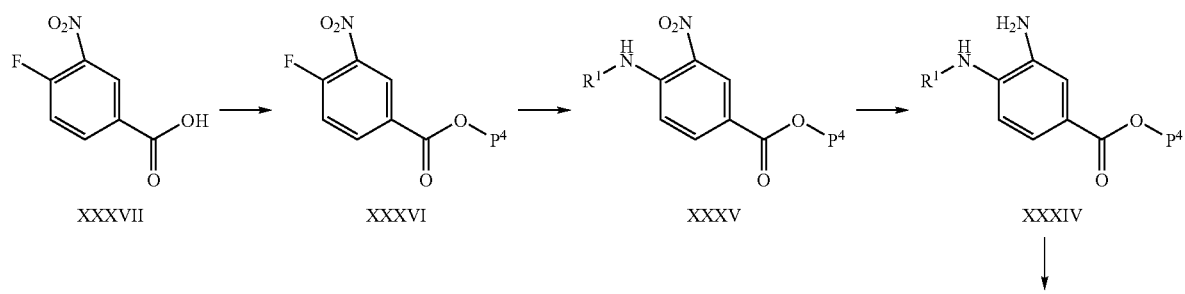
Scheme 6

-continued
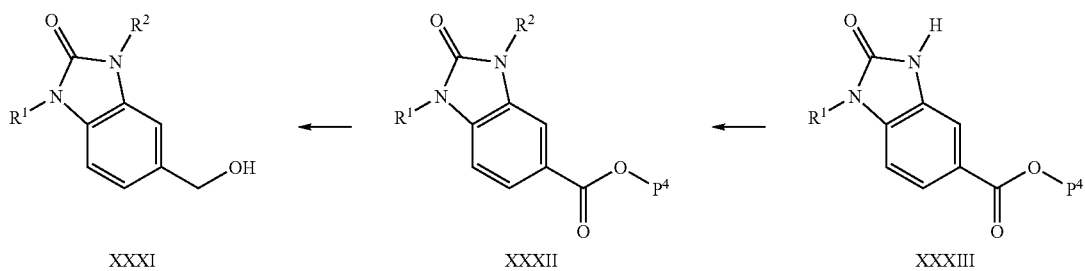
XXXI      XXXII      XXXIII
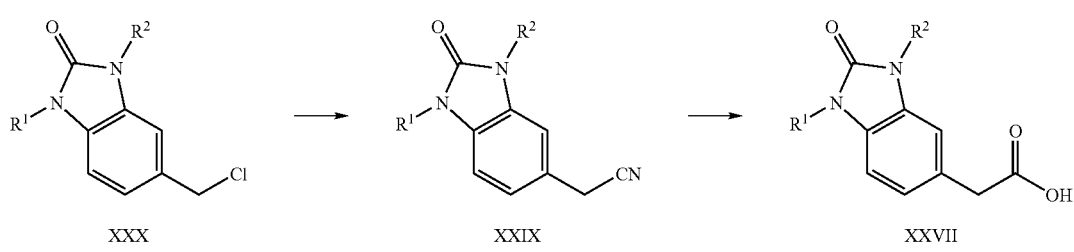
XXX      XXIX      XXVII
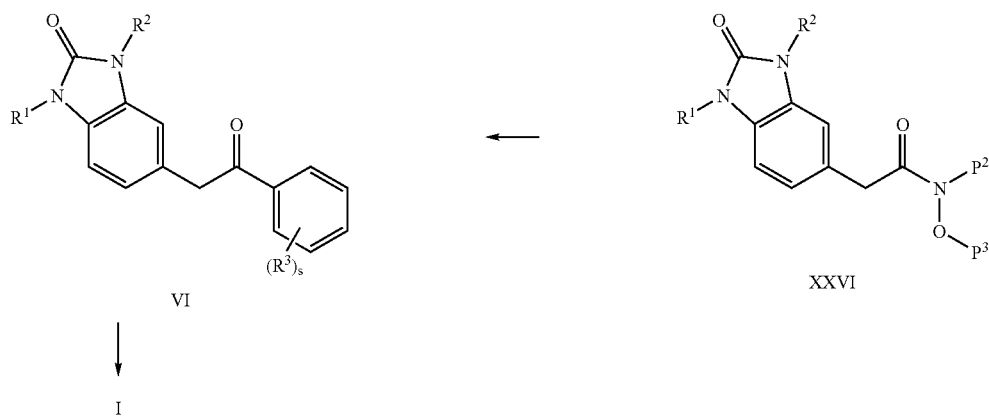
VI      XXVI
I Scheme 7
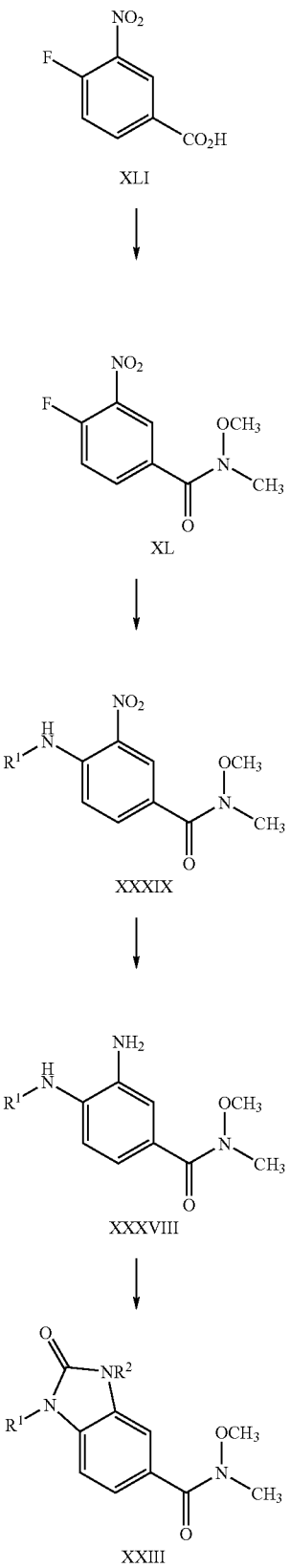
Scheme 8
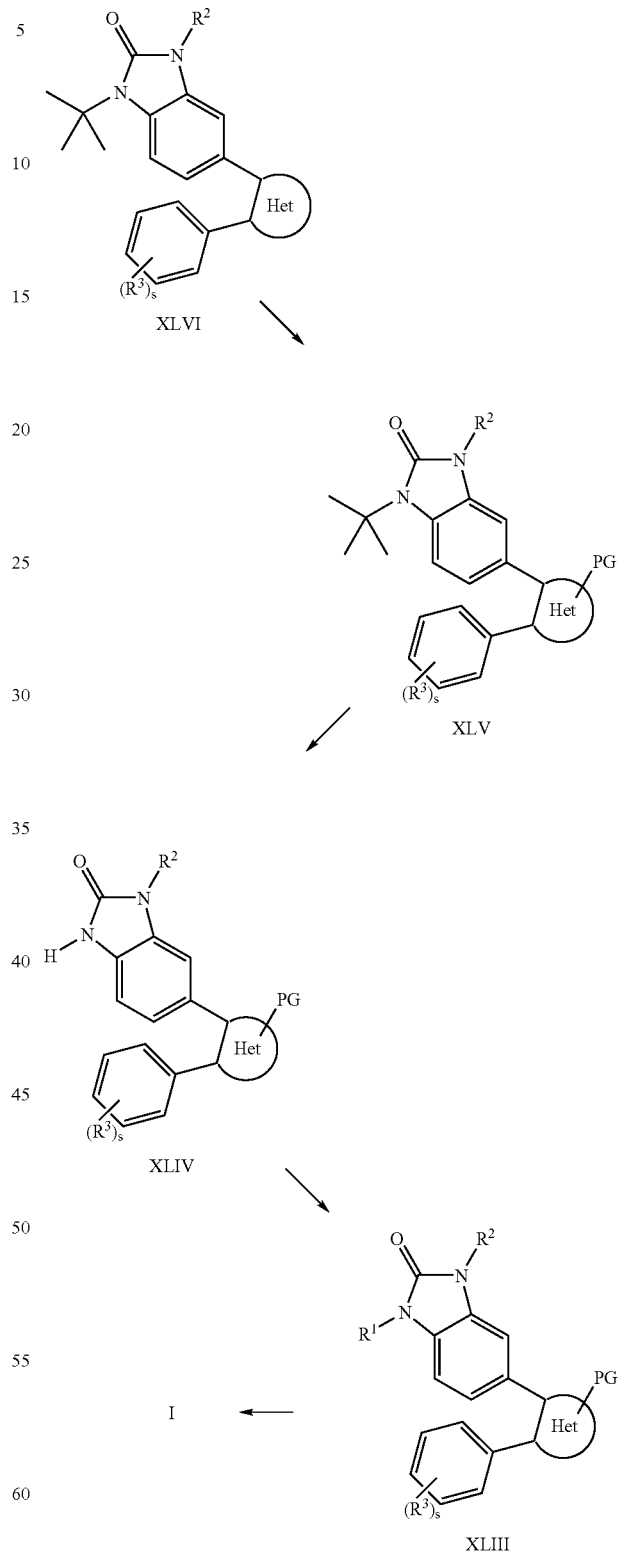
Scheme I refers to the preparation of compounds of the formula I. Referring to Scheme 1, a compound of the formula I, wherein $(R^3)_s$-phenyl-Het is (c) or (f), can be prepared from compounds of the formula II by reaction with an aminating reagent. Suitable aminating reagents include hydrazines of the formula $H_2N-NH-R^7$, in a polar solvent. Suitable solvents include alcohols such as ethanol, propanol or butanol or mixtures of alcohols and acetic acid, preferably ethanol. The aforesaid reaction is conducted at a temperature of about 10° C. to about 30° C., preferably at about 22° C., for a period from about 1 hour to about 7 hours, preferably about 3 hours.

The compound of formula 11 is prepared from a compound of formula VI by reaction with an acetal, such as dimethylformamide—dimethylacetal, at a temperature of about 60° C. to about 90° C., preferably about 80° C. for a period from about 1 hour to about 6 hours, preferably about 3 hours.

Alternatively, compounds of the formula I, wherein $(R^3)_s$-phenyl-Het is (c) or (f), can be prepared from compounds of the formula III by reaction with an aminating reagent such as $H_2N-NH-R^7$ according to methods analogous to the conversion of compounds of formula II to formula I, above.

The compound of formula III is prepared from a compound of formula VI by reaction with an isothioyanate. Suitable isothiocyanates include compounds of the formula $R^4-N=C=S$. Reactions with isothiocyanates are facilitated by the addition of a base, such as sodium hydride, lithium diisopropylamide or other suitable strong bases. Suitable solvents for the aforesaid reaction include pyridine, N,N-dimethylformamide or tetrahydrofuran, preferably pyridine. The aforesaid reaction is performed from a period of about 0.5 hour to about 4 hours at a temperature of about 0° C. to about 30° C. The deprotonation reaction with above said bases is followed by the addition of a suitable isothiocyanate and is performed for a period from about 10 minutes to about 20 hours, at a temperature of about 0° C. to about 30° C., preferably about 22° C. for a period from about 0.5 hour to about 24 hours.

Compounds of the formula I, wherein $(R^3)_s$-phenyl-Het is (b), can be prepared from compounds of the formula IV, by reaction with an aldehyde of the formula $R^6-(C=O)H$ in the presence of an ammonia source and cuprous acetate and a polar solvent. Suitable ammonia sources include ammonium trifluoroacetate, ammonia, and ammonium acetate, preferably ammonium acetate. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

Compounds of the formula I, wherein $(R^3)_s$-phenyl-Het is (d) can be prepared from compounds of the formula IV, by reaction with an acylating reagent of the formula $R^6(C=O)-L$, wherein L is a leaving group such as halo or anhydrido, using method well known to those skilled in the art. The acyl derivative, so formed, is converted to the compound of formula I by cyclodehydration in the presence of a source of ammonia. Suitable solvents include acetic acid and tetrahydrofuran. The aforesaid reaction can be run at a temperature from about 22° C. to about 80° C., preferably 50° C., for a period from about 1 hour to about 24 hours, preferably 2 hours.

The compound of formula IV is prepared from a compound of formula V by reaction with sodium methoxide, or sodium ethoxide, or sodium tert-butoxide, preferably sodium methoxide, in an alcohol solvent, such as methanol, ethanol, isopropanol, preferably methanol. The aforesaid reaction can be conducted at a temperature of 0° C. to about 30° C., preferably at about 22° C., for a period of time from 15 minutes to about 3 hours, preferably about 30 minutes. The aforesaid reaction is followed by an aqueous acidic work-up.

The compound of formula V is prepared from a compound of formula VI by reaction with with $Br_2$ in a polar solvent. Suitable solvents include acetic acid, chloroform or methylene chloride, preferably acetic acid. The aforesaid reaction is conducted at a temperature of about 0° C. to about 30° C. preferably at about 22° C. (room temperature) for a period from about 10 minutes to about 4 hours, preferably about 30 minutes.

Compounds of the formula I, wherein $(R^3)_s$-phenyl-Het is (a), can be prepared from compounds of the formula VII, by reaction with an ammonia source and cuprous acetate and a polar solvent. Suitable ammonia sources include ammonium trifluoroacetate, ammonia, and ammonium acetate, preferably ammonium acetate. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

The compound of formula VII is prepared from a compound of formula VI by reaction with a reagent of the formula

VIII wherein L is a leaving group such as chloro, bromo, iodo or mesylate, in the presence of a base and a solvent. Suitable bases include NaH and n-butyllithium. Suitable solvents include THF and DMF. The aforesaid reaction can be conducted at a temperature from about −30° C. to about the reflux temperature of the solvent, for a period of about 5 minutes to about 24 hours.

The compound of formula VI is prepared according to the methods of Scheme 6. The compound of formula VII is prepared by methods well known to those skilled in the art.

Scheme 2 refers to an alternate preparation of compounds of formula I, wherein $(R^3)_s$-phenyl-Het is (b), from compounds of the formula XIV. Compounds of the formula XIV can be prepared by the methods of Scheme 4.

Referring to Scheme 2, a compound of the formula I, wherein $(R^3)_s$-phenyl-Het is a group of the formula (b), can be prepared from a compound of the formula X by reaction with a compound of the formula

XI wherein $R^5$ is hydrogen, in the presence of a polar solvent. Suitable solvents include dimethyl formamide, chloroform, DMSO, THF and ethanol, preferably dimethylformamide.

The aforesaid reaction is conducted at a temperature of about 15° C. to about 80° C., preferably about 60° C., for a period from about 4 hours to about 4 days, preferably 4 hours.

Alternatively, a compound of the formula I, wherein wherein $(R^3)_s$-phenyl-Het is a group of the formula (b), can be prepared from a compound of formula XII by reaction with $R^6$—(C=O)H in the presence of an ammonia source. Suitable ammonia sources include ammonium trifluoroacetate, ammonia, and ammonium acetate, preferably ammonium acetate. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

The compound of formula XII is prepared from a compound of the formula XIII by reaction with an oxidizing reagent in a polar protic solvent. Suitable oxidizing reagents include copper acetate, pyridiniumchlorochromate (PCC) and tetrapropylammonium peruthenate/N-methyl morpholine-N-oxide (TPAP/NMO), preferably cuprous acetate. Suitable solvents include acetic acid. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

Alternatively, a compound of the formula I, wherein $(R^3)_s$-phenyl-Het is a group of the formula (b), can be prepared from a compound of formula XIII, by reaction with an aldehyde of the formula $R^6$—(C=O)—H in the presence of cuprous acetate and an ammonia source according to methods analogous to those for the conversion of compounds of formula IV to formula I in Scheme 1.

The compound of formula XIII is prepared from a compound of the formula X by reaction with a methoxide such as described in Scheme 1 for the preparation of compounds of formula IV from compounds of formula V.

The compound of formula X is prepared from a compound of the formula XIV by reaction with $Br_2$ in a polar solvent. Suitable solvents include acetic acid, chloroform or methylene chloride, preferably acetic acid. The aforesaid reaction is conducted at a temperature of about 0° C. to about 30° C. preferably at about 22° C. (room temperature) for a period from about 10 minutes to about 4 hours, preferably about 30 minutes.

Scheme 3 refers to an alternate preparation of compounds of formula I, wherein $(R^3)$s phenyl-Het is a group of the formula (b) or (d) and $R^6$ is hydrogen. Referring to Scheme 3, a compound of formula I, wherein $(R^3)_s$-phenyl-Het is of the formula (d) and $R^6$ is hydrogen, is prepared from a compound of formula XVII by reaction with an isocyamide of formula

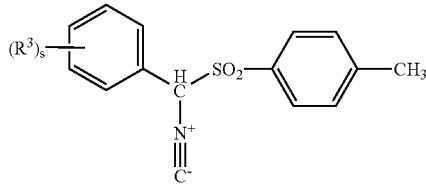

XVI in the presence of a base. Suitable bases include potassium carbonate, triethylamine, and piperazine, preferably potassium carbonate. Suitable solvents include polar solvents such as tetrahydrofuran, or N,N-dimethylformamide, preferably in N,N-dimethylformamide. The aforesaid reaction may be run at a temperature between about 22° C. and about 70° C., preferably at about 22° C. for a period from about 2 hours to about 4 hours, followed by about 6 hours to about 10 hours at a temperature of about 70° C.

Compounds of formula I, wherein $(R^3)_s$-phenyl-Het is of the formula (b) and $R^6$ is hydrogen, can be prepared in an analogous way by first preparation of the intermediate imine of formula XV by reaction of compounds of formula XVII with a suitable amine of the formula $NH_2R^5$ under dehydrating conditions. Such conditions include the treatment of compounds of formula XVII and an amine $NH_2R^5$ in a solvent such as tetrahydrofuran or dichlormethane with a dehydrating agent such as anhydrous magnesium sulfate or molecular sieves. Alternatively, the imine of formula XV can be prepared and subsequently reacted in an aqueous media as described in the literature: (Sisko, J.; Kassik, A. J.; Mellinger, M.; Filan, J. J.; Allen, A.; Olsen, M. A.; J. Org. Chem. 2000, 65, 1516–1524). Reactions of imines of formula XV with suitable isocynamides of formula XVI are conducted at about 22° C. for a time period from about 1 day to about 21 days, preferably about 1 day.

A compound of formula XVII is prepared from a compound of formula XXIII in Scheme 4.

Scheme 4 refers to an alternate preparation of compounds of the formula I, wherein $(R^3)_s$-phenyl-Het is a group of the formula (b). Referring to Scheme 4, compounds of the formula I are prepared from compounds of the formula XVIII by reaction with an ammonia source. Suitable ammonia sources include ammonium trifluoroacetate, ammonia, and ammonium acetate, preferably ammonium trifluoroacetate. The aforesaid reaction can be run neat or in the presence of a solvent such as alcohols (methanol, ethanol or butanol) and acetic acid. The aforesaid reaction can be run at a temperature from about 60° C. to about 150° C. for a period from about 15 minutes to about 3 hours, preferably neat conditions at about 150° C. for about 1 hour.

The compound of formula XVIII is prepared form a compound of formula XIX by reaction with, an oxidizing reagent such as N-methyl morpholine N-oxide/TPAP, Dess-Martin reagent, PCC or oxalyl chloride-DMSO, preferably N-methyl morpholine N-oxide/TPAP. Suitable solvents for the aforesaid reaction include methylene chloride, chloroform, THF or dichloromethane. The aforesaid reaction is conducted at a temperature from about 10° C. to about 30° C. for a time from about 15 minutes to about 3 hours, preferably about 1 hour.

The compound of formula XIX is prepared from a compound of the formula XX by reaction with an acylating reagent of the formula,

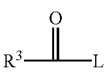

XXI wherein L is a leaving group, and a base. Suitable bases include triethylamine, Hunig's base, or DBU, preferably triethylamine. Suitable leaving groups include Cl, Br or activated acids. Suitable solvents for the aforesaid reaction include methylene chloride, dimethyl formamide, THF or DMF, and mixtures thereof, preferably methylene chloride. The aforesaid reaction is conducted at a temperature from about 10° C. to about 30° C. preferably about 22° C. (room temperature) for a period from about 1 hour to about 6 hours preferably about 1 hour.

The compound of the formula XX is prepared form a compound of formula XXII by reaction with a reducing agent. Reducing agents are well known to those skilled in the art. For example, reduction of the double bond may be effected with hydrogen gas ($H_2$), using catalysts such as palladium on carbon (Pd/C), palladium on barium sulfate (Pd/BaSO$_4$), platinum on carbon (Pt/C), or tris(triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis,* Paul Rylander, Academic Press Inc., San Diego, 31–63 (1979). The following conditions are preferred: Pd on carbon, methanol at 25° C. and 50 psi of hydrogen gas pressure. This method also provides for introduction of hydrogen isotopes (i.e., deuterium, tritium) by replacing $^1H_2$ with $^2H_2$ or $^3H_2$ in the above procedure.

The compound of the formula XXII is prepared from a compound of formula XIV by reaction with a base or acid and a alkyl nitrite. Suitable nitrites include n-butyl nitrite, t-butyl, or iso-amyl, preferably n-butyl nitrite. Suitable bases include sodium ethoxide, sodium methoxide or potassium t-butoxide, preferably sodium ethoxide. Suitable solvents for the aforesaid reaction include alcohols (such as methanol, ethanol, propanol or butanol) or DMSO, preferably ethanol. The aforesaid reaction is conducted at a temperature of about-10° C. to about 5° C. preferably 0° C., for a period from about 1 hour to about 48 hours, preferably about 24 hours.

The compound of the formula XIV is prepared from a compound of the formula XXIII by reaction with a Grignard reagent of the formula ($R^3$)$_s$-phenyl-CH$_2$—M, wherein M is magnesium chloride or magnesium bromide. Suitable solvents for the aforesaid reaction are ethers (such as dimethyl ether THF, DME or dioxane), preferably THF. The aforesaid reaction is conducted at a temperature from about 0° C. to about 30° C., preferably at about 22° C. (room temperature), for a period from about 1 hour to about 48 hours, preferably about 6 hours.

Compounds of the formula XXIII can be made according to the methods of Scheme 7.

Scheme 5 refers to the preparation of compounds of the formula 1, wherein ($R^3$)s phenyl-Het is a group of the formula (e). Referring to Scheme 5, a compound of the formula I can be prepared from compound of formula XXIV by reaction with a hydroxylamine (preferably a salt thereof such as the hydrochloride salt), and a base. Suitable bases include pyridine or a trialkylamine, preferably pyridine. Suitable solvents include N,N-dimethylformamide, tetrahydrofuran or pyridine, preferably pyridine. The aforesaid reaction is conducted at a temperature from about 0° C. to about 100° C., preferably about 60° C., for a period from about 1 hour to about 48 hours, preferably about 20 hours.

The compound of formula XXIV can be prepared from a compound of formula XXV by reaction with an ester of the formula ($R^3$)$_s$-phenyl-CO$_2$P$^1$, wherein P$^1$ is methyl or ethyl, in the presence of a base and a solvent. Suitable bases include sodium hydride, lithium diisopropylamide, or sodium alkoxides, preferably sodium ethoxide. Suitable solvents include alcohols such as methanol, ethanol, propanol, butanol, or tetrahydrofuran, preferably ethanol. The aforesaid reaction is conducted at a temperature from about 23° C. to about 65° C., preferably at about 50° C., for a period from about 2 hours to about 24 hours, preferably about 20 hours.

The compound of formula XXV can be made by methods well known to those of ordinary skill in the art and in Scheme 6.

Scheme 6 refers to the preparation of compounds of the formula VI which are intermediates for the preparation of compounds of formula I in Scheme 1. Referring to Scheme 6, a compound of the formula VI is prepared from a compound of formula XXVI by reaction with a Grignard reagent of the formula ($R^3$)$_s$-phenyl-M, wherein M is an activating group such as magnesium bromide or magnesium chloride in a solvent. Suitable solvents include tetrahydrofuran, dioxane, dimethylethyl ether or diethyl ether, preferably tetrahydrofuran. The aforesaid reaction is conducted at a temperature of about −78° C. to 0° C. for a period from about 10 minutes to about 24 hours preferably about 2 hours (See Pirrung, M.; Shuey, S. W.; *J. Org. Chem.* 1994, 59, 3890–3897).

The compound of formula XXVI is prepared from a compound of formula XXVII by reaction with a hydroxylamine of the formula

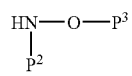

XXVIII wherein P$^2$ and P$^3$ are independently (C$_1$–C$_6$)alkyl, preferably methyl, and an activating agent. Suitable activating agents include carbonyldiimidazole or oxalyl chloride, preferably carbonyldiimidazole. Suitable solvents include methylene chloride or dichloroethane.

The compound of formula XXVII is prepared from a compound of formula XXIX by acid or base hydrolysis, such as by reaction with sulfuric acid/water (preferably 1:1) at a temperature of about 100° C. to about 120° C., preferably about 110° C. for a period from about 1 hour to about 6 hours, preferably about 4 hours.

The compound of formula XXIX is prepared from a compound of formula XXX by reaction with a nitrile in a solvent. Suitable nitriles includes potassium cyamide or sodium cyamide, preferably potassium cyamide. Suitable solvents include dimethyl sulfoxide, N,N-dimethylformamide, preferably dimethyl sulfoxide. The aforesaid reaction is conducted at a temperature from about 80° C. to about 100° C., preferably about 90° C., for a period from about 1 hour to about 3 hours, preferably about 2 hours.

The compound of formula XXX is prepared from a compound of formula XXXI by reaction with a halogenating reagent such as oxalyl chloride, thionyl chloride, phosphorous pentachloride and phosphourous oxychloride, bromine in acetic acid, at a temperature from about about 10° C. to about 65° C., preferably at about 50° C., for a period from about 1 hour to about 4 hours, preferably about 2 hours.

The compound of formula XXXI can be prepared from a compound of formula XXXII by reduction. Suitable reducing agents include lithium borohydride, sodium borohydride (NaBH$_4$), sodium cyanoborohydride (NaCNBH$_3$), lithium aluminum hydride (LiAlH$_4$) and borane in THF (BH$_3$·THF). Suitable solvents include methanol, ethanol, THF, diethyl ether, dioxane and tetrahydrofuran. The aforesaid reaction is conducted at a temperature from about 0° C. to about 70° C., preferably 65° C., for a period from about 10 minutes to about 1 hour, preferably about 30 minutes.

The compound of formula XXXII, wherein $P^4$ is $(C_1-C_6)$ alkyl, can be prepared from a compound of formula XXXIII, wherein $P^4$ is $(C_1-C_6)$alkyl, by reaction with an alkylating reagent of the formula $R^2L$, wherein L is a leaving group such as iodo and bromo, in the presence of a base. Suitable bases include sodium hydride and cesium carbonate. Suitable solvents include dimethyl sulfoxide, NN-dimethylformamide. The aforesaid reaction is conducted at a temperature from about 0° C. to about 30° C., preferably about 22° C., for a period from about 10 minutes to about 2 hours, preferably about 1 hour.

The compound of formula XXXIII, wherein $P^4$ is $(C_1-C_6)$ alkyl, is prepared from a compound of formula XXXIV, wherein $P^4$ is $(C_1-C_6)$alkyl, by reaction with a phosgene equivalent. Suitable phosgene equivalents include phosgene, triphosgene and carbonyldiimidazole. Suitable solvents include dichloromethane, THF, benzene and dichloroethane. The aforesaid reaction is run at a temperature from about 10° C. to about 30° C., preferably at about 22° C. (room temperature) for a period from about 10 minutes to about 2 hours, preferably about 30 minutes.

The compound of formula XXXIV can be prepared from a compound of formula XXXV by reaction with a reducing agent using standard techniques that are well known to those skilled in the art. For example, reduction may be effected with hydrogen gas ($H_2$), using catalysts such as palladium on carbon (Pd/C), palladium on barium sulfate (Pd/BaSO$_4$), platinum on carbon (PVC), or tris(triphenylphosphine) rhodium chloride (Wilkinson's catalyst), as described in *Catalytic Hydrogenation in Organic Synthesis*, Paul Rylander, Academic Press Inc., San Diego, 31–63 (1979). The following conditions are preferred: 10% palladium on carbon, ethanol at 22° C. and 50 psi of hydrogen gas pressure. Suitable solvents include alcohols such as methanol, ethanol in an appropriate solvent such as methanol, ethanol, THF, dioxane or ethyl acetate, at a pressure from about 1 to about 5 atmospheres. The aforesaid reaction is run at a temperature from about 10° C. to about 60° C., preferably about 22° C., for a period from about 1 hour to about 3 hours, preferably about 2 hours.

The compound of formula XXXV is prepared from a compound of formula XXXVI by reaction with an amine of the formula $R^1NH_2$ in the presence of a base. Suitable bases include the amine of the formula $R^1NH_2$, triethylamine and dimethylaminopyridine, preferably the base is the amine of the formula $R^1NH_2$. Suitable solvents include dichloromethane, chloroform, DCE and THF, preferably methylene chloride. The aforesaid reaction is run at a temperature from about 0° C. to about 30° C., preferably 22° C. (room temperature) for a period from about 6 hours to about 48 hours, preferably about 12 hours.

The compound of formula XXXVI, wherein $P^4$ is $(C_1-C_6)$ alkyl, is prepared from a compound of formula XXXVII by reaction with an activating reagent, an alcohol and a base. Suitable activating agents include oxalyl chloride with catalytic NN-dimethylformamide, thionyl chloride, and carbodiimide. Suitable alcohols include methanol, ethanol or propanol. Suitable bases include triethylamine or diisopropylethylamine. The aforesaid reaction is conducted at a temperature of about −10° C. to about 5° C., preferably at about 0° C., for a period from about 1 hour to about 3 hours, preferably 2 hours.

The compound of the formula XXXVII can be prepared by methods well known to those skilled in the art.

Scheme 7 refers to the preparation of compounds of the formula XXIII, which are intermediates useful in the preparation of compounds of formula I in Scheme 4. Referring to Scheme 7, a compound of the formula XXIII is prepared from a compound of the formula XXXVIII by reaction with an acylating reagent in a polar solvent. Suitable acylating reagents include phosgene, triphosgene, CDI and ethyl chloroformate, preferably triphosgene. Suitable solvents include methylene chloride, THF, acetic acid and chloroform, preferably methylene chloride. The aforesaid reaction is run at a temperature from about 0° C. to about 30° C., preferably 22° C. (room temperature) for a period from about 6 hours to about 24 hours, preferably about 12 hours.

The compound of formula XXXVIII can be prepared from compounds of the formula XXXIX by hydrogenation conditions such as described in Scheme 6 for the conversion of compounds of formula XXXV to compounds of the formula XXXIV.

Compounds of the formula XXXIX can be prepared from compounds of the formula XL according to conditions such as described in Scheme 6 for the conversion of compounds of formula XXXVI to compounds of the formula XXXV.

Compounds of the formula XL can be prepared from compounds of the formula XLI by reaction with a suitable activating agent and a compound of the formula,

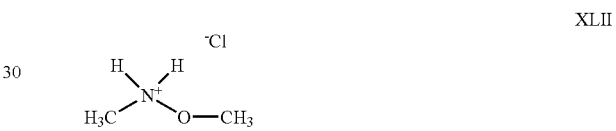

XLII and a base. Suitable activating agents include thionyl chloride, EDCI and DCC, preferably oxalyl chloride. Suitable bases include triethylamine, Hunig's base, or DBU, preferably triethylamine. Suitable solvents for the aforesaid reaction include methylene chloride, dimethyl formamide, THF or DMF, and mixture thereof, preferably methylene chloride. The aforesaid reaction is conducted at a temperature from about 0° C. to about 30° C. preferably about 22° C. (room temperature) for a period from about 6 hours to about 48 hours preferably about 12 hours.

Compounds of the formula XLI and XLII are commercially available or can be made by methods well known to those skilled in the art.

Scheme 8 refers to the preparation of compounds of formula I from other compounds of formula I, wherein $R^1$ is t-butyl. Referring to Scheme 8, a compound of the formula I is prepared from a compound of the formula XLIII by reaction with a deprotection reagent. Suitable deprotection reagents include aqueous acids such as hydrochloric and sulfuric acids, preferably hydrochloric acid. Suitable solvents for the aforesaid reaction include methylene chloride, dimethyl formamide, THF or dioxane, and mixture thereof with water, preferably THF/water. The aforesaid reaction is conducted at a temperature from about 0° C. to about 30° C. preferably about 22° C. (room temperature) for a period from about 6 hours to about 48 hours preferably about 12 hours.

A compound of formula XLIII is prepared from a compound of formula XLIV by reaction with a borate ester of the formula $R^1$—$B(OH)_2$, wherein $R^1$ is aryl or heteroaryl, and a catalyst in the presence of a base. Suitable bases include triethylamine, Hunig's base, and pyridine, preferably triethylamine. Suitable catalysts include copper acetate. Suitable solvents for the aforesaid reaction include methylene chloride, chloroform and dichloromethane, preferably methylene chloride. The aforesaid reaction is conducted at a temperature from about −70° C. to about 30° C. preferably about 22° C. (room temperature) for a period from about 6 hours to about 48 hours preferably about 12 hours.

The compound of formula XLIV is prepared from a compound of formula XLV by reaction with an acid. Suitable acids include methane sulfonic acid, trifluoromethanesulfonic acid and sulfuric acid, preferably methanesulfonic acid. Suitable solvents for the aforesaid reaction include acetic acid and triflouoacetic acid, preferably trifluoroacetic acid. The aforesaid reaction is conducted at a temperature from about 0° C. to about 30° C. preferably about 22° C. (room temperature) for a period from about 12 hours to about 48 hours preferably about 24 hours.

The compound of formula XLV is prepared from a compound of formula XLVI by reaction with a protecting group and a base. Suitable protecting groups include tosyl chloride, benzenesulfonyl chloride, methoxybenzene sulfonyl chloride, preferably tosyl chloride. Suitable bases include sodium hydride, triethylamine, Hunig's base and DBU, preferably sodium hydride. Suitable solvents for the aforesaid reaction include dimethyl formamide and dimethylsulfoxide, preferably dimethylsulfoxide. The aforesaid reaction is conducted at a temperature from about 0° C. to about 30° C. preferably about 22° C. (room temperature) for a period from about 6 hours to about 24 hours preferably about 12 hours.

The compounds of formula XLVI are compounds of formula I wherein $R^2$ is t-butyl and can be prepared according to Scheme 1.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate (i.e., 1,1′-methylene-bis-(2-hydroxy-3-naphthoate)] salts.

Those compounds of the formula I which are also acidic in nature, e.g., where $R^3$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The activity of the compounds of the invention for the various disorders described above can be determined according to one or more of the following assays. All of the compounds of the invention, that were tested, had an $IC_{50}$ of less than 10 μM in the TNFα and MAPKAP in vitro assays and an $ED_{50}$ of less than 50 mg/kg in the in vivo TNFα assay.

The compounds of the present invention also possess differential activity (i.e. are selective for) for one or more p38 kinases (i.e. α, β, γ, and δ). Certain compounds are selective for p38α over p38β, γ, and δ, other compounds are selective for p38β over p38α, γ, and δ, other compounds are selective for p38 α and β over p38 γ and δ. Selectivity is measured in standard assays as a $IC_{50}$ ratio of inhibition in each assay.

Inhibition of TNF-Alpha Production by Human LPS-Treated Monocytes

Mononuclear cells are isolated from heparinized blood (1.5 ml of 1000 units/ml heparin for injection, Elkins-Sinn, Inc. added to each 50 ml sample) using Accuspin System-Histopaque-1077 tubes (Sigma A-7054). Thirty-five milliliters of whole blood are added to each tube and the tubes are centrifuged at 2100 rpm for 20 minutes in a Beckman GS-6KR centrifuge with the brake off at room temperature. The mononuclear cells which collect at the interface are removed, diluted with Macrophage serum free medium (Gibco-BRL) (Medium) to achieve a final volume of 50 ml, and collected by centrifugation for 10 minutes. The supernatant is discarded and the cell pellet is washed 2 times with 50 ml of Medium. A sample of the suspended cells is taken before the second wash for counting. Based on this count, the washed cells are diluted with Medium containing 1% FBS to a final concentration of $2.7 \times 10^6$ cells/ml and 75l of the cell suspension is added to each well of a 96 well plate.

Compound Preparation:

Compounds are routinely tested at final concentrations from 2 μM to 0.016 μM, but may be tested at other concentrations, depending on activity. Test agents are diluted with DMSO to a final concentration of 2 mM. From this stock solution, compounds are first diluted 1:25 (5 μl of 2 mM stock+120 μl Medium containing 400 ng/ml LPS and 1% FBS then 40 μl of this dilution is diluted with 360 μl of Medium with LPS. Serial dilutions (⅕) are performed by transferring 20 μl of this dilution to 80 μl of Medium containing both LPS and 0.4% DMSO, resulting in solutions containing 8 μM, 1.6 μM, 0.32 μM and 0.064 μM of test agent.

Assay:

The assay is initiated by adding 25 µl of the diluted compounds to the mononuclear cell suspension and incubating the cells at 37 C and 5% $CO_2$ for 4 hours.

The 96-well plates are then centrifuged for 10 minutes at 2000 rpm at 4° C. in a Beckman GS-6KR centrifuge to remove cells and cell debris. A 90 µl aliquot of each supernatant is removed and transferred to a 96 well round bottom plate, and this plate is centrifuged a second time to insure that all cell debris is removed. 80 µl of the supernatant is removed and transferred to a new round bottom plate.

Supernatants are analyzed for TNF-α content using R&D ELISA. 25 µl of each sample is added to an ELISA well containing 25 µl of assay diluent RD1F and 75 µl of assay diluent RD5. The assay is run following kit directions except 100 µl of conjugate and substrate solutions are used.

Interpretation

The amount of TNF-α immunoreactivity in the samples is calculated as follows:

% Control=$(X-B)/(TOT-B) \times 100$ where X=$OD_{450}$ nm of the test compound well
B=$OD_{450}$ of Reagent Blank wells on the ELISA
Total=$OD_{450}$ of cells that were treated with 0.1% DMSO only.

MAPKAP Kinase-2 Assay

Monocyte Preparation.

Mononuclear cells are collected from heparinized human blood as detailed above. The washed cells are seeded into 6-well cluster plates at a density of $1 \times 10^7$ cells/well (in 2 ml of Medium). The plates are incubated at 37° C. in a 5% $CO_2$ environment for 2 hours to allow adherence of the monocytes, after which time media supernatants containing non-adherent cells are removed by aspiration and 2 ml of fresh medium are added to each well. Plates are incubated overnight at 37° C. in a 5% $CO_2$ environment.

Cell Activation:

Media are removed by aspiration. The attached cells are rinsed twice with fresh Medium, then 2 ml of D-MEM medium containing 10% heat inactivated FBS are added to each well. Test compounds are prepared as 30 mM stock solutions in DMSO and diluted to 1250, 250, 50, 10, 2, and 0.4 µM in D-MEM containing 1% DMSO and 10% FBS. To individual wells of the monocyte cultures, 20 µl of these test agent dilutions are added resulting in final test agent concentrations of 12.5, 2.5, 0.5, 0.1, 0.02 and 0.004 µM. After a 10 minute preincubation period, 20 µl of a 10 µg/ml LPS solution are added to each well and the plates are incubated at 37° C. for 30 min. Media subsequently are removed by aspiration, the attached monocytes are rinsed twice with phosphate buffered saline, then 1 ml of phosphate buffered saline containing 1% Triton X-100 (Lysis Buffer; also containing 1 Complete™ tablet [Boehringer #1697498] per 10 ml of buffer) is added to each well. The plates are incubated on ice for 10 minutes, after which the lysates are harvested and transferred to centrifugation tubes. After all samples are harvested, they are clarified by centrifugation (45,000 rpm for 20 min) and the supernatants recovered.

MAPKAP Kinase-2 Immunoprecipitation:

5 µl of anti-MAPKAP kinase-2 antiserum (Upstate Biotechnology #06–534) is added to a microcentrifuge tube (1 tube for each of the above cell lysates) containing 1 ml of a 5% suspension of Protein G-Sepharose (Sigma #P3296) in PBS. These mixtures are incubated for 1 hour at 4° C. (with rocking) after which the beads, containing bound IgG, are recovered by centrifugation and washed twice with 1 ml of 50 mM Tris, pH 7.5, 1 mM EDTA, 1 mM EGTA, 0.5 mM orthovanadate, 0.1% 2-mercaptoethanol, 1% Triton X-100, 5 mM sodium pyrophosphate, 10 mM sodium P-glycerophosphate, 0.1 mM phenylmethylsulfonyl fluoride, 1 µg/ml leupeptin, 1 µg/ml pepstatin, and 50 mM sodium fluoride (Buffer A) by repeated centrifugation. An individual monocyte cell extract (prepared above) is then transferred to each tube containing a pellet of IgG-coated Protein G-Sepharose, and these mixtures are incubated for 2 hours at 4° C. (with rocking). The beads subsequently are harvested by centrifugation, and the resulting bead pellets are washed once with 0.5 ml of Buffer A containing 0.5 M NaCl, once with 0.5 ml of Buffer A, and once with 0.1 ml of a buffer composed of 20 mM MOPS, pH 7.2, 25 mM sodium β-glycerophosphate 5 mM EGTA, 1 mM orthovanadate, and 1 mM dithiothreitol (Buffer B).

MAPKAP Kinase-2 Activity Assessment.

A kinase reaction mixture stock is prepared as follows: 2.2 µl of 10 mCi/ml γ[$^{32}$P]ATP, 88 µl of 1.3 µg/ml solution of MAPKAP Kinase-2 substrate peptide (Upstate Biotechnology #12–240), 11 µl of 10 mM ATP, 8.8 µl of 1 M $MgCl_2$, and 770 µl of Buffer B. To each of the immune complex-Protein G-pellets, 40 µl of the kinase reaction mixture are added and the tubes are incubated for 30 minutes at 30° C. The tubes then are clarified by centrifugation and 25 µl of each supernatant is spotted onto a P81 filter paper disk (Whatman #3698–023). After allowing all fluid to soak into the filter, each disk is placed into an individual well of 6-well cluster plates and the filters are washed sequentially with 2 ml of 0.75% phosphoric acid (3 washes/15 min each) and once with acetone (10 min). The filters then are air dried and transferred to liquid scintillation vials containing 5 ml of scintillation fluid. Radioactivity is determined in a liquid scintillation counter. The amount of radioactivity bound to the filter at each test agent concentration is expressed as a percentage of that observed from cells stimulated with LPS in the absence of a test agent.

In vivo Inhibition of TNFα

Rats were weighed and dosed with vehicle (0.5% methyl cellulose, Sigma) or drug. One hour later, animals were injected i.p. with LPS (50 ug/rat, Sigma L-4130). Ninety minutes later, animals were sacrificed by asphyxiation with $CO_2$ and bled by cardiac puncture. Blood was collected in Vaccutainer tubes and spun for 20 minutes at 3000 rpm. Serum was assayed for TNFα levels using an ELISA (R&D Systems).

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregela tinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl β-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (inflammation) is 0.1 to 200 mg of the active ingredient per unit dose which could be administered, for example, 1 to 4 times per day.

Aerosol formulations for treatment of the conditions referred to above in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of an ERK kinase inhibitor, preferably from about 1 mg to about 200 mg of p38 kinase inhibitor. Administration may be several times daily, for example 2, 3, 4 or 8 times, giving for example, 1, 2 or 3 doses each time.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N-dimethylformamide. Chroma tography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" (2$^{nd}$ Ed, John Wiley & Sons 1991).

EXAMPLE 1

1,3-Diethyl-5-(3R-pyrrolidin-3-yl-5-M-tolyl-3H-imidazol-4-yl)-1,3-dihydro-benzoimidazol-2-one Hydrochloride Salt

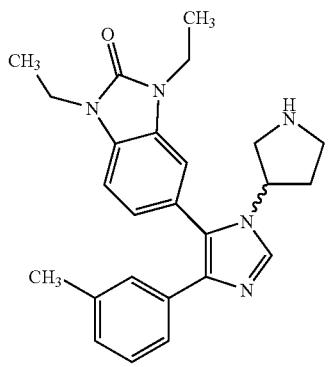

A) 5-[((3R)-1-Benzyl-pyrrolidin-3-ylimino)-methyl]-1,3-diethyl-1,3-dihydro-benzoimidazol-2-one To a dry flask charged with a stir bar was added (3R)-(−)-1-benzyl-3-aminopyrrolidine (202 mg, 1.15 mmoles) (commercial from TCI-US), 1,3-Diethyl-2-oxo-2,3-dihydro-1H-benzoimidazole-5-carbaldehyde (250 mg, 1.15 mmoles), magnesium sulfate (500 mg) and 5 ml of dichloromethane (0.23 M). The flask was sealed with a plastic cap and the resulting mixture was stirred for 20 hours at 22° C. The mixture was filtered through a nylon disk via syringes, rinsing with dichloromethane and the yellow filtrate was concentrated to give 450 mg of the title compound as a yellow gum/foam.

B) 5-[3-((3R)-1-Benzyl-pyrrolidin-3-yl)-5-m-tolyl-3H-imidazol-4-yl]-1,3-diethyl-1,3-dihydro-benzoimidazol-2-one To a flask charged with 5-[((3R)-1-Benzyl-pyrrolidin-3-ylimino)-methyl]-1,3-diethyl-1,3-dihydro-benzoimidazol-2-one was added a stir bar and 4-methylphenyl-toylsulfonomethylisocyanide (326 mg, 1.15 mmoles) (Joseph Sisko, Mark Mellinger, Peter W. Sheldrake, and Neil H. Baine, *Organic Synthesis*, Vol. 77, 198–205 (1999); Joseph Sisko, Mark Mellinger, Peter W. Sheldrake, and Neil H. Baine, *Tetrahedron Letters*, Vol. 37, No. 45, 8113–8116, (1996); U.S. Pat. No. 5,756,499; prepared in an analogous manner starting with 3-methylbenzylaldehyde). N,N-dimethylformamide (2 mL, 0.58 M) was added and within 5 minutes a light yellow solution was obtained. To this stirred solution was added MP-carbonate (498 mg, 1.37 mmoles) (Argonaut Tech); the flask was sealed with a plastic cap and the mixture was stirred for 40 hours. The mixture was filtered into a separatory funnel with ethyl acetate. The ethyl acetate layer was extracted with 3 N HCl (3 times). The aqueous extracts were made basic to approximately pH 9.5 with solid potassium carbonate. The basic mixture was extracted with ethyl acetate (3 times). These ethyl acetate extracts were washed with water (2 times), dried with sodium sulfate, filtered and the filtrate was concentrated to give a yellow oil. This oil was purified by flash chromatography (95:5 ethyl acetate/methyl alcohol) to give 240 mg of the named compound as a light yellow foam/gum.

C) 1,3-Diethyl-5-(3R-pyrrolidin-3-yl-5-m-tolyl-3H-imidazol-4-yl)-1,3-dihydro-benzoimidazol-2-one hydrochloride salt A mixture of 5-[3-((3R)-1-Benzyl-pyrrolidin-3-yl)-5-m-tolyl-3H-imidazol-4-yl]-1,3-diethyl-1,3-dihydro-benzoimidazol-2-one (235 mg, 0.47 mmoles), 10% palladium on carbon (200 mg), and concentrated hydrochloric acid (77 µL, 0.93 mmoles), in 20 mL methyl alcohol was shaken under hydrogen atmosphere (50 psi) for 5.5 hours. The mixture was filtered through nylon and the filtrate was concentrated to give 183 mg of a light yellow foam. The foam was taken up in approximately 2 ml hexanes/ethyl acetate (1:1) and stirred as a suspension for 18 hours. The white crystals where collected by filtration, washed with hexanes and dried to give 86 mg of the title compound. MS (APCI) m/z 416 (M+1).

The compounds of Examples 2–53, were prepared according to methods analogous to those of Example 1, substituting the appropriate aldehyde, amine and isocyamide where required.

TABLE 1

| Ex. | Structure | Data |
|---|---|---|
| 2 | 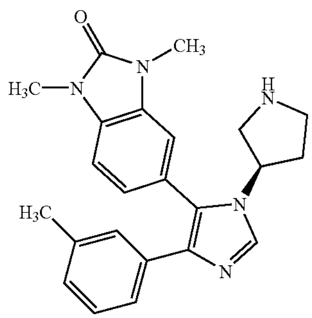 | MS (APCI) m/z 388 (M + 1). |
| 3 | 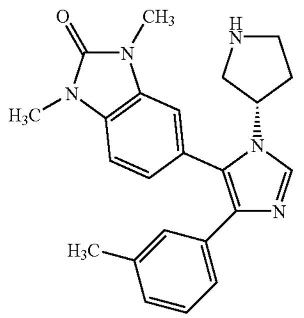 | MS (APCI) m/z 388 (M + 1). |
| 4 | 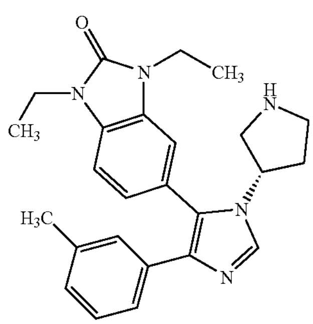 | MS (APCI) m/z 416 (M + 1). |
| 5 | 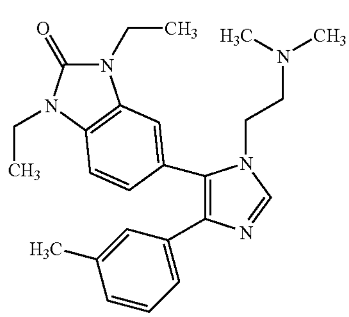 | MS (APCI) m/z 390 (M + 1). |

TABLE 1-continued

| Ex. | Structure | Data |
|---|---|---|
| 6 | 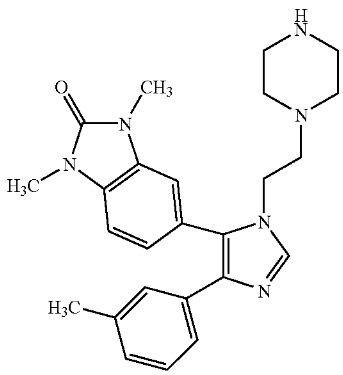 | MS (APCI) m/z 431 (M + 1) |
| 7 | 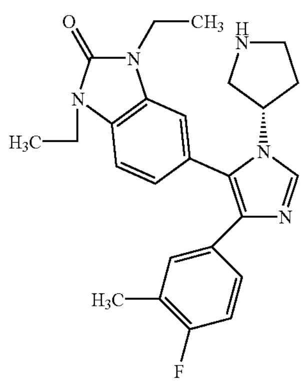 | MS (APCI) m/z 434 (M + 1). |
| 8 | 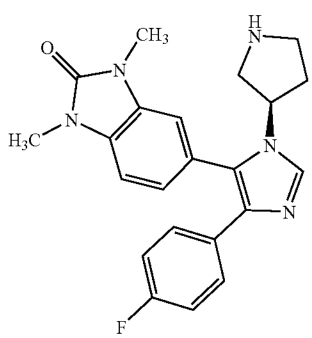 | MS (APCI) m/z 392 (M + 1) |
| 9 | 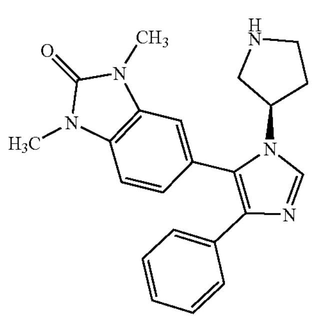 | MS (APCI) m/z 374 (M + 1) |

TABLE 1-continued

| Ex. | Structure | Data |
|---|---|---|
| 10 | 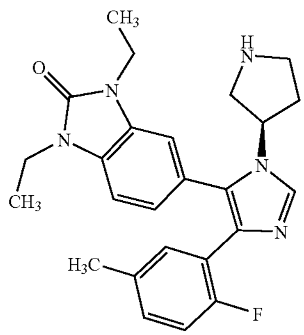 | MS (APCI) m/z 434 (M + 1) |
| 11 | 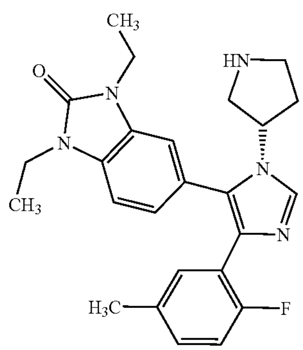 | MS (APCI) m/z 434 (M + 1) |
| 12 | 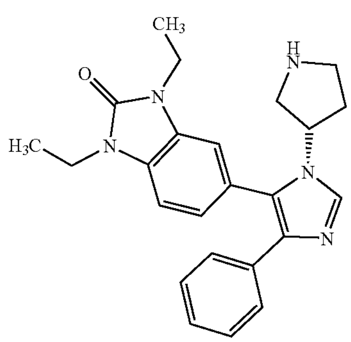 | MS (APCI) m/z 402 (M + 1) |
| 13 | 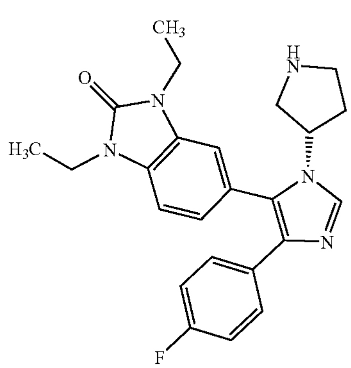 | MS (APCI) m/z 420 (M + 1) |

TABLE 1-continued

| Ex. | Structure | Data |
|---|---|---|
| 14 | 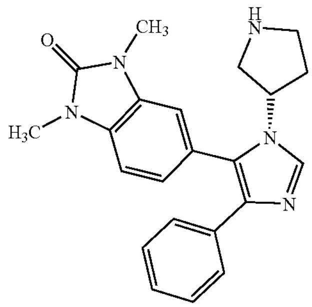 | MS (APCI) m/z 374 (M + 1) |
| 15 | 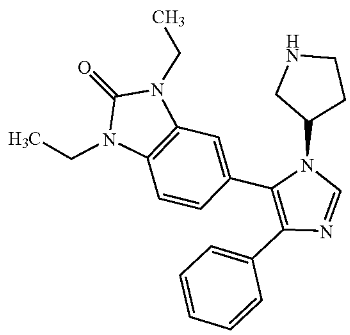 | MS (APCI) m/z 402 (M + 1) |
| 16 | 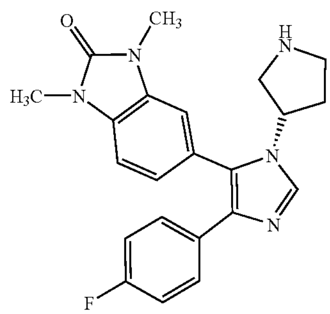 | MS (APCI) m/z 392 (M + 1) |
| 17 | 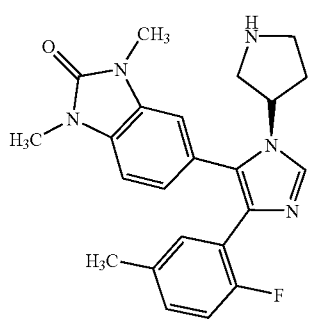 | MS (APCI) m/z 406 (M + 1) |
| 18 | 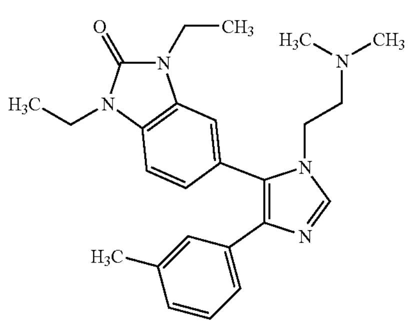 | MS (APCI) m/z 418 (M + 1) |

TABLE 1-continued
| Ex. | Structure | Data |
|---|---|---|
| 19 | 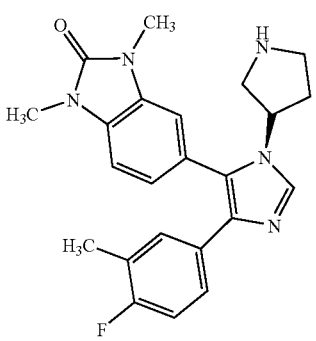 | MS (APCI) m/z 406 (M + 1) |
| 20 | 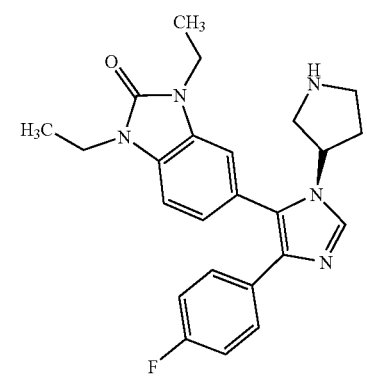 | MS (APCI) m/z 420 (M + 1) |
| 21 | 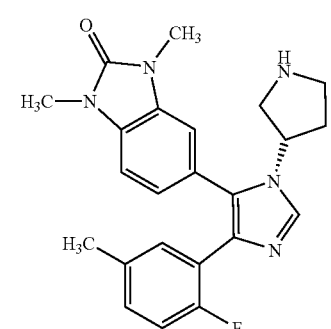 | MS (APCI) m/z 406 (M + 1) |
| 22 | 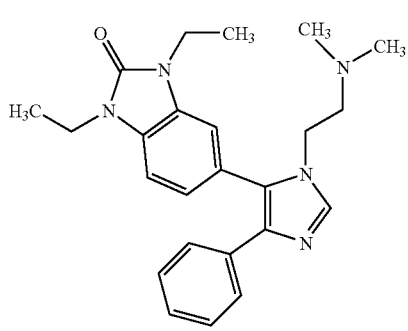 | MS (APCI) m/z 404 (M + 1) |

TABLE 1-continued

| Ex. | Structure | Data |
|---|---|---|
| 23 | 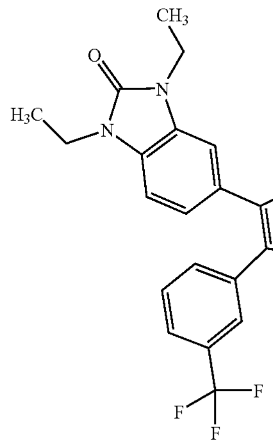 | MS (APCI) m/z 470 (M + 1) |
| 24 | 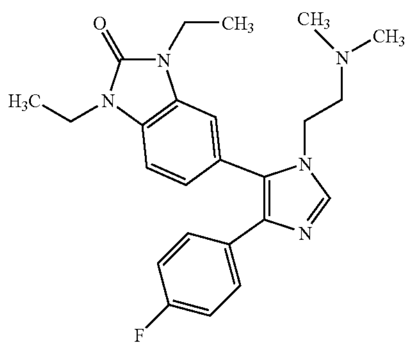 | MS (APCI) m/z 422 (M + 1) |
| 25 | 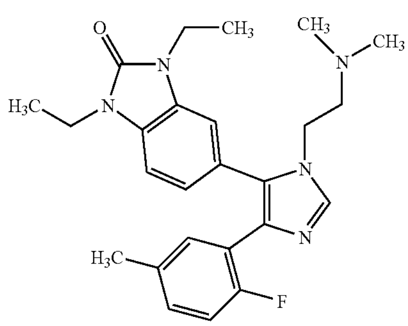 | MS (APCI) m/z 436 (M + 1) |
| 26 | 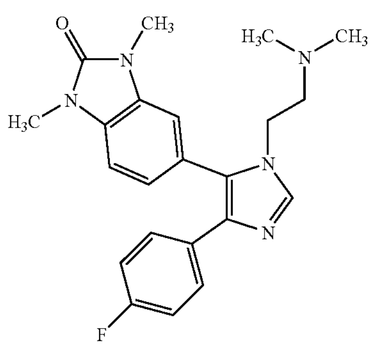 | MS (APCI) m/z 394 (M + 1) |

TABLE 1-continued

| Ex. | Structure | Data |
|---|---|---|
| 27 | 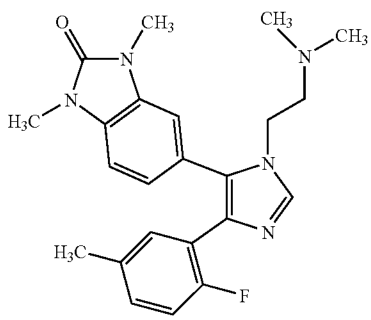 | MS (APCI) m/z 408 (M + 1) |
| 28 | 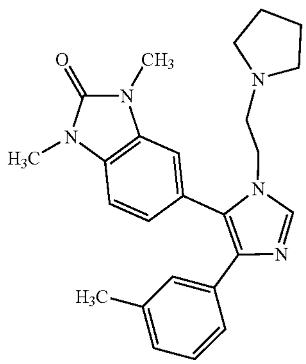 | MS (APCI) m/z 416 (M + 1) |
| 29 | 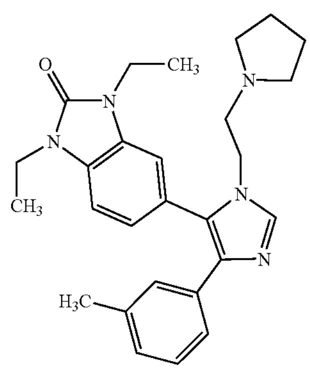 | MS (APCI) m/z 444 (M + 1) |
| 30 | 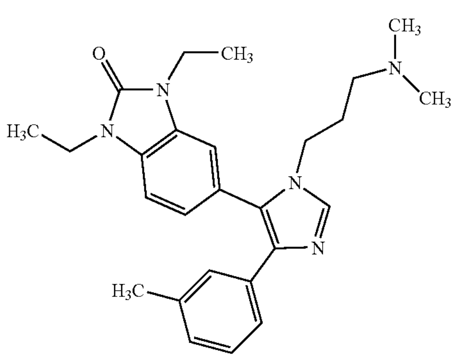 | MS (APCI) m/z 432 (M + 1) |

TABLE 1-continued

| Ex. | Structure | Data |
|---|---|---|
| 31 | 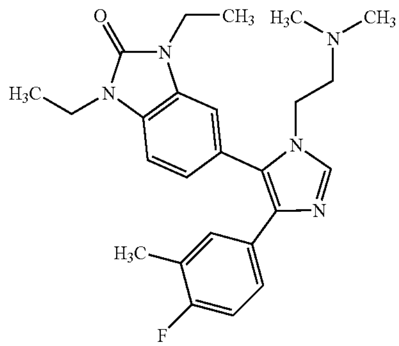 | MS (APCI) m/z 436 (M + 1) |
| 32 | 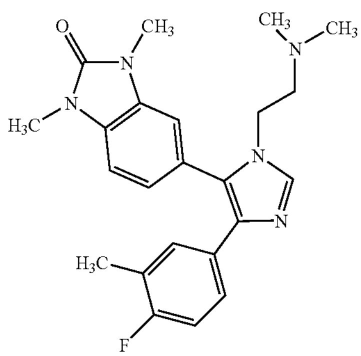 | MS (APCI) m/z 408 (M + 1) |
| 33 | 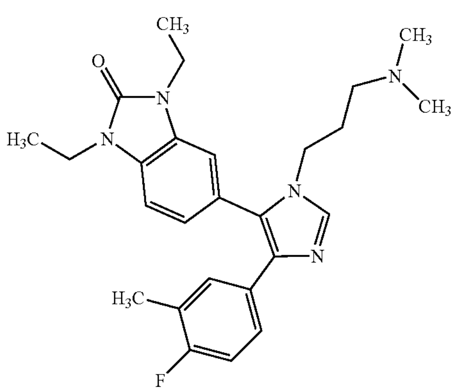 | MS (APCI) m/z 450 (M + 1) |
| 34 | 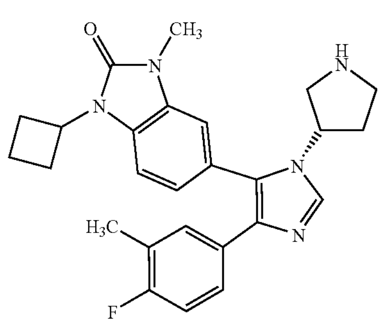 | MS (APCI) m/z 446 (M + 1) |

TABLE 1-continued
| Ex. | Structure | Data |
|---|---|---|
| 35 | 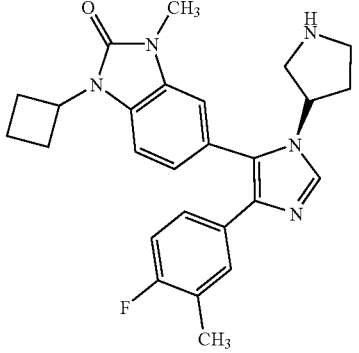 | MS (APCI) m/z 446 (M + 1) |
| 36 | 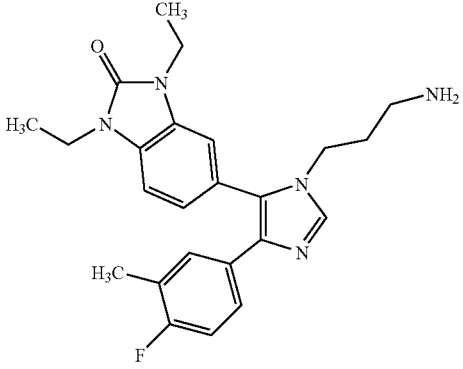 | MS (APCI) m/z 422 (M + 1) |
| 37 | 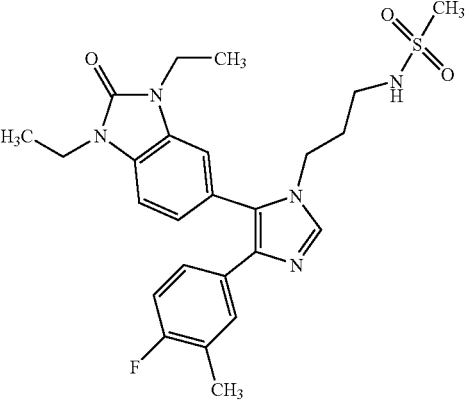 | Purified by flash chromatography (95:5 EtOA/MeOH). MS (APCI) m/z 500 (M + 1) |
| 38 | 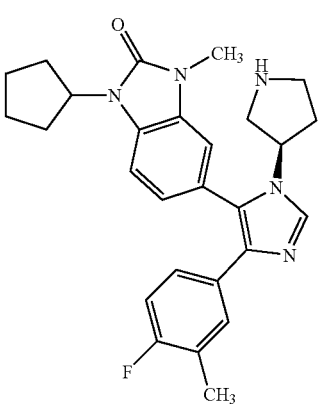 | MS (APCI) m/z 460 (M + 1) |

TABLE 1-continued

| Ex. | Structure | Data |
|---|---|---|
| 39 | 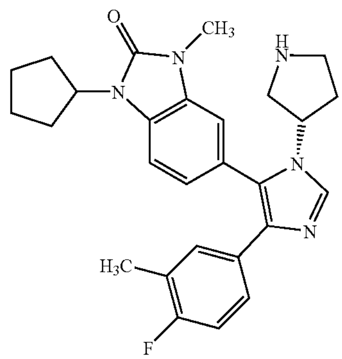 | MS (APCI) m/z 460 (M + 1) |
| 40 | 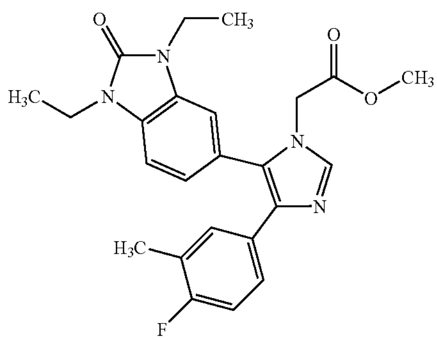 | MS (APCI) m/z 437 (M + 1) |
| 41 | 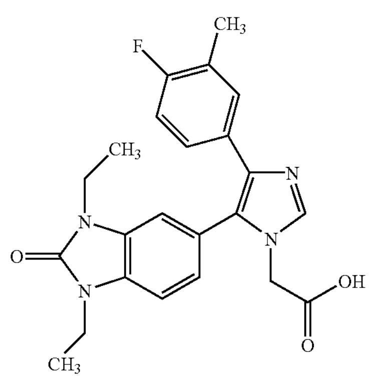 | MS 322 (m + 1) |
| 42 | 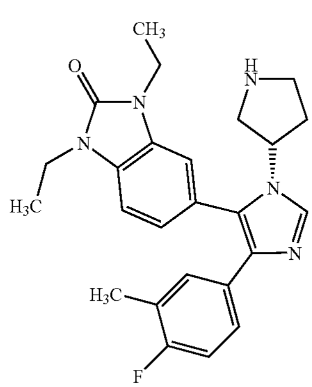 | MS (APCI) m/z 434 (M + 1) |

TABLE 1-continued

| Ex. | Structure | Data |
|---|---|---|
| 43 | 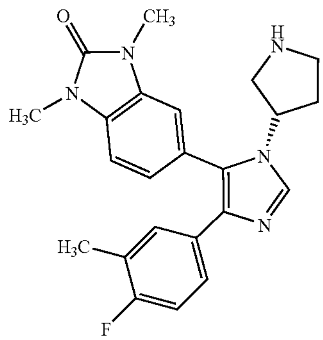 | MS (APCI) m/z 406 (M + 1) |
| 44 | 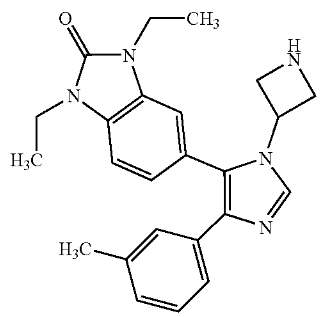 | MS (APCI) m/z 402 (M + 1) |
| 45 | 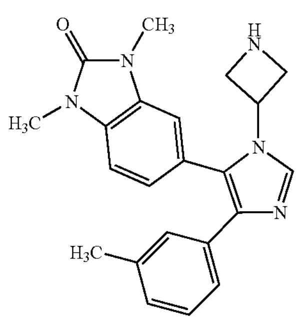 | MS (APCI) m/z 374 (M + 1) |
| 46 | 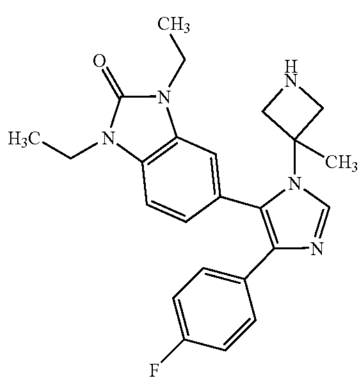 | MS (APCI) m/z 420 (M + 1) |

TABLE 1-continued

| Ex. | Structure | Data |
|---|---|---|
| 47 | 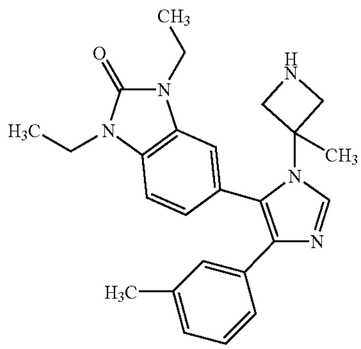 | MS (APCI) m/z 416 (M + 1) |
| 48 | 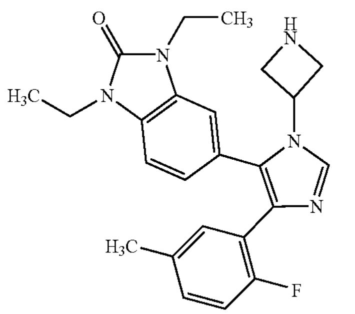 | MS (APCI) m/z 420 (M + 1) |
| 49 | 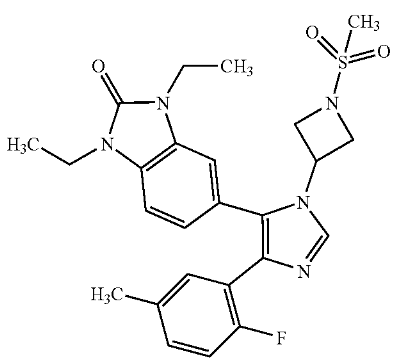 | |
| 50 | 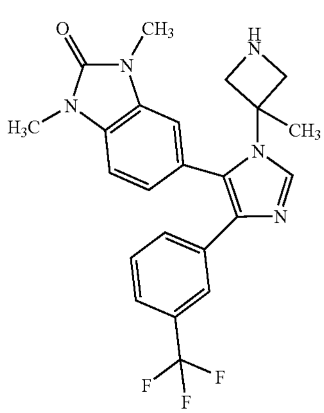 | MS (APCI) m/z 442 (M + 1) |

TABLE 1-continued
| Ex. | Structure | Data |
|---|---|---|
| 51 | 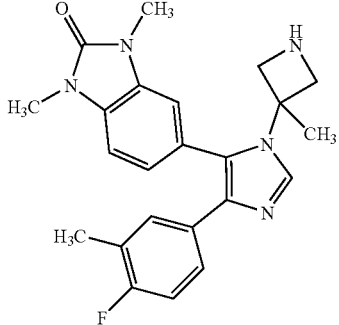 | MS (APCI) m/z 406 (M + 1) |
| 52 | 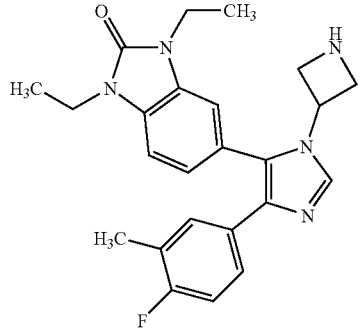 | MS (APCI) m/z 420 (M + 1) |
| 53 | 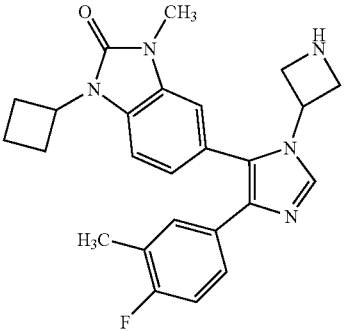 | MS (APCI) m/z 432 (M + 1) |

EXAMPLE 54

5-[3-(2-Amino-ethyl)-5-m-tolyl-3H-imidazol-4-yl]-1,3-dimethyl-1,3-dihydro-benzoimidazol-2-one

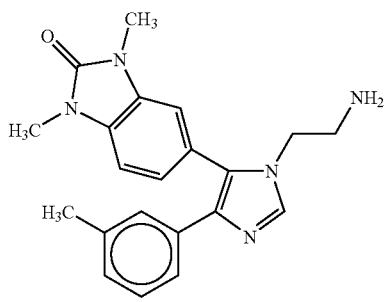

A. To a dry flask charged with a stir bar was added 2-(2-amino-ethyl)-isoindole-1,3-dione hydrochloride salt (100 mg, 0.53 mmoles) (Burgess, K.; Ibarzo, J. D.; Linthicum S.; Russell, D. H.; Shin, H.; Shitangkoon, A.; Totani, R.; and Zhang, A.; *J. Am. Chem. Soc.* 1997, 119, 1556), 1,3-Dimethyl-2-oxo-2,3-dihydro-1H-benzoimidazole-5-carbaldehyde (156 mg, 0.68 mmoles), MP-carbonate (254 mg, 0.79 mmoles) (Argonaut Tech), 3 Å sieves (1.2 g) and 4 mL of dichloromethane. The flask was sealed with a plastic cap and the resulting mixture was stirred for 48 hours at 22° C. The mixture was filtered through a nylon disk via syringes, rinsing with dichloromethane and the filtrate was concentrated to give 154 mg of 2-{2-[(1,3-Dimethyl-2-oxo-2,3-dihydro-1H-benzoimidazol-5-ylmethylene)-amino]-ethyl}-isoindole-1,3-dione as a light yellow solid.

B. To a flask charged with 2-{2-[(1,3-Dimethyl-2-oxo-2,3-dihydro-1H-benzoimidazol-5-ylmethylene)-amino]-ethyl}-isoindole-1,3-dione was added a stir bar and 4-methylphenyl-toylsulfonomethylisocyanide (120 mg, 0.42 mmoles) (Joseph Sisko, Mark Mellinger, Peter W. Sheldrake, and Neil H. Baine, *Organic Synthesis*, Vol. 77, 198–205 (1999); Joseph Sisko, Mark Mellinger, Peter W. Sheldrake, and Neil H. Baine, *Tetrahedron Letters*, Vol. 37, No. 45, 8113–8116, (1996); US5756499; prepared in an analogous manner starting with 3-methylbenzylaldehyde). dichloromethane (4 mL) was added and within 5 minutes a light yellow solution was obtained. To this stirred solution was added MP-carbonate (250 mg, 0.78 mmoles) (Argonaut Tech); the flask was sealed with a plastic cap and the mixture was stirred for 5 days. The mixture was filtered, washing with dichloromethane and ethyl acetate. The filtrate was concentrated to give a yellow oil. this oil was purified by flash chromatography (5% methanol in ethyl acetate) to give 105 mg of 2-{2-[5-(1,3-Dimethyl-2-oxo-2,3-dihydro-1H-benzoimidazol-5-yl)-4-m-tolyl-imidazol-1-yl]-ethyl}-isoindole-1,3-dione as a light yellow film/solid.

C. To a stirred, hot solution of 2-{2-[5-(1,3-Dimethyl-2-oxo-2,3-dihydro-1H-benzoimidazol-5-yl)-4-m-tolyl-imidazol-1-yl]-ethyl}-isoindole-1,3-dione (90 mg, 0.18 mmoles) in 5 mL ethanol was added aqueous 35 wt % hydrazine (50 pL). The resulting mixture was heated at reflux for 4 hours. The mixture (white precipitate visible) was cooled to 23° C. and concentrated in vacuo. The residue was taken up in 3 N HCl and methanol and extracted with ethyl acetate. The ethyl acetate extract was washed with 3 N HCl. The combined acidic aqueous layers were extracted with ethyl acetate (2 times). The acidic aqueous layer was made basic (pH 10–11) with $Na_2CO_3$ and extracted with ethyl acetate (3 times). These ethyl acetate extracts were combined and dried ($Na_2SO_4$), filtered, and the filtrate was concentrated to give 48 mg of 5-[3-(2-Amino-ethyl)-5-m-tolyl-3H-imidazol-4-yl]-1,3-dimethyl-1,3-dihydro-benzoimidazol-2-one as an off white film/solid. MS (APCI) m/z 362 (M+1).

The compounds of Examples 55–58, were prepared according to the method of claim 54, substituting the appropriate aldehyde, amine and isocyanate where appropriate.

TABLE 2

| Example | Structure | Data |
|---|---|---|
| 55 | 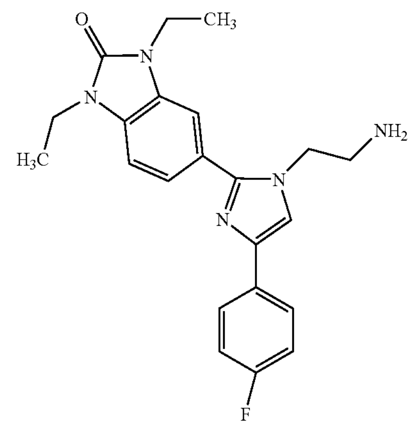 | |
| 56 | 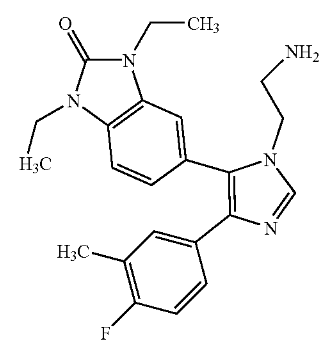 | |
| 57 | 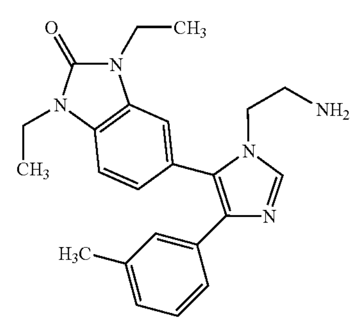 | MS (APCI) m/z 390 (M + 1) |

TABLE 2-continued

| Example | Structure | Data |
|---|---|---|
| 58 | 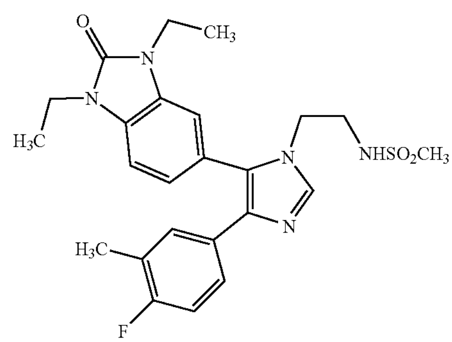 | MS (APCI) m/z 486 (M + 1) |

EXAMPLE 59

5-[5-(4-Fluoro-phenyl)-3-(1-methyl-pyrrolidin-3-yl)-3H-imidazol-4-yl]-1,3-dimethyl-1,3-dihydro-benzoimidazol-2-one

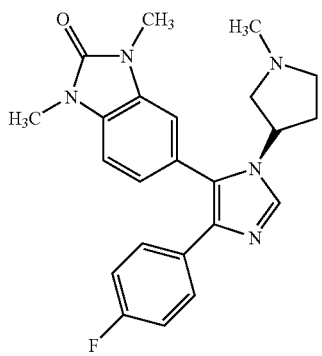

To a stirred solution of the title compound of Example 8 (57 mg, 0.133 mmoles) and formaldehyde 37% in water (0.0176 mL, 0.217 mmoles) in dichloromethane was added sodium cyanoborohydride (27.5 mg, 0.437 mmoles) and acetic acid to a pH of 5.0. After 1 hour the reaction mixture was diluted with dichloromethane and washed once with 1 N NaOH, once with water, and once with brine. The organic layer was dried with magnesium sulfate, filtered, and the filtrate was concentrated to give 37 mg of crude product. This residue was purified by flash chromatography (2% methanol in dichloromethane) to give 6 mg of the title compound.

The compounds of Examples 59 and 60 were prepared according to the method of Example 58 substituting the appropriate amine.

TABLE 3

| Example | Structure | Data |
|---|---|---|
| 60 | 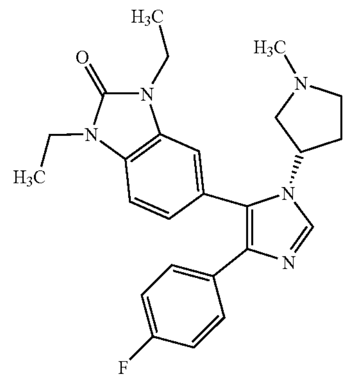 | |
| 61 | 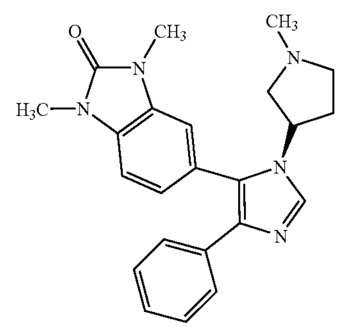 | |

EXAMPLE 62

3-Methyl-1-phenyl-5-(3-pyrazin-2-yl-5-m-tolyl-1H-imidazol-4-yl)-1,3-dihydro-benzoimidazol-2-one To a stirred solution of 3-Methyl-1-phenyl-5-(5-m-tolyl-1H-imidazol-4-yl)-1,3-dihydro-benzoimidazol-2-one (prepared as described previously in Example 200, 33 mg, 0.087 mmol) in DMF (0.1 mL) was added NaH (4 mg, 0.095 mmol). After stirring for 20 min, 2-chloropyrazine (9.3 mL, 0.10 μmol) was added and the reaction mixture was heated to 120° C. for 14 hours. The reaction mixture was cooled to room temperature and concentrated in vacuo. The residue was purified by LC (Waters Symmetry C8, formic acid/acetonitrile/water) to afford 2 mg of the title compound.

EXAMPLE 63

1-Isopropyl-3-methyl-5-(2-pyrimidin-5-yl-5-m-tolyl-1H-imidazol-4-yl)-1,3-dihydro-benzoimidazol-2-one

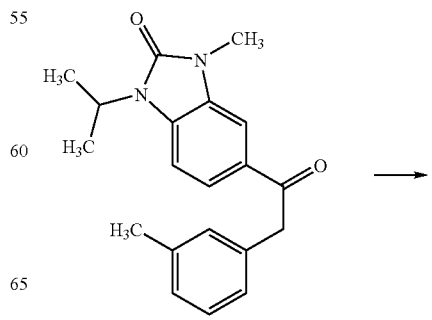

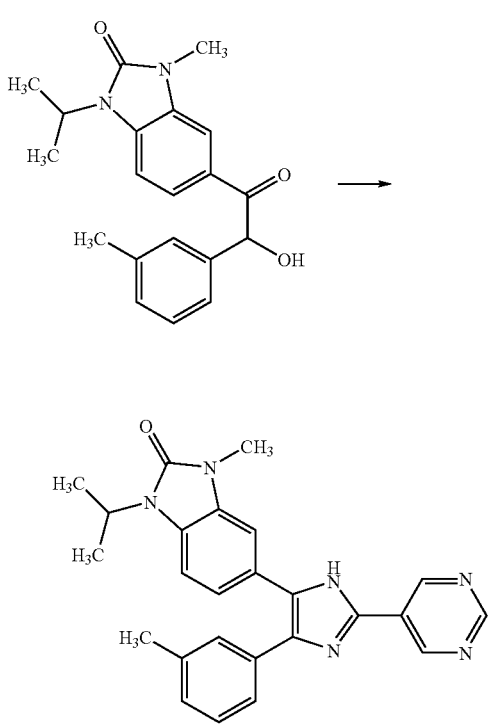

To a stirred solution of 1-isopropyl-3-methyl-5-m-tolylacetyl-1,3-dihydro-benzoimidazol-2-one (prepared as described in the preparations 1–8, 10.0 gm, 31 mmol) in acetic acid (60 mL) was added bromine (1.63 mL, 31.6 mmol) in one portion. The reaction was allowed to stir overnight (c.a. 14 hours) after which time it was found to be complete by 1H NMR. The reaction was concentrated in vacuo and the residue was taken up in ethyl acetate (150 mL) and washed twice with saturated sodium bicarbonate solution. The organic phase was dried with anhydrous sodium sulfate and concentrated in vacuo to afford 12.1 gm of a tan solid which was used without purification.

To a stirred solution of 5-(bromo-m-tolyl-acetyl)-1-isopropyl-3-methyl-1,3-dihydro-benzoimidazol-2-one (2.0 gm, 4.98 mmol) in methanol (10 mL) was added sodium methoxide (2.4 mL of a 25% solution in methanol, 9.97 mmol). After 10 minutes, the reaction was determined to be complete by LCMS. Methylene chloride (30 mL) and 6N HCl were added to the reaction mixture. After stirring for 30 min, the layers were separated and the aqueous layer was extracted with three more portions of methylene chloride. The combined methylene chloride extracts were dried over anhydrous sodium sulfate and concentrated in vacuo to afford 1.2 gm of a tan solid which was used in the next step without further purification.

To a stirred solution of 5-(hydroxy-m-tolyl-acetyl)-1-isopropyl-3-methyl-1,3-dihydro-benzoimidazol-2-one (prepared above, 300 mg, 0.88 mmol) in acetic acid was added copper acetate (320 mg, 1.8 mmol), ammonium acetate (680 mg, 8.9 mmol), and pyrimidine-5-carboxaldehyde (*Synthetic Communications*, 1994, 253–256, 150 mg, 1.33 mmol). The reaction mixture was heated to reflux. After three hours, the starting material was completely consumed. The reaction mixture was cooled to room temperature and ammonium hydroxide was added cautiously to the stirred solution until pH=8–9. After stirring for 10 minutes, the blue solution was extracted with methylene chloride (3×30 mL). The combined organic extracts were washed with brine and dried over anhydrous sodium sulfate. Removal of the solvent in vacuo afforded 280 mg of crude material which was purified by flash chromatography (ethyl acetate) to afford 60 mg of the title compound. MS (M+1)=425.2.

The following compounds were prepared using the procedure described in Example 63 above.

| EXAMPLE | Structure | Data MS (M + 1) |
|---|---|---|
| 64 | 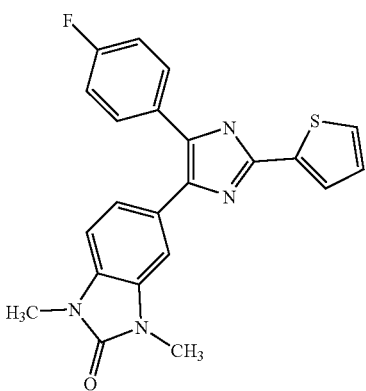 | 405.2 |

-continued

| EXAMPLE | Structure | Data MS (M + 1) |
| --- | --- | --- |
| 65 | 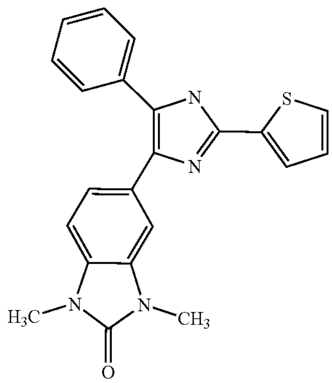 | 387.2 |
| 66 | 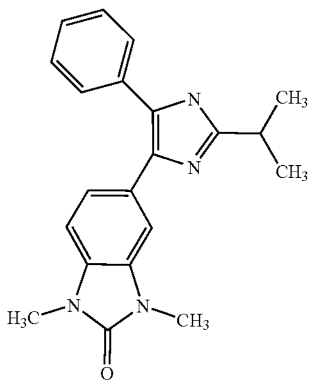 | 347.3 |
| 67 | 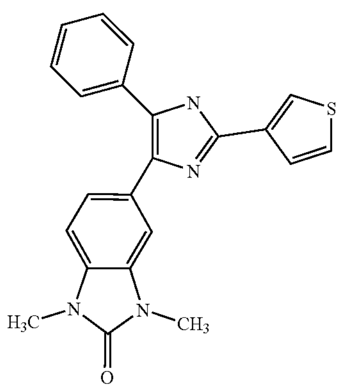 | 387.2 |
| 68 | 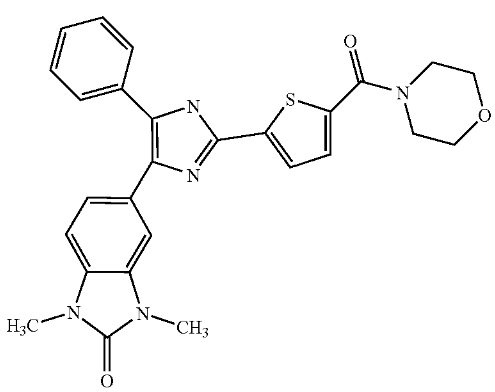 | 500.2 |

-continued
| EXAMPLE | Structure | Data MS (M + 1) |
|---------|-----------|-----------------|
| 69 | 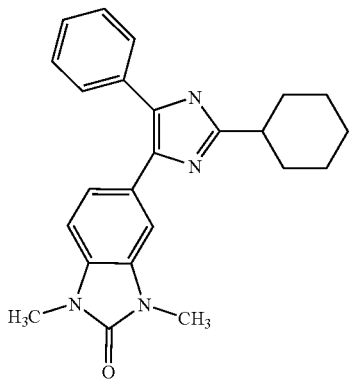 | 387.3 |
| 70 | 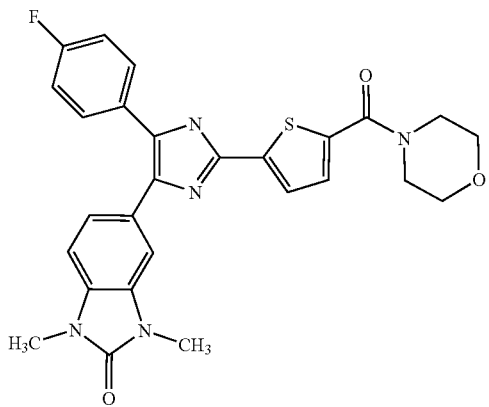 | 518.2 |
| 71 | 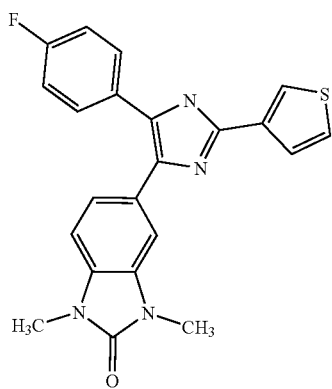 | 405.2 |

-continued
| EXAMPLE | Structure | Data MS (M + 1) |
|---|---|---|
| 72 | 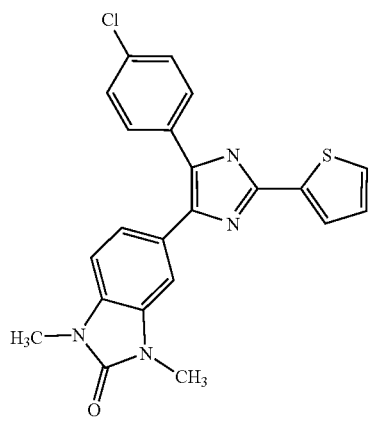 | 421.1 |
| 73 | 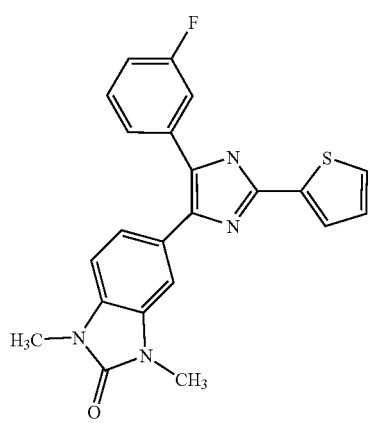 | 405.2 |
| 74 | 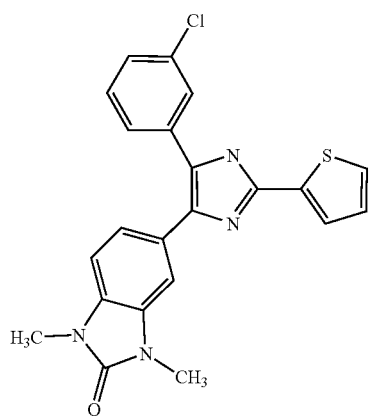 | 421.2 |

-continued

| EXAMPLE | Structure | Data MS (M + 1) |
| --- | --- | --- |
| 75 | 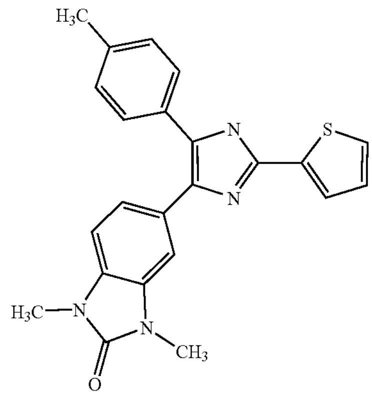 | 401.2 |
| 76 | 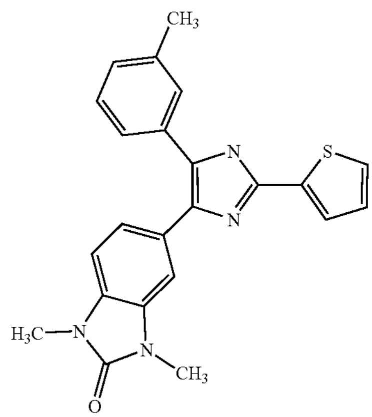 | 401.2 |
| 77 | 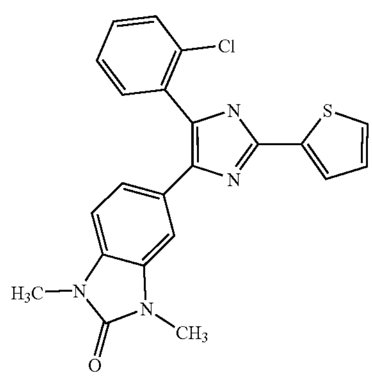 | 421.1 |
| 78 | 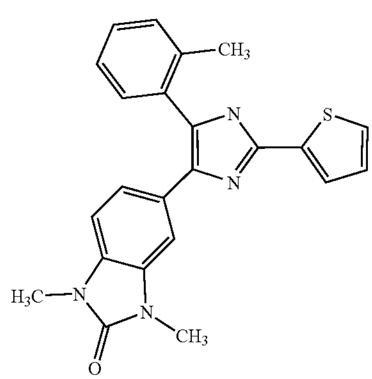 | 401.2 |

-continued

| EXAMPLE | Structure | Data MS (M + 1) |
|---|---|---|
| 79 | 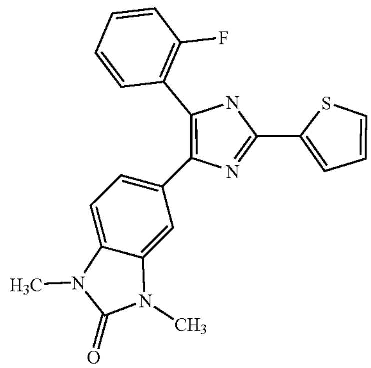 | 405.2 |
| 80 | 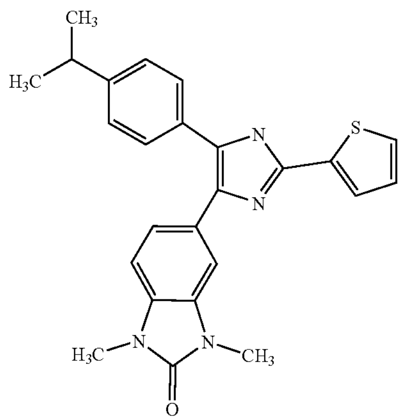 | 429.0 |
| 81 | 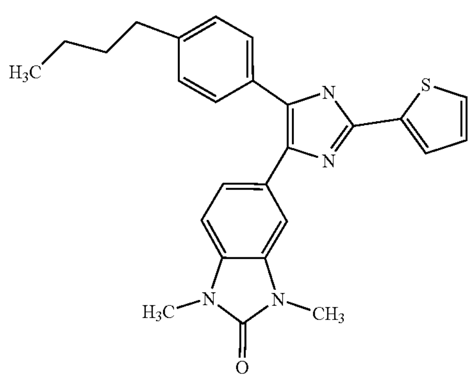 | 443.2 |
| 82 | 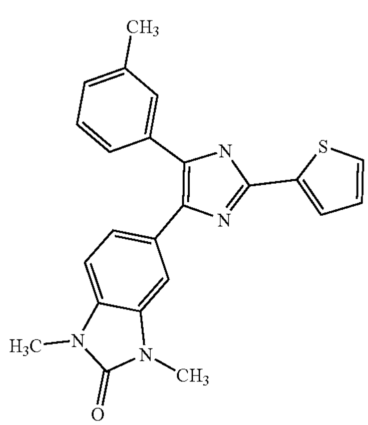 | 401.2 |

-continued
| EXAMPLE | Structure | Data MS (M + 1) |
|---|---|---|
| 83 | 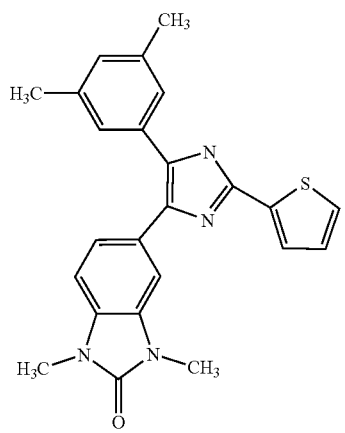 | 415.2 |
| 84 | 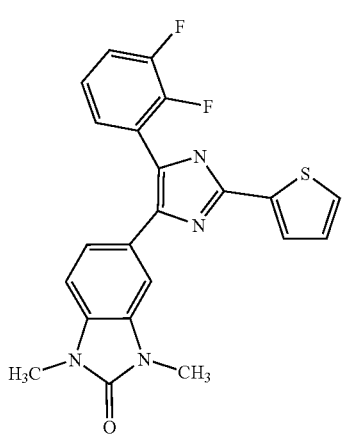 | 423.2 |
| 85 | 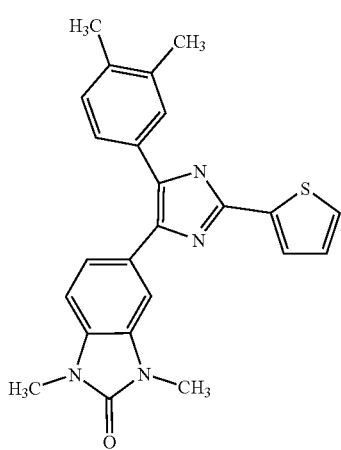 | 415.3 |

-continued
| EXAMPLE | Structure | Data MS (M + 1) |
|---|---|---|
| 86 | 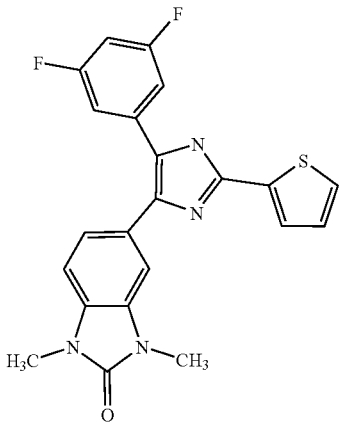 | 423.1 |
| 87 | 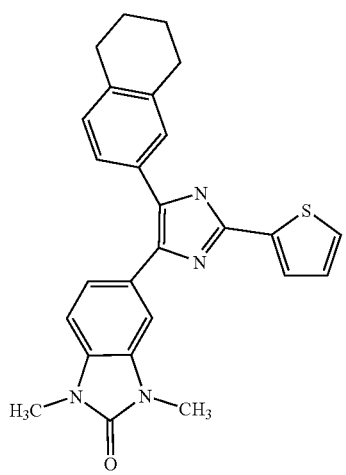 | 441.2 |
| 88 | 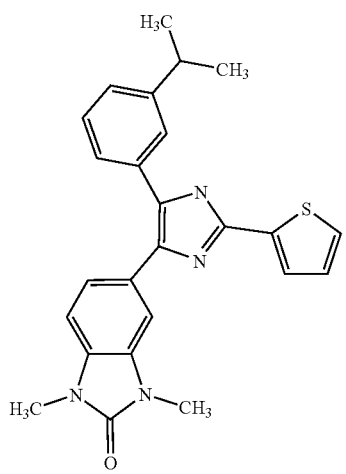 | 429.2 |

-continued
| EXAMPLE | Structure | Data MS (M + 1) |
|---|---|---|
| 89 | 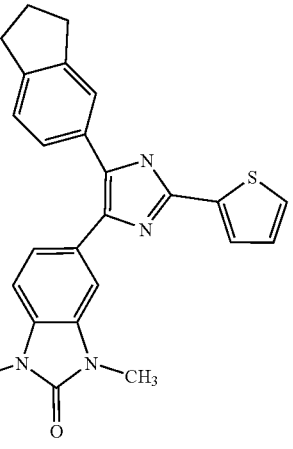 | 427.2 |
| 90 | 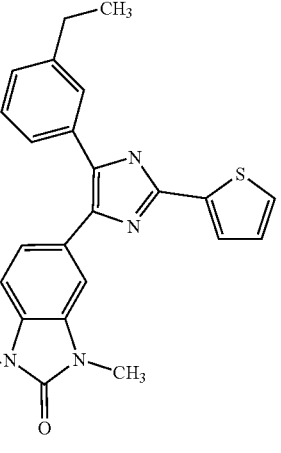 | 415.2 |
| 91 | 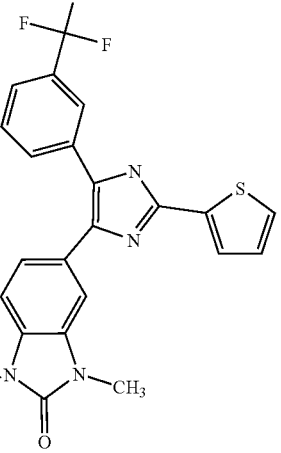 | 455.1 |

-continued

| EXAMPLE | Structure | Data MS (M + 1) |
| --- | --- | --- |
| 92 | 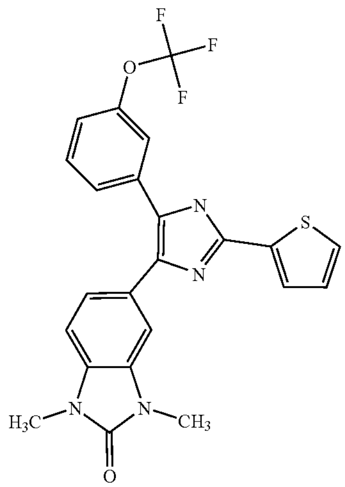 | 471.1 |
| 93 | 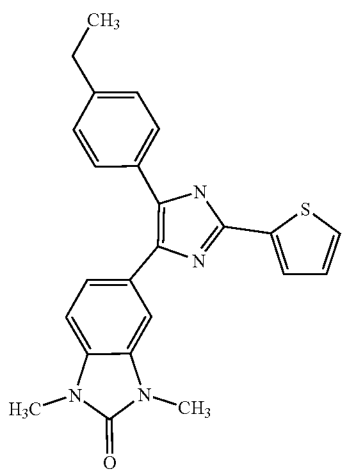 | 415.2 |
| 94 | 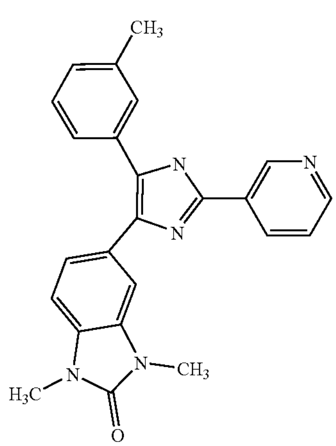 | 396.2 |

-continued
| EXAMPLE | Structure | Data MS (M + 1) |
|---|---|---|
| 95 | 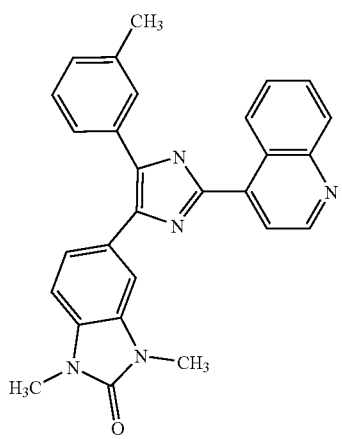 | 446.2 |
| 96 | 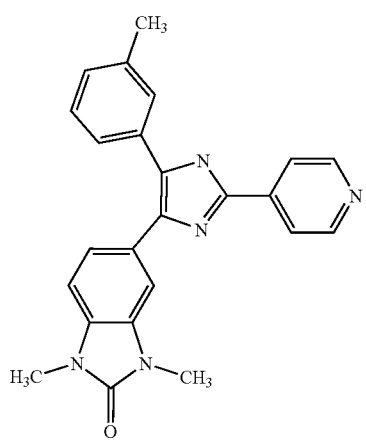 | 396.1 |
| 97 | 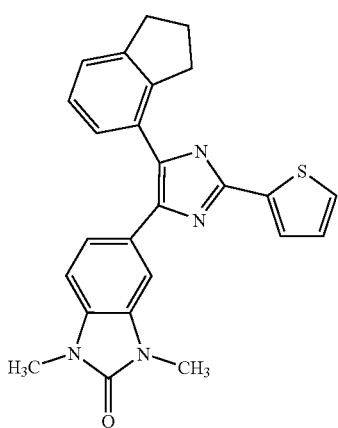 | 427.1 |

-continued
| EXAMPLE | Structure | Data MS (M + 1) |
|---|---|---|
| 98 | 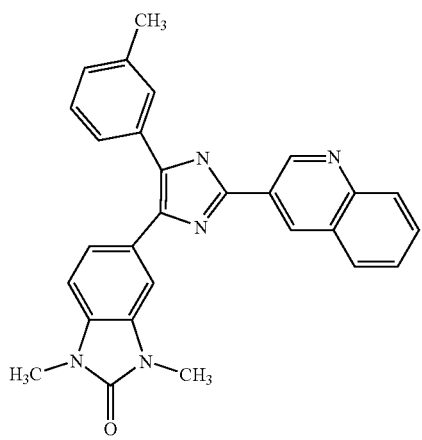 | 446.2 |
| 99 | 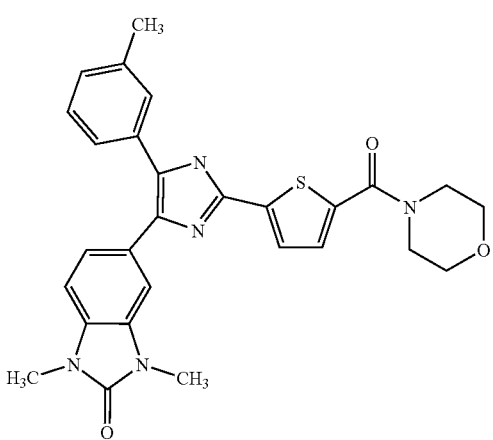 | 514.1 |
| 100 | 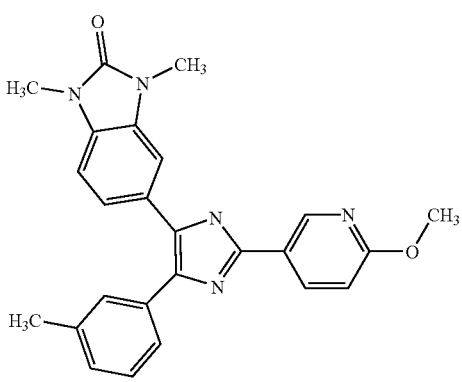 | 426.1 |

-continued

| EXAMPLE | Structure | Data MS (M + 1) |
|---|---|---|
| 101 | 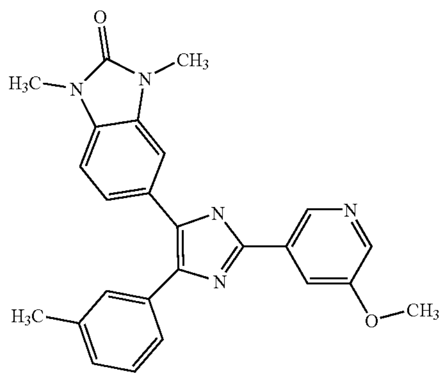 | 426.0 |
| 102 | 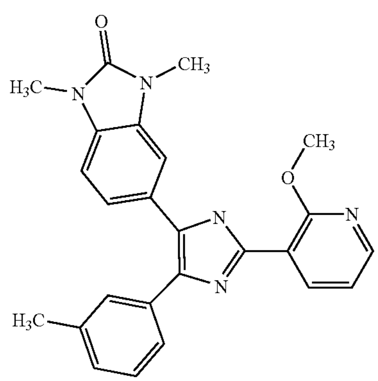 | 426.1 |
| 103 | 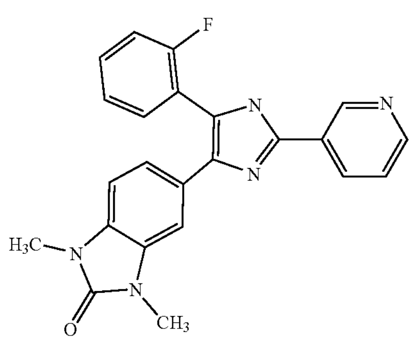 | 400.0 |
| 104 | 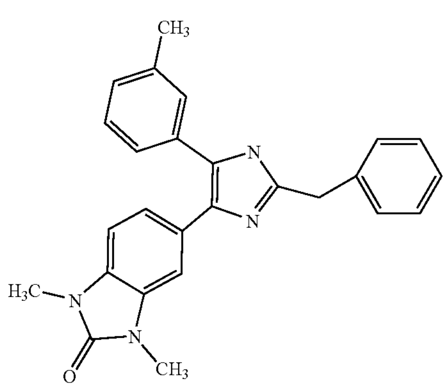 | 409.3 |

-continued
| EXAMPLE | Structure | Data MS (M + 1) |
| --- | --- | --- |
| 105 | 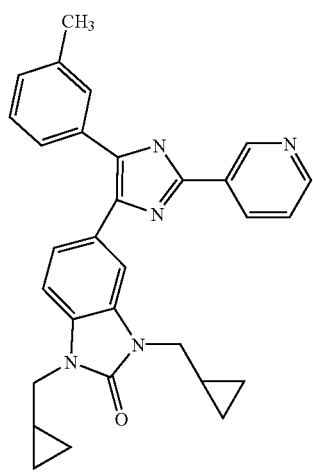 | 476.4 |
| 106 | 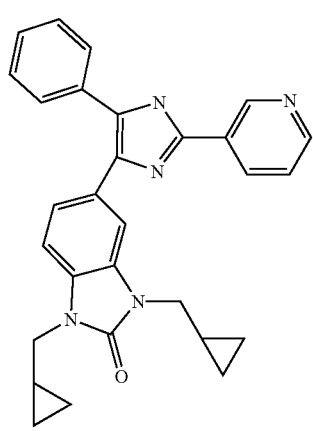 | 462.5 |
| 107 | 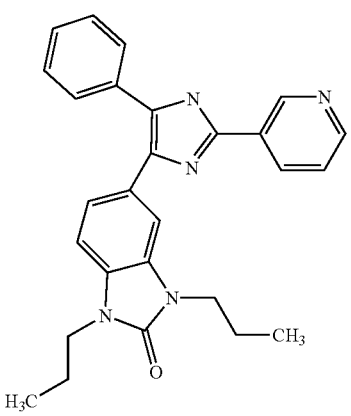 | 438.2 |

-continued

| EXAMPLE | Structure | Data MS (M + 1) |
|---------|-----------|-----------------|
| 108 | 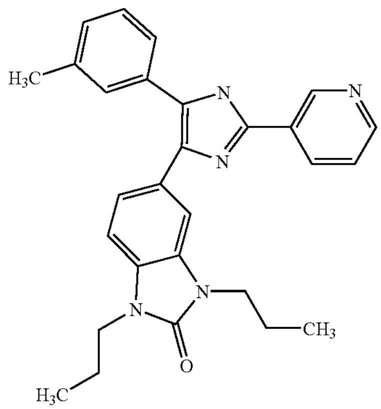 | 452.2 |
| 109 | 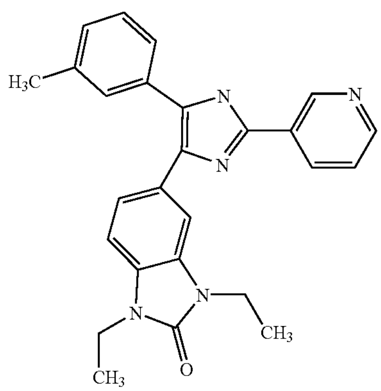 | 424.1 |
| 110 | 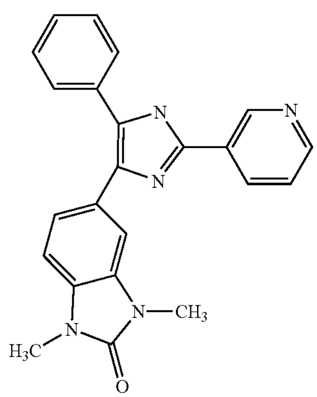 | 382.1 |
| 111 | 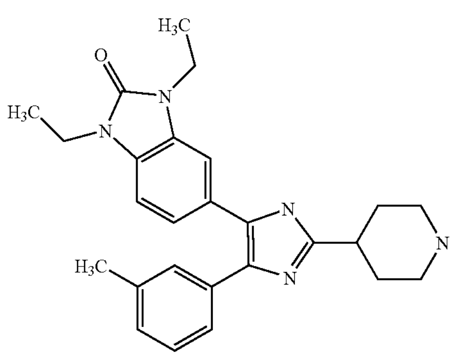 | 430.3 |

-continued
| EXAMPLE | Structure | Data MS (M + 1) |
|---|---|---|
| 112 | 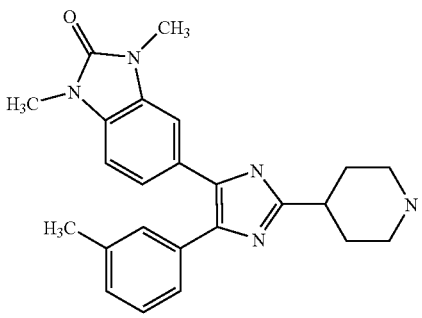 | 403.3 |
| 113 | 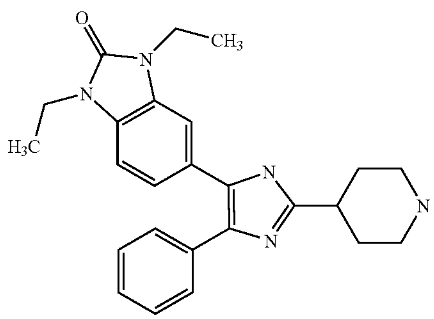 | 416.4 |
| 114 | 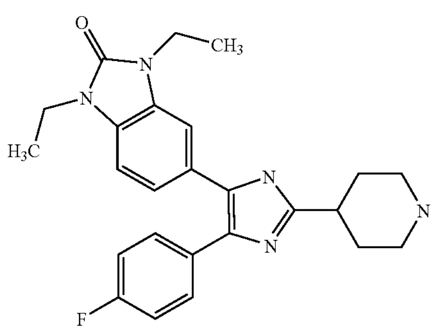 | 434.4 |
| 115 | 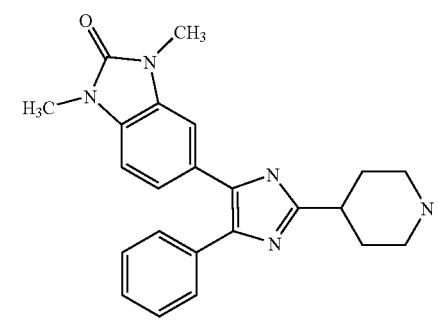 | 388.3 |

-continued

| EXAMPLE | Structure | Data MS (M + 1) |
| --- | --- | --- |
| 116 | 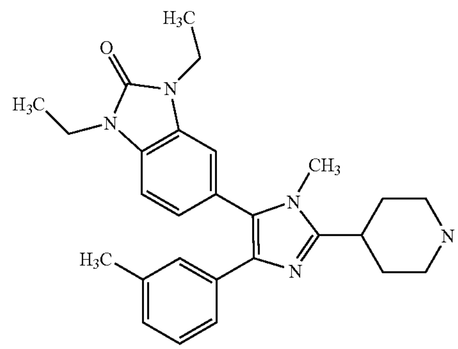 | 444.4 |
| 117 | 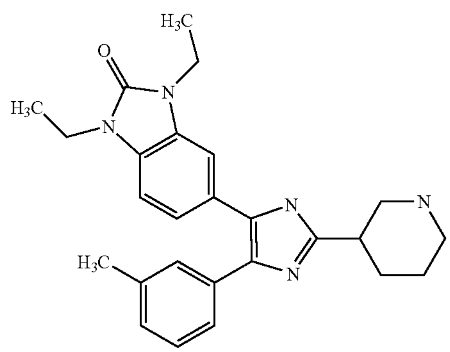 | 430.3 |
| 118 | 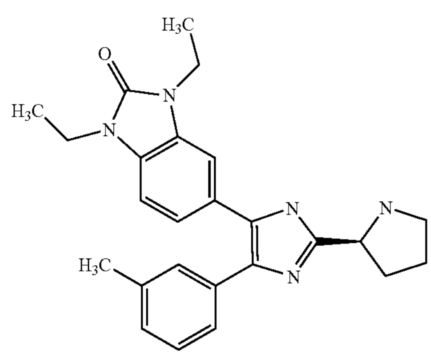 | 417 |
| 119 | 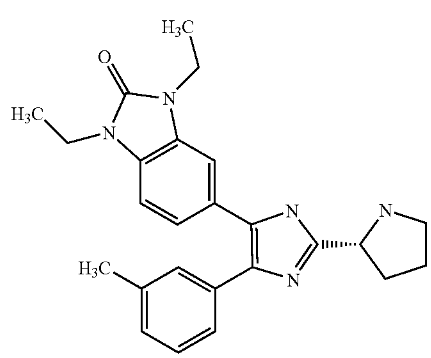 | 416.4 |

| EXAMPLE | Structure | Data MS (M + 1) |
|---------|-----------|-----------------|
| 120 | 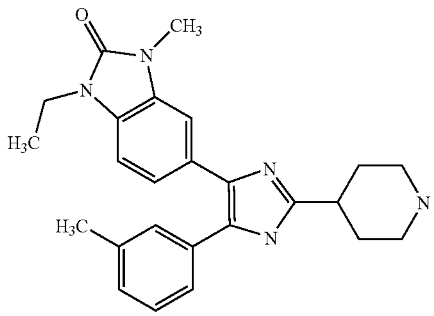 | 416.4 |
| 121 | 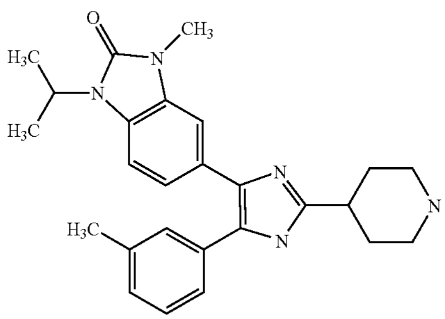 | 430.4 |
| 122 | 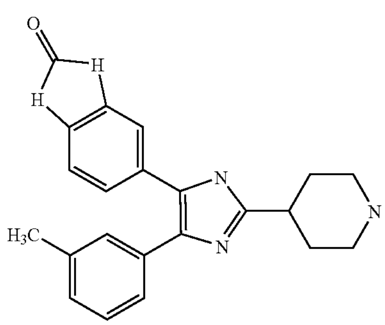 | 374.3 |
| 123 | 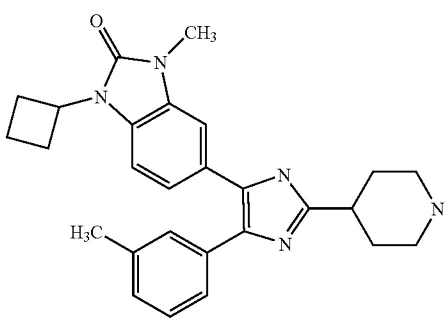 | 442.2 |

-continued
| EXAMPLE | Structure | Data MS (M + 1) |
|---|---|---|
| 124 | 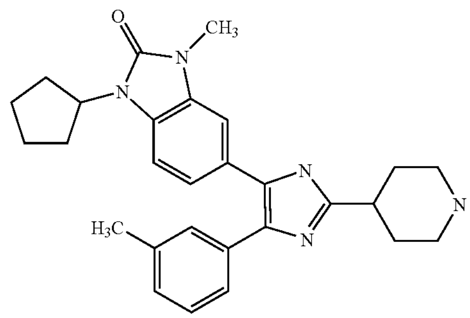 | 456.2 |
| 125 | 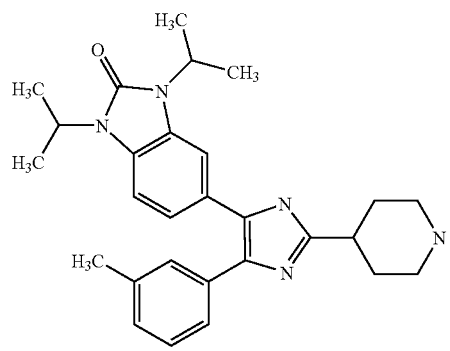 | 458.2 |
| 126 | 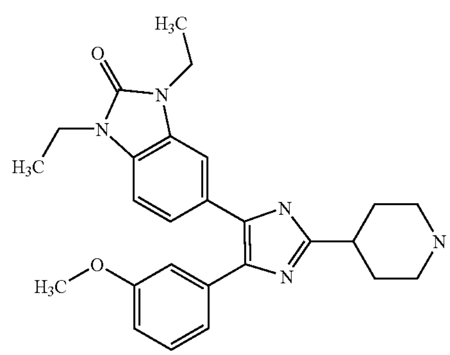 | 446.2 |
| 127 | 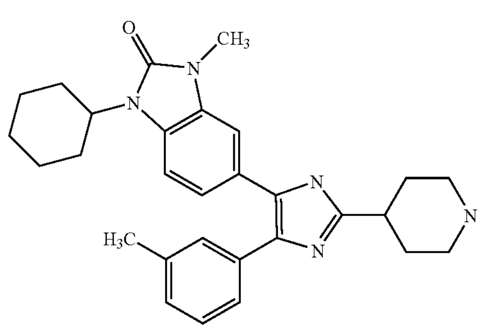 | 470.3 |

-continued
| EXAMPLE | Structure | Data MS (M + 1) |
|---|---|---|
| 128 | 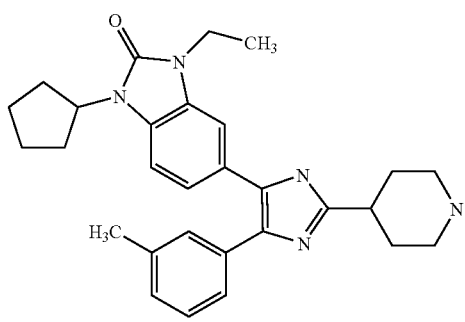 | 470.3 |
| 129 | 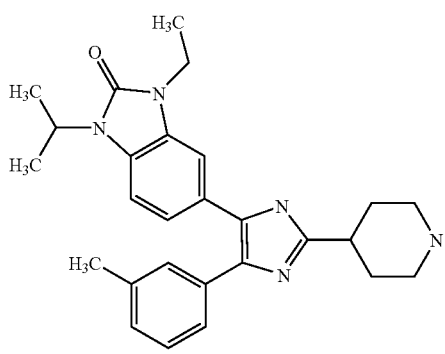 | 444.3 |
| 130 | 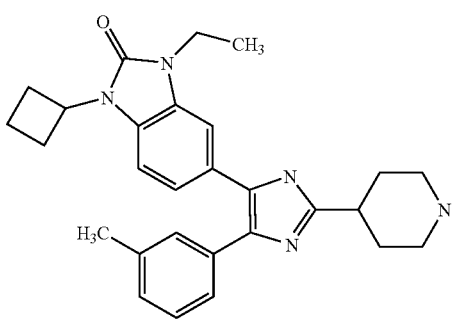 | 456.2 |
| 131 | 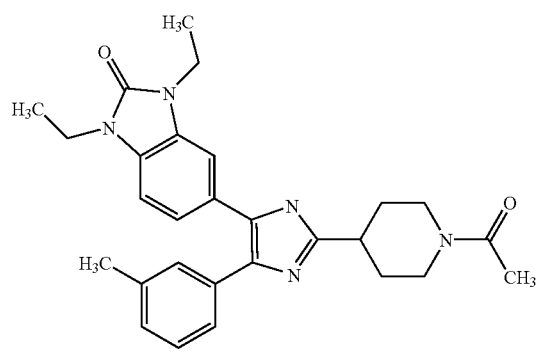 | 472.3 |

-continued

| EXAMPLE | Structure | Data MS (M + 1) |
|---|---|---|
| 132 | 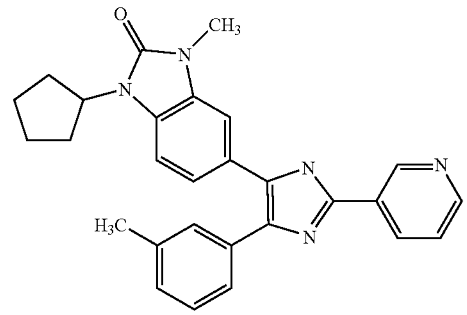 | 450.1 |
| 133 | 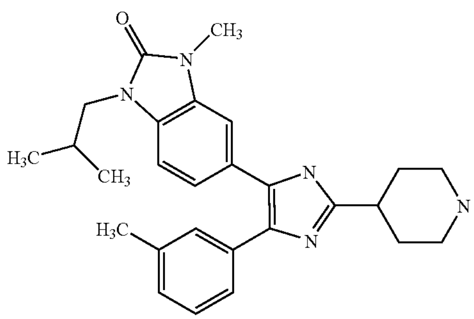 | 444.3 |
| 134 | 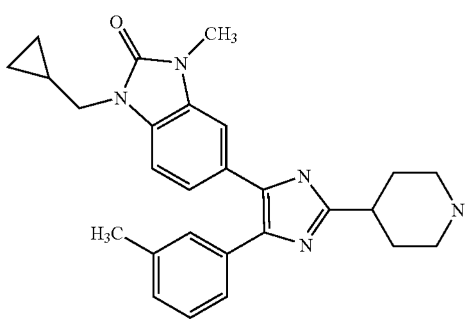 | 442.2 |
| 135 | 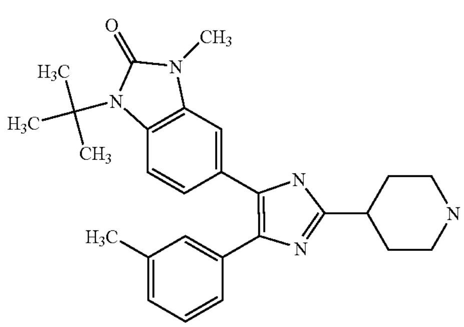 | |

-continued
| EXAMPLE | Structure | Data MS (M + 1) |
|---------|-----------|-----------------|
| 136 | 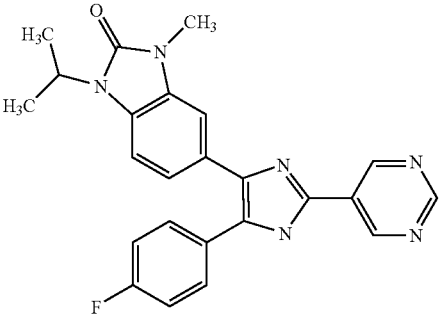 | 429.2 |
| 137 | 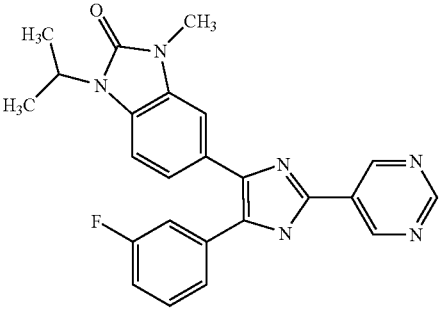 | 429.2 |
| 138 | 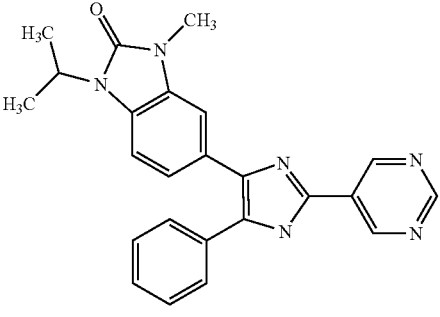 | 411.2 |
| 139 | 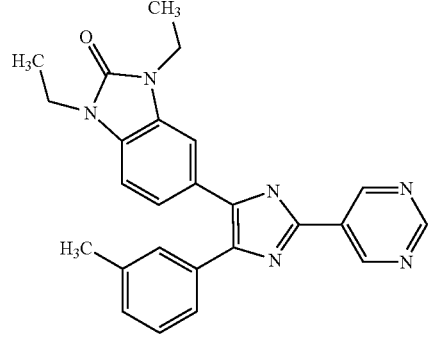 | 425.2 |

| EXAMPLE | Structure | Data MS (M + 1) |
|---|---|---|
| 140 | 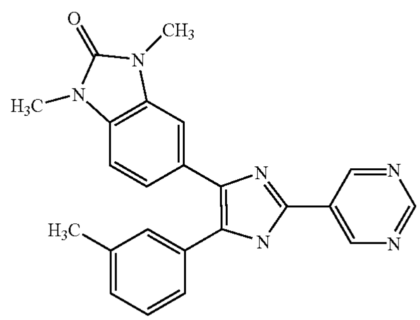 | 397.2 |
| 141 | 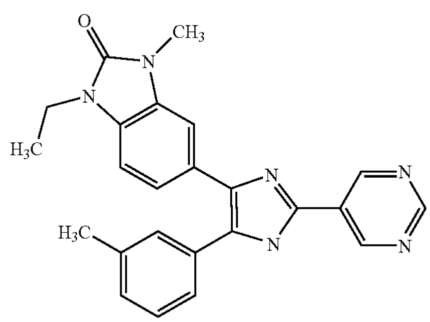 | 411.2 |

EXAMPLE 142 AND 143

N-[5-(1-Isobutyl-3-methyl-2-oxo-2,3-dihydro-1H-benzoimidazol-5-yl)-4-m-tolyl-1H-imidazol-2-yl]-acetamide and 5-[2-Amino-5-(3-chloro-phenyl)-3H-imidazol-4-yl]-1-cyclopentyl-3-methyl-1,3-dihydro-benzoimidazol-2one hydrochloride.

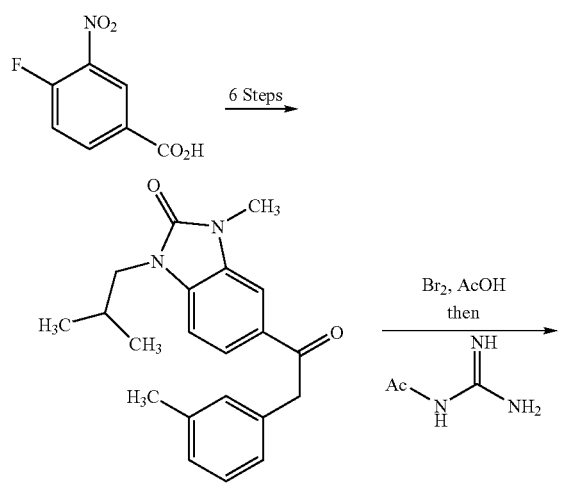

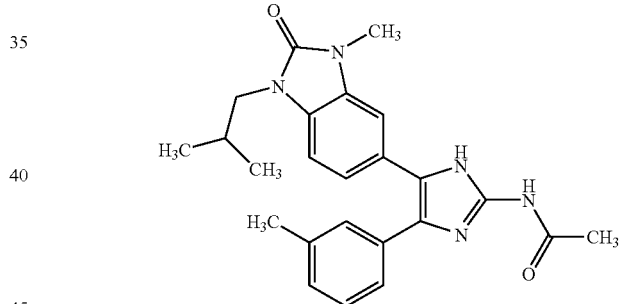

To a stirred solution of 1-isobutyl-3-methyl-5-m-tolylacetyl-1,3-dihydro-benzoimidazol-2-one (1.0 gm, 2.97 mmol) in acetic acid (11 mL) was added bromine (2.97 mL of a 1M solution of bromine in acetic acid, 2.97 mmol). After 2 hours, $^1$HNMR of an aliquot of the reaction mixture showed complete reaction. The acetic acid was removed in vacuo, and residual acetic acid was removed by azeotroping with methanol. The residue was taken up in DMF (11 mL) and treated with N-acetyl guanidine (0.90 gm, 8.92 mmol). The reaction mixture was stirred for 3 days at room temperature. LCMS of the reaction mixture indicated the starting material was consumed. The reaction mixture was poured into water (150 mL) and the white precipitate was filtered and dried in vacuo. Chromatography (Flash 40, ethyl acetate) afforded 262 mg of a light yellow solid. MS (M+1)=418.2

To a stirred solution of N-[4-(3-chloro-phenyl)-5-(1-cyclopentyl-3-methyl-2-oxo-2,3-dihydro-1H-benzoimidazol-5-yl)-1H-imidazol-2-yl]-acetamide (prepared as described above, 102 mg) in methanol:water (1:1, 10 mL) was added concentrated sulfuric acid (ca. 0.5 mL). The mixture was heated to reflux for 4 hours, after which the reaction was cooled to room temperature and the concentrated in vacuo.

The resulting aqueous solution was diluted with water and the pH was adjusted to 10 with aqueous ammonium hydroxide. The mixture was filtered and the resulting white powder was taken up in 1M HCl in ether and concentrated in vacuo to afford 70 mg of the title compound as the HCl salt. MS (M+1)=408.1 (free base).

The following compounds were prepared using the procedure described in Example 142 and 143 above.

| EXAMPLE | Structure | Data MS (M + 1) |
|---|---|---|
| 144 | 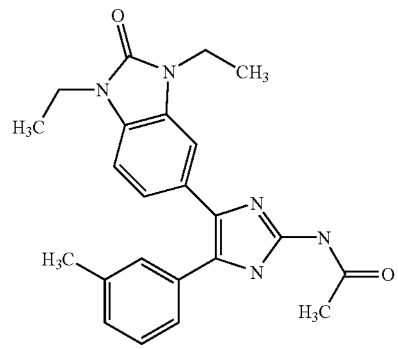 | 404.6 |
| 145 | 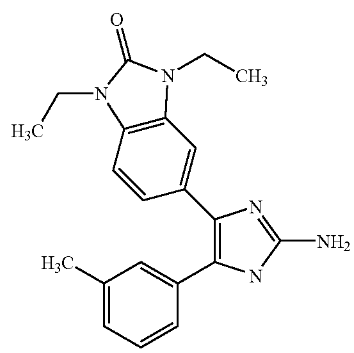 | 362.3 |
| 146 | 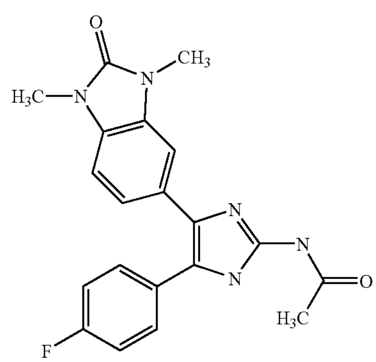 | 380.6 |
| 147 | 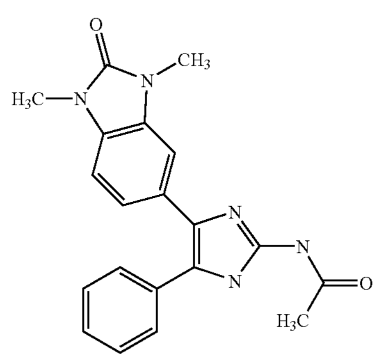 | 362.3 |

-continued

| EXAMPLE | Structure | Data MS (M + 1) |
| --- | --- | --- |
| 148 | 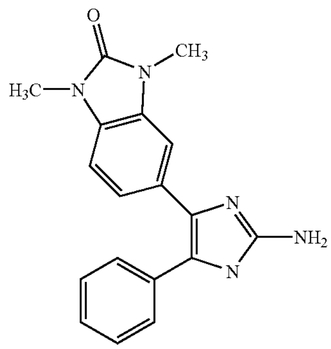 | 320.2 |
| 149 | 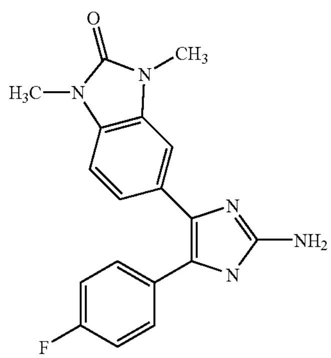 | 338.2 |
| 150 | 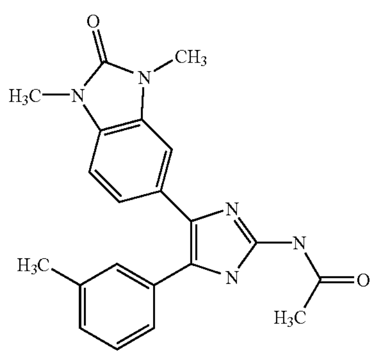 | 376.4 |
| 151 | 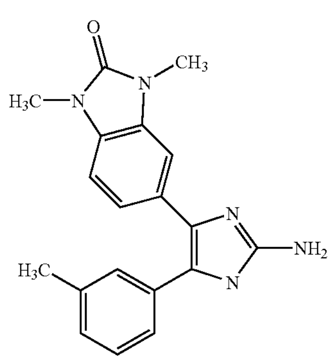 | |

| EXAMPLE | Structure | Data MS (M + 1) |
|---------|-----------|-----------------|
| 152 | 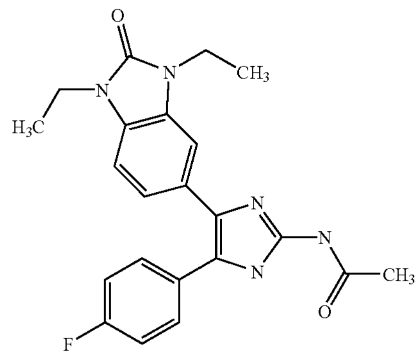 | 408.0 |
| 153 | 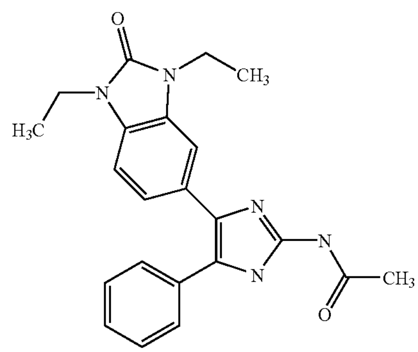 | 390.3 |
| 154 | 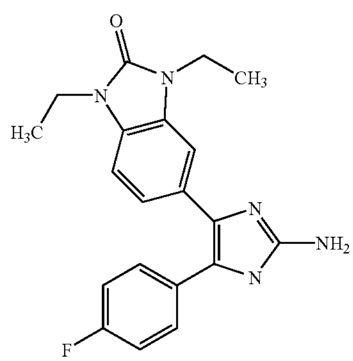 | 366.3 |
| 155 | 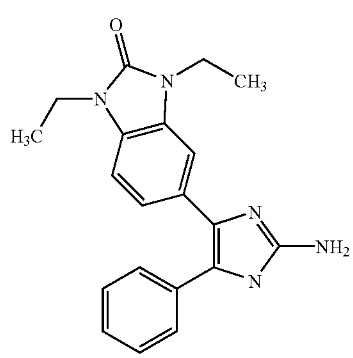 | 348.3 |

-continued
| EXAMPLE | Structure | Data MS (M + 1) |
|---|---|---|
| 156 | 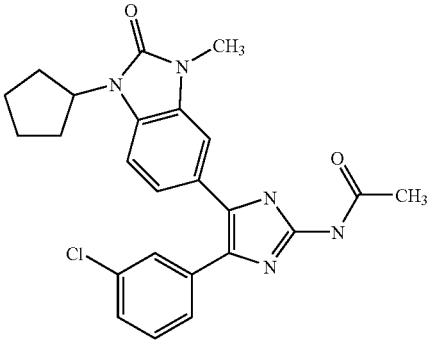 | 451.9 |
| 157 | 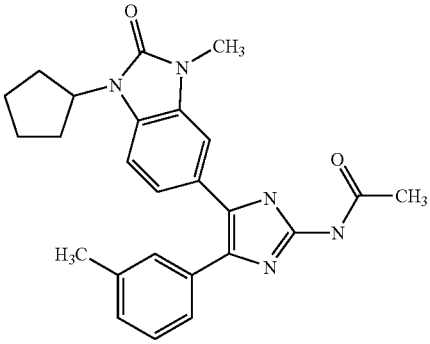 | 430.1 |
| 158 | 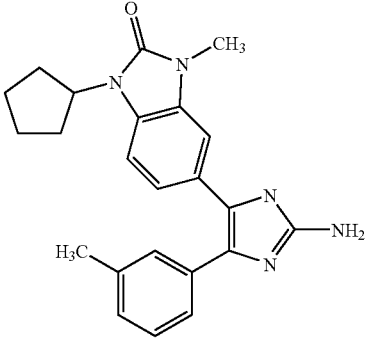 | | 
| 159 | 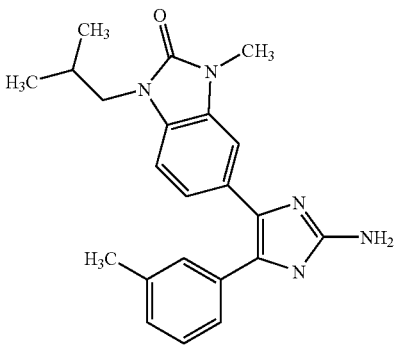 | 376.0 |

-continued

| EXAMPLE | Structure | Data MS (M + 1) |
| --- | --- | --- |
| 160 | 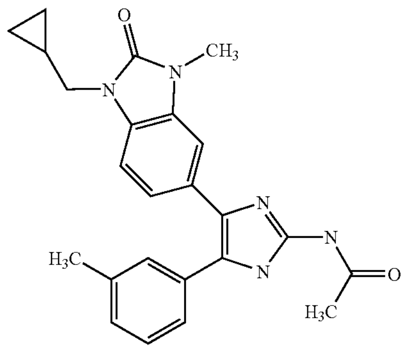 | 416.0 |
| 161 | 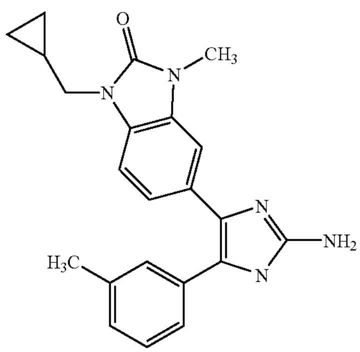 | 374.1 |
| 162 | 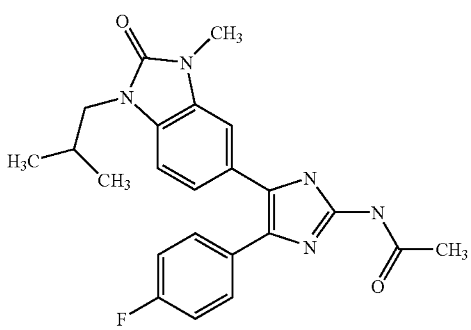 | 422.2 |
| 163 | 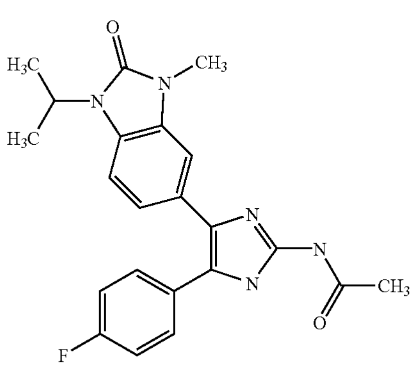 | 408.1 |

-continued
| EXAMPLE | Structure | Data MS (M + 1) |
|---------|-----------|-----------------|
| 164 | 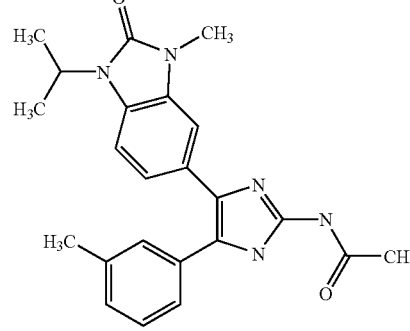 | 404.2 |
| 165 | 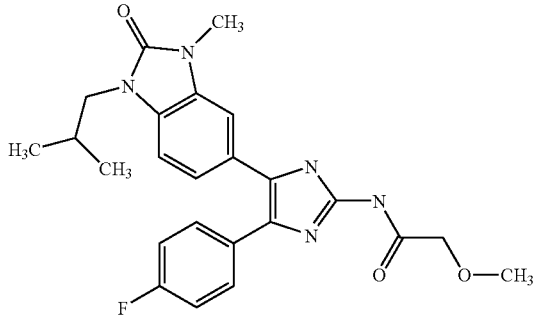 | 452.1 |
| 166 | 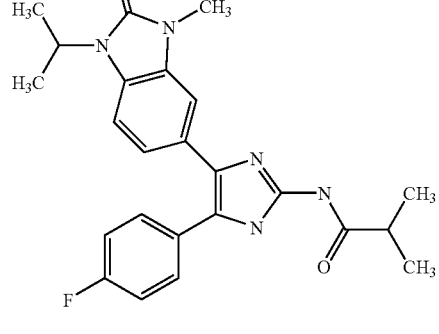 | 436.1 |
| 167 | 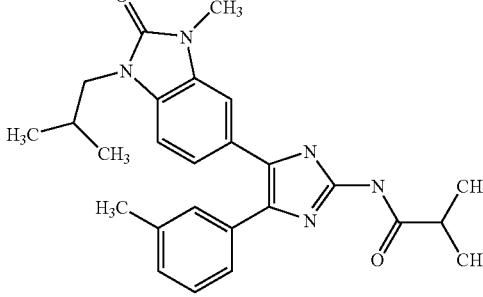 | 446.2 |

-continued
| EXAMPLE | Structure | Data MS (M + 1) |
| --- | --- | --- |
| 168 | 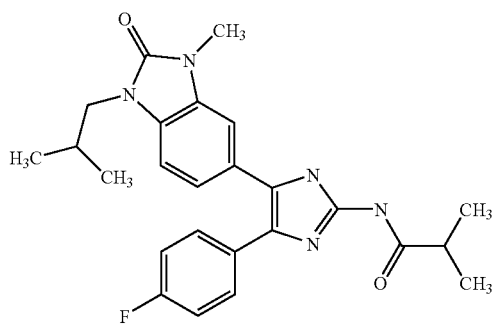 | 450.1 |
| 169 | 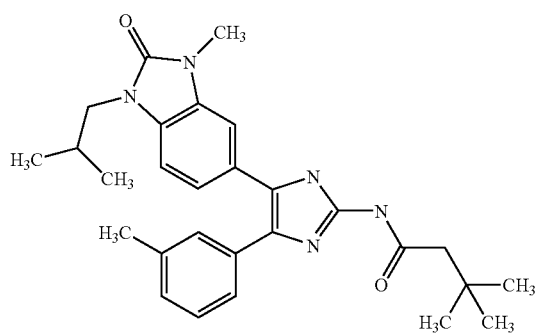 | 474.2 |
| 170 | 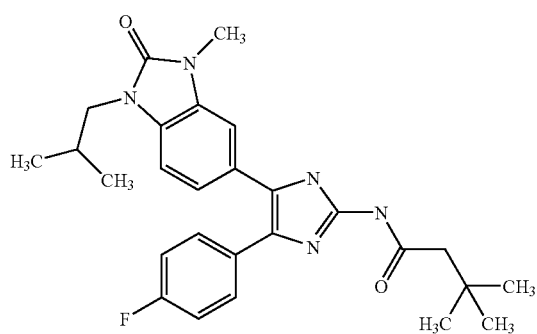 | 478.2 |
| 171 | 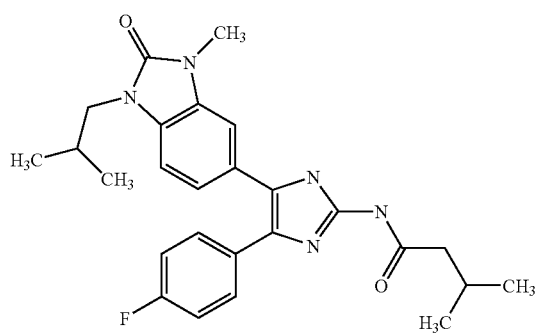 | 464.2 |

-continued
| EXAMPLE | Structure | Data MS (M + 1) |
|---|---|---|
| 172 | 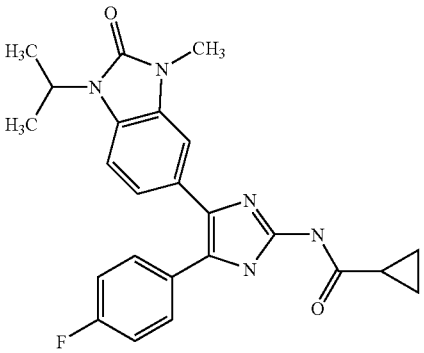 | 434.1 |
| 173 | 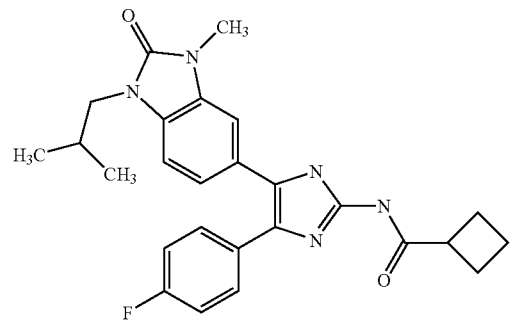 | 462.2 |
| 174 | 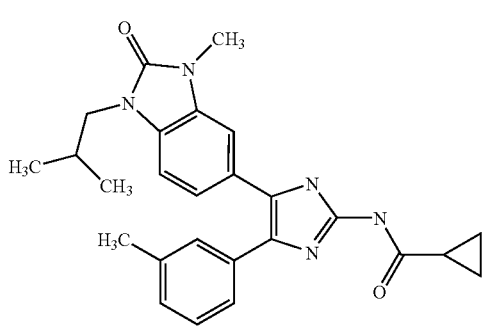 | 444.2 |
| 175 | 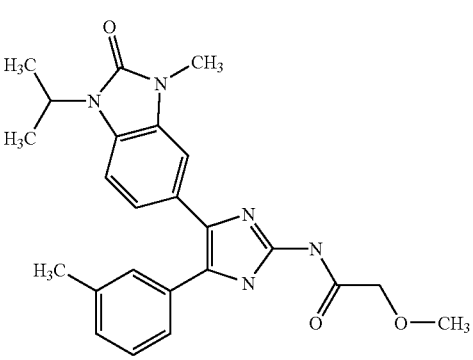 | 434.2 |

-continued
| EXAMPLE | Structure | Data MS (M + 1) |
|---|---|---|
| 176 | 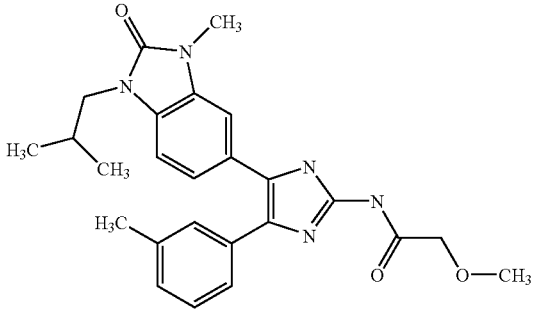 | 448.2 |
| 177 | 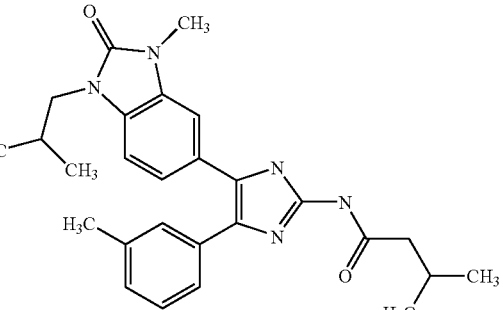 | 460.2 |
| 178 | 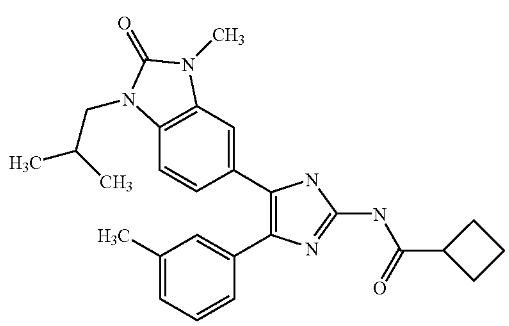 | 458.2 |
| 179 | 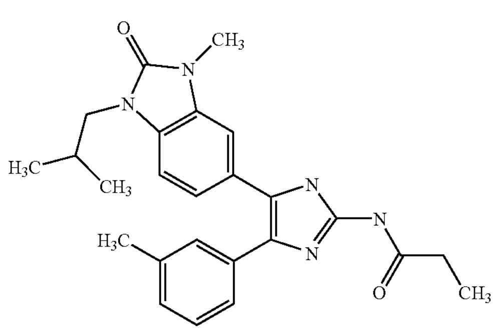 | 432.1 |

-continued

| EXAMPLE | Structure | Data MS (M + 1) |
|---------|-----------|-----------------|
| 180 | 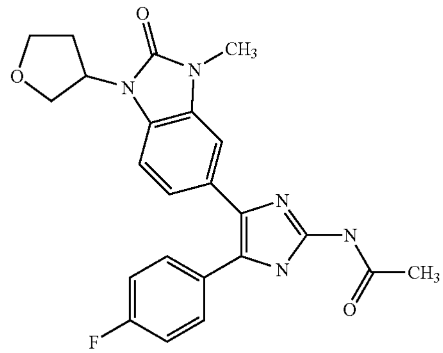 | 436.1 |
| 181 | 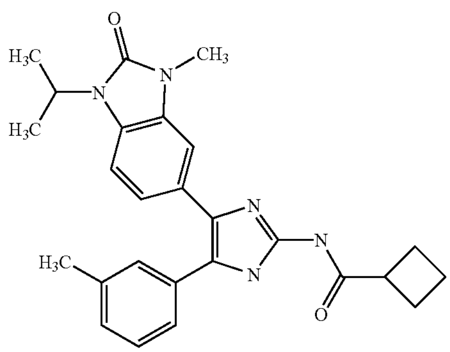 | 444.2 |
| 182 | 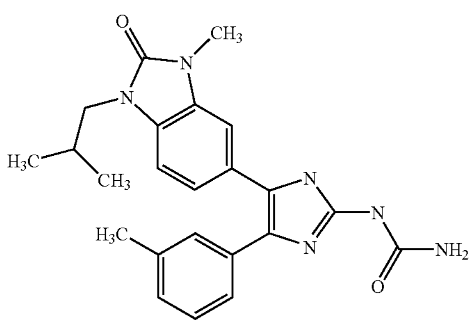 | 419.2 |
| 183 | 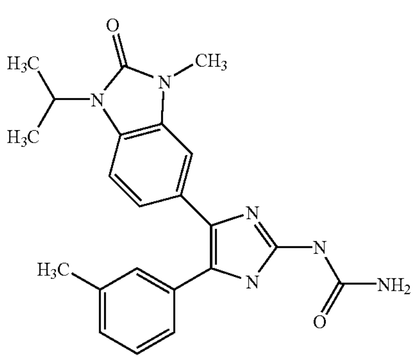 | 405.2 |

-continued

| EXAMPLE | Structure | Data MS (M + 1) |
|---------|-----------|-----------------|
| 184 | 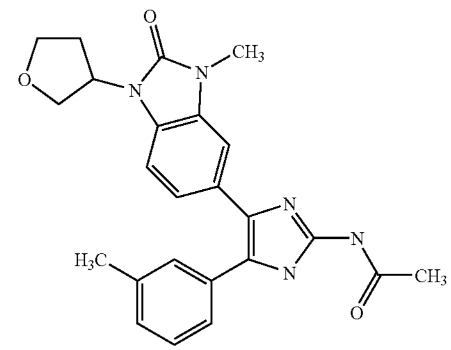 | 432.2 |
| 185 | 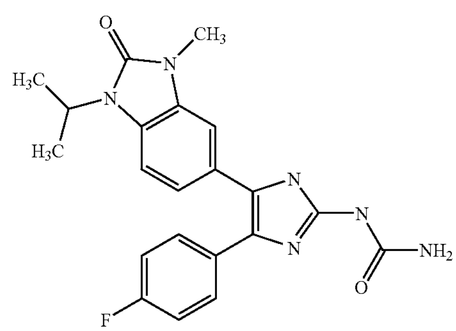 | 409.2 |
| 186 | 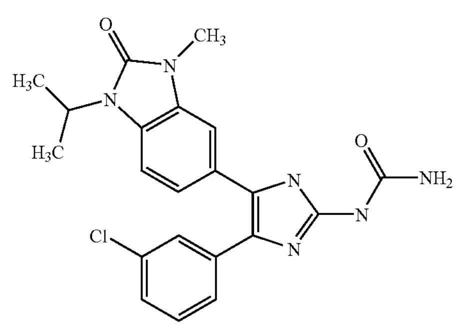 | 425.1 |
| 187 | 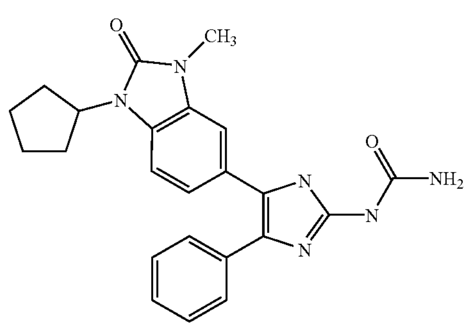 | 417.2 |

-continued

| EXAMPLE | Structure | Data MS (M + 1) |
| --- | --- | --- |
| 188 | 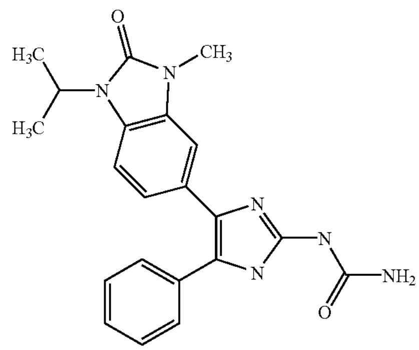 | 391.2 |
| 189 | 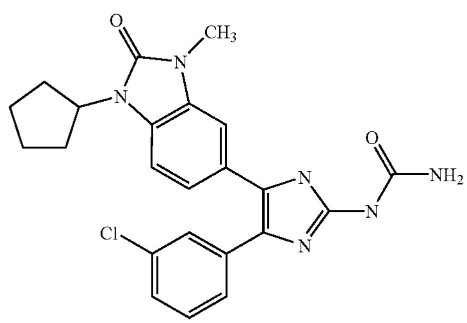 | 451.1 |
| 190 | 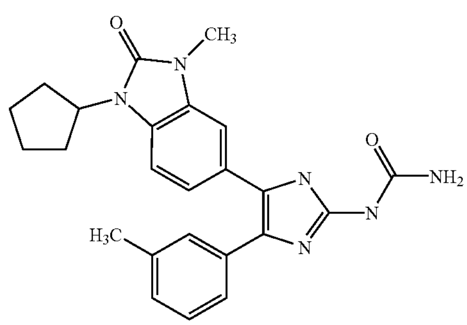 | 431.2 |
| 191 | 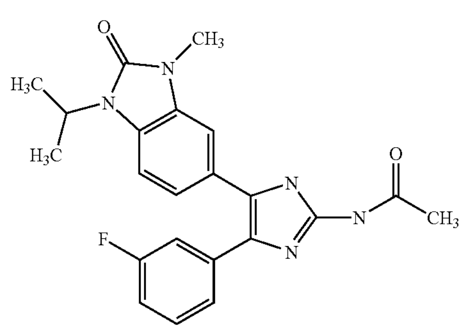 | 408.2 |

-continued

| EXAMPLE | Structure | Data MS (M + 1) |
|---------|-----------|-----------------|
| 192 | 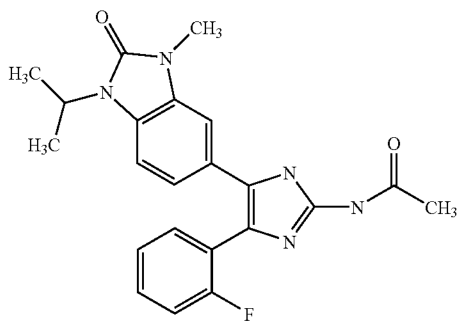 | 408.2 |
| 193 | 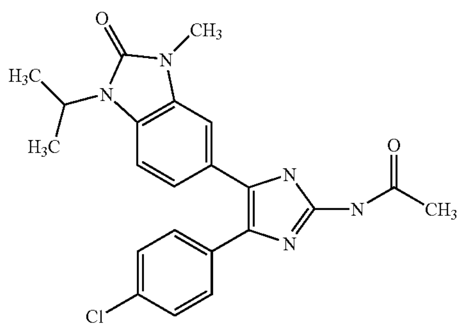 | 424.2 |
| 194 | 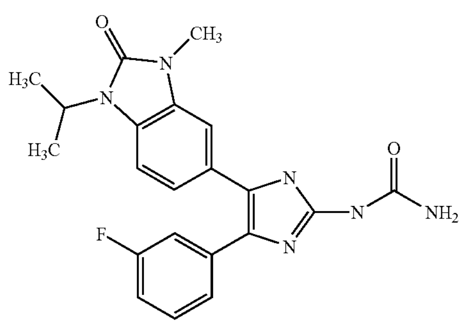 | 409.2 |
| 195 | 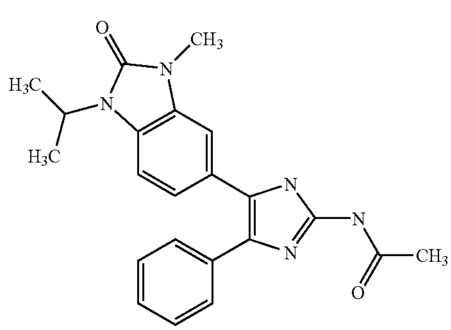 | 390.2 |

-continued

| EXAMPLE | Structure | Data MS (M + 1) |
|---------|-----------|-----------------|
| 196 | 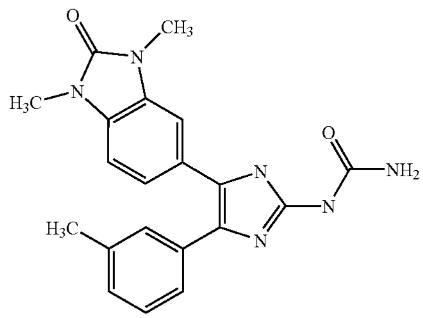 | 377.2 |
| 197 | 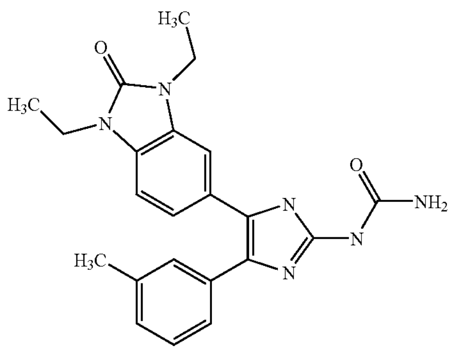 | 405.2 |
| 198 | 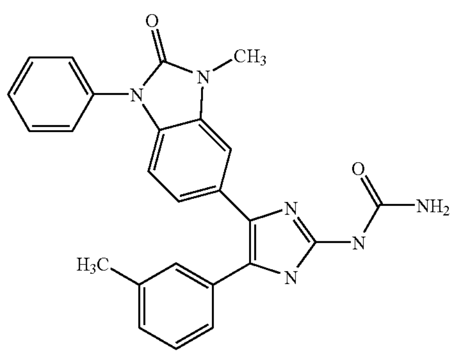 | 439.2 |
| 199 | 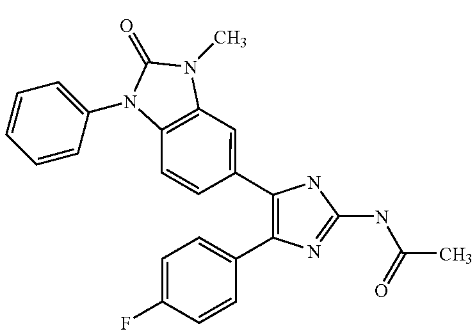 | 442.2 |

EXAMPLE 200 And 201

3-Methyl-1-phenyl-5-(5-m-tolyl-1H-imidazol-4-yl)-1,3-dihydro-benzoimidazol-2-one and 5-(3-benzyl-5-m-tolyl-3H-imidazol-4-yl)-1,3-diethyl-1,3-dihydro-benzoimidazol-2-one

3-Nitro-4-phenylamino-benzoic acid

A mixture of 4-chloro-3-nitrobenzoic acid (5.70 gm, 23 mmol), aniline (3.17 mL, 35 mmol), N-methylmorpholine (3.24 mL, 25 mmol), copper powder (0.1 gm, 1.57 mmol) and isoamyl alcohol (200 mL) was heated to reflux with stirring for 6 days. The mixture was then cooled to room temperature and filtered through a pad of celite. The filtrate was concentrated in vacuo and the residue taken up in ethyl acetate. The organic phase was washed with 3N HCl (2×1 L). The resulting organic phase was then extracted with saturated aqueous sodium carbonate solution. The aqueous phase was then washed with diethyl ether, followed by ethyl acetate. The aqueous phase was cautiously acidified to pH=1 with 6N HCl, and the resulting precipitate was filtered and dried to afford 2.54 gm of the title compound which was used without further purification.

2-Oxo-1-phenyl-2,3-dihydro-1H-benzoimidazole-5-carboxylic acid methoxy-methyl-amide To a stirred solution of 3-amino-4-phenylamino-benzoic acid (prepared from 3-nitro-4-phenylamino-benzoic acid as described in the general procedure, 2.04 gm, 8.94 mmol) in THF (25 mL) was added carbonyl diimidazole (3.62 gm, 22.34 mmol). After stirring for 1 hour at room temperature, N,O-dimethylhydroxyl amine (1.31 gm, 13.41 mmol) was added in one portion. Stirring was continued at room temperature for an additional 2 hours after which time the reaction was determined to be complete by LC-MS. The THF was removed in vacuo and the residue was diluted with water and extracted with methylene chloride three times. The combined methylene chloride extracts were dried over anhydrous sodium sulfate and concentrated in vacuo to afford 2.23 gm of the title compound as a tan solid which was used without further purification.

3-Methyl-1-phenyl-5-(5-m-tolyl-1H-imidazol-4-yl)-1,3-dihydro-benzoimidazol-2-one 5-(Bromo-m-tolyl-acetyl)-3-methyl-1-phenyl-1,3-dihydro-benzoimidazol-2-one (prepared from 2-oxo-1-phenyl-2,3-dihydro-1H-benzoimidazole-5-carboxylic acid methoxy-methyl-amide as described in the general procedure, 0.26 gm, 0.60 mmol) was added to 5 mL of 8% water/formamide and the mixture was heated to 140° C. for 14 hours. The reaction mixture was then cooled to room temperature and diluted with 20 mL of ammonium hydroxide with rapid stirring. After stirring for ½ hour, the solid precipitate was filtered and purified by column chromatography (0.5% methanol in ethyl acetate) to afford 75 mg of the title compound. MS (M+1)=381.2

5-(3-Benzyl-5-m-tolyl-3H-imidazol-4-yl)-1,3-diethyl-1,3-dihydro-benzoimidazol-2-one To a slurry of sodium hydride (254 mg of a 60% dispersion in mineral oil, 6.4 mmol) in DMF (79 mL) was added 1,3-diethyl-5-(5-m-tolyl-3H-imidazol-4-yl)-1,3-dihydro-benzoimidazol-2-one (prepared as described above, 2.0 gm, 5.8 mmol). The resulting mixture was stirred for 15 minutes, then benzyl bromide (0.76 mL, 6.4 mmol) was added all in one portion. The reaction was stirred for an additional 30 minutes, and was then quenched with water. The aqueous mixture was extracted with ethyl acetate, and the combined organic extracts were dried over anhydrous sodium sulfate and concentrated in vacuo to afford a yellow oil. The oil was purified by flash chromatography eluting with ethyl acetate to afford 540 mg of the title compound as the less polar constituent. MS (M+1)=437.0

The following compounds were prepared using methods analogous to those described in Example 200 and 201 above.

| EXAMPLE | Structure | Data MS (M + 1) |
|---|---|---|
| 202 | (structure) | 347.2 |
| 203 | (structure) | 333.6 |
| 204 | (structure) | 375.4 |

-continued
| EXAMPLE | Structure | Data MS (M + 1) |
|---|---|---|
| 205 | 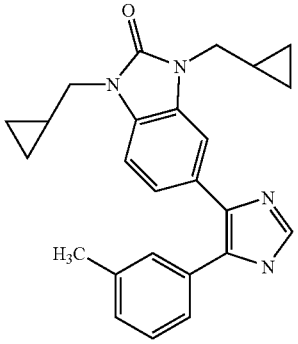 | 399.4 |
| 206 | 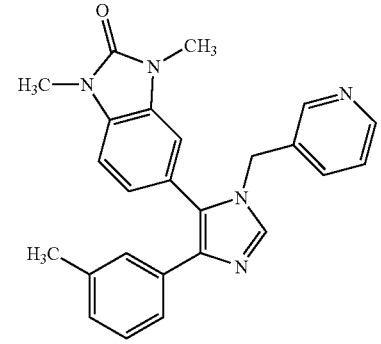 | 410.3 |
| 207 | 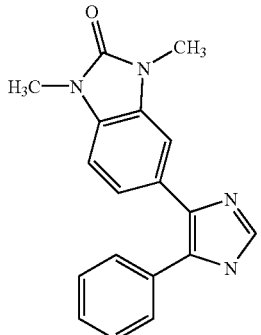 | 305.5 |
| 208 | 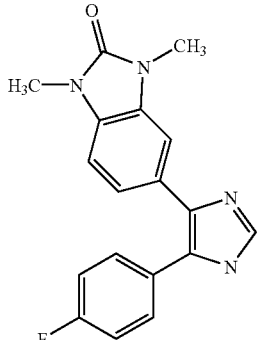 | 323.3 |
-continued
| EXAMPLE | Structure | Data MS (M + 1) |
|---|---|---|
| 209 | 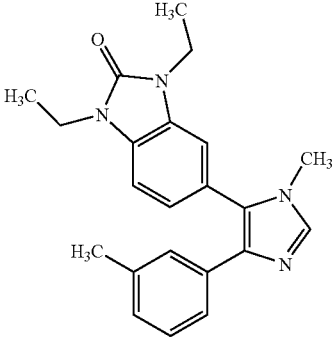 | 361.3 |
| 210 | 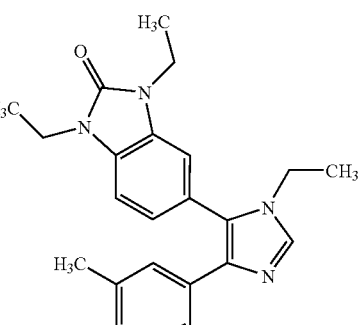 | 375.0 |
| 211 | 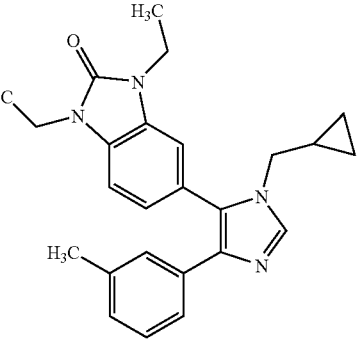 | |
| 212 | 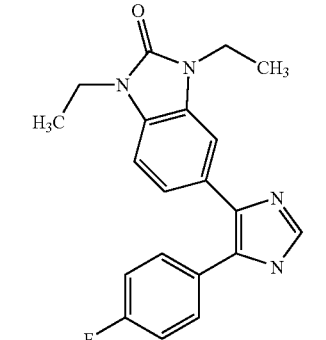 | |

-continued
| EXAMPLE | Structure | Data MS (M + 1) |
|---|---|---|
| 213 | 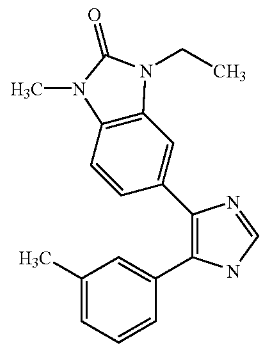 | 333.4 |
| 214 | 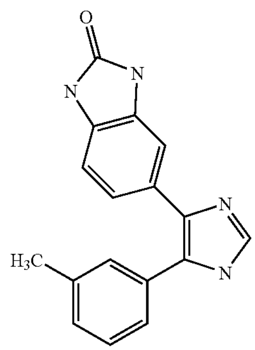 | 291.3 |
| 215 | 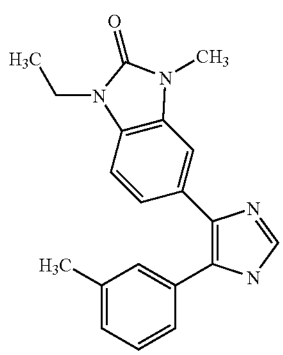 | 333.3 |
| 216 | 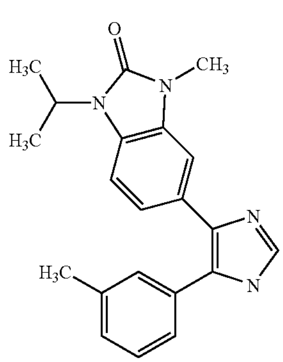 | 347.3 |
-continued
| EXAMPLE | Structure | Data MS (M + 1) |
|---|---|---|
| 217 | 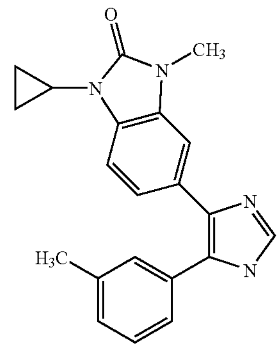 | 345.3 |
| 218 | 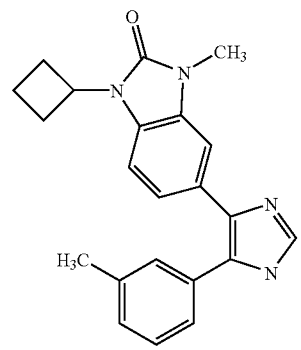 | 359.4 |
| 219 | 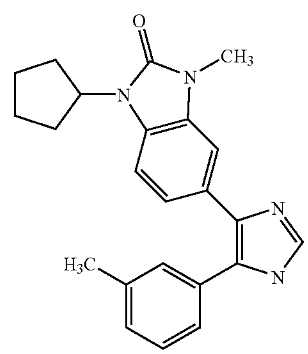 | 373.3 |
| 220 | 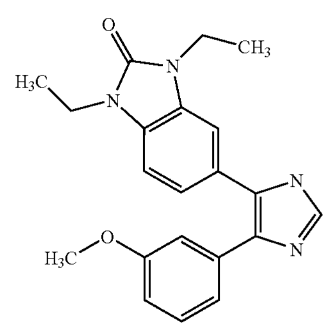 | 363.2 |

-continued
| EXAMPLE | Structure | Data MS (M + 1) |
|---|---|---|
| 221 | 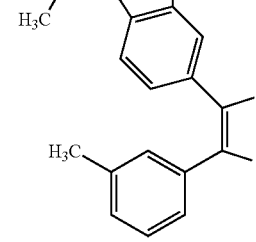 | 347.3 |
| 222 | 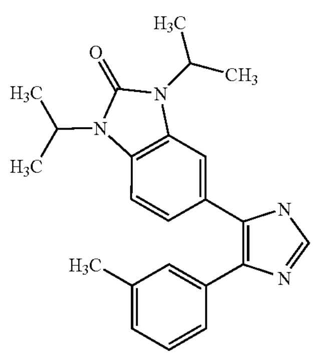 | 375.2 |
| 223 | 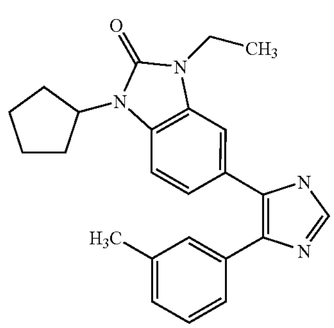 | 387.2 |
| 224 | 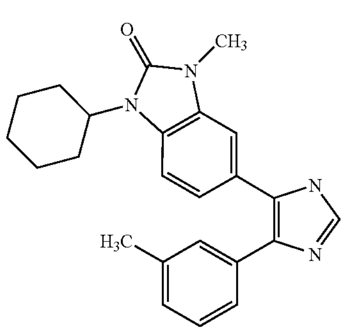 | 387.2 |
-continued
| EXAMPLE | Structure | Data MS (M + 1) |
|---|---|---|
| 225 | 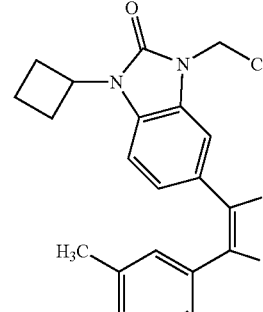 | 361.2 |
| 226 | 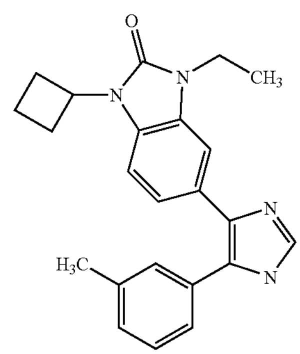 | 373.2 |
| 227 | 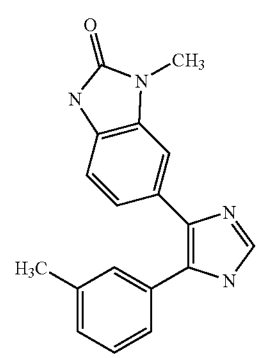 | 305.2 |
| 228 | 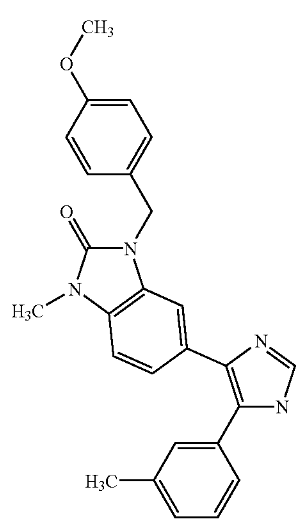 | 425.2 |

-continued

| EXAMPLE | Structure | Data MS (M + 1) |
|---|---|---|
| 229 | 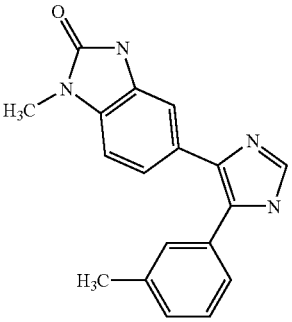 | 305.2 |
| 230 | 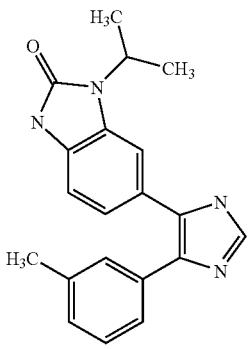 | 333.2 |
| 231 | 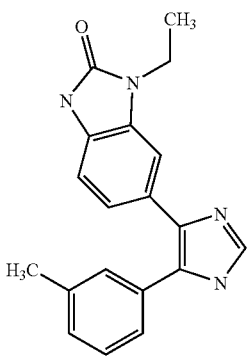 | 319.2 |
| 232 | 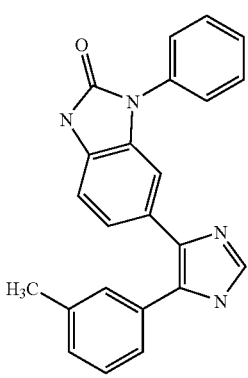 | 367.2 |

-continued

| EXAMPLE | Structure | Data MS (M + 1) |
|---|---|---|
| 233 | 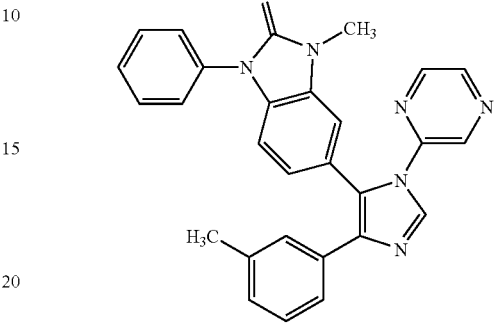 | 459.2 |
| 234 | 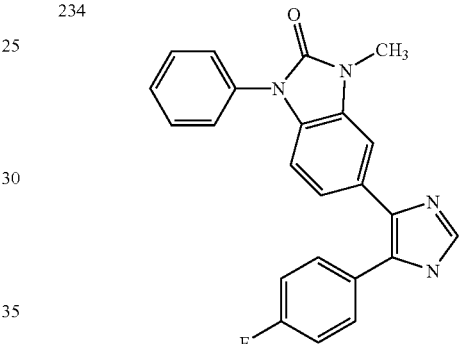 | 385.2 |

EXAMPLE 235, 236 AND 237

1-Isobutyl-3-methyl-5-(5-m-tolyl-2-trifluoromethyl-3H-imidazol-4-yl)-1,3-dihydro-benzoimidazol-2-one 5-(1-Isobutyl-3-methyl-2-oxo-2,3-dihydro-1H-benzoimidazol-5-yl)-4-m-tolyl-1H-imidazole-2-carbonitrile and 1-ethyl-3-methyl-5-[2-(morpholine-4-carbonyl)-5-m-tolyl-3H-imidazol-4yl]-1,3-dihydro-benzoimidazol-2-one Examples 235 and 236 were prepared using the method of Kimoto, H.; Cohen, L. A. *J. Org. Chem.* 1980, 45, 3831–3835.

5-(1-Isobutyl-3-methyl-2-oxo-2,3-dihydro-1H-benzoimidazol-5-yl)-4-m-tolyl-1H-imidazole-2-carboxylic acid 1-Isobutyl-3-methyl-5-(5-m-tolyl-2-trifluoromethyl-3H-imidazol-4-yl)-1,3-dihydro-benzoimidazol-2-one (prepared as described previously using the method described for example 63 and Lombardino, J. G.; Wiseman, E. H. *J. Med. Chem.* 1974, 17(11), 1182–1188, 34 mg, 0.08 mmol) was suspended in 0.5M sodium hydroxide solution (1.27 mL). The suspension was stirred for 3 days, after which time the reaction was taken to pH=2 with 1N HCl and concentrated in vacuo. The residue was taken up in ethanol and cooled to 0° C., at which time sodium chloride was filtered off. The ethanol was concentrated in vacuo and the residue was purified by LC (Waters Symmetry C8, formic acid/acetonitrile/water) to afford 8 mg of the title compound as a white solid. MS (M+1)=405.1

5-(1-Isobutyl-3-methyl-2-oxo-2,3-dihydro-1H-benzoimidazol-5-yl)-4-m-tolyl-1H-imidazole-2-carbonitrile 1-Isobutyl-3-methyl-5-(5-m-tolyl-2-trifluoromethyl-3H-imidazol-4-yl)-1,3-dihydro-benzoimidazol-2-one (prepared as described previously using the method described for example 63 and Lombardino, J. G.; Wiseman, E. H. *J. Med. Chem.* 1974, 17(11), 1182–1188, 20 mg, 0.05 mmol) was suspended in 5% aqueous ammonium hydroxide solution (4.7 mL). The suspension was stirred for 5 days, after which time the reaction was concentrated in vacuo. The resulting material was purified by LC (Waters Symmetry C8, acetonitrile/water 40% to 100%) to afford 8 mg of the title compound as a white solid. MS (M+1)=386.2

1-Ethyl-3-methyl-5-[2-(morpholine-4-carbonyl)-5-m-tolyl-3H-imidazol-4-yl]-1,3-dihydro-benzoimidazol-2-one A mixture of 1-ethyl-3-methyl-5-(5-m-tolyl-2-trifluoromethyl-3H-imidazol-4-yl)-1,3-dihydro-benzoimidazol-2-one (prepared as described above, 50 mg, 0.13 mmol), N,N-dimethylaminopyridine (48.7 mg, 0.40 mmol), EDCI (38.3 mg, 0.20 mmol) and morpholine (17.4 mg, 0.20 mmol) was stirred at room temperature in THF (1.33 mL) at room temperature. One drop of DMF was added to ensure solubility. The reaction mixture was allowed to stir overnight. The mixture was concentrated in vacuo, taken up in methylene chloride and washed with 10% aqueous citric acid. The organic phase was dried over anhydrous sodium sulfate and concentrated in vacuo to afford a reddish-brown solid, which was recrystallized in diisopropyl ether to give 19 mg of the title compound. MS (M+1)=446.5.

The following examples were prepared using the methods described for examples 235, 236, and 237.

| EXAMPLE | Structure | Data MS (M + 1) |
| --- | --- | --- |
| 238 | 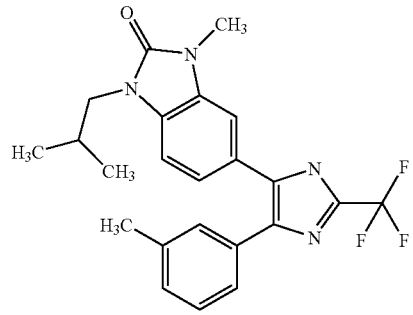 | 429.2 |
| 239 | 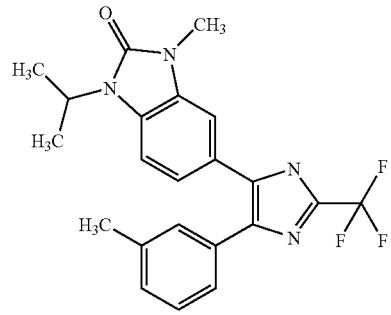 | 415.2 |

-continued

| EXAMPLE | Structure | Data MS (M + 1) |
|---------|-----------|-----------------|
| 240 | 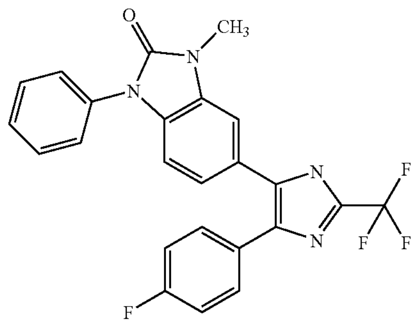 | 453.1 |
| 241 | 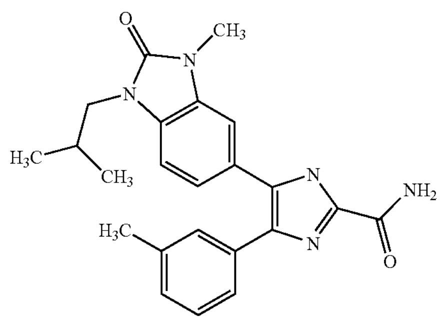 | 404.2 |
| 242 | 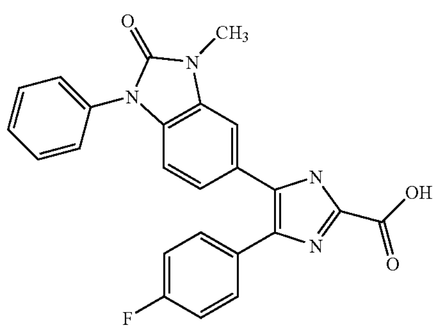 | 429.1 |
| 243 | 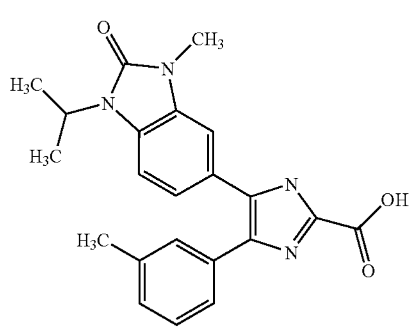 | 391.2 |

-continued

| EXAMPLE | Structure | Data MS (M + 1) |
| --- | --- | --- |
| 244 | 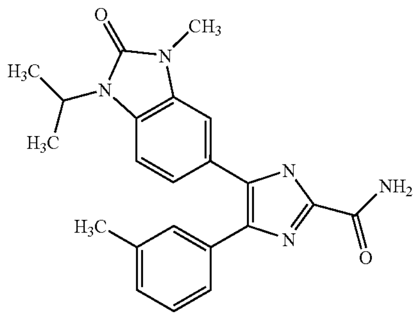 | 390.2 |
| 245 | 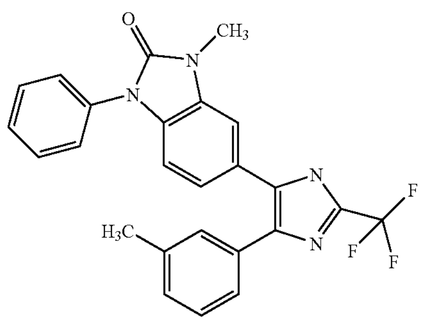 | 449.2 |
| 246 | 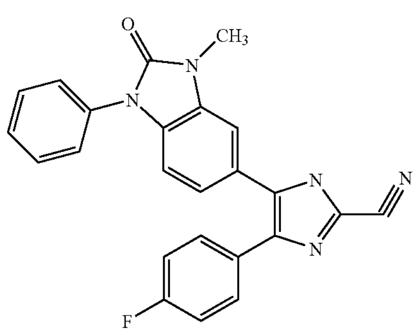 | 410.1 |
| 247 | 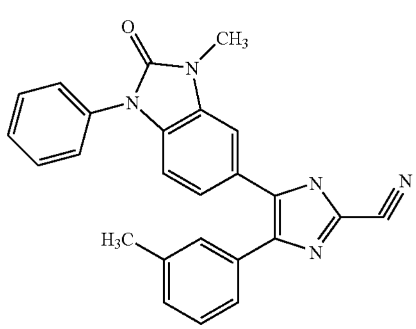 | 406.3 |

-continued

| EXAMPLE | Structure | Data MS (M + 1) |
|---------|-----------|-----------------|
| 248 | 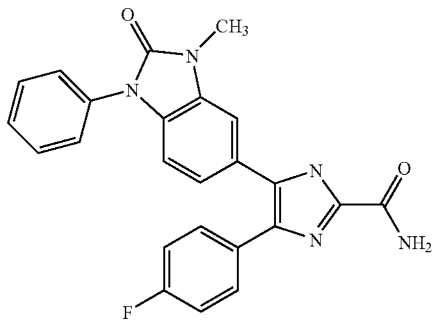 | 428.4 |
| 249 | 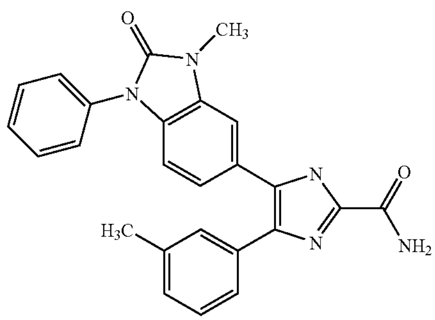 | 424.3 |
| 250 | 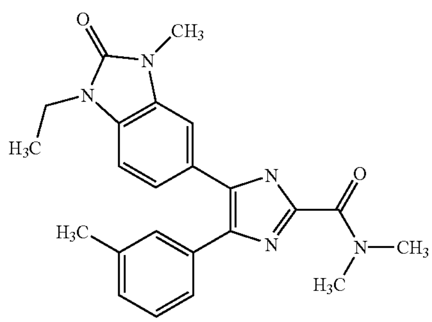 | 404.3 |
| 251 | 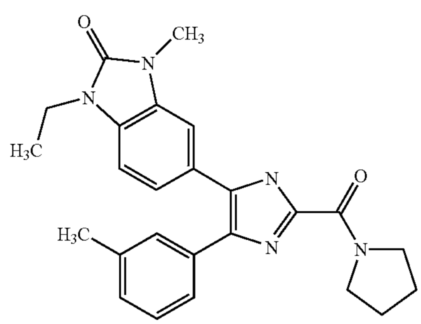 | 430.3 |

-continued
| EXAMPLE | Structure | Data MS (M + 1) |
|---|---|---|
| 252 | 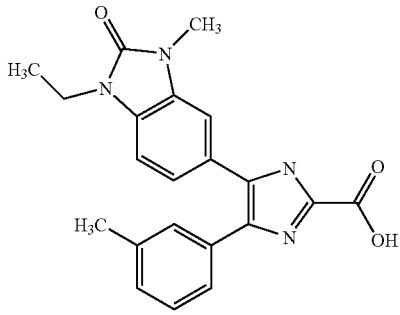 | 377.2 |
| 253 | 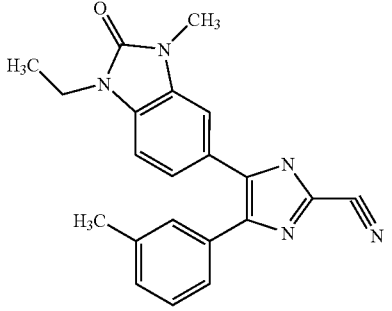 | 358.1 |
| 254 | 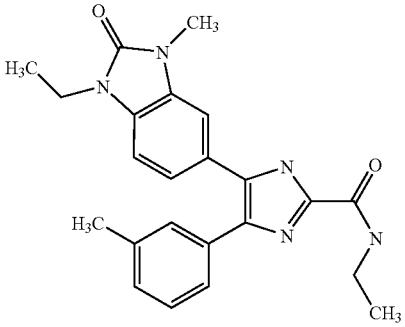 | 404.0 |
| 255 | 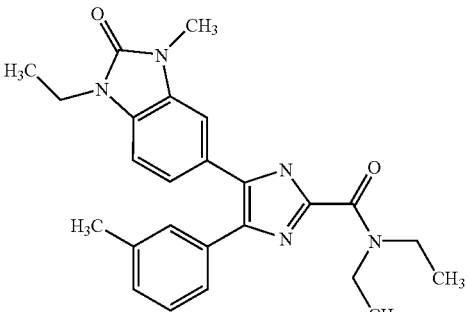 | 432.3 |

-continued

| EXAMPLE | Structure | Data MS (M + 1) |
|---|---|---|
| 256 | 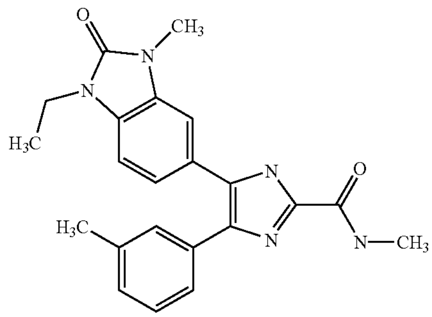 | 390.2 |
| 257 | 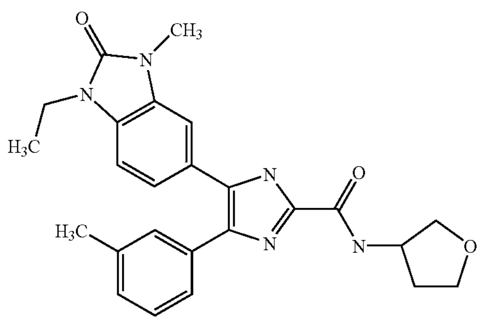 | 446.3 |
| 258 | 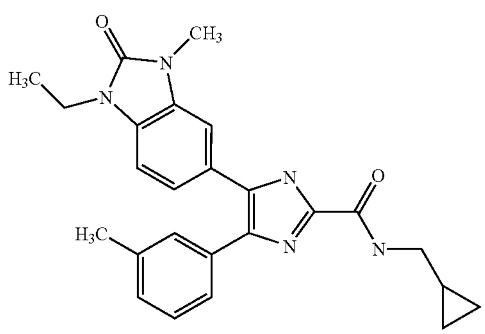 | 430.2 |
| 259 | 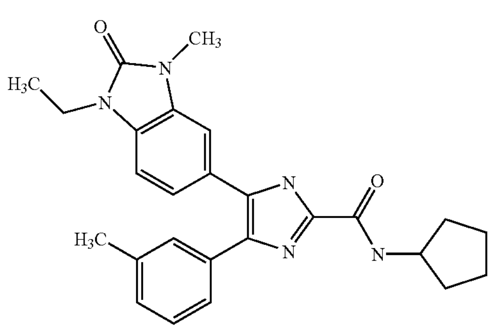 | 444.0 |

-continued
| EXAMPLE | Structure | Data MS (M + 1) |
|---|---|---|
| 260 | 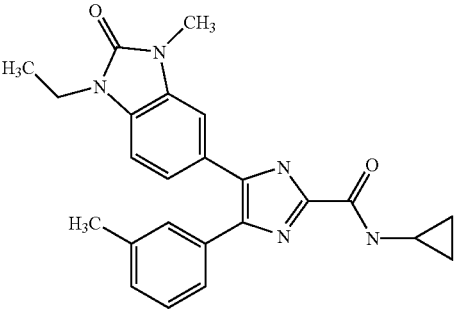 | 416.1 |
| 261 | 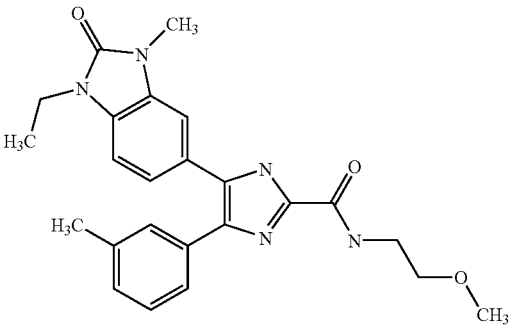 | 434.4 |
| 262 | 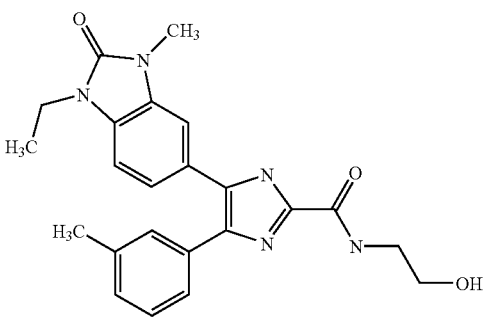 | 420.2 |

EXAMPLE 263

1-Isopropyl-3-methyl-5-(2-pyrazin-2-yl-5-m-tolyl-1H-imidazol-4-yl)-1,3-dihydro-benzoimidazol-2-one

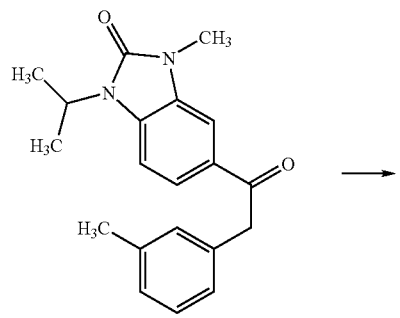

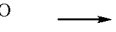

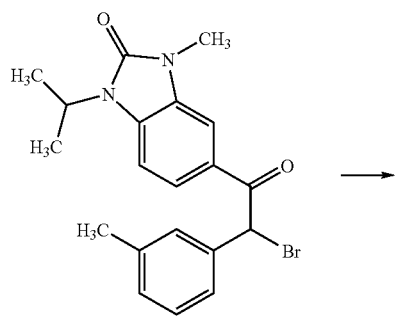

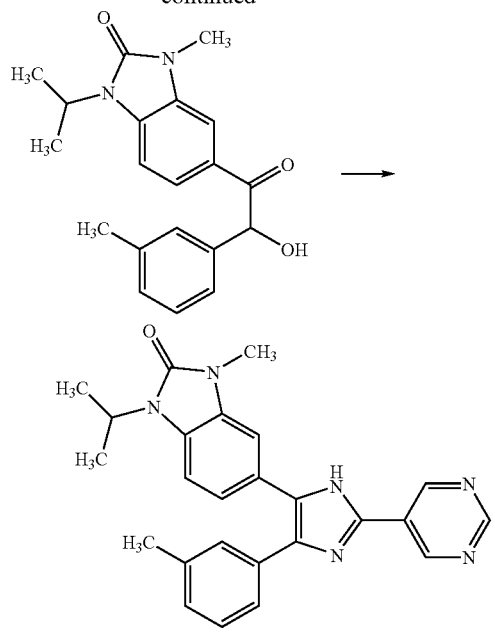

A stirred mixture of 5-(bromo-m-tolyl-acetyl)-1-isopropyl-3-methyl-1,3-dihydro-benzoimidazol-2-one (prepared as described in example 142, 0.5 gm, 1.25 mmol), pyrazine-2-carboxamidine hydrochloride (0.395 gm, 2,49 mmol) cesium carbonate (1.22 gm, 3.74 mmol) and DMF (4.0 mL) was heated to 60° C. After 1 hour, the reaction was determined to be complete by LCMS. The reaction was cooled to room temperature and diluted with water (40 mL). After stirring for 1 hour, the crude suspension was filtered and the solids were purified by flash chromatography (diethyl ether, followed by ethyl acetate) to afford 40 mg of the title compound as a light tan solid. MS (M+1)=425.1

The following examples were prepared using the method described for example 263.

| EXAMPLE | Structure | Data MS (M + 1) |
|---|---|---|
| 264 | 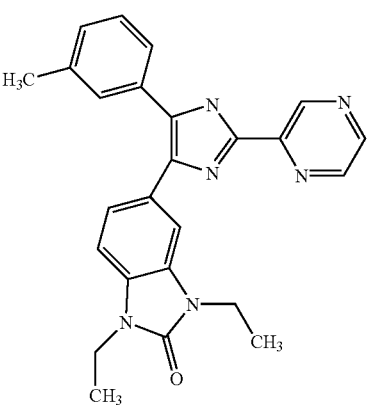 | 425.2 |

-continued

| EXAMPLE | Structure | Data MS (M + 1) |
| --- | --- | --- |
| 265 | 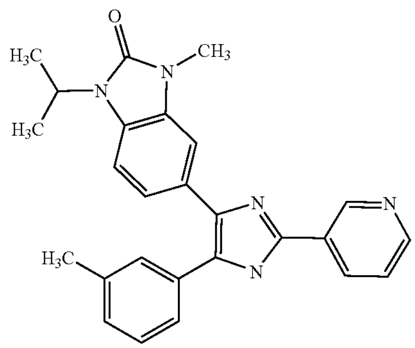 | 424.2 |
| 266 | 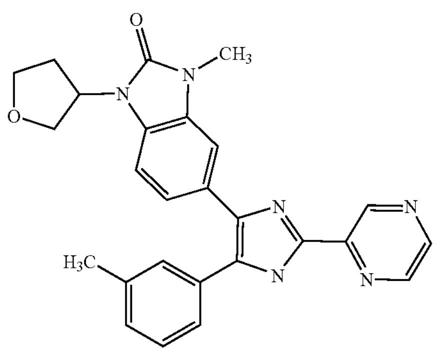 | 453.2 |
| 267 | 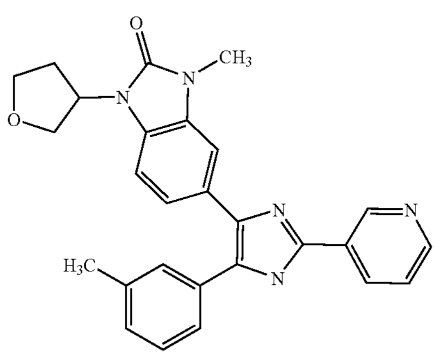 | 452.2 |
| 268 | 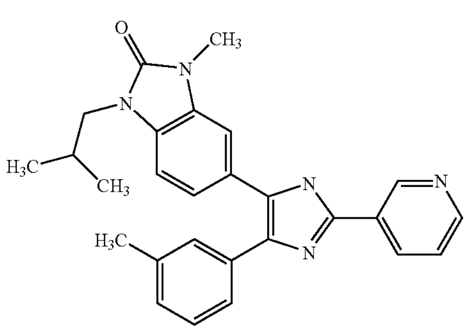 | 438.2 |

-continued

| EXAMPLE | Structure | Data MS (M + 1) |
|---------|-----------|-----------------|
| 269 | 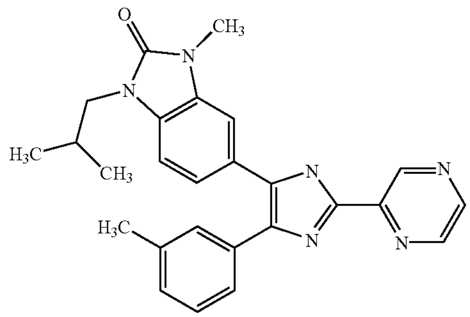 | 439.2 |
| 270 | 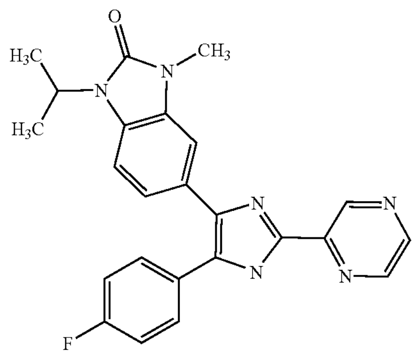 | 429.1 |
| 271 | 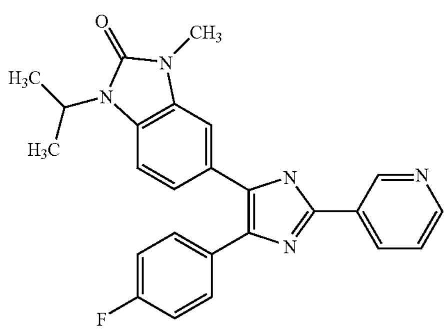 | 428.1 |
| 272 | 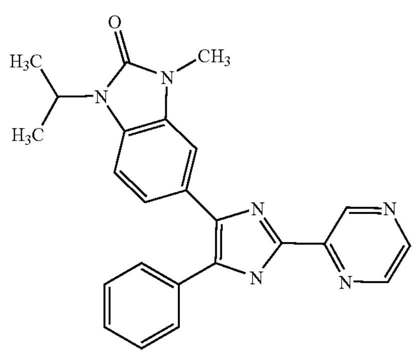 | 411.2 |

-continued
| EXAMPLE | Structure | Data MS (M + 1) |
|---|---|---|
| 273 | 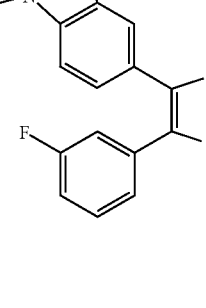 | 429.1 |
| 274 | 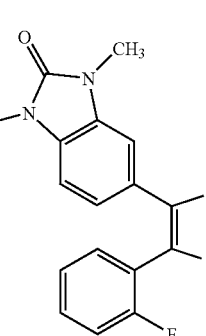 | 429.2 |
| 275 | 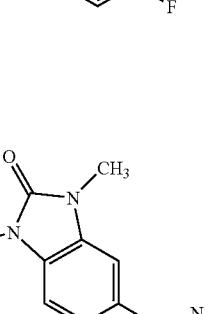 | 397.0 |
| 276 | 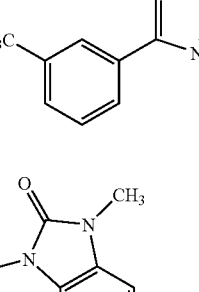 | 445.4 |

-continued

| EXAMPLE | Structure | Data MS (M + 1) |
|---------|-----------|-----------------|
| 277 | 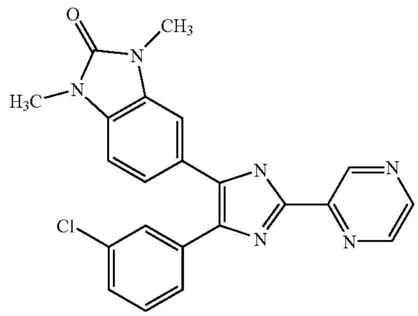 | 417.4 |
| 278 | 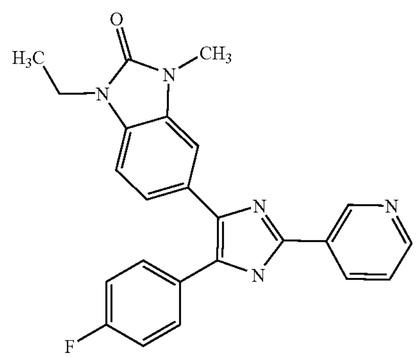 | 414.2 |
| 279 | 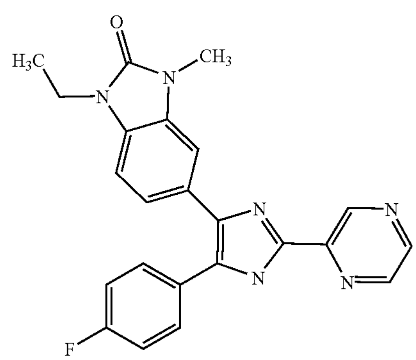 | 415.2 |
| 280 | 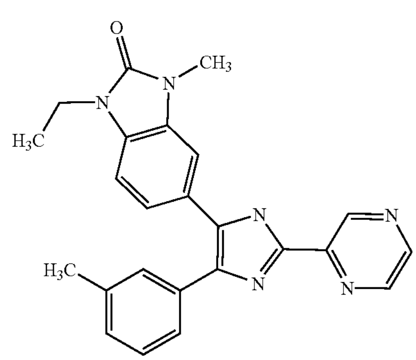 | 411.2 |

-continued

| EXAMPLE | Structure | Data MS (M + 1) |
|---------|-----------|-----------------|
| 281 | 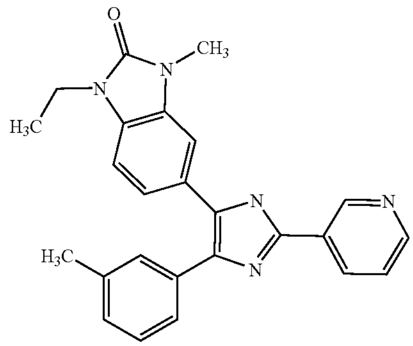 | 410.2 |
| 282 | 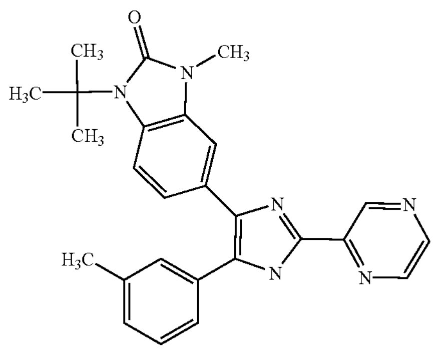 | 439.3 |
| 283 | 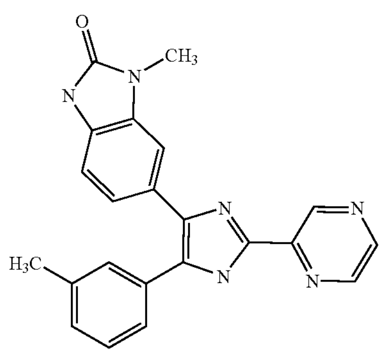 | 383.2 |
| 284 | 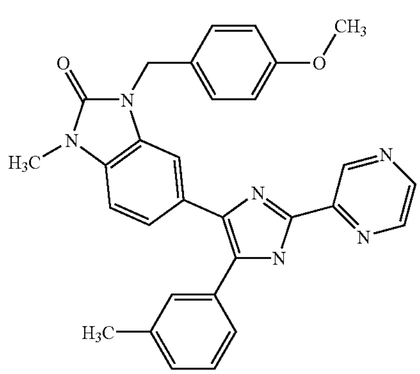 | 503.2 |

-continued

| EXAMPLE | Structure | Data MS (M + 1) |
|---------|-----------|-----------------|
| 285 | 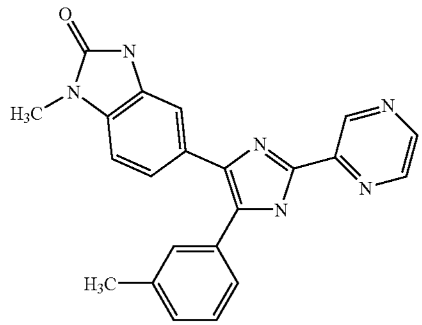 | 383.2 |
| 286 | 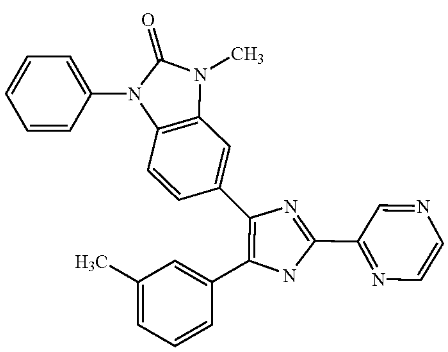 | 459.2 |
| 287 | 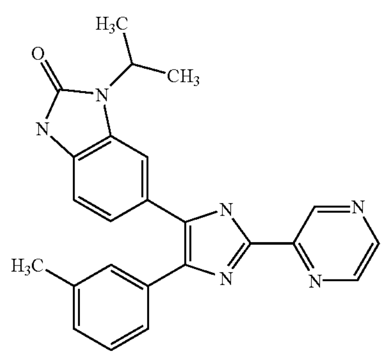 | 411.1 |
| 288 | 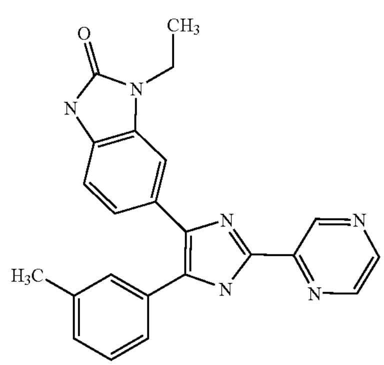 | 397.1 |

-continued

| EXAMPLE | Structure | Data MS (M + 1) |
|---|---|---|
| 289 | 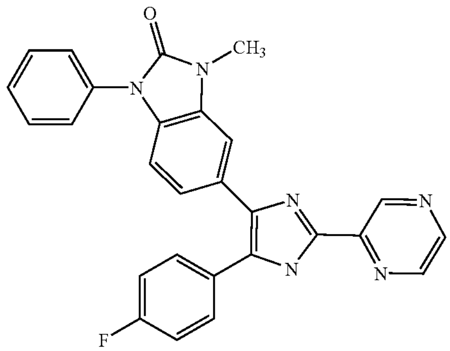 | 463.2 |
| 290 | 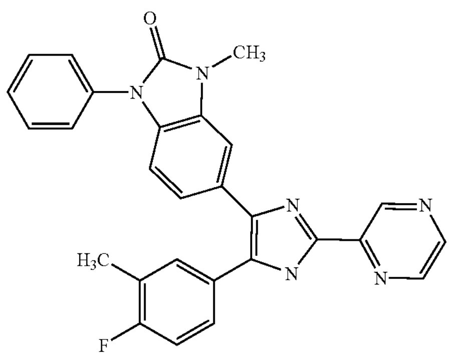 | 477.3 |

EXAMPLE 291

3-METHYL-1-THIOPHEN-3-YL-5-(5-M-TOLYL-3H-IMIDAZOL-4-YL)-1,3-DIHYDRO-BENZOIMIDAZOL-2-ONE

To a solution of 1-tert-butyl-3-methyl-5-(5-m-tolyl-1H-imidazol-4-yl)-1,3-dihydro-benzoimidazol-2-one (prepared as described previously, 100 mg, 0.277 mmol) in THF (1 mL) was added sodium hydride (12 mg of a 60% dispersion in mineral oil, 0.31 mmol). After 5 minutes, p-toluenesulfonyl chloride (58 mg, 0.31 mmol) was added, and the reaction was allowed to stir overnight. The reaction mixture was diluted with water and extracted with ethyl acetate. The organic phase was dried over anhydrous sodium sulfate and concentrated in vacuo to afford 140 mg of tolylated imidazole as a 1:1 mixture of regioisomers which was taken up in 1 mL of trifluoroacetic acid and treated with 0.25 mL of methanesulfonic acid. The mixture was allowed to stir for 2 hours, then diluted with methylene chloride and cautiously neutralized with aqueous sodium bicarbonate solution. The methylene chloride phase was dried over anhydrous sodium sulfate and concentrated in vacuo to afford 120 of a mixture of 1-methyl-6-[1-(toluene-4-sulfonyl)-5-m-tolyl-1H-imidazol-4-yl]-1,3-dihydro-benzoimidazol-2-one and 1-methyl-6-[3-(toluene-4-sulfonyl)-5-m-tolyl-3H-imidazol-4-yl]-1,3-dihydro-benzoimidazol-2-one. The following reaction was carried out using a modification of the procedure found in Chan, D. M. T.; Monaco, K. L.; Wang, R—P.; Winters, M. P. Tetrahedron Lett 1998, 39, 2933–2936. A mixture of the tosylated imidazoles (100 mg, 0.22 mmol), 3-thiopheneboronic acid (55.8 mg, 0.44 mmol), $Cu(OAc)_2$ (39.6 mg, 0.22 mmol), powdered molecular sieves (400 mg), triethylamine (60.8 μL, 0.44 mmol) in methylene chloride (1 mL) was stirred for three days. The mixture was poured on to a celite pad and the pad was eluted with ethyl acetate. The ethyl acetate was concentrated in vacuo to afford a tan solid that was taken up in THF (1 mL) and treated with concentrated aqueous HCl (1 mL). After 2 hours, the reaction was diluted with water and washed with diethyl ether. The aqueous phase was basified with aqueous ammonium hydroxide, then extracted with methylene chloride (2×40 mL). The methylene chloride was dried over anhydrous sodium sulfate and concentrated in vacuo to afford 65 mg of 3-methyl-1-thiophen-3-yl-5-(5-m-tolyl-3H-imidazol-4-yl)-1,3-dihydro-benzoimidazol-2-one. MS (M+1)=387.2

The following examples were prepared using the method described for example 291.

| EXAMPLE | Structure | Data MS (M + 1) |
|---|---|---|
| 291 | 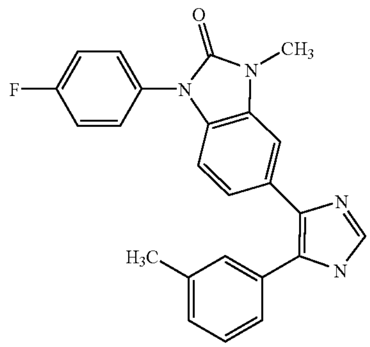 | 399.2 |
| 293 | 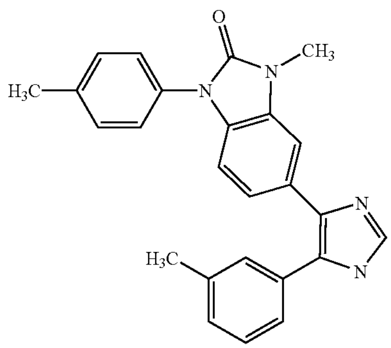 | 395.2 |
| 294 | 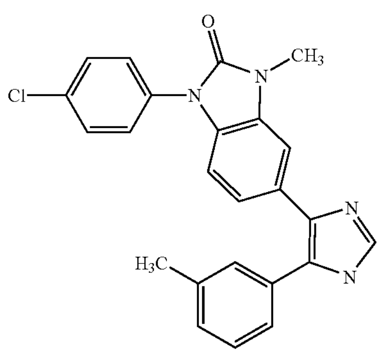 | 415.2 |
| 295 | 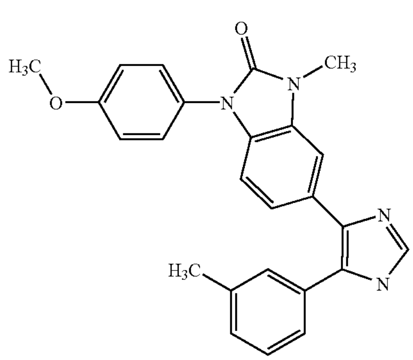 | 411.2 |

-continued

| EXAMPLE | Structure | Data MS (M + 1) |
|---------|-----------|-----------------|
| 296 | 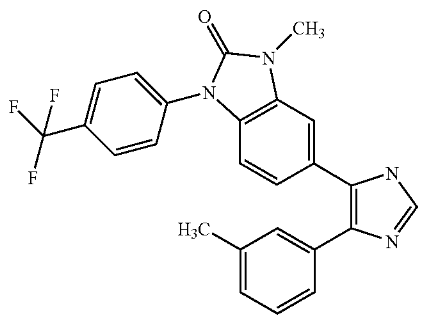 | 449.4 |
| 297 | 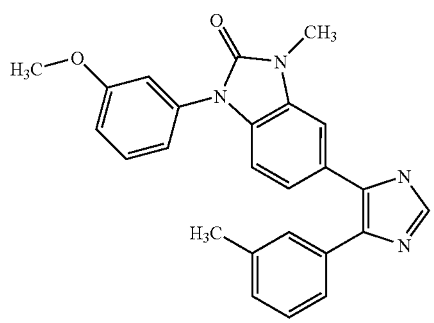 | 411.1 |
| 298 | 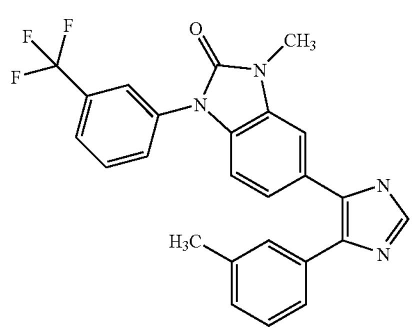 | 449.2 |
| 299 | 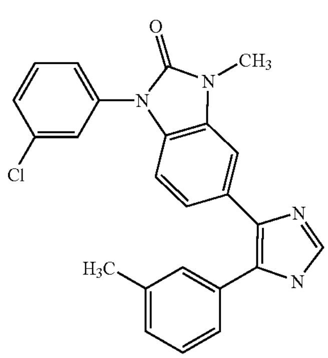 | 415.2 |

-continued

| EXAMPLE | Structure | Data MS (M + 1) |
| --- | --- | --- |
| 300 | 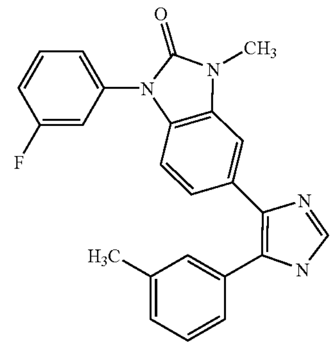 | 399.2 |
| 301 | 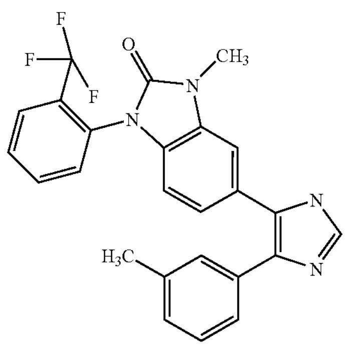 | 449.2 |
| 302 | 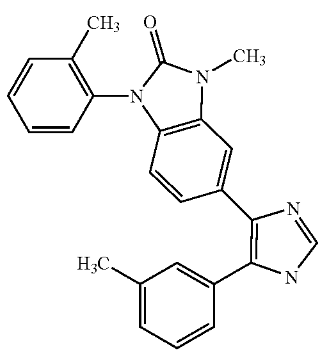 | 395.3 |
| 303 | 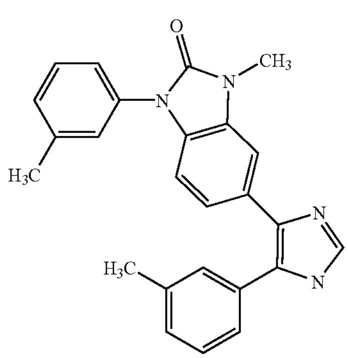 | 395.2 |

-continued

| EXAMPLE | Structure | Data MS (M + 1) |
|---|---|---|
| 304 | 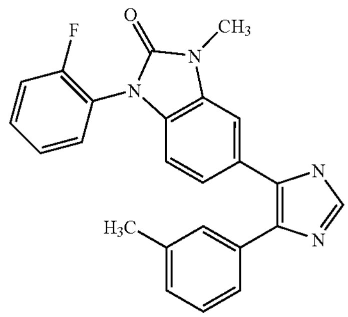 | 399.2 |
| 305 | 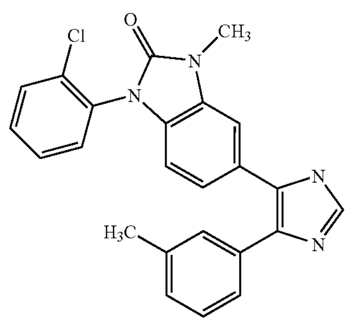 | 415.1 |
| 306 | 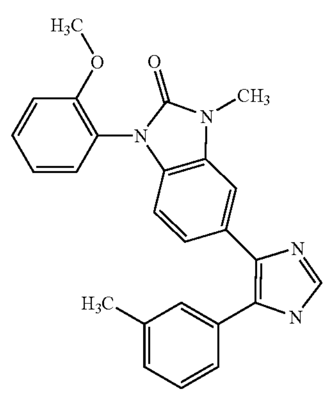 | 411.2 |
| 307 | 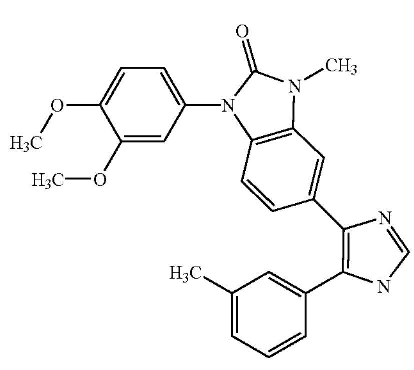 | 441.2 |

-continued

| EXAMPLE | Structure | Data MS (M + 1) |
|---------|-----------|-----------------|
| 308 | 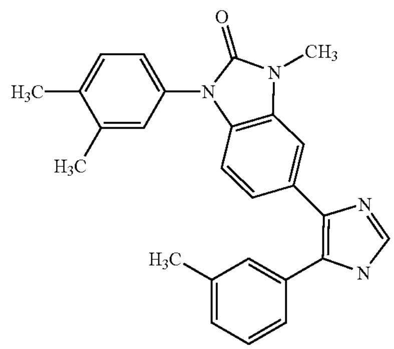 | 409.3 |
| 309 | 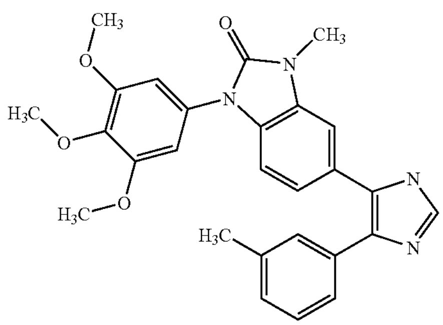 | 471.3 |
| 310 | 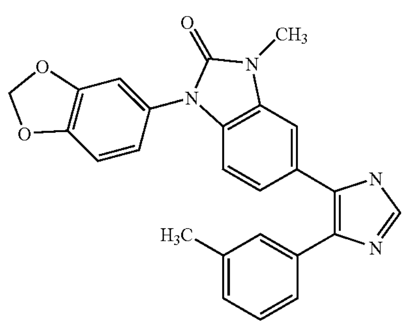 | 425.2 |
| 311 | 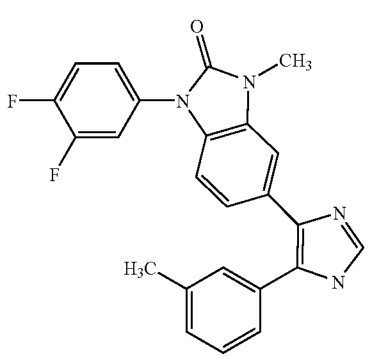 | 417.2 |

| EXAMPLE | Structure | Data MS (M + 1) |
|---|---|---|
| 312 | 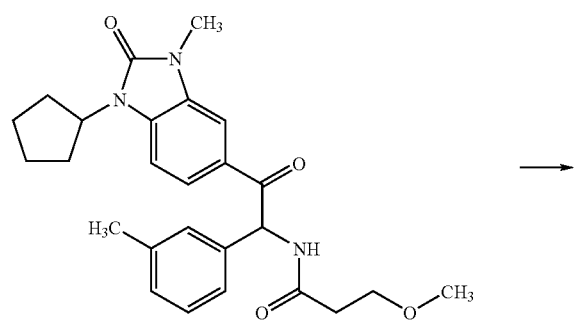 | 441.2 |

EXAMPLE 313

1(1-CYCLOPENTYL-3-METHYL-2-OXO-2,3-DIHYDRO-1H-BENZOIMIDAZOL-5-YL)-2-M-TOLYL-ETHANE-1,2-DIONE 2-OXIME

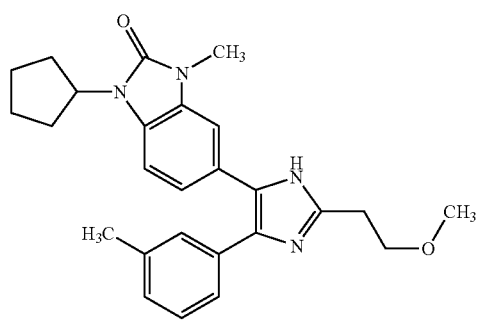

Sodium ethoxide (9.27 mL of a 21% solution in ethanol, 28.6 mmol) was added to ethanol (12 mL) at 0 deg C. After 5 minutes, 1-cyclopentyl-3-methyl-5-m-tolylacetyl-1,3-dihydro-benzoimidazol-2-one (prepared as described in the general procedure, 5 gm, 14.3 mmol) was added. n-Butyl nitrite (3.34 mL, 28.6 mmol) was then added dropwise over 5 minutes. When the addition was complete, the flask was covered with a septum and allowed to stand in the refrigerator overnight, after which time LCMS of an aliquot showed essentially complete reaction. The reaction mixture was diluted with 300 mL of water and allowed to stir at room temperature overnight. The resulting precipitate was filtered and dried in vacuo. The yellow solid was slurried with benzene for 2 hours and filtered to afford 4.0 gm of a pale tan solid. The title oxime is formed a ca. 10:1 mixture of isomers.

5-(2-Amino-1-hydroxy-2-m-tolyl-ethyl)-1-cyclopentyl-3-methyl-1,3-dihydro-benzoimidazol-2-one hydrochloride 1-(1-Cyclopentyl-3-methyl-2-oxo-2,3-dihydro-1H-benzoimidazol-5-yl)-2-m-tolyl-ethane-1,2-dione 2-oxime (5 gm, 13.2 mmol) was dissolved in ethanol (300 mL) in a Parr bottle. Concentrated HCl (3.3 mL, 40 mmol) was added, followed by 10% Pd on carbon (approximately 0.5 gm). The resulting mixture was placed on a Parr hydrogenation apparatus and hydrogenated at a hydrogen pressure of 40 psi. Hydrogen consumption slowed considerably after 3 hours, with the amino ketone being formed initially. Hydrogenation was continued overnight, after which time the reaction was determined to be complete. The mixture was filtered through a celite plug and the filtrate was concentrated in vacuo to afford a viscous yellow oil, which was triturated/repulped in diethyl ether to afford 4.90 gm of a white solid.

N-[2-(1-Cyclopentyl-3-methyl-2-oxo-2,3-dihydro-1H-benzoimidazol-5-yl)-2-hydroxy-1-m-tolyl-ethyl]-3-methoxy-propionamide To a stirred solution of 3-methoxypropionic acid (93.5 µL, 0.99 mmol) in methylene chloride (6 mL) and DMF (200 µL) was added oxalyl chloride (86.8 µL, 0.99 mmol). The resulting clear solution was stirred for 2 hours, then added via canula to a stirred solution of 5-( 2-amino-1-hydroxy-2-m-tolyl-ethyl)-1-cyclopentyl-3-methyl-1,3-dihydro-benzoimidazol-2-one hydrochloride (400 mg, 0.99 mmol) and triethyl amine (306 µL) in methylene chloride (4 mL). After 1 hour, LCMS showed complete reaction. Water was added to the reaction mixture and the organic phase was separated and washed with brine. The organic phase was dried over anhydrous sodium sulfate and concentrated in vacuo to afford 433 mg of the amide, which was used without further purification.

233

N-[2-(1-Cyclopentyl-3-methyl-2-oxo-2,3-dihydro-1H-benzoimidazol-5-yl)-2-oxo-1-m-tolyl-ethyl]-3-methoxy-propionamide N-[2-(1-Cyclopentyl-3-methyl-2-oxo-2,3-dihydro-1H-benzoimidazol-5-yl)-2-hydroxy-1-m-tolyl-ethyl]-3-methoxy-propionamide (433 mg, 0.96 mmol) was dissolved in methylene chloride (9.6 mL) and N-methylmorpholine N-oxide (168.7 mg, 1.44 mmol) was added. After stirring for ten minutes, TPAP (20.2 mg, 0.06 mmol) was added. The reaction was stirred for 1 hour, after which time LCMS and TLC (ethyl acetate) indicated complete reaction. The reaction mixture was poured into saturated aqueous sodium bicarbonate and additional methylene chloride was added. The organic phase was separated and washed with brine, followed by aqueous copper sulfate. The organic phase was then filtered through a plug of silica gel, eluting with ethyl acetate. Concentration of the filtrate afforded 294 mg of a white X solid that was used without further purification.

234

1-Cyclopentyl-5-[2-(2-methoxy-ethyl)-5-m-tolyl-3H-imidazol-4-yl]-3-methyl-1,3-dihydro-benzoimidazol-2-one N-[2-(1-Cyclopentyl-3-methyl-2-oxo-2,3-dihydro-1H-benzoimidazol-5-yl)-2-oxo-1-m-toly-ethyl]-3-methoxy-propionamide (294 mg, 0.65 mmol) was stirred with ammonium trifluoroacetate (857 mg, 6.5 mmol) and the mixture was heated to 150 deg C. in an oil bath. Occasionally, the sides of the flask were rinced down with methanol to insure all reactants were heated uniformly. A TLC (ethyl acetate) of the reaction mixture after 1 hour of heating showed complete reaction. The oil bath was removed, and hot water was added to the reaction mixture as it cooled. When the mixture reached room temperature, no precipitate formed, so the aqueous mixture was extracted with ethyl acetate (2×20 mL). The combined organic phase was washed with water and dried over anhydrous sodium sulfate to afford 240 mg of a tan solid. MS (M+1)=431.3.

The following examples were prepared using the method described for example 313.

| EXAMPLE | Structure | Data MS (M + 1) |
| --- | --- | --- |
| 314 | 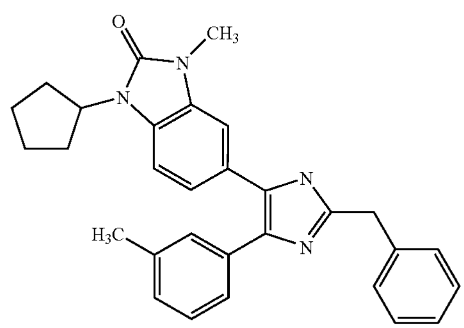 | 463.1 |
| 315 | 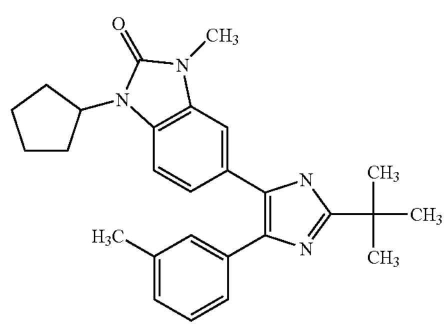 | 429.0 |
| 316 | 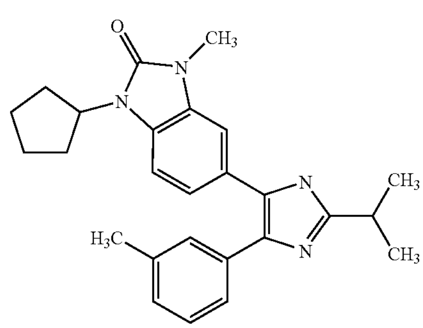 | 415.3 |

-continued
| EXAMPLE | Structure | Data MS (M + 1) |
|---|---|---|
| 317 | 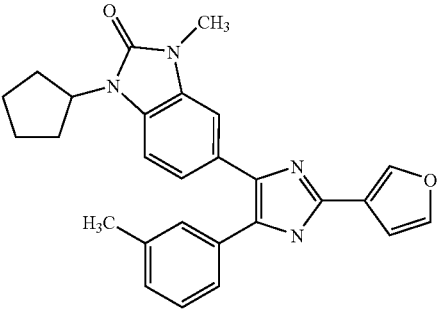 | 439.0 |
| 318 | 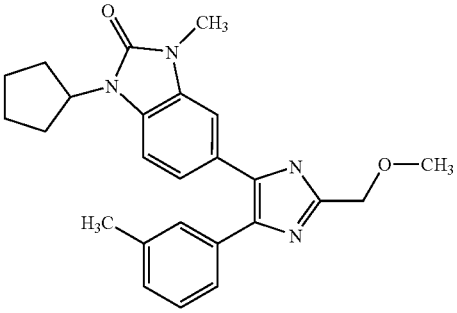 | 417.1 |
| 319 | 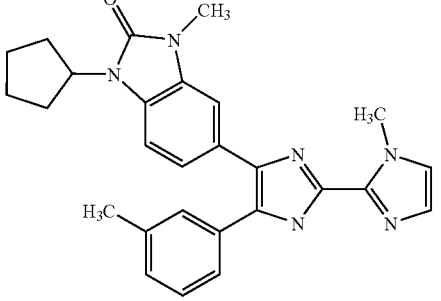 | 453.1 |
| 320 | 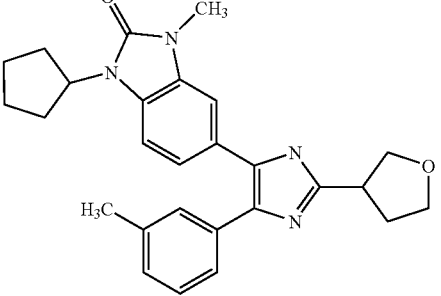 | 443.3 |

-continued
| EXAMPLE | Structure | Data MS (M + 1) |
|---------|-----------|-----------------|
| 321 | 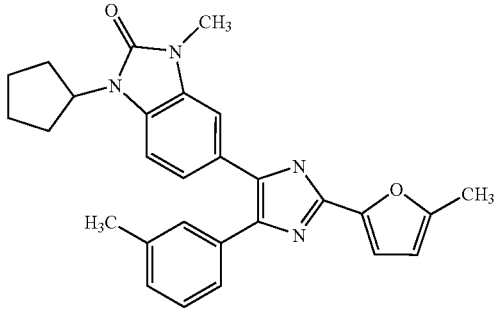 | 453.1 |
| 322 | 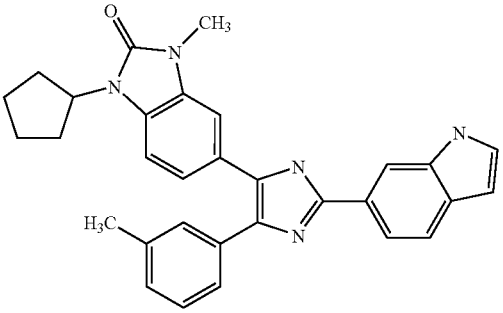 | 488.0 |
| 323 | 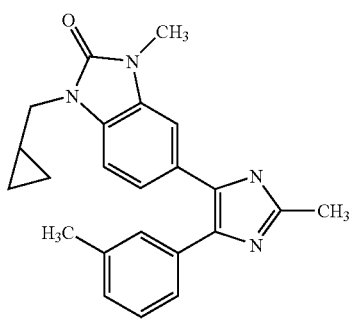 | 373.2 |
| 324 | 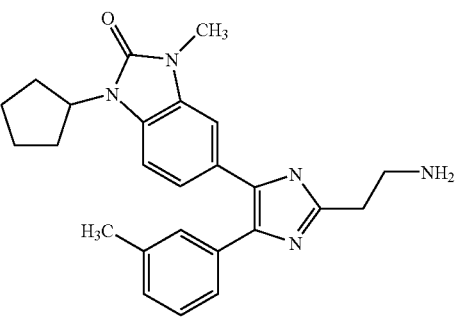 | 416.3 |

| EXAMPLE | Structure | Data MS (M + 1) |
|---------|-----------|-----------------|
| 325 | 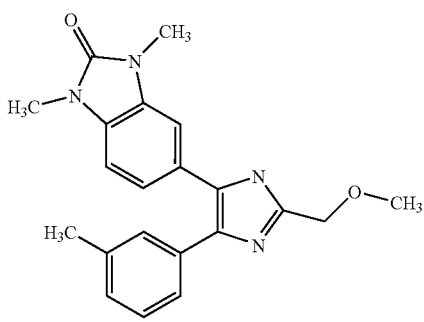 | 363.2 |
| 326 | 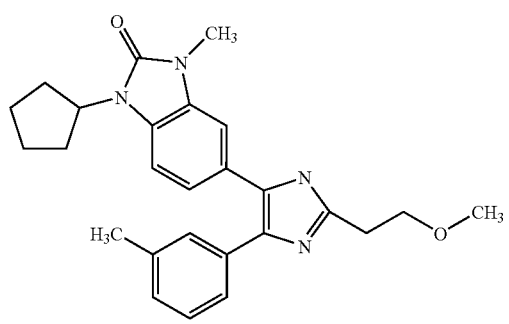 | 431.3 |
| 327 | 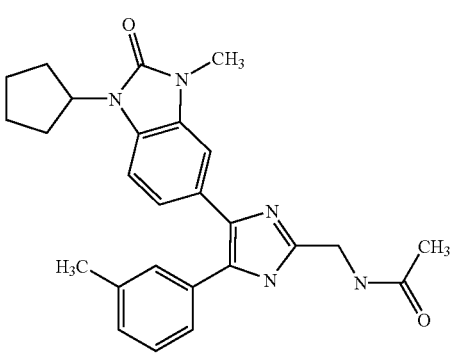 | 444.2 |
| 328 | 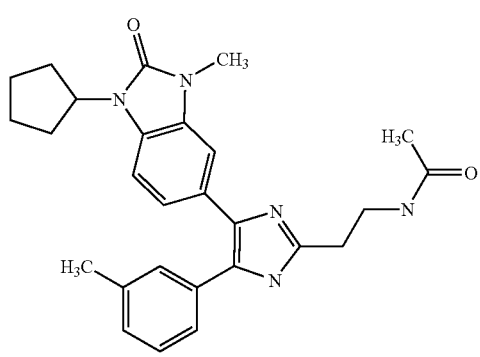 | 458.2 |

| EXAMPLE | Structure | Data MS (M + 1) |
|---|---|---|
| 329 | 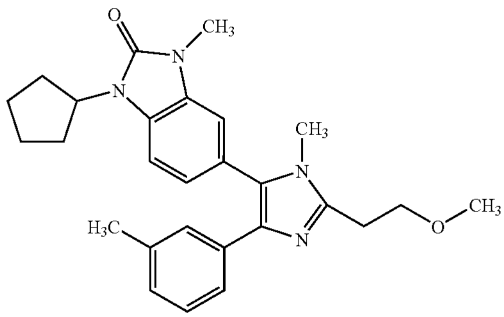 | 445.1 |

EXAMPLE 330

1,3-DIETHYL-5-(5-PYRIDIN-3-YL-2-M-TOLYL-1H-PYRROL-3-YL)-1,3-DIHYDRO-BENZOIMIDAZOL-2-ONE

2-(1,3-diethyl-2-oxo-2,3-dihydro-1H-benzoimidazol-5-yl)-4-pyridin-3-yl-1-m-tolyl-butane-1,4-dione To a cooled (0° C.) solution of 1,3-diethyl-5-(2-oxo-2-m-tolyl-ethyl)-1,3-dihydro-benzoimidazol-2-one (prepared as described previously, 500 mg, 1.55 mmol) in N,N-dimethylacetamide (DMA, 2.35 mL) was added NaH (124 mg of a 60% dispersion in mineral oil, 3.1 mmol). The slurry was stirred for 10 minutes, then a solution of 3-(Bromoacetyl) pyridine (310 mg, 1.55 mmol) in DMA (0.470 mL) was added. After 1 hour, the reaction was quenched with 3 mL of acetic acid and diluted with water. The aqueous was extracted with EtOAc (3×10 mL), the organics combined and washed with water, saturated sodium bicarbonate, then again with water. The organics were dried over anhydrous sodium sulfate and concentrated in vacuo to afford 600 mg of the title compound.

1,3-Diethyl-5-(5-pyridin-3-yl-2-m-tolyl-1H-pyrrol-3-yl)-1,3-dihydro-benzoimidazol-2-one A solution of 2-(1,3-diethyl-2-oxo-2,3-dihydro-1H-benzoimidazol-5-yl)-4-pyridin-3-yl-1-m-tolyl-butane-1,4-dione (600 mg, 1.13 mmol) and ammonium acetate (871 mg, 11.3 mmol) in acetic acid (3.77 mL) was heated at 110° C. for 4 hours. The reaction was then poured over a mixture of ice and NH₄OH and stirred for 5 minutes. The aqueous mixture was extracted with EtOAc (3×10 mL). The organics were combined, washed with brine, dried over sodium sulfate, and concentrated in vacuo to give a orange oil. The oil was purified by flash chromatography using a gradient of Et₂O to 50% EtOAc/Et₂O, affording 30 mg of the title compound. MS (M+1)=423.2.

EXAMPLE 331

1-(2-Chloro-phenyl)-3-methyl-5-(4-m-tolyl-oxazol-5-yl)-1,3-dihydro-benzoimidazol-2-one A slurry of 1-(2-chloro-phenyl)-3-methyl-2-oxo-2,3-dihydro-1H-benzoimidazole-5-carbaldehyde (prepared as described previously, 100 mg, 0.35 mmol), [(toluene-4-sulfonyl)-m-tolyl-methyl]-isonitrile (prepared as described previously, 110 mg, 0.38 mmol) and potassium carbonate (53.1 mg, 0.38 mmol) in DMF was heated to 60° C. overnight. The reaction mixture was cooled to room temperature and quenched with water. The resulting aqueous solution was extracted with ethyl acetate and the combined organic extracts were washed with brine, dried over anhydrous sodium sulfate and concentrated in vacuo to afford a brown oil. Purification by HPLC (30–80% acetonitrile/water gradient) afforded 40 mg of the title compound. MS (M+1)=416.3

The following examples were prepared using the method described for example 331.

| EXAMPLE | Structure | Data MS (M + 1) |
|---|---|---|
| 332 | 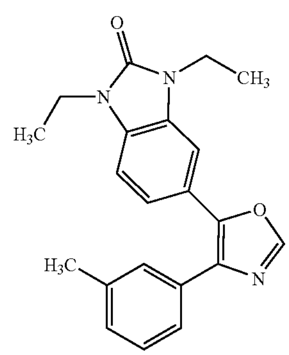 | 348.4 |
| 333 | 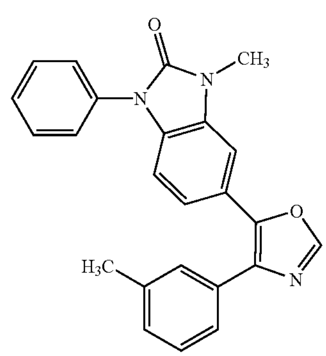 | 382.2 |

EXAMPLE 334

1-Cyclobutyl-3-methyl-5-(3-m-tolyl-1H-pyrazol-4-yl)-1,3-dihydro-benzoimidazol-2-one

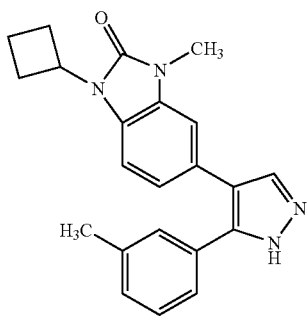

4-Fluoro-3-nitro-benzoic acid methyl ester

To a solution of 4-fluoro-3-nitro-benzoic acid (25 g, 0.135 mol) in dichloromethane (250 ml) at 23° C. was added dimethylformamide (0.5 ml) followed by dropwise addition of oxalyl chloride (15 ml, 0.172 mol). After stirring for 2 hours an aliquot was removed and confirmed to be product by $^1$H NMR. The entire sample was then concentrated under reduced pressure, diluted with dichloromethane (250 ml) and cooled to 0° C. The sample was then treated with a solution of triethylamine (37 ml, 0.266 mol) and methyl alcohol (43 ml, 0.939 mol) in dichloromethane (50 ml) added dropwise over 30 minutes. The reaction was allowed to warm to 23° C. After 2 hours the reaction was poured onto aqueous sodium bicarbonate and extracted with dichloromethane. The organic layer was dried with sodium sulfate and concentrated in vacuo to give 26.5 g of 4-fluoro-3-nitro-benzoic acid methyl ester as a solid.

4-Cyclobutylamino-3-nitro-benzoic acid methyl ester

To a solution of 4-fluoro-3-nitro-benzoic acid methyl ester (14.51 g, 50.9 mmol) in dichloromethane (150 ml) was added cyclobutylamine (14 ml, 164 mmol) slowly with cooling on an ice bath. After 2 hours at 23° C. the reaction was diluted with water and extracted with dichloromethane. The organic layer was dried with sodium sulfate and concentrated in vacuo to give 18.95 g of 4-cyclobutylamino-3-nitro-benzoic acid methyl ester.

3-Amino-4-cyclobutylamino-benzoic acid methyl ester

To a solution of 4-cyclobutylamino-3-nitro-benzoic acid methyl ester (18.959, 56.3 mmol) in ethyl alcohol (300 ml) in a Parr shaker was added 10% Pd/C (0.67 g). The reaction was subjected to an atmosphere of hydrogen (50 psi) until the consumption of hydrogen ceased (2 hours). The reaction mixture was filtered through a pad of Celite® and concentrated to give 15.94 g of 3-Amino-4-cyclobutylamino-benzoic acid methyl ester as a solid.

1-Cyclobutyl-2-oxo-2,3-dihydro-1H-benzoimidazole-5-carboxylic acid methyl ester To a solution of 3-amino-4-cyclobutylamino-benzoic acid methyl ester (15.94 g, 72.3 mmol) in dichloromethane (250 ml) at 23 C was added phosgene (38.3 ml of a 20% solution in toluene) dropwise over 30 minutes. The reaction was allowed to stand for 2 hours then was diluted with water and extracted with ethyl acetate. The organic layer was dried with sodium sulfate and concentrated in vacuo to give 17.01 g of 1-cyclobutyl-2-oxo-2,3-dihydro-1H-benzoimidazole-5-carboxylic acid methyl ester.

1-Cyclobutyl-3-methyl-2-oxo-2,3-dihydro-1H-benzoimidazole-5-carboxylic acid methyl ester To a solution of 1-cyclobutyl-2-oxo-2,3-dihydro-1H-benzoimidazole-5-carboxylic acid methyl ester (17.01 g, 69.1 mmol) in methyl sulfoxide (60 ml) was added sodium hydride (2.76 g as a 60% dispersion in oil, 69 mmol). The reaction mixture was stirred for 30 minutes prior to the dropwise addition of iodomethane (4.3 ml, 69.1 mmol). The reaction was stirred for 1 hour, was diluted with water and extracted with ethyl acetate. The organic layer was dried with sodium sulfate and concentrated in vacuo to give 17.76 g of 1-Cyclobutyl-3-methyl-2-oxo-2,3-dihydro-1H-benzoimidazole-5-carboxylic acid methyl ester.

1-Cyclobutyl-5-hydroxymethyl-3-methyl-1,3-dihydro-benzoimidazol-2-one

To a tetrahydrofuran (150 mL) solution of 1-Cyclobutyl-2-oxo-2,3-dihydro-1H-benzoimidazole-5-carboxylic acid methyl ester 16.35 g, 62.8 mmol) was added lithium borohydride (63 mL, 2.0 M in tetrahydrofuran). The mixture was heated to 65° C. then methanol (2.5 mL) was added. The reaction was complete after 0.5 hours and was cooled and extracted into ethyl acetate from saturated ammonium chloride. The organic layer was washed with water and brine, dried over sodium sulfate and concentrated to give 13.79 g of 1-Cyclobutyl-5-hydroxymethyl-3-methyl-1,3-dihydro-benzoimidazol-2-one.

5-Chloromethyl-1-cyclobutyl-3-methyl-1,3-dihydro-benzoimidazol-2-one

1-Cyclobutyl-5-hydroxymethyl-3-methyl-1,3-dihydro-benzoimidazol-2-one (13.79 g, 59.4 mmol) was diluted with dichloromethane (300 mL) and triethylamine (12.4 mL). The reaction was cooled to 0° C. and methanesulfonyl chloride (6.9 mL, 89.1 mmol) was added. The mixture was stirred for 1 hour at 0° C. then was diluted with saturated sodium bicarbonate and extraced into dichloromethane. The organic layer was dried over sodium sulfate and concentrated. The resulting oil was filtered through silica gel using ethyl acetate containing 1% triethylamine as eluent to give 11.92 g of 5-Chloromethyl-1-cyclobutyl-3-methyl-1,3-dihydro-benzoimidazol-2-one.

1-Cyclobutyl-3-methyl-2-oxo-2,3-dihydro-1H-benzoimidazol-5-yl)-acetonitrile

To a solution of 5-Chloromethyl-1-cyclobutyl-3-methyl-1,3-dihydro-benzoimidazol-2-one (11.92 g, 47.5 mmol) in methyl sulfoxide (50 mL) was added sodium cyanide (6.6 g). The reaction was heated to 90° C. for 2 hours then was cooled, diluted with water and extracted into ethyl acetate.

The organic layer was washed with brine, dried over sodium sulfate and concentrated to give (1-Cyclobutyl-3-methyl-2-oxo-2,3-dihydro-1H-benzoimidazol-5-yl)-acetonitrile (11.5 g).

1-Cyclobutyl-3-methyl-2-oxo-2,3-dihydro-1H-benzoimidazol-5-yl)-acetic Acid (1-Cyclobutyl-3-methyl-2-oxo-2,3-dihydro-1H-benzoimidazol-5-yl)-acetonitrile (11.5 g) was diluted with sulfuric acid:water (1:1, 25 mL) and was heated to 110° C. for 4 hour then cooled and extracted into ethyl acetate, dried over sodium sulfate and concentrated to give 11.99 g of (1-Cyclobutyl-3-methyl-2-oxo-2,3-dihydro-1H-benzoimidazol-5-yl)-acetic acid.

2-(3-Cyclobutyl-1-methyl-2-oxo-2,3-dihydro-1H-benzoimidazol-5-yl)-N-methoxy-N-methyl-acetamide (1-Cyclobutyl-3-methyl-2-oxo-2,3-dihydro-1H-benzoimidazol-5-yl)-acetic acid (11.99 g) was diluted with dichloromethane (200 mL) and was treated with carbonyl diimidazole (7.5 g). After 0.5 hour the mixture was treated with N,O-dimethylhydroxylamine hydrochloride (4.4 g) and was stirred at 23° C. for 18 hours. The mixture was then diluted with saturated sodium bicarbonate and extracted into dichloromethane. The organic layer was dried over sodium sulfate and concentrated to give 7.21 g of 2-(3-Cyclobutyl-1-methyl-2-oxo-2,3-dihydro-1H-benzoimidazol-5-yl)-N-methoxy-N-methyl-acetamide.

3-Cyclobutyl-1-methyl-5-(2-oxo-2-m-tolyl-ethyl)-1,3-dihydro-benzoimidazol-2-one

To a tetrahydrofuran (40 mL) solution of Cyclobutyl-1-methyl-2-oxo-2,3-dihydro-1H-benzoimidazol-5-yl)-N-methoxy-N-methyl-acetamide (2.83 g, 9.3 mmol) at −78° C. was added 3-methylphenyl magnesium bromide (11.2 mL, 1M in tetrahydrofuran). The mixture was allowed to warm to 23° C., was diluted with saturated ammonium chloride and extracted into ethyl acetate. The organic layer was dried with sodium sulfate and concentrated. Subsequent chromatography on silica gel gave 3-Cyclobutyl-1-methyl-5-(2-oxo-2-m-tolyl-ethyl)-1,3-dihydro-benzoimidazol-2-one (1.38 g).

1-Cyclobutyl-3-methyl-5-(3-m-tolyl-1H-pyrazol-4-yl)-1,3-dihydro-benzoimidazol-2-one To a flask containing 3-Cyclobutyl-1-methyl-5-(2-oxo-2-m-tolyl-ethyl)-1,3-dihydro-benzoimidazol-2-one (0.469 g, 1.4 mmol) was added dimethylformamide-dimethyl acetal (3 mL). The mixture was heated to 80° C. for 3 hours. After cooling, the reaction mixture was concentrated then diluted with ethanol (5 mL) and hydrazine (0.5 mL) and allowed to stand for 3 hours. Upon concentration of this mixture 1-Cyclobutyl-3-methyl-5-(3-m-tolyl-1H-pyrazol-4-yl)-1,3-dihydro-benzoimidazol-2-one (400 mg) was obtained.

EXAMPLE 335

1-Cyclobutyl-5-[5-(3-dimethylamino-propylamino)-3-m-tolyl-1H-pyrazol-4-yl]-3-methyl-1,3-dihydro-benzoimidazol-2-one

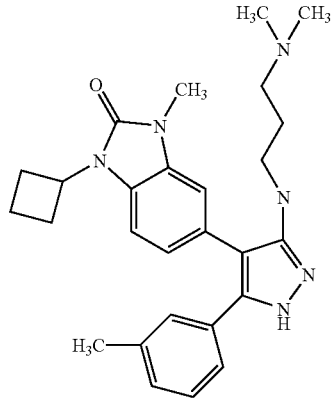

A pyridine (2 mL) solution of 3-Cyclobutyl-1-methyl-5-(2-oxo-2-m-tolyl-ethyl)-1,3-dihydro-benzoimidazol-2-one (220.7 mg, 0.66 mmol) was treated with sodium hydride (37,5 mg, 60% oil dispersion). After 0.5 hours (3-Isothiocyanato-propyl)-dimethyl-amine (2 equivalents) was added. After 1 hour the reaction was diluted with water and ethyl acetate and extracted into ethyl acetate. The organic layer was dried with sodium sulfate and concentrated. The residue was diluted with ethanol (2 mL) and hydrazine (0.5 mL) and allowed to stand for 18 hours at 23° C. The mixture was extracted with ethyl acetate and water, dried over sodium sulfate and concentrated. Preparative thin layer chromatography followed by the addition of hydrochloric acid in ether and concentrate ion gave 1-Cyclobutyl-5-[5-(3-dimethylamino-propylamino)-3-m-tolyl-1H-pyrazol-4-yl]-3-methyl-1,3-dihydro-benzoimidazol-2-one (50.1 mg) as the hydrochloride salt.

EXAMPLE 336

5-[5-Amino-1-(2-hydroxy-ethyl)-3-m-tolyl-1H-pyrazol-4-yl]-1-cyclobutyl-3-methyl-1,3-dihydro-benzoimidazol-2-one

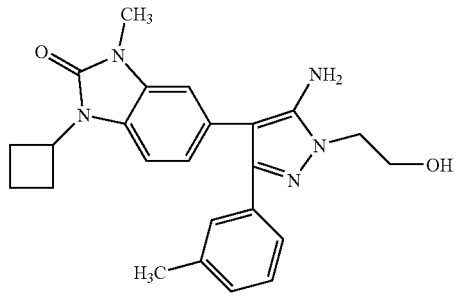

2-(1-Cyclobutyl-3-methyl-2-oxo-2,3-dihydro-1H-benzoimidazol-5-yl)-3-oxo-3-m-tolyl-propionitrile Sodium metal (1.2 g) was diluted with ethanol (12 mL). After dissolution (1-Cyclobutyl-3-methyl-2-oxo-2,3-dihydro-1H-benzoimidazol-5-yl)-acetonitrile (2.0 g, 8.29 mmol) was added followed by ethyl 3-methyl benzoate (2.0 mL). The reaction was heated to 75° C. for 2.5 hours then cooled and extracted into ethyl acetate from saturated sodium bicarbonate. Chromatography on silica gel gave the desired 2-(1-Cyclobutyl-3-methyl-2-oxo-2,3-dihydro-1H-benzoimidazol-5-yl)-3-oxo-3-m-tolyl-propionitrile.

5-[5-Amino-1-(2-hydroxy-ethyl)-3-m-tolyl-1H-pyrazol-4-yl]-1-cyclobutyl-3-methyl-1,3-dihydro-benzoimidazol-2-one 2-(1-Cyclobutyl-3-methyl-2-oxo-2,3-dihydro-1H-benzoimidazol-5-yl)-3-oxo-3-m-tolyl-propionitrile (66.5 mg, 0.19 mmol) was diluted with 2-propanol (0.4 mL) and acetic acid (0.8 mL). Hydroxyethyl hydrazine was then added (0.1 mL) and the mixture was heated to 70° C. for 8 hours. The reaction was cooled, poured onto saturated sodium bicarbonate and extracted with ethyl acetate. The organic layer was dried with sodium sulfate and concentrated. Preparative thin layer chromatography gave 5-[5-Amino-1-(2-hydroxy-ethyl)-3-m-tolyl-1H-pyrazol-4-yl]-1-cyclobutyl-3-methyl-1,3-dihydro-benzoimidazol-2-one (27.6 mg).

EXAMPLE 337

1,3-Dimethyl-5-(3-methyl-5-m-tolyl-1H-pyrazol 4-yl)-1,3-dihydro-benzoimidazol-2-one

1,3-Diethyl-2-oxo-2,3-dihydro-1H-benzoimidazole-5-carbaldehyde

To a dichloromethane (50 mL) solution of oxalyl chloride (1.47 mL, 16.8 mmol) at −78° C. was added methyl sulfoxide (1.47 mL, 20.5 mmol). After 15 minutes 1-Cyclobutyl-5-hydroxymethyl-3-methyl-1,3-dihydro-benzoimidazol-2-one (2.21 g, 10.0 mmol, in 20 mL dichloromethane) was added. After 20 minutes triethylamine (4.26 mL, 20.6 mmol) was added and the reaction was allowed to warm to 23° C. Upon dilution with saturated sodium bicarbonate and dichloromethane the product was extracted into dichloromethane. The organic layer was dried over sodium sulfate and concentrated to give 1,3-Diethyl-2-oxo-2,3-dihydro-1H-benzoimidazole-5-carbaldehyde (2.17 g).

1,3-Dimethyl-5-(2-nitro-propenyl)-1,3-dihydro-benzoimidazol-2-one 1,3-Dimethyl-2-oxo-2,3-dihydro-1H-benzoimidazole-5-carbaldehyde (2.48 g, 13.1 mmol, obtained using the same procedure used for 1,3-Diethyl-2-oxo-2,3-dihydro-1H-benzoimidazole-5-carbaldehyde) in n-butanol (25 mL) was treated with □-alanine (298.0 mg) and nitroethane (1.85 mL). The mixture was heated to 115° C. for 4 hours, more nitroethane (0.5 mL) was added and the heating was continued for 2 hours. The reaction was allowed to cool, was filtered and washed with ether then dried to give 1,3-Dimethyl-5-(2-nitro-propenyl)-1,3-dihydro-benzoimidazol-2-one (2.229 g).

1,3-Dimethyl-5-(2-oxo-Propyl)-1,3-dihydro-benzoimidazol-2-one 1,3-Dimethyl-5-(2-nitro-propenyl)-1,3-dihydro-benzoimidazol-2-one (2.23 g) was dissolved in methanol (15 mL) and water (40 mL) and treated sequentially with iron (1.67 g) and iron trichloride hexahydrate (174.3 mg). After heating to 75° C. concentrated hydrochloric acid (8 mL) was added in portions over 0.5 hours. The mixture was stirred at 75° C. for 2.5 hours, cooled, treated with saturated sodium bicarbonate and extracted into ethyl acetate The organic layer was dried over sodium sulfate, and concentrated to give 1,3-Dimethyl-5-(2-oxo-propyl)-1,3-dihydro-benzoimidazol-2-one (1.465 g).

5-(1-Acetyl-2-m-tolyl-vinyl)-1,3-dimethyl-1,3-dihydro-benzoimidazol-2-one 1,3-Dimethyl-5-(2-oxo-propyl)-1,3-dihydro-benzoimidazol-2-one was diluted with toluene (30 mL) and treated with 3-methylbenzaldehyde (0.82 mL) and piperidine (0.3 mL). The mixture was placed in an oil bath set to a temperature of 145° C. and the flask was fitted with a pressure equalizing funnel containing 4 Å molecular sieves and equipped with a condenser. After 18 hours the mixture was allowed to cool and was concentrated. Chromatography on silica gel afforded 5-(1-Acetyl-2-m-tolyl-vinyl)-1,3-dimethyl-1,3-dihydro-benzoimidazol-2-one (1.077 g).

1,3-Dimethyl-5-(3-methyl-5-m-tolyl-1H-pyrazol-4-yl)-1,3-dihydro-benzoimidazol-2-one 5-(1-Acetyl-2-m-tolyl-vinyl)-1,3-dimethyl-1,3-dihydro-benzoimidazol-2-one (1.07 g) in acetic acid (5 mL) was treated with p-toluenesulfonhydrazide (0.685 g). The reaction mixture was heated to 115° C. for 5 hours. Additional p-toluenesulfonhydrazide (0.601 g) was added and the reaction was heated for an additional 4 hours. The mixture was then allowed to cool, was poured onto saturated sodium bicarbonate and extracted into ethyl acetate. Chromatography on silica gel afforded 1,3-Dimethyl-5-(3-methyl-5-m-tolyl-1H-pyrazol-4-yl)-1,3-dihydro-benzoimidazol-2-one (0.263 g).

EXAMPLE 338

2-[4-(1,3-Diethyl-2-oxo-2,3-dihydro-1H-benzoimidazol-5-yl)-3-m-tolyl-pyrazol-1-yl]-N-ethyl-acetamide

[4-(1,3-Diethyl-2-oxo-2,3-dihydro-1H-benzoimidazol-5-yl)-3-m-tolyl-pyrazol-1-yl]-acetic acid tert-butyl ester 1,3-Diethyl-5-(3-m-tolyl-1H-pyrazol-4-yl)-1,3-dihydro-benzoimidazol-2-one (310 mg, 0.896 mmol) was diluted with dioxane (4 mL) and treated with sodium hydride (61.4 mg, 60% oil dispersion). After stirring at 23° C. for 0.5 hour t-butyl bromoacetate (0.25 mL) was added and the mixture was allowed to stir for 1 hour then was poured onto saturated sodium bicarbonate and extracted with ethyl acetate. The organic layer was dried with sodium sulfate and concentrated. Silica gel chromatography gave [4-(1,3-Diethyl-2-oxo-2,3-dihydro-1H-benzoimidazol-5-yl)-3-m-tolyl-pyrazol-1-yl]-acetic acid tert-butyl ester (0.122 g) and [4-(1,3-Diethyl-2-oxo-2,3-dihydro-1H-benzoimidazol-5-yl)-5-m-tolyl-pyrazol-1-yl]-acetic acid tert-butyl ester (0.135 g).

[4-(1,3-Diethyl-2-oxo-2,3-dihydro-1H-benzoimidazol-5-yl)-3-m-tolyl-pyrazol-1-yl]-acetic acid

[4-(1,3-Diethyl-2-oxo-2,3-dihydro-1H-benzoimidazol-5-yl)-3-m-tolyl-pyrazol-1-yl]-acetic acid tert-butyl ester (0.122 g) was diluted with dichloromethane (1 mL) and trifluoroacetic acid (0.5 mL). Upon stirring for 18 hours at 23° C. the mixture was concentrated to give [4-(1,3-Diethyl-2-oxo-2,3-dihydro-1H-benzoimidazol-5-yl)-3-m-tolyl-pyrazol-1-yl]-acetic acid (0.107 g).

2-[4-(1,3-Diethyl-2-oxo-2,3-dihydro-1H-benzoimidazol-5-yl)-3-m-tolyl-pyrazol-1-yl]-N-ethyl-acetamide To a dichloromethane (2 mL) solution of [4-(1,3-Diethyl-2-oxo-2,3-dihydro-1H-benzoimidazol-5-yl)-3-m-tolyl-pyrazol-1-yl]-acetic acid (0.106 g) was added carbonyldiimidazole (0.055 g). After stirring at 23° C. for 0.5 hours ethyl amine (0.2 mL, 2M in tetrahydrofuran) was added. The reaction was stirred at 23° C. for an additional hour then was concentrated. Preparative thin layer chromatography gave 2-[4-(1,3-Diethyl-2-oxo-2,3-dihydro-1H-benzoimidazol-5-yl)-3-m-tolyl-pyrazol-1-yl]-N-ethyl-acetamide (0.075 g).

EXAMPLE 339

1,3-Diethyl-5-{1-[2-(2-methoxy-ethylamino)-ethyl]-3-m-tolyl-1H-pyrazol-4-yl}-1,3-dihydro-benzoimidazol-2-one

[4-(1,3-Diethyl-2-oxo-2,3-dihydro-1H-benzoimidazol-5-yl)-3-m-tolyl-pyrazol-1-yl]-acetaldehyde 5-(1-Allyl-3-m-tolyl-1H-pyrazol-4-yl)-1,3-diethyl-1,3-dihydro-benzoimidazol-2-one (obtained in the using the same procedure as utilized for the preparation of [4-(1,3-Diethyl-2-oxo-2,3-dihydro-1H-benzoimidazol-5-yl)-5-m-tolyl-pyrazol-1-yl]-acetic acid tert-butyl ester (0.135 g), substituting allyl iodide for t-butyl bromoacetate) (0.107 g) was diluted with t-butanol (3 mL). To this solution was added water (3 mL), sodium periodate (0.120 g) and catalytic osmium tetroxide (0.1 mL, 2.5% solution in t-butanol). The mixture was stirred at 23° C. for 2 hours then was diluted with ethylacetate and saturated sodium bicarbonate and extracted. The organic layer was dried over sodium sulfate and concentrated. Subsequent chromatography on silica gel gave [4-(1,3-Diethyl-2-oxo-2,3-dihydro-1H-benzoimidazol-5-yl)-3-m-tolyl-pyrazol-1-yl]-acetaldehyde (0.06 g).

1,3-Diethyl-5-{1-[2-(2-methoxy-ethylamino)-ethyl]-3-m-tolyl-1H-pyrazol-4-yl}-1,3-dihydro-benzoimidazol-2-one To a benzene (3 mL) solution of [4-(1,3-Diethyl-2-oxo-2,3-dihydro-1H-benzoimidazol-5-yl)-3-m-tolyl-pyrazol-1-yl]-acetaldehyde (0.034 g) was added methoxyethylamine (0.03 mL) and 4 Å molecular sieves. The reaction was allowed to stand at 23° C. for 1 hour then was filtered and concentrated. The resulting oil was diluted with methanol (2 mL), 4 Å molecular sieves were added and the mixture was treated with sodium cyanoborohydride (0.02 g). After stirring for 18 hours the mixture was poured onto ethyl acetate/saturated sodium bicarbonate and extracted. The organic layer was dried over sodium sulfate and concentrated. Preparative thin layer chromatography gave 1,3-Diethyl-5-{1-[2-(2-methoxy-ethylamino)-ethyl]-3-m-tolyl-1H-pyrazol-4-yl}-1,3-dihydro-benzoimidazol-2-one (0.014 g). Subsequent treatment with 1M hydrochloric acid in ether gave the hydrochloride salt.

EXAMPLE 340

1,3-Diethyl-5-[1-(3-ethylamino-2-hydroxy-propyl)-3-m-tolyl-1H-pyrazol-4-yl]-1,3-dihydro-benzoimidazol-2-one 1,3-Diethyl-5-(1-oxiranylmethyl-3-m-tolyl-1H-pyrazol-4-yl)-1,3-dihydro-benzoimidazol-2-one (obtained using a method similar to that for [4-(1,3-Diethyl-2-oxo-2,3-dihydro-1H-benzoimidazol-5-yl)-3-m-tolyl-pyrazol-1-yl]-acetaldehyde, substituting epibromohydrin for allyl iodide) (0.016 g) was diluted with diethylamine (0.3 mL, as a 70% solution in water) and stirred at 23° C. for 0.5 hours. Azeotropic removal of the water with toluene gave 1,3-Diethyl-5-[1-(3-ethylamino-2-hydroxy-propyl)-3-m-tolyl-1H-pyrazol-4-yl]-1,3-dihydro-benzoimidazol-2-one.

EXAMPLE 341

5-(5-Amino-3-m-tolyl-isoxazol-4-yl)-1,3-diethyl-1,3-dihydro-benzoimidazol-2-one

To a pyridine (1.5 mL) solution of 2-(1,3-Diethyl-2-oxo-2,3-dihydro-1H-benzoimidazol-5-yl)-3-oxo-3-m-tolyl-propionitrile (0.113 g) at 23° C. was added hydroxylamine hydrochloride (0.071 g). The reaction was heated to 30° C. for 1 hour then to 55° C. for 3 hours, cooled and extracted into ethyl acetate from 10% citric acid. The organic layer was dried over sodium sulfate and concentrated. The resulting powder was triturated with methanol and filtered to give 5-(5-Amino-3-m-tolyl-isoxazol-4-yl)-1,3-diethyl-1,3-dihydro-benzoimidazol-2-one (0.085 g).

EXAMPLE 342

1,3-Dimethyl-5-(5-methyl-3-phenyl-1H-pyrazol-4-yl)-1,3-dihydro-benzoimidazol-2-one is prepared according to the procedures outlined in Example 337. 1,3-Dimethyl-5-(5-methyl-3-phenyl-1H-pyrazol-4-yl)-1,3-dihydro-benzoimidazol-2-one (70.9 mg) is diluted with dichloromethane and is treated with triethylamine (0.1 mL) and acetyl chloride (0.05 mL). The mixture is allowed to stir for 20 minutes then is diluted with saturated sodium bicarbonate and extracted into dichloromethane. The organic layer is dried over sodium sulfate and concentrated to give 8 mg 5-(1-Acetyl-5-methyl-3-m-tolyl-1H-pyrazol-4-yl)-1,3-dimethyl-1,3-dihydro-benzoimidazol-2-one.

EXAMPLE 343

5-[2-(1-Benzyl-piperidin-4-yl)-3-m-tolyl-1H-pyrazol-4-yl]-1,3-diethyl-1,3-dihydro-benzoimidazol-2-one is prepared according to the procedures described in Example 334. 5-[2-(1-Benzyl-piperidin-4-yl)-3-m-tolyl-1H-pyrazol-4-yl]-1,3-diethyl-1,3-dihydro-benzoimidazol-2-one (180 mg) is diluted with ethanol (5 mL) and acetic acid (5 drops). The mixture is then treated with 5% Pd/C and shaken under an atmosphere of hydrogen for 8 hours. The mixture is then filtered and concentrated to give 1,3-Diethyl-5-(2-piperidin-4-yl-3-m-tolyl-1H-pyrazol-4-yl)-1,3-dihydro-benzoimidazol-2-one.

EXAMPLE 344

[4-(1,3-Diethyl-2-oxo-2,3-dihydro-1H-benzoimidazol-5-yl)-5-m-tolyl-pyrazol-1-yl]-acetic acid ethyl ester is prepared according to the procedures outlined in Example 334. [4-(1,3-Diethyl-2-oxo-2,3-dihydro-1H-benzoimidazol-5-yl)-5-m-tolyl-pyrazol-1-yl]-acetic acid ethyl ester (388 mg) is diluted with tetrahydrofuran (3 mL) and methanol (4 mL). Lithium borohydride (39 mg) is added and the mixture is stirred at 23° C. for 20 hours. The reaction mixture is diluted with saturated ammonium chloride and extracted with ethyl acetate. The organic layer is dried with sodium sulfate and concentrated. Chromatography on silica gel gave 3-Diethyl-5-[1-(2-hydroxy-ethyl)-5-m-tolyl-1H-pyrazol-4-yl]-1,3-dihydro-benzoimidazol-2-one. 3-Diethyl-5-[-(2-hydroxy-ethyl)-5-m-tolyl-1H-pyrazol-4-yl]-1,3-dihydro-benzoimidazol-2-one (86.5 mg) is diluted with pyridine, (1 mL) cooled to 0° C., and treated with methanesulfonyl chloride (0.02 mL). The reaction mixture is allowed to stir for 20 hours then is treated with water and extracted with dichloromethane. The organic layer is dried with sodium sulfate and concentrated to give Methanesulfonic acid 2-[4-(1,3-diethyl-2-oxo-2,3-dihydro-1H-benzoimidazol-5-yl)-5-m-tolyl-pyrazol-1-yl]-ethyl ester. Methanesulfonic acid 2-[4-(1,3-diethyl-2-oxo-2,3-dihydro-1H-benzoimidazol-5-yl)-5-m-tolyl-pyrazol-1-yl]-ethyl ester (104 mg) is diluted with morpholine (0.15 mL) and methanol (0.9 mL). The reaction is heated to 65° C. for 5 hours then allowed to stand at 23° C. for 20 hours. The reaction mixture is diluted with saturated sodium bacarbonate and extracted with ethyl acetate. Chromatography on silica gel gave 1,3-Diethyl-5-[1-(2-morpholin-4-yl-ethyl)-5-m-tolyl-1H-pyrazol-4-yl]-1,3-dihydro-benzoimidazol-2-one.

EXAMPLE 345

[4-(1,3-Diethyl-2-oxo-2,3-dihydro-1H-benzoimidazol-5-yl)-3-m-tolyl-pyrazol-1-yl]-acetaldehyde is prepared according to the procedures described in Example 339. [4-(1,3-Diethyl-2-oxo-2,3-dihydro-1H-benzoimidazol-5-yl)-3-m-tolyl-pyrazol-1-yl]-acetaldehyde (0.03 g) is diluted with methanol (0.5 mL) and is treated with sodium borohydride (0.005 g). The reaction is held at 23° C. for 20 hours. The product is purified on silica gel to give 1,3-Diethyl-5-[1-(2-hydroxy-ethyl)-3-m-tolyl-1H-pyrazol-4-yl]-1,3-dihydro-benzoimidazol-2-one.

EXAMPLE 346

[5-Amino-4-(1,3-diethyl-2-oxo-2,3-dihydro-1H-benzoimidazol-5-yl)-3-m-tolyl-pyrazol-1-yl]-acetic acid tert-butyl ester is prepared according to Example 338. [5-Amino-4-(1,3-diethyl-2-oxo-2,3-dihydro-1H-benzoimidazol-5-yl)-3-m-tolyl-pyrazol-1-yl]-acetic acid tert-butyl ester (0.06 g) is diluted with 50% trifluoroacetic acid is chloroform and stirred for 5 hours. The reaction is concentrated then treated sequentially with chloroform (2 mL) 1-hydroxybenzotriazole hydrate (0.026 g), diisopropylethylamine (0.06 mL) and 1-[3-(dimethylamino)propyl]-3-ethylcarbodiimide hydrochloride (0.036 g). The mixture is allowed to stir for 20 hours, is diluted with saturated sodium bicarbonate and extracted with ethyl acetate. After concentration the product is purified on silica gel to give 1,3-Diethyl-5-(2-oxo-6-m-tolyl-2,3-dihydro-1H-imidazo[1,2-b]pyrazol-7-yl)-1,3-dihydro-benzoimidazol-2-one.

EXAMPLE 347

5-(5-Amino-1-methyl-3-phenyl-1H-pyrazol-4-yl)-1-cyclobutyl-3-methyl-1,3-dihydro-benzoimidazol-2-one is prepared according to the methods described in Example 336. 5-(5-Amino-1-methyl-3-phenyl-1H-pyrazol-4-yl)-1-cyclobutyl-3-methyl-1,3-dihydro-benzoimidazol-2-one (0.05 g) is diluted with chloroform (0.5 mL) and is treated with triethyl amine (0.04 mL) and acetyl chloride (0.02 mL). The reaction is allowed to stir for 1 hour then is diluted with saturated sodium bicarbonate and extracted with ethyl acetate. After concentration of the organic layer the product is purified by silica gel chromatography to give N-[4-(1-Cyclobutyl-3-methyl-2-oxo-2,3-dihydro-1H-benzoimidazol-5-yl)-2-methyl-5-phenyl-2H-pyrazol-3-yl]-acetamide. Similar reaction conditions utilizing the appropriate isocyanate, chloroformate or sulfonyl halide can be used to prepare ureas, carbamates and sulfonamides.

The compounds of Example 348–628, were prepared according to one or more of the methods of Examples 334–347. Specific Examples methods used to prepare final products are identifed in the Method column in the Table below, although one skilled in the art will appreciate that certain products were prepared by the conversion of other final products.

TABLE 12

| EXAMPLE | MOLSTRUCTURE | | Method |
|---|---|---|---|
| 348 | (structure) | 319 (M + 1) | 337 |

TABLE 12-continued

| EXAMPLE | MOLSTRUCTURE | | Method |
|---|---|---|---|
| 349 | [structure] | 333.1 (M + 1) | 337 |
| 350 | [structure] | 337.1 (M + 1) | 337 |
| 351 | [structure] | 347.2 (M + 1) | 337 |
| 352 | [structure] | 361.2 (M + 1) | 337 |

TABLE 12-continued

| EXAMPLE | MOLSTRUCTURE | | Method |
|---|---|---|---|
| 353 | | 362.2 (M + 1) | 336 |
| 354 | | 375.1 (M + 1) | 342 |
| 355 | | 437.4 (M + 1) | 342 |
| 356 | | | 342 |

TABLE 12-continued
| EXAMPLE | MOLSTRUCTURE | | Method |
|---|---|---|---|
| 357 | 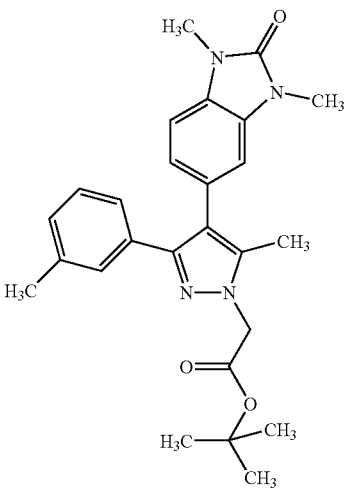 | 447.4 (M + 1) | 338 |
| 358 | 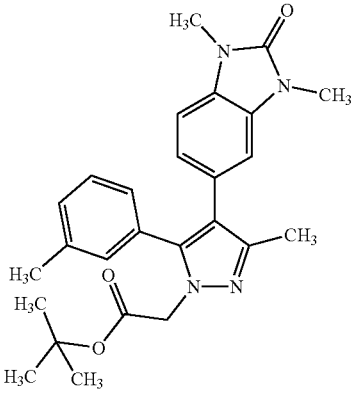 | 447.3 (M + 1) | 338 |
| 359 | 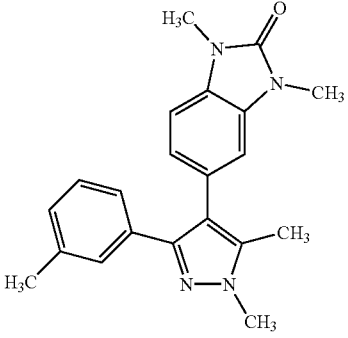 | 347.3 (M + 1) | 339 |

TABLE 12-continued
| EXAMPLE | MOLSTRUCTURE | | Method |
|---|---|---|---|
| 360 | 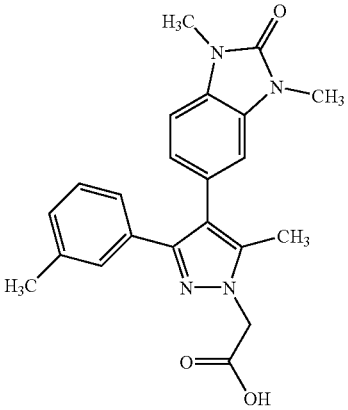 | 391.1 (M + 1) | 338 |
| 361 | 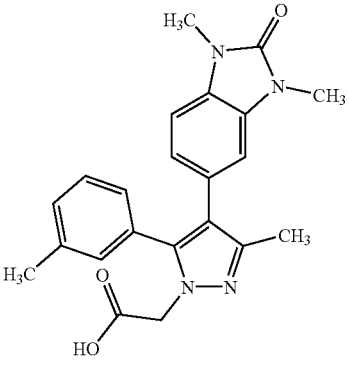 | 391.1 (M + 1) | 338 |
| 362 | 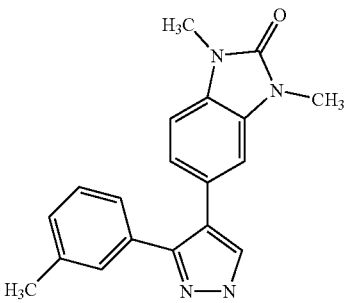 | | 334 |

TABLE 12-continued
| EXAMPLE | MOLSTRUCTURE | | Method |
|---|---|---|---|
| 363 | 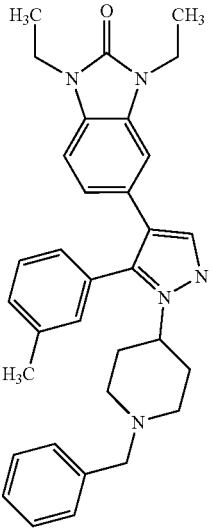 | 520.1 (M + 1) | 334 |
| 364 | 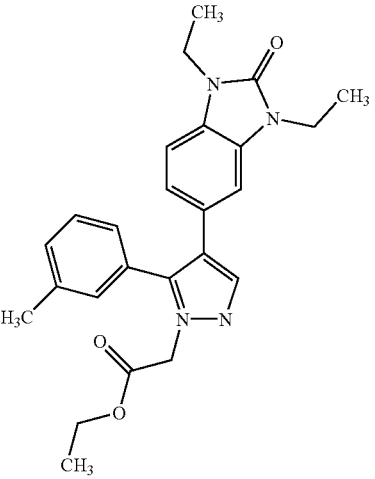 | 433 (M + 1) | 338 |
| 365 | 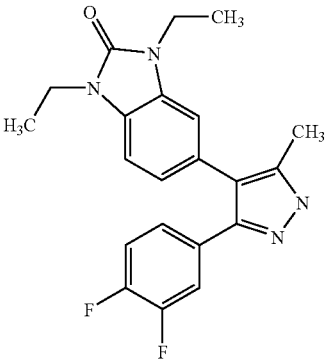 | 383.0 (M + 1) | 337 |

TABLE 12-continued
| EXAMPLE | MOLSTRUCTURE | | Method |
|---|---|---|---|
| 366 | 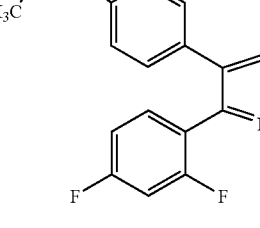 | 383.0 (M + 1) | 337 |
| 367 | 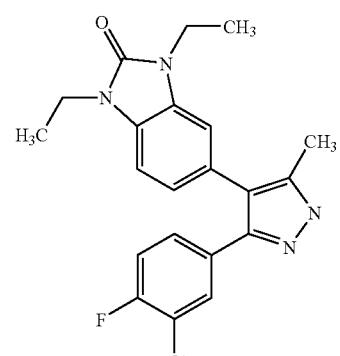 | 399.0 (M + 1) | 337 |
| 368 | 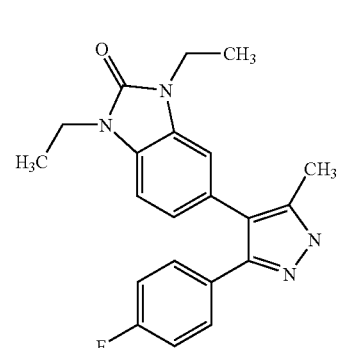 | 365.3 (M + 1) | 337 |
| 369 | 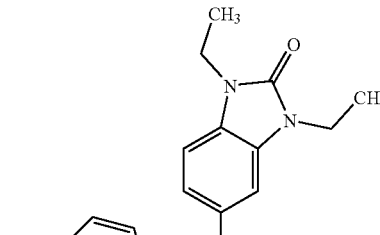 | 361.1 (M + 1) | 339 |

TABLE 12-continued

| EXAMPLE | MOLSTRUCTURE | | Method |
|---|---|---|---|
| 370 | | 430.2 (M + 1) | 343 |
| 371 | | 347.3 (M + 1) | 334 |
| 372 | | 424.4 (M + 1) | 334 |

TABLE 12-continued

| EXAMPLE | MOLSTRUCTURE | | Method |
|---|---|---|---|
| 373 | | 305.2 (M + 1) | 334 |
| 374 | | 376.2 (M + 1) | 335 |
| 375 | | 333.3 (M + 1) | 334 |
| 376 | | 376.1 (M + 1) | 335 |

TABLE 12-continued

| EXAMPLE | MOLSTRUCTURE | | Method |
|---------|---|---|--------|
| 377 | | 406.3 (M + 1) | 335 |
| 378 | | 478 (M + 1) | 334 |
| 379 | | 430.1 (M + 1) | 335 |

TABLE 12-continued
| EXAMPLE | MOLSTRUCTURE | | Method |
|---------|--------------|---|--------|
| 380 | 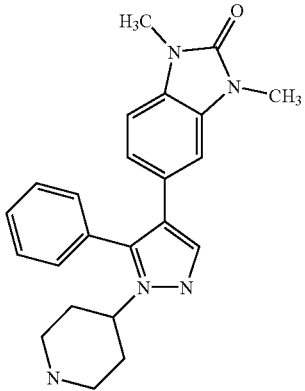 | 388 (M + 1) | 343 |
| 381 | 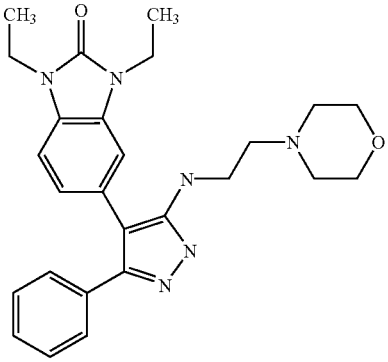 | 461.3 (M + 1) | 335 |
| 382 | 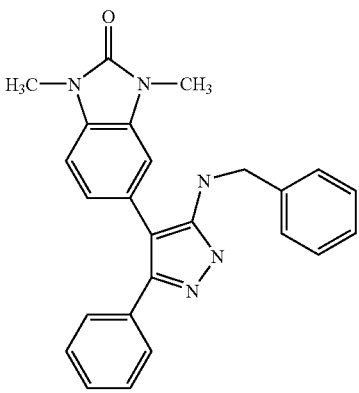 | 410.2 (M + 1) | 335 |

TABLE 12-continued
| EXAMPLE | MOLSTRUCTURE | | Method |
|---|---|---|---|
| 383 | 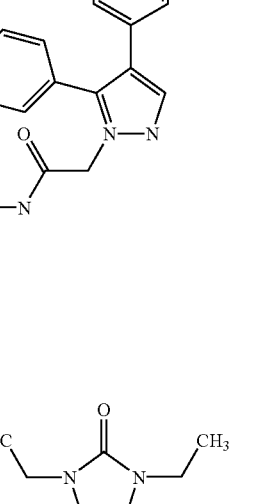 | 432.1 (M + 1) | 338 |
| 384 | 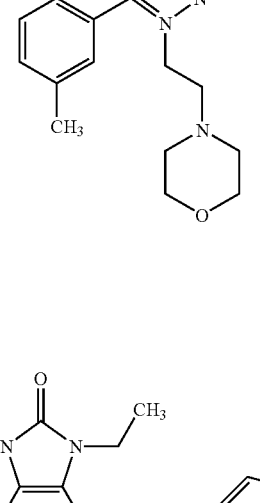 | 460.3 (M + 1) | 344 |
| 385 | 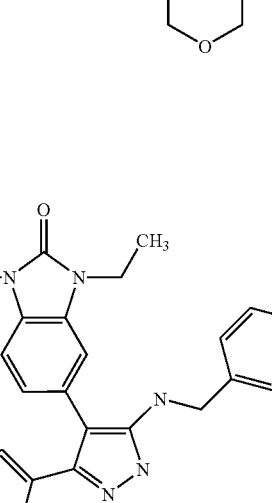 | 452.0 (M + 1) | 335 |

TABLE 12-continued
| EXAMPLE | MOLSTRUCTURE | | Method |
|---|---|---|---|
| 386 | 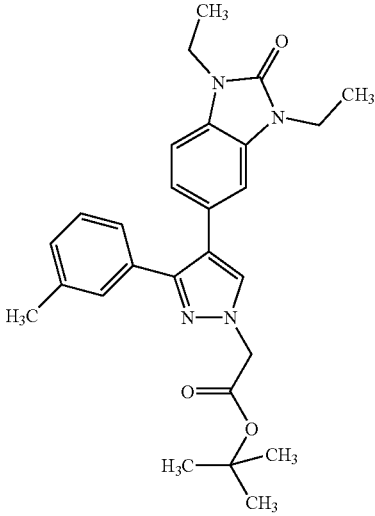 | 461.3 (M + 1) | 338 |
| 387 | 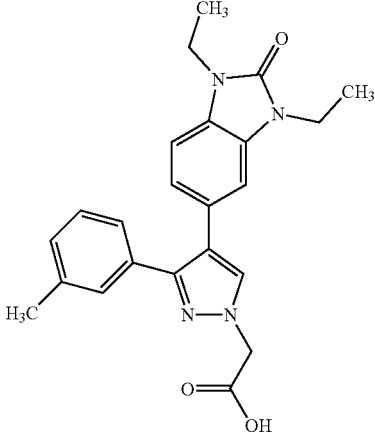 | | 338 |
| 388 | 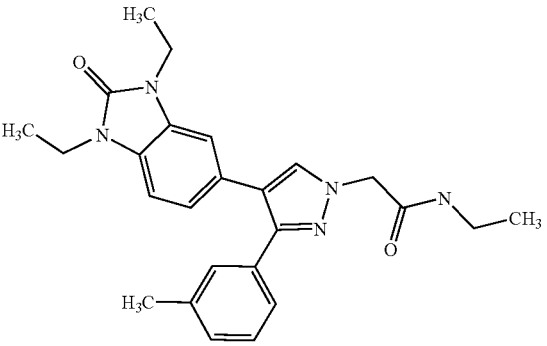 | | 338 |

TABLE 12-continued

| EXAMPLE | MOLSTRUCTURE | | Method |
|---|---|---|---|
| 389 | | 433.2 (M + 1) | 338 |
| 390 | | 377.3 (M + 1) | 338 |
| 391 | | 387.2 (M + 1) | 339 |
| 392 | | 474.2 (M + 1) | 338 |

TABLE 12-continued

| EXAMPLE | MOLSTRUCTURE | | Method |
|---|---|---|---|
| 393 | | 462.3 (M + 1) | 338 |
| 394 | | 487.4 (M + 1) | 338 |
| 395 | | 446.1 (M + 1) | 338 |

TABLE 12-continued
| EXAMPLE | MOLSTRUCTURE | | Method |
|---|---|---|---|
| 396 | 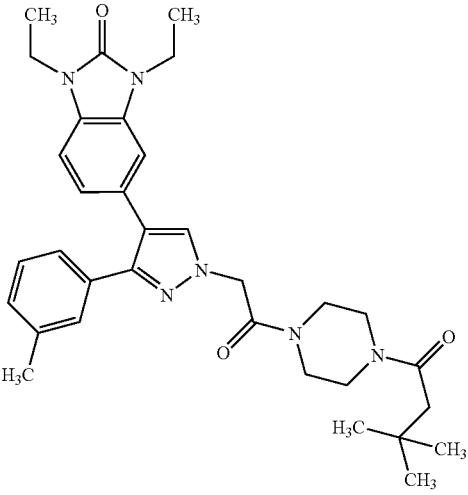 | 573.3 (M + 1) | 338 |
| 397 | 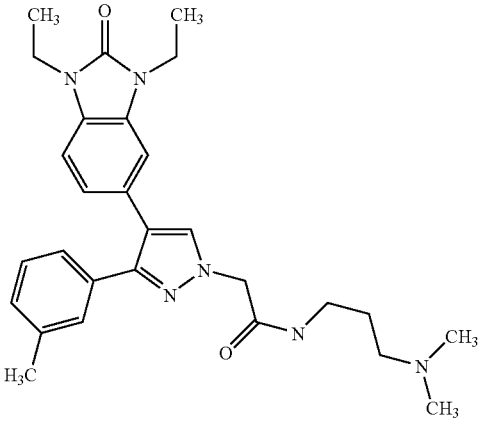 | 489.1 (M + 1) | 338 |
| 398 | 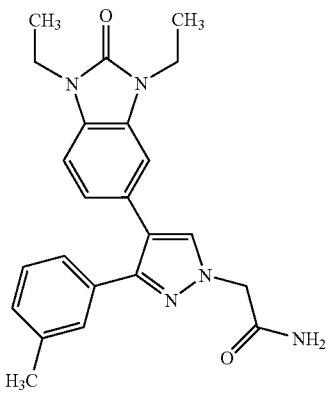 | 404.2 (M + 1) | 338 |

TABLE 12-continued

| EXAMPLE | MOLSTRUCTURE | | Method |
|---|---|---|---|
| 399 | | 404.2 (M + 1) | 338 |
| 400 | | 515.3 (M + 1) | 338 |
| 401 | | | 338 |

TABLE 12-continued
| EXAMPLE | MOLSTRUCTURE | | Method |
|---|---|---|---|
| 402 | 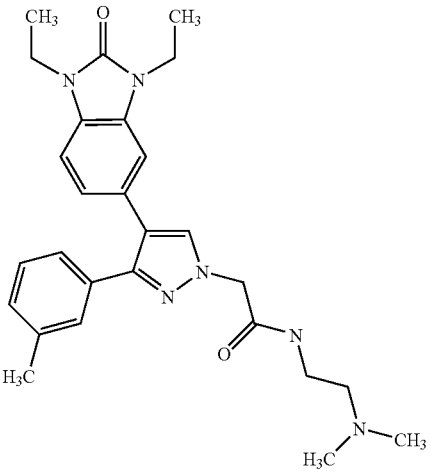 | 475.3 (M + 1) | 338 |
| 403 | 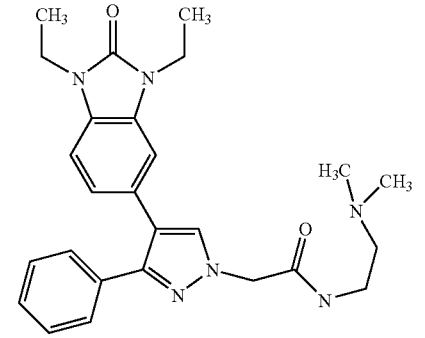 | 461.2 (M + 1) | 338 |
| 404 | 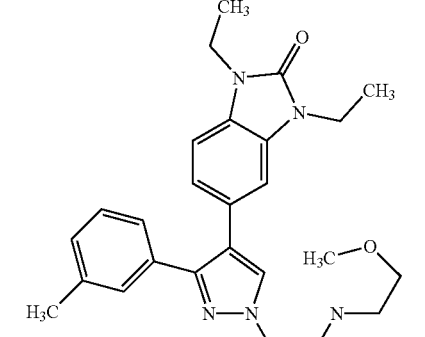 | 448.2 (M + 1) | 339 |

TABLE 12-continued
| EXAMPLE | MOLSTRUCTURE | | Method |
|---|---|---|---|
| 405 | 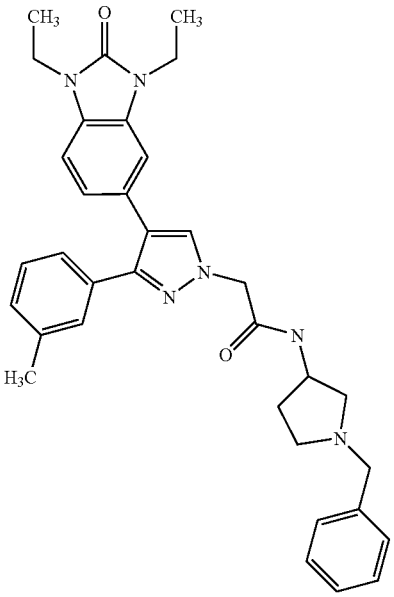 | 563.2 (M + 1) | 338 |
| 406 | 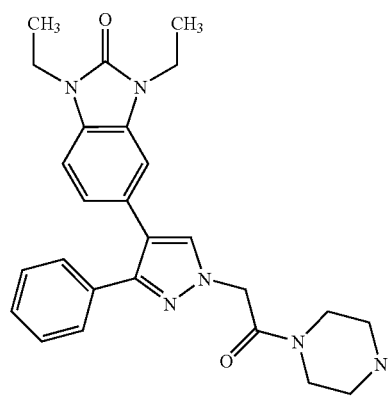 | 459.1 (M + 1) | 338 |
| 407 | 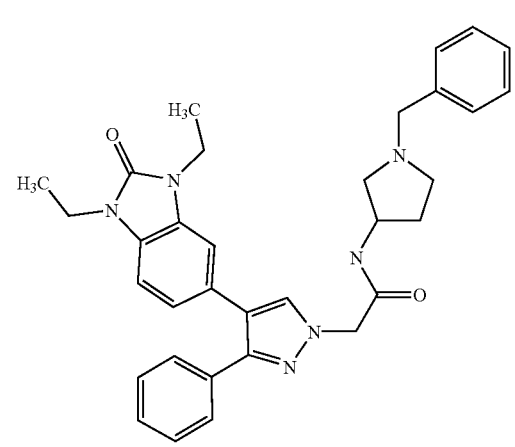 | 549.2 (M + 1) | 338 |

TABLE 12-continued
| EXAMPLE | MOLSTRUCTURE | | Method |
|---|---|---|---|
| 408 | 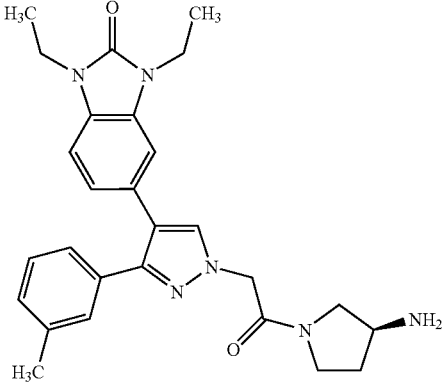 | 473.3 (M + 1) | 338 |
| 409 | 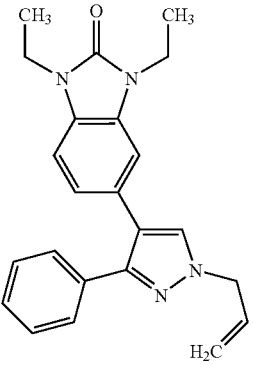 | 373.2 (M + 1) | 339 |
| 410 | 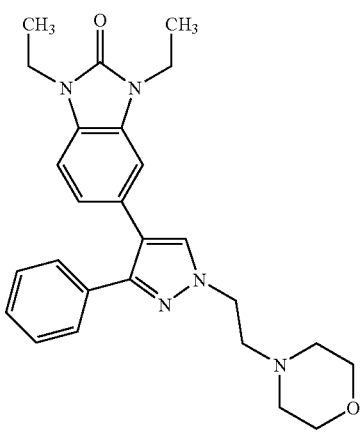 | 446.1 (M + 1) | 339 |

TABLE 12-continued
| EXAMPLE | MOLSTRUCTURE | | Method |
|---|---|---|---|
| 411 | 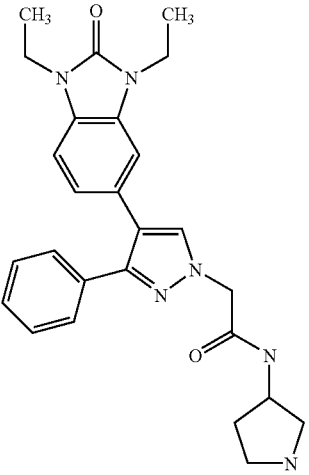 | 459.3 (M + 1) | 338 |
| 412 | 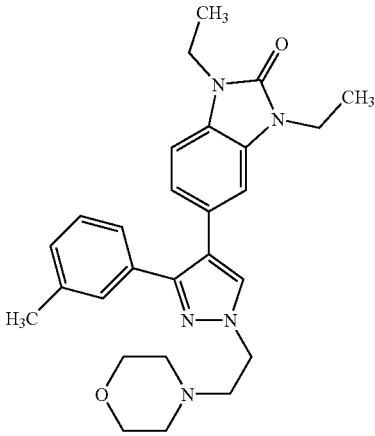 | 460.3 (M + 1) | 339 |
| 413 | 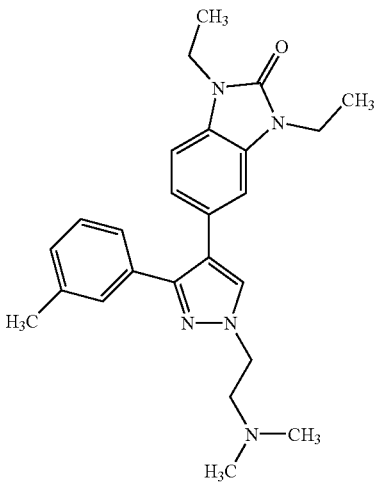 | 418.3 (M + 1) | 339 |

TABLE 12-continued
| EXAMPLE | MOLSTRUCTURE | | Method |
|---|---|---|---|
| 414 | 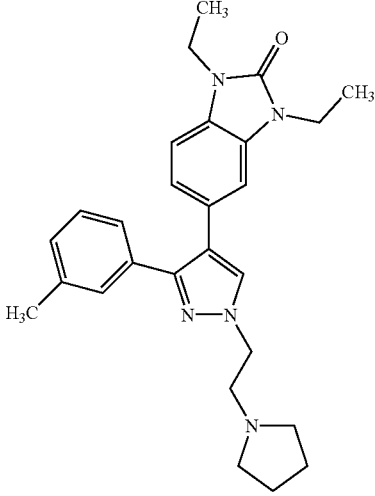 | 444.3 (M + 1) | 339 |
| 415 | 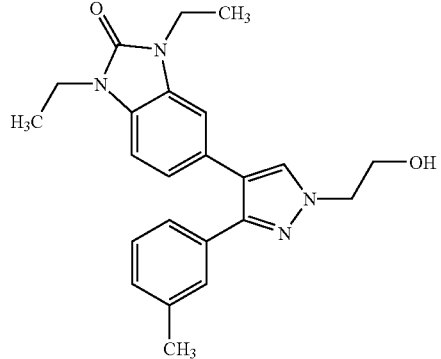 | 391.2 (M + 1) | 345 |
| 416 | 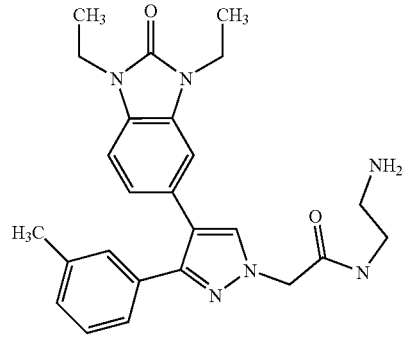 | 447.2 (M + 1) | 338 |

TABLE 12-continued

| EXAMPLE | MOLSTRUCTURE | | Method |
|---|---|---|---|
| 417 | | 501.1 (M + 1) | 338 |
| 418 | | 501.2 (M + 1) | 338 |
| 419 | | 515.2 (M + 1) | 338 |

TABLE 12-continued
| EXAMPLE | MOLSTRUCTURE | | Method |
|---|---|---|---|
| 420 | 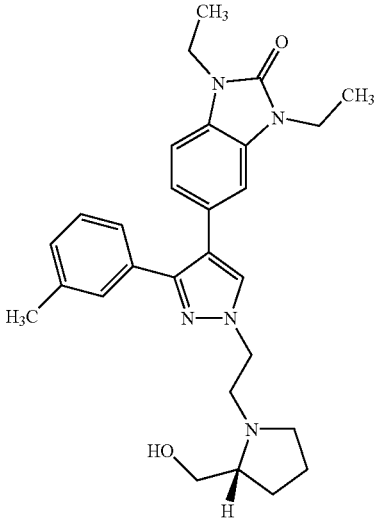 | 474.2 (M + 1) | 339 |
| 421 | 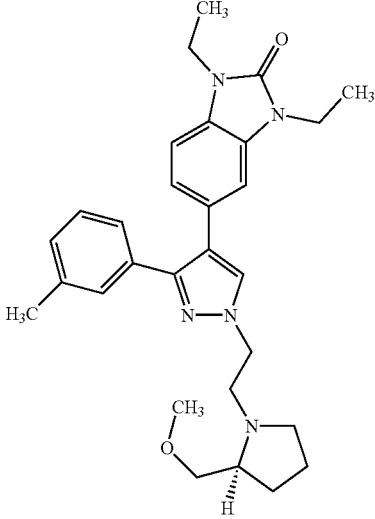 | 488.3 (M + 1) | 339 |
| 422 | 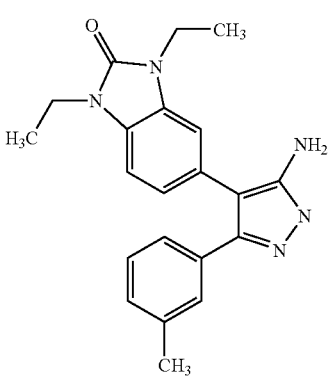 | 396.2 (M − 1) | 336 |

TABLE 12-continued
| EXAMPLE | MOLSTRUCTURE | | Method |
|---|---|---|---|
| 423 | 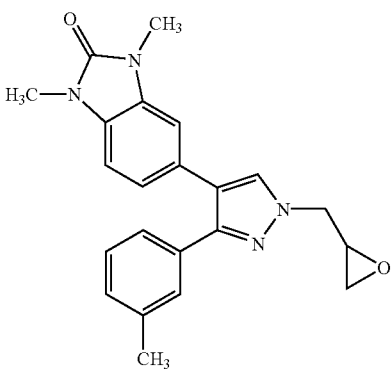 | 375.2 (M + 1) | 340 |
| 424 | 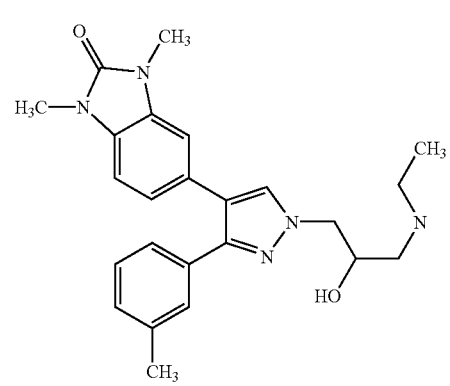 | | 340 |
| 425 | 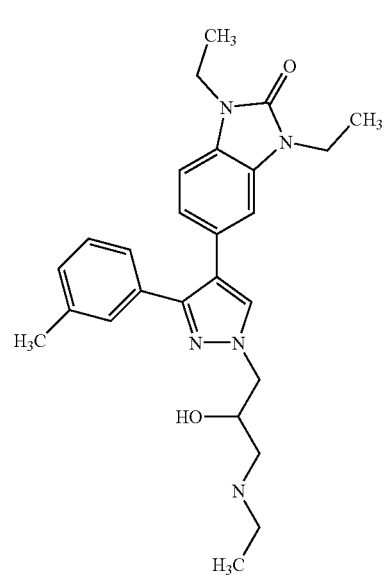 | 448.2 (M + 1) | 340 |

TABLE 12-continued
| EXAMPLE | MOLSTRUCTURE | | Method |
|---|---|---|---|
| 426 | 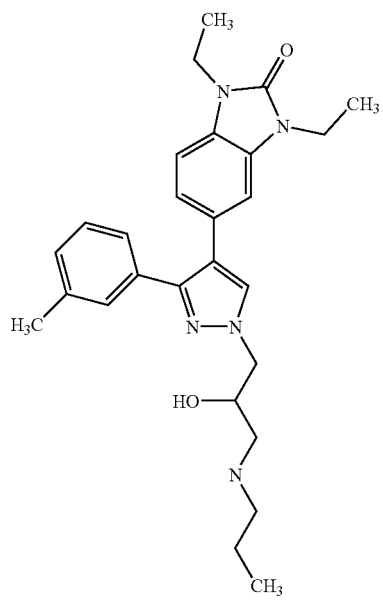 | 462.2 (M + 1) | 340 |
| 427 | 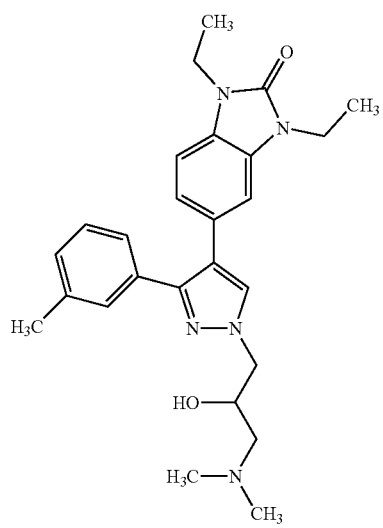 | 448.2 (M + 1) | 340 |

TABLE 12-continued
| EXAMPLE | MOLSTRUCTURE | | Method |
|---|---|---|---|
| 428 | 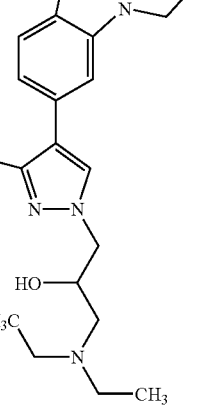 | 476.3 (M + 1) | 340 |
| 429 | 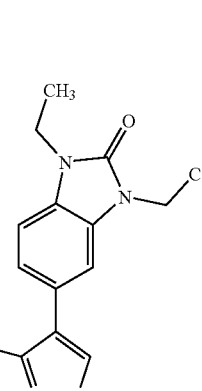 | 421.1 (M + 1) | 340 |
| 430 | 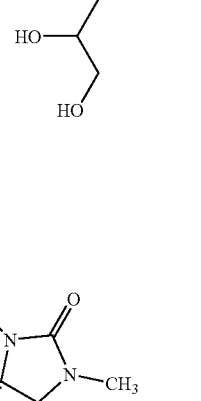 | 473.3 (M + 1) | 335 |

TABLE 12-continued
| EXAMPLE | MOLSTRUCTURE | | Method |
|---|---|---|---|
| 431 | 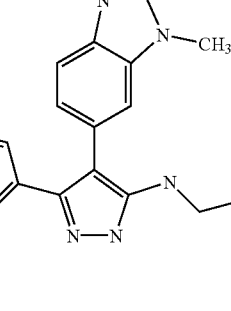 | 459.3 (M + 1) | 335 |
| 432 | 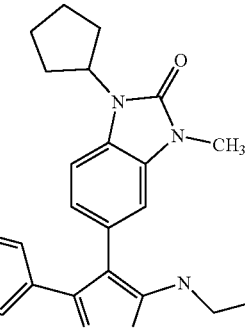 | 478.1 (M + 1) | 335 |
| 433 | 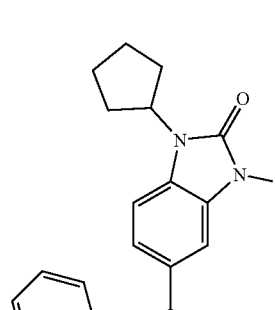 | 373.1 (M + 1) | 334 |
| 434 | 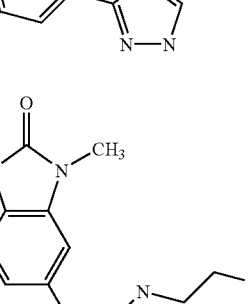 | 501.2 (M + 1) | 335 |

TABLE 12-continued

| EXAMPLE | MOLSTRUCTURE | | Method |
|---|---|---|---|
| 435 | | 535.2 (M − 1) | 338 |
| 436 | | 454.2 (M − 1) | 340 |
| 437 | | 387.2 (M + 1) | 334 |

TABLE 12-continued

| EXAMPLE | MOLSTRUCTURE | | Method |
|---|---|---|---|
| 438 | | 388.1 (M + 1) | 336 |
| 439 | | 445.1 (M + 1) | 338 |
| 440 | | | 338 |
| 441 | | 487.1 (M + 1) | 335 |

TABLE 12-continued

| EXAMPLE | MOLSTRUCTURE | | Method |
|---|---|---|---|
| 442 | | 515.3 (M + 1) | 338 |
| 443 | | 473.2 (M + 1) | 335 |
| 444 | | 402.2 (M + 1) | 335 + 346 |
| 445 | | 507.3 (M − 1) | 338 |

TABLE 12-continued
| EXAMPLE | MOLSTRUCTURE | | Method |
|---|---|---|---|
| 446 | 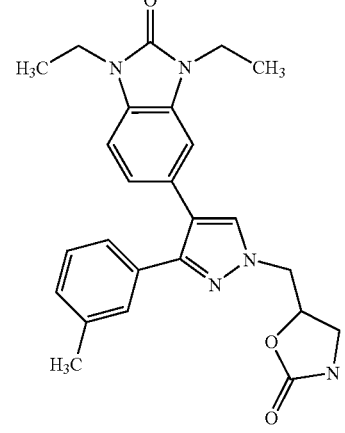 | 446.2 (M + 1) | 338 |
| 447 | 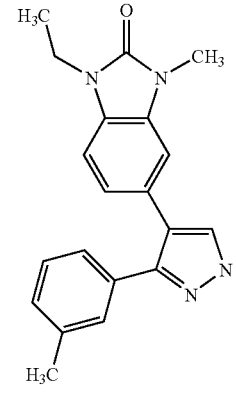 | 333.3 (M + 1) | 334 |
| 448 | 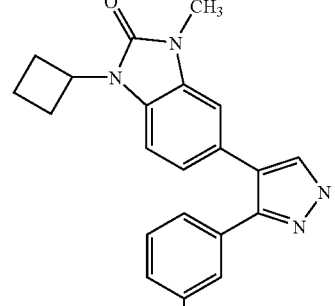 | 359.2 (M + 1) | 334 |

TABLE 12-continued

| EXAMPLE | MOLSTRUCTURE | | Method |
|---|---|---|---|
| 449 | | 429.2 (M + 1) | 340 |
| 450 | | 459.2 (M + 1) | 335 |
| 451 | | 446.2 (M + 1) | 340 |
| 452 | | 474.2 (M + 1) | 340 |

TABLE 12-continued
| EXAMPLE | MOLSTRUCTURE | | Method |
|---|---|---|---|
| 453 | 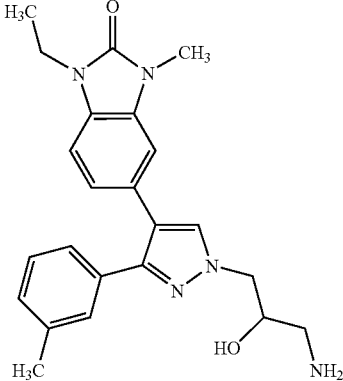 | 406.2 (M + 1) | 340 |
| 454 | 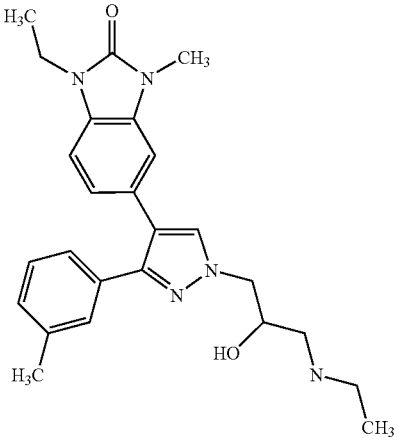 | 434.2 (M + 1) | 340 |
| 455 | 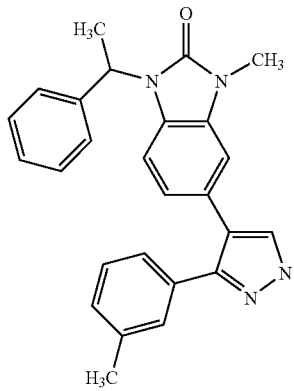 | 409.3 (M + 1) | 334 |

TABLE 12-continued
| EXAMPLE | MOLSTRUCTURE | | Method |
|---|---|---|---|
| 456 | 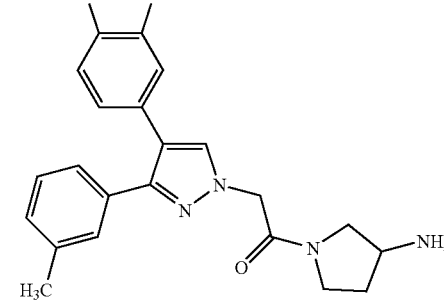 | 459.1 (M + 1) | 338 |
| 457 | 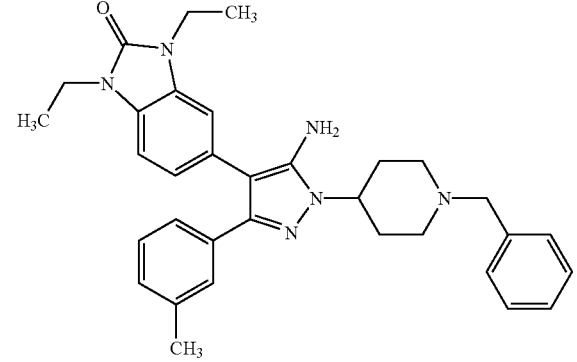 | 535.2 (M + 1) | 336 |
| 458 | 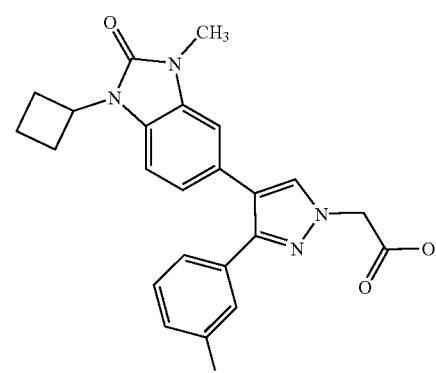 | 417.2 (M + 1) | 338 |
| 459 | 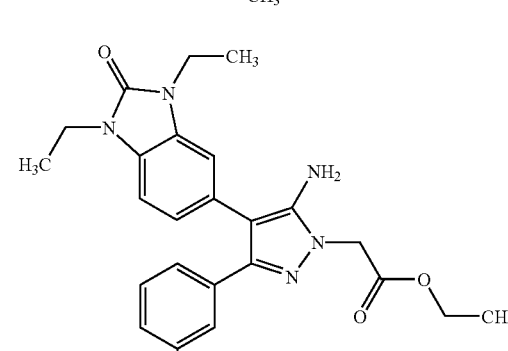 | 448.2 (M + 1) | 338 |

TABLE 12-continued

| EXAMPLE | MOLSTRUCTURE | | Method |
|---|---|---|---|
| 460 | | | 336 |
| 461 | | 439.2 (M + 1) | 336 |
| 461 | | 460.2 (M + 1) | 338 |
| 462 | | | 336 |

TABLE 12-continued

| EXAMPLE | MOLSTRUCTURE | | Method |
|---|---|---|---|
| 463 | | | 338 |
| 464 | | 374.2 (M + 1) | 336 |
| 465 | | 360.1 (M + 1) | 336 |
| 466 | | 376.2 (M + 1) | 336 |

TABLE 12-continued

| EXAMPLE | MOLSTRUCTURE | | Method |
|---|---|---|---|
| 467 | | 430.2 (M + 1) | 336 + 347 |
| 468 | | 446.2 (M + 1) | 338 |
| 469 | | 416.2 (M + 1) | 336 + 347 |
| 470 | | 544.1 (M + 1) | 336 + 347 |

TABLE 12-continued

| EXAMPLE | MOLSTRUCTURE | | Method |
|---|---|---|---|
| 471 | | 418.2 (M + 1) | 338 |
| 472 | | | 336 |
| 473 | | 406.1 (M + 1) | 336 |
| 474 | | 459.2 (M + 1) | 347 |

TABLE 12-continued

| EXAMPLE | MOLSTRUCTURE | | Method |
|---|---|---|---|
| 474 | | 400.2 (M + 1) | 346 |
| 475 | | 460.2 (M + 1) | 347 |
| 476 | | 466.1 (M + 1) | 347 |
| 477 | | 362.2 (M + 1) | 336 |

TABLE 12-continued

| EXAMPLE | MOLSTRUCTURE | | Method |
|---|---|---|---|
| 478 | | 445.1 (M + 1) | 347 |
| 479 | | 431.2 (M + 1) | 347 |
| 480 | | 444.0 (M + 1) | 347 |
| 481 | | 406.0 (M + 1) | 336 |

TABLE 12-continued

| EXAMPLE | MOLSTRUCTURE | | Method |
|---|---|---|---|
| 482 | | 404.2 (M + 1) | 347 |
| 483 | | 404.2 (M + 1) | 347 |
| 484 | | 484.2 (M + 1) | 347 |
| 484 | | 348.2 (M + 1) | 336 |

TABLE 12-continued

| EXAMPLE | MOLSTRUCTURE | | Method |
|---|---|---|---|
| 485 | | 376.2 (M + 1) | 339 |
| 486 | | 416.1 (M + 1) | 347 |
| 487 | | 535.0 (M + 1) | 343 |
| 488 | | 414.2 (M + 1) | 346 |

TABLE 12-continued
| EXAMPLE | MOLSTRUCTURE | | Method |
|---|---|---|---|
| 489 | 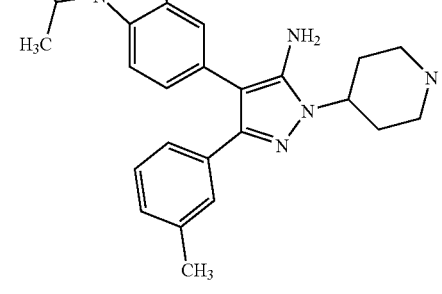 | 445.2 (M + 1) | 343 |
| 490 | 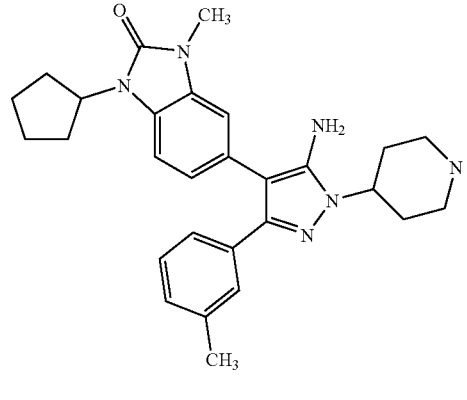 | 471.2 (M + 1) | 343 |
| 491 | 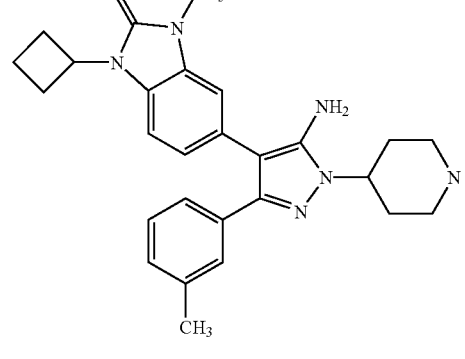 | | 343 |
| 492 | 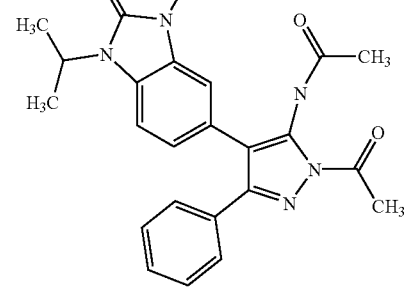 | 432.2 (M + 1) | 347 |

TABLE 12-continued

| EXAMPLE | MOLSTRUCTURE | | Method |
|---|---|---|---|
| 493 | | 390.2 (M + 1) | 347 |
| 494 | | 363.2 (M + 1) | 341 |
| 495 | | 406.2 (M + 1) | 346 |
| 495 | | 449.2 (M + 1) | 343 |

TABLE 12-continued

| EXAMPLE | MOLSTRUCTURE | | Method |
|---|---|---|---|
| 496 | | 487.3 (M + 1) | 338 |
| 497 | | 389.2 (M + 1) | 341 |
| 498 | | 375.2 (M + 1) | 341 |
| 499 | | 545.1 (M + 1) | 341 + 347 |

TABLE 12-continued
| EXAMPLE | MOLSTRUCTURE | | Method |
|---|---|---|---|
| 500 | 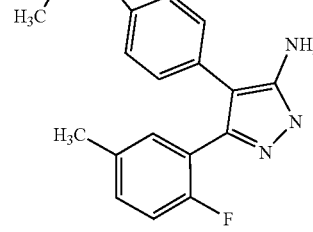 | 380.1 (M + 1) | 336 |
| 501 | 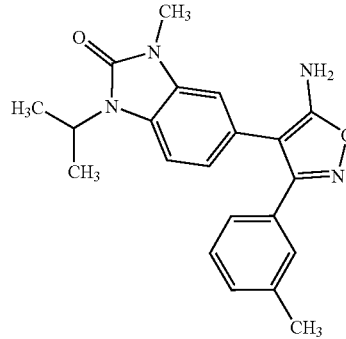 | 363.2 (M + 1) | 341 |
| 502 | 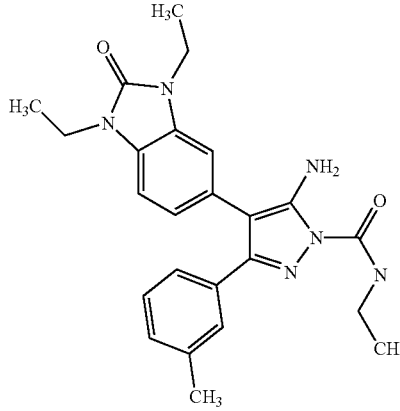 | 433.2 (M + 1) | 347 |
| 503 | 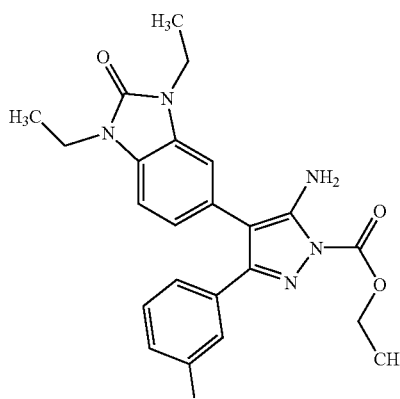 | 434.2 (M + 1) | 347 |

TABLE 12-continued
| EXAMPLE | MOLSTRUCTURE | | Method |
|---|---|---|---|
| 504 | 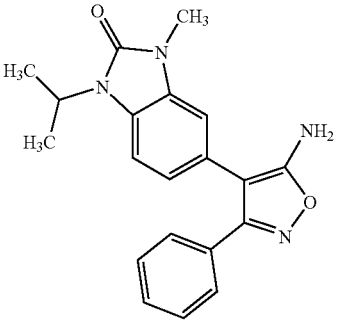 | 349.2 (M + 1) | 341 |
| 505 | 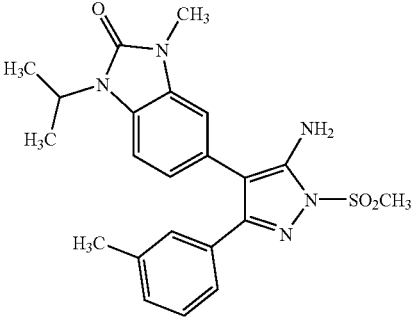 | 440.2 (M + 1) | 347 |
| 506 | 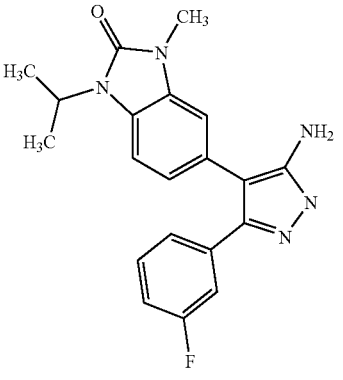 | 366.1 (M + 1) | 336 |
| 507 | 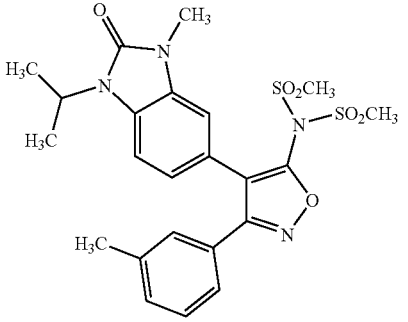 | 519.1 (M + 1) | 341 |

TABLE 12-continued

| EXAMPLE | MOLSTRUCTURE | | Method |
|---|---|---|---|
| 508 | [structure: 1-isopropyl-3-methyl-benzimidazol-2-one with 5-amino-3-(3-fluorophenyl)isoxazol-4-yl substituent] | 367.0 (M + 1) | 341 |
| 509 | [structure: 1-isopropyl-3-methyl-benzimidazol-2-one with 3-(3-methylphenyl)-5-(methylsulfonylamino)isoxazol-4-yl substituent] | 441.3 (M + 1) | 341 |
| 510 | [structure: 1-isopropyl-3-methyl-benzimidazol-2-one with 5-amino-3-(2-fluoro-5-methylphenyl)isoxazol-4-yl substituent] | 381.1 (M + 1) | 341 |
| 510 | [structure: 1-isopropyl-3-methyl-benzimidazol-2-one with 5-amino-3-(4-fluorophenyl)pyrazol-4-yl substituent] | | 336 |

TABLE 12-continued

| EXAMPLE | MOLSTRUCTURE | | Method |
|---|---|---|---|
| 511 | | 434.2 (M + 1) | 341 |
| 512 | | 347.4 (M + 1) | 334 |
| 513 | | 445.3 (M + 1) | 343 |
| 514 | | 425.2 (M + 1) | 342 |

TABLE 12-continued

| EXAMPLE | MOLSTRUCTURE | | Method |
|---|---|---|---|
| 515 | | 458.2 (M + 1) | 342 |
| 516 | | 464.1 (M + 1) | 338 |
| 517 | | 418.2 (M + 1) | 346 |
| 518 | | 450.1 (M + 1) | 342 + 340 |

TABLE 12-continued

| EXAMPLE | MOLSTRUCTURE | | Method |
|---------|--------------|---|--------|
| 519 | | 448.2 (M + 1) | 338 |
| 520 | | 379.2 (M + 1) | 341 |
| 521 | | 461.0 (M + 1) | 335 |
| 522 | | 447.3 (M + 1) | 335 |

TABLE 12-continued

| EXAMPLE | MOLSTRUCTURE | | Method |
|---|---|---|---|
| 523 | | 419.0 (M + 1) | 335 |
| 524 | | 360.3 (M + 1) | 335 |
| 526 | | 461.0 (M + 1) | 335 |
| 527 | | 447.2 (M + 1) | 335 |

TABLE 12-continued

| EXAMPLE | MOLSTRUCTURE | | Method |
|---|---|---|---|
| 528 | | 447.1 (M + 1) | 335 |
| 529 | | 433.1 (M + 1) | 335 |
| 530 | | 348.1 (M + 1) | 335 |
| 531 | | | 335 |

TABLE 12-continued

| EXAMPLE | MOLSTRUCTURE | | Method |
| --- | --- | --- | --- |
| 532 | | 459.2 (M + 1) | 335 |
| 533 | | | 335 |
| 534 | | 422.3 (M + 1) | 335 |
| 535 | | 447.0 (M + 1) | 335 |

TABLE 12-continued
| EXAMPLE | MOLSTRUCTURE | | Method |
|---|---|---|---|
| 536 | 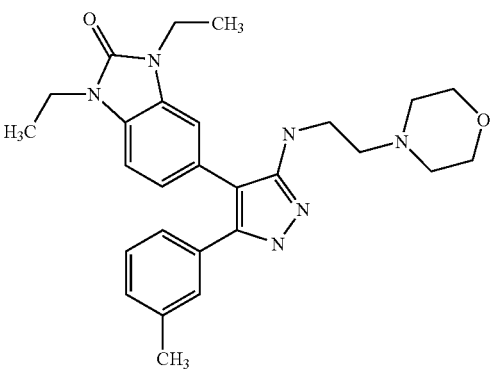 | 475.3 (M + 1) | 335 |
| 537 | 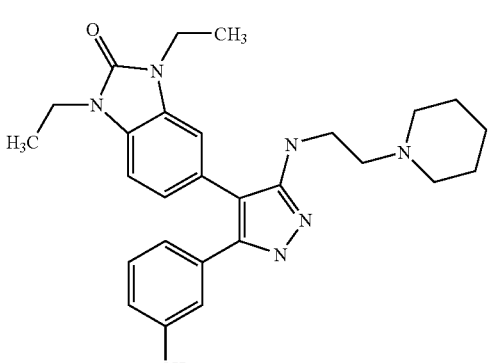 | 473.3 (M + 1) | 335 |
| 538 | 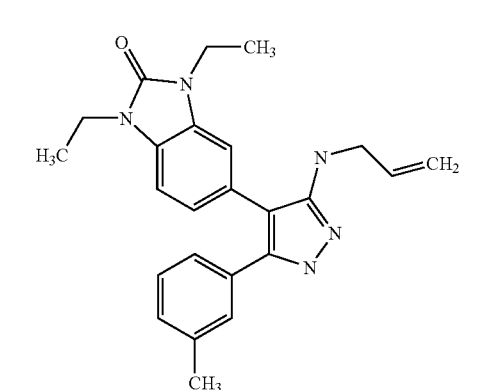 | 402.2 (M + 1) | 335 |
| 539 | 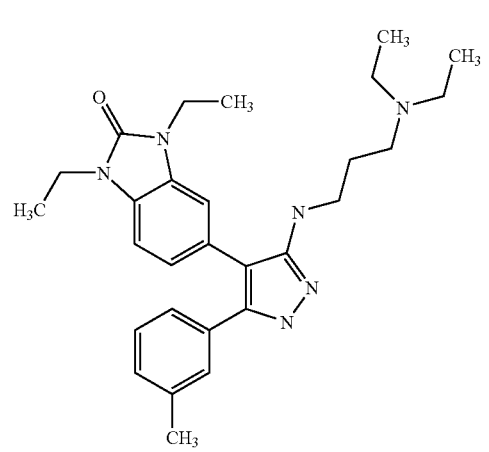 | 475.3 (M + 1) | 335 |

TABLE 12-continued
| EXAMPLE | MOLSTRUCTURE | | Method |
|---------|--------------|--|--------|
| 540 | 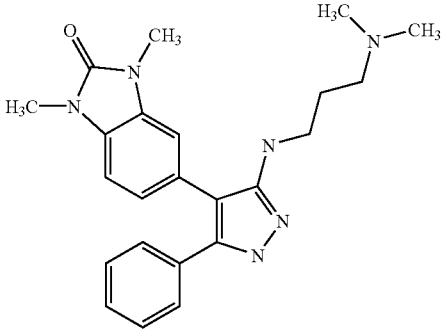 | 405.2 (M + 1) | 335 |
| 541 | 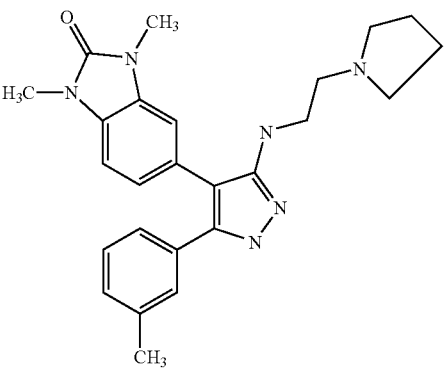 | | 335 |
| 542 | 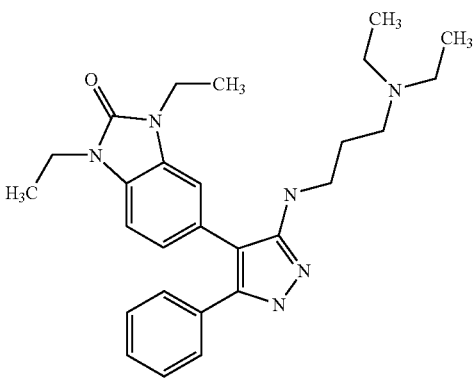 | 461.2 (M + 1) | 335 |
| 543 | 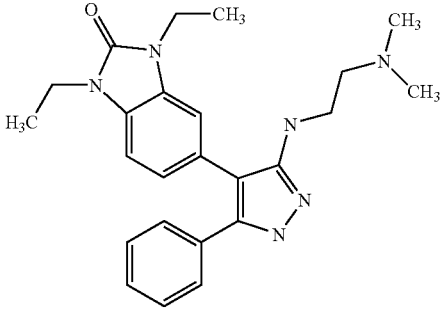 | 419.1 (M + 1) | 335 |

TABLE 12-continued

| EXAMPLE | MOLSTRUCTURE | | Method |
|---|---|---|---|
| 544 | | 419.3 (M + 1) | 335 |
| 545 | | 433.3 (M + 1) | 335 |
| 546 | | 445.2 (M + 1) | 335 |
| 547 | | 433.2 (M + 1) | 335 |

TABLE 12-continued

| EXAMPLE | MOLSTRUCTURE | | Method |
|---|---|---|---|
| 548 | | 433.3 (M + 1) | 335 |
| 549 | | 447.3 (M + 1) | 335 |
| 550 | | 365.1 (M + 1) | 334 |
| 551 | | 351.1 (M + 1) | 334 |

TABLE 12-continued
| EXAMPLE | MOLSTRUCTURE | | Method |
|---|---|---|---|
| 552 | 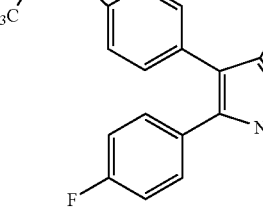 | 366.1 (M + 1) | 336 |
| 553 | 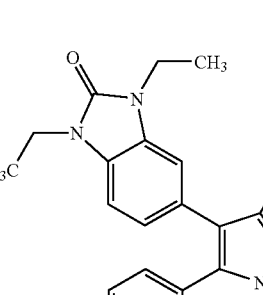 | 380.1 (M + 1) | 336 |
| 554 | 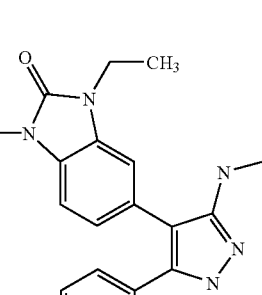 | 416.1 (M + 1) | 335 |
| 555 | 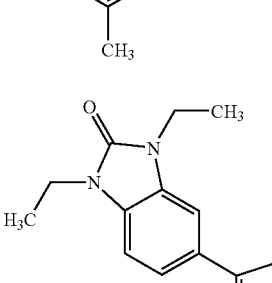 | 401.2 (M + 1) | 334 |

TABLE 12-continued

| EXAMPLE | MOLSTRUCTURE | | Method |
|---|---|---|---|
| 556 | | 419.1 (M + 1) | 334 |
| 557 | | 469.1 (M + 1) | 334 |
| 558 | | 484.1 (M + 1) | 336 |
| 559 | | 374.1 (M + 1) | 336 |

TABLE 12-continued

| EXAMPLE | MOLSTRUCTURE | | Method |
|---|---|---|---|
| 560 | | 387.1 (M + 1) | 336 |
| 661 | | 461.0 (M + 1) | 335 |
| 562 | | 447.3 (M + 1) | 335 |
| 563 | | 419.0 (M + 1) | 335 |

TABLE 12-continued

| EXAMPLE | MOLSTRUCTURE | | Method |
|---------|---|---|---|
| 564 | | 360.3 (M + 1) | 335 |
| 565 | | 461.0 (M + 1) | 335 |
| 566 | | 447.2 (M + 1) | 335 |
| 567 | | 447.1 (M + 1) | 335 |

TABLE 12-continued

| EXAMPLE | MOLSTRUCTURE | | Method |
|---|---|---|---|
| 568 | | 433.1 (M + 1) | 335 |
| 569 | | 348.1 (M + 1) | 335 |
| 570 | | | 335 |
| 571 | | 459.2 (M + 1) | 335 |

TABLE 12-continued

| EXAMPLE | MOLSTRUCTURE | | Method |
|---|---|---|---|
| 572 | | | 335 |
| 573 | | 422.3 (M + 1) | 335 |
| 574 | | 447.0 (M + 1) | 335 |
| 575 | | 475.3 (M + 1) | 335 |

TABLE 12-continued
| EXAMPLE | MOLSTRUCTURE | | Method |
|---|---|---|---|
| 576 | 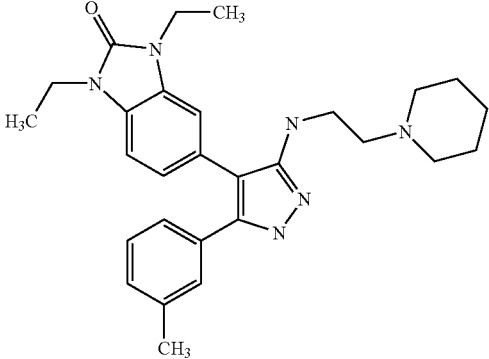 | 473.3 (M + 1) | 335 |
| 577 | 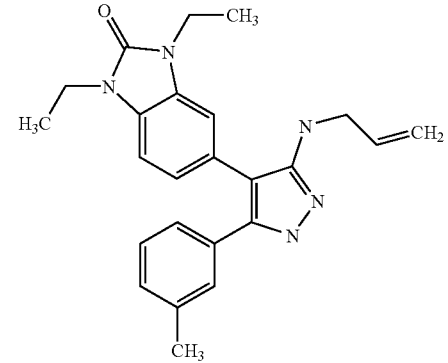 | 402.2 (M + 1) | 335 |
| 578 | 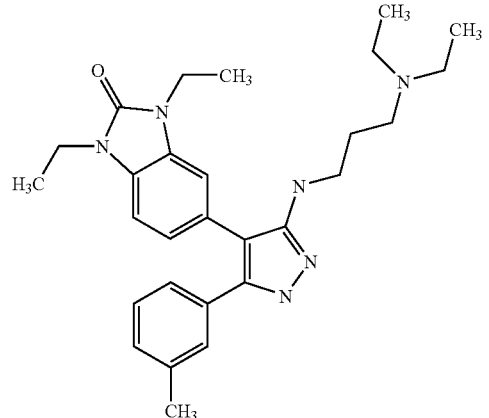 | 475.3 (M + 1) | 335 |
| 579 | 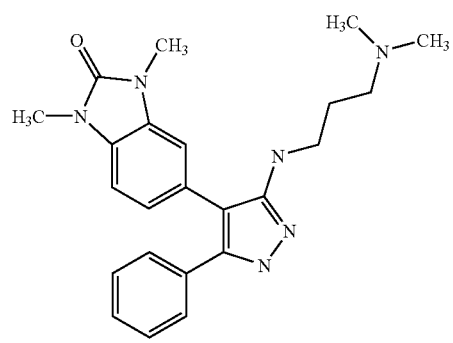 | 405.2 (M + 1) | 335 |

TABLE 12-continued

| EXAMPLE | MOLSTRUCTURE | | Method |
|---|---|---|---|
| 580 | (structure) | | 335 |
| 581 | (structure) | 461.2 (M + 1) | 335 |
| 582 | (structure) | 419.1 (M + 1) | 335 |
| 583 | (structure) | 419.3 (M + 1) | 335 |

TABLE 12-continued
| EXAMPLE | MOLSTRUCTURE | | Method |
|---|---|---|---|
| 584 | 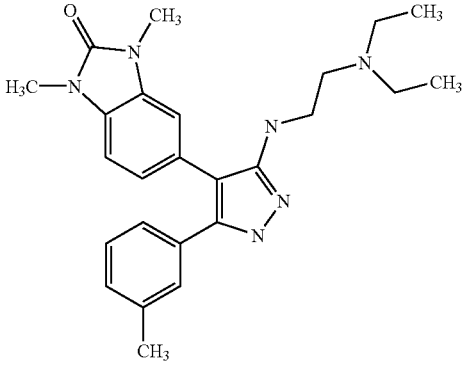 | 433.3 (M + 1) | 335 |
| 585 | 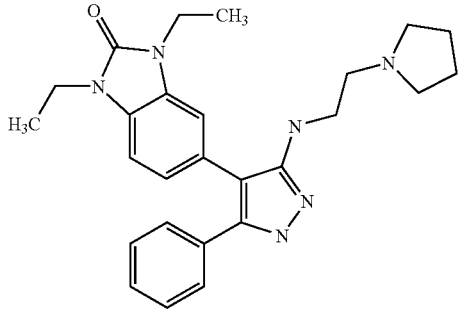 | 445.2 (M + 1) | 335 |
| 586 | 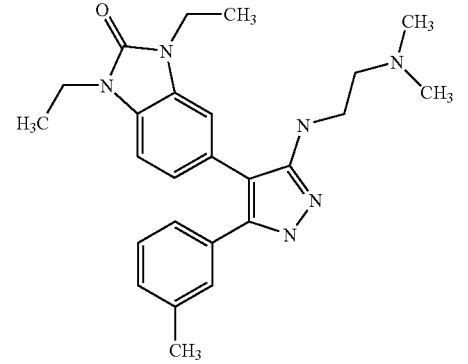 | 433.2 (M + 1) | 335 |
| 587 | 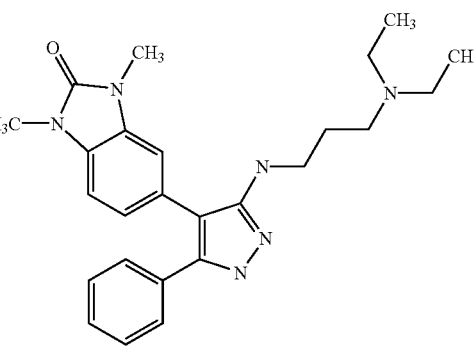 | 433.3 (M + 1) | 335 |

TABLE 12-continued
| EXAMPLE | MOLSTRUCTURE | | Method |
|---|---|---|---|
| 588 | 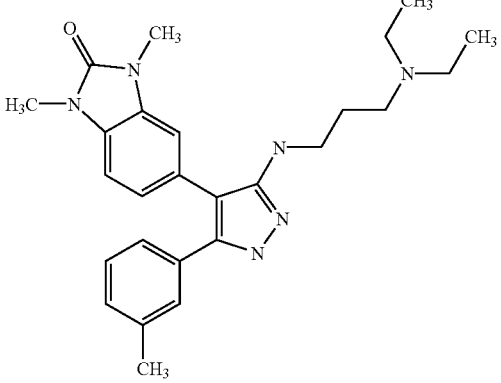 | 447.3 (M + 1) | 335 |
| 589 | 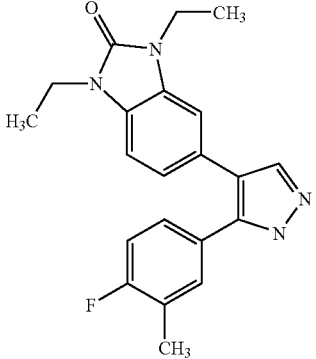 | 365.1 (M + 1) | 334 |
| 590 | 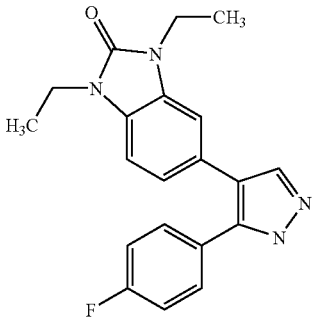 | 351.1 (M + 1) | 334 |
| 591 | 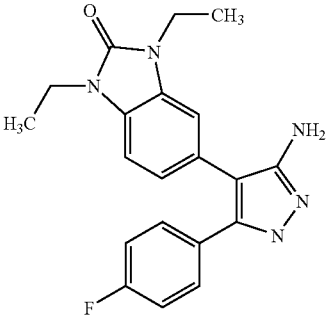 | 366.1 (M + 1) | 336 |

TABLE 12-continued
| EXAMPLE | MOLSTRUCTURE | | Method |
|---|---|---|---|
| 592 | 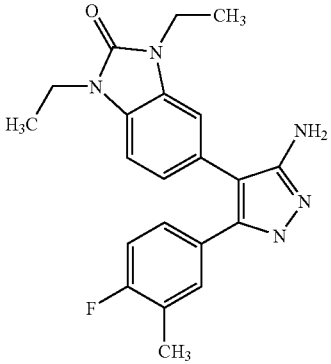 | 380.1 (M + 1) | 336 |
| 593 | 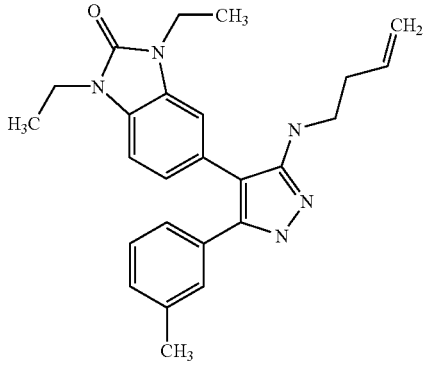 | 416.1 (M + 1) | 335 |
| 594 | 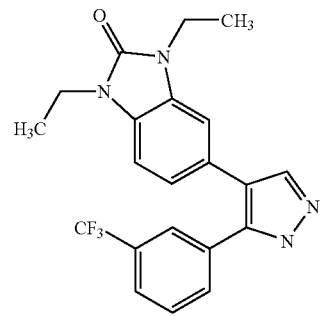 | 401.2 (M + 1) | 334 |
| 595 | 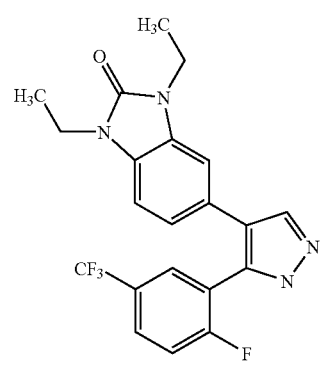 | 419.1 (M + 1) | 334 |

TABLE 12-continued

| EXAMPLE | MOLSTRUCTURE | | Method |
|---------|--------------|---|--------|
| 596 | | 469.1 (M + 1) | 334 |
| 597 | | 484.1 (M + 1) | 336 |
| 598 | | 374.1 (M + 1) | 336 |
| 599 | | 387.1 (M + 1) | 336 |

TABLE 12-continued

| EXAMPLE | MOLSTRUCTURE | | Method |
|---|---|---|---|
| 600 | | 423.3 (M + 1) | 334 |
| 601 | | 501.2 (M + 1) | 334 |
| 602 | | 424.3 (M + 1) | 334 |

TABLE 12-continued
| EXAMPLE | MOLSTRUCTURE | | Method |
|---|---|---|---|
| 603 | 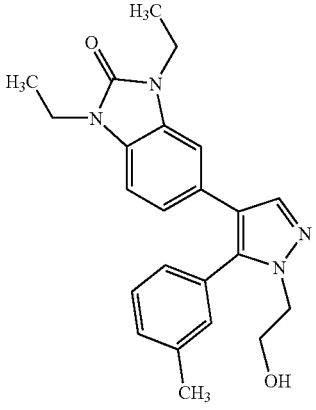 | 391.3 (M + 1) | 334 |
| 604 | 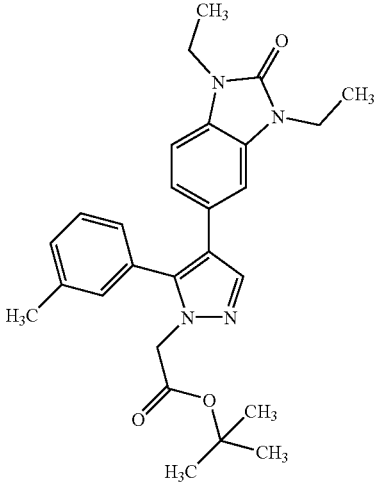 | 461.3 (M + 1) | 334 |
| 605 | 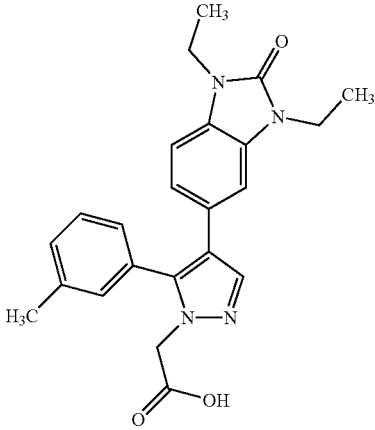 | | |

TABLE 12-continued
| EXAMPLE | MOLSTRUCTURE | | Method |
|---|---|---|---|
| 606 | 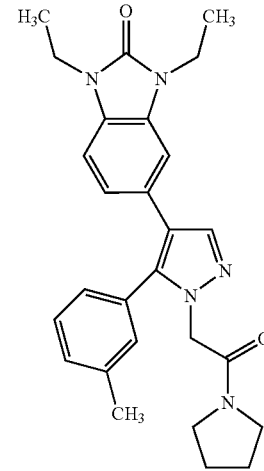 | 458.1 (M + 1) | 338 |
| 607 | 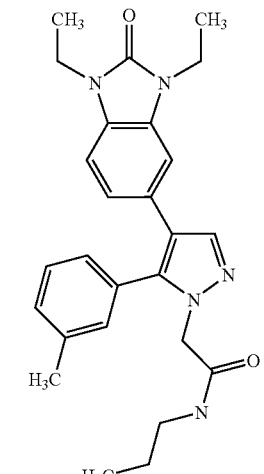 | 446.1 (M + 1) | 338 |
| 608 | 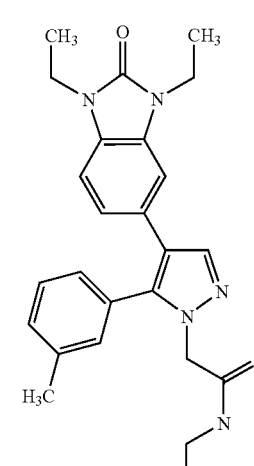 | 476.1 (M + 1) | 338 |

TABLE 12-continued
| EXAMPLE | MOLSTRUCTURE | | Method |
|---|---|---|---|
| 609 | 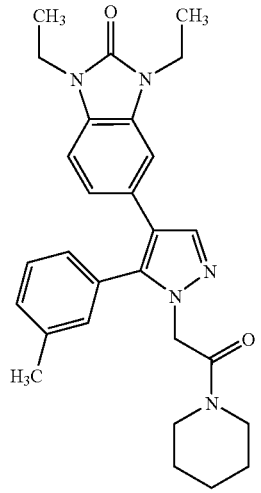 | 472.3 (M + 1) | 338 |
| 610 | 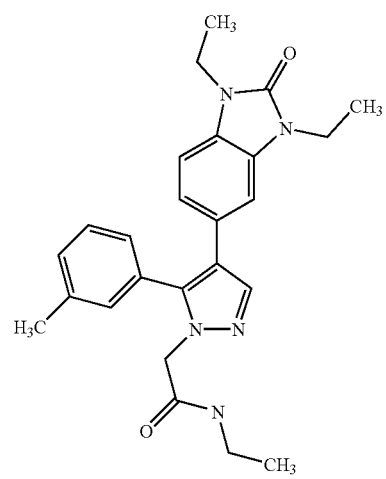 | 432.2 (M + 1) | 338 |
| 611 | 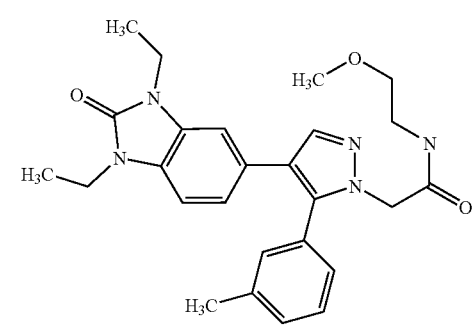 | 462.3 (M + 1) | 338 |

TABLE 12-continued
| EXAMPLE | MOLSTRUCTURE | | Method |
|---|---|---|---|
| 612 | 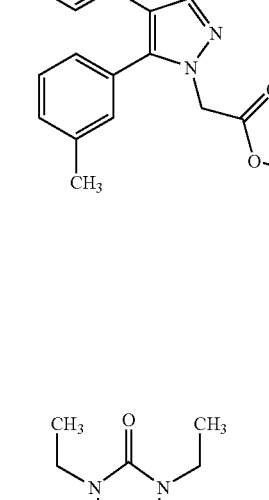 | 433.2 (M + 1) | 338 |
| 613 | 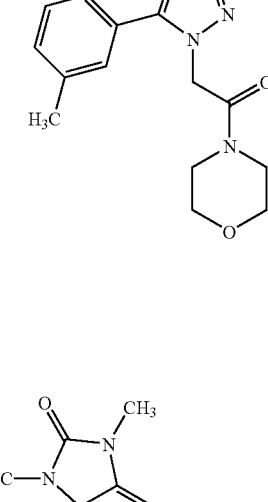 | 474.3 (M + 1) | 338 |
| 614 | 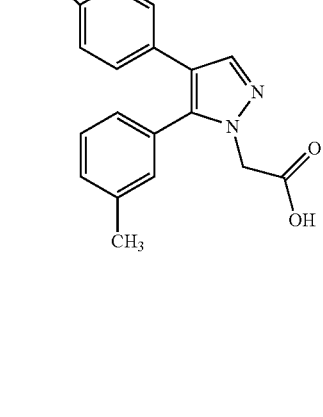 | 377.3 (M + 1) | 338 |

TABLE 12-continued
| EXAMPLE | MOLSTRUCTURE | | Method |
|---|---|---|---|
| 615 | 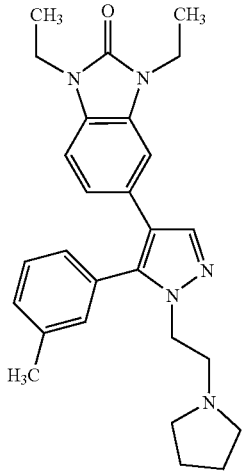 | 444.2 (M + 1) | 344 |
| 616 | 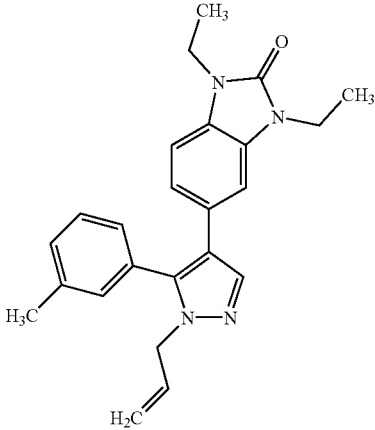 | | 338 |
| 617 | 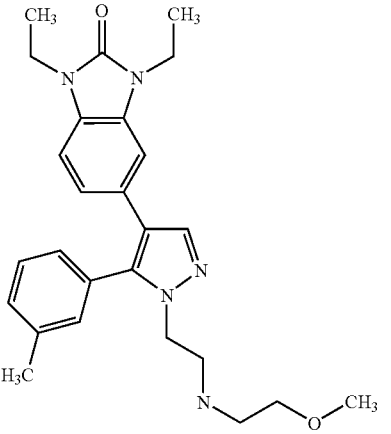 | 448.4 (M + 1) | 334 |

TABLE 12-continued
| EXAMPLE | MOLSTRUCTURE | | Method |
|---------|--------------|--------|--------|
| 618 | 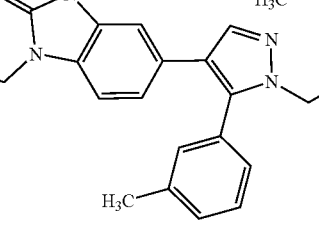 | 418.3 (M + 1) | 334 |
| 619 | 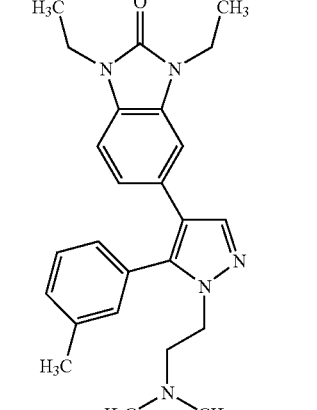 | 418.3 (M + 1) | 345 |
| 620 | 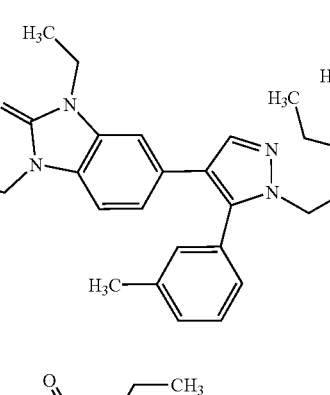 | 446.4 (M + 1) | 345 |
| 621 | 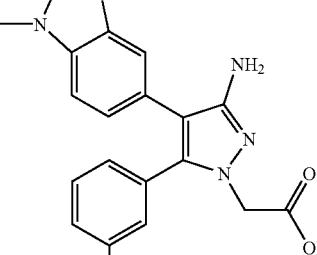 | | 338 |

TABLE 12-continued
| EXAMPLE | MOLSTRUCTURE | | Method |
|---|---|---|---|
| 622 | 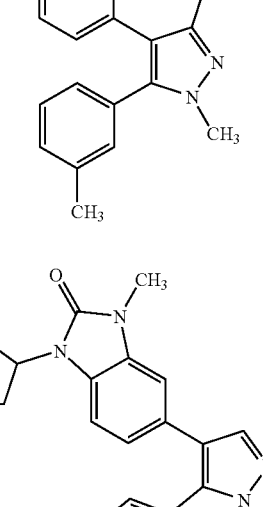 | 461.3 (M + 1) | 335 |
| 623 | 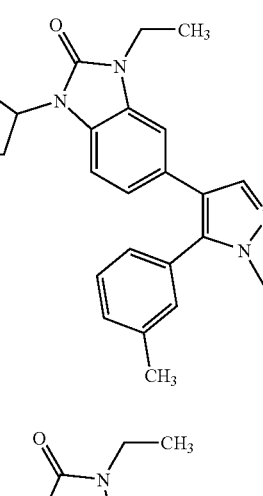 | 431.2 (M + 1) | 338 |
| 624 | 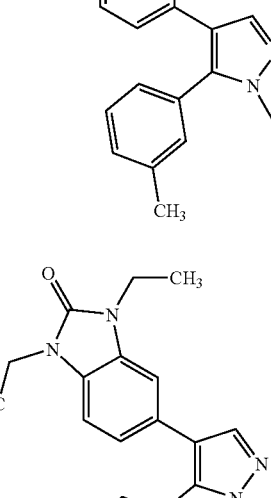 | 445.2 (M + 1) | 338 |
| 625 | 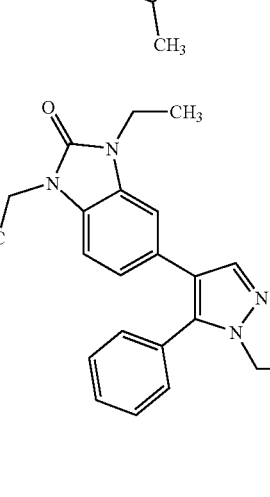 | 391.2 (M + 1) | 338 |

TABLE 12-continued
| EXAMPLE | MOLSTRUCTURE | | Method |
|---|---|---|---|
| 626 | | 417.1 (M + 1) | 338 |
| 627 | | 447.2 (M + 1) | 338 |
| 628 | | 476.2 (M + 1) | 338 |
Preparation 1
4-Fluoro-N-methoxy-N-methyl-3-nitro-benzamide.
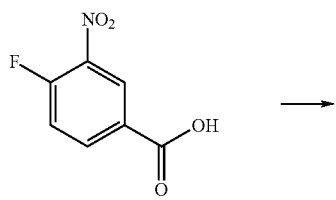
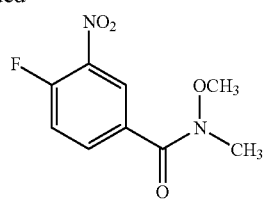
4-Fluoro-3-nitrobenzoic acid (100 gm, 0.54 mol) was taken up in dry methylene chloride (1 L) and 1.5 mL of DMF was added. To this solution was added oxalyl chloride (61 mL, 0.702 mol). After 1.5 hours, the solvent was removed in vacuo and the crude acid chloride (yellow oil) was taken up in methylene chloride (50 mL) and slowly added to a stirring mixture of triethylamine (150.5 mL, 1.08 mol) and Weinreb amine hydrochloride (68.5 gm, 0.702 mol) in methylene chloride (950 mL) at 0 deg C. The reaction was allowed to warm to room temperature and stirred overnight. The reaction mixture was washed with saturated sodium dihydrogen phosphate, followed by water. The organic phase was dried over anhydrous sodium sulfate and concentrated in vacuo to an orange-yellow oil. The crude oil was triturated with pentane to give 110.28 gm (90%) of a yellow to off white powder.

Preparation 2

4-Cyclopentylamino-N-methoxy-N-methyl-3-nitro-benzamide

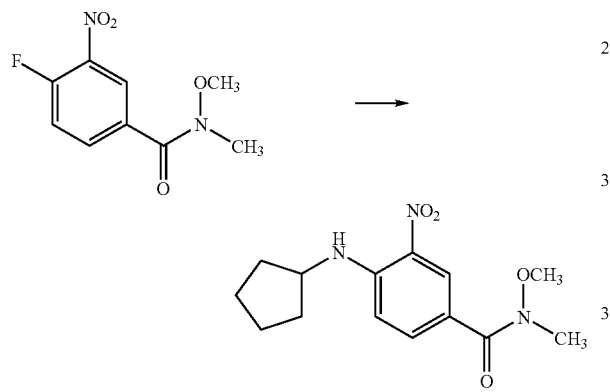

To a solution of the Weinreb amide (20 gm, 87.6 mmol, preparation described above) in methylene chloride (250 mL) was added cyclopentyl amine (19.0 mL, 192.8 mmol) in several portions. The reaction was stirred overnight at room temperature; the reaction was determined to be complete by $^1$HNMR the following morning. The reaction mixture was washed with water (2×100 mL) and the organic phase was dried over anhydrous sodium sulfate and concentrated in vacuo to afford 24.95 gm (97%) of a bright yellow solid.

Preparation 3

3-Amino-4-cyclopentylamino-N-methoxy-N-methyl-benzamide.

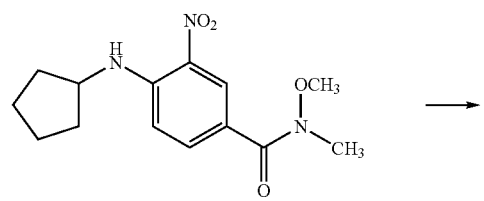

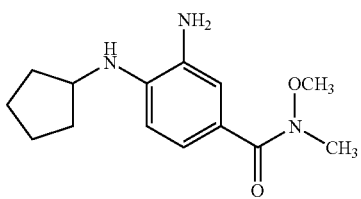

To a solution/slurry of the cyclopentyl Weinreb amide (24.95 gm, 85 mmol, preparation described above) in ethanol (500 mL) was added 10% Pd on carbon (approximately 1 gm). The resulting black slurry was hydrogenated on a Parr shaker for 5 hours, after which TLC (ethyl acetate) showed complete consumption of starting material. (Also, the color of the ethanol solution goes from bright yellow to clear, indicating complete consumption of starting material.) The catalyst was removed by filtration through Celite®, and the solvent was removed in vacuo to give 21.95 gm (98%) of the substituted aniline as a dark purple, viscous oil which was used without further purification.

Preparation 4

1-Cyclopentyl-2-oxo-2,3-dihydro-1H-benzoimidazole-5-carboxylic acid methoxy-methyl-amide

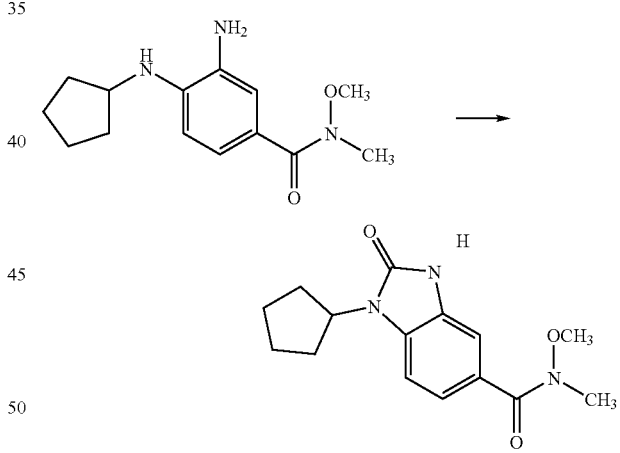

To a solution of substituted aniline (21.95 gm, 83 mmol, preparation described above) in methylene chloride (300 mL) was added triphosgene (9.79 gm, 33 mmol) in small portions (CAUTION: GAS EVOLUTION). After the addition of the triphosgene was complete, the reaction was stirred overnight at room temperature, after which time $^1$H NMR and TLC showed complete reaction. The organic phase was washed three times with saturated sodium bicarbonate solution, the organic phase was dried over anhydrous sodium sulfate and concentrated in vacuo to give 26.2 gm (quantitative) of a dark red foam which was used without further purification.

Preparation 5

1-tert-Butyl-2-oxo-2,3-dihydro-1H-benzoimidazole-5-carboxylic acid methoxy-methyl-amide

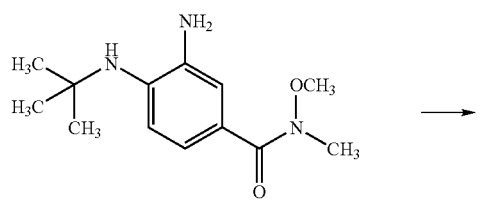

To a stirred solution of aniline (22.5 gm, 89.5 mmol) in dry methylene chloride (250 mL) was added carbonyl diimidazole (16.0 gm 98.5 mmol) in small portions (heat evolution). After stirring for 4 hours, $^1$HNMR of an aliquot of the reaction showed no starting material. Saturated sodium bicarbonate solution was added to the reaction mixture and the organic phase was separated, washed with saturated bicarbonate solution and brine, then dried over anhydrous sodium sulfate. Concentration in vacuo afforded 25.68 gm of a dark foam which was used without further purification.

Preparation 6

1-Cyclopentyl-3-methyl-2-oxo-2,3-dihydro-1H-benzoimidazole-5-carboxylic acid methoxy-methyl-amide

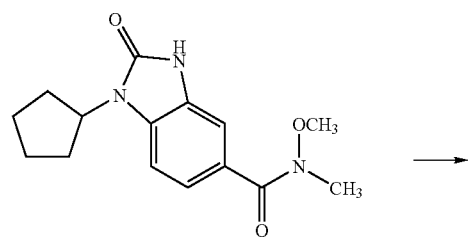

To a slurry of sodium hydride (720 mg of a 60% dispersion in mineral oil, 18 mmol) in dry DMSO (25 mL) was added the benzimidazolone (5.0 gm, 16 mmol, preparation described above) in small portions (CAUTION: GAS EVOLUTION). The resulting mixture was stirred for 30 minutes during which time the solution turned brown. A solution of methyl iodide (1.5 mL, 24 mmol) in DMSO (10 mL) was then added dropwise and the resulting solution stirred until TLC (ethyl acetate) showed complete reaction. The reaction was quenched with water (15 fold volume excess) and the aqueous phase was extracted with ethyl acetate (3×200 mL). The combined organic phases were washed with water and brine. The organic phase was dried over anhydrous sodium sulfate and concentrated in vacuo to afford 5.0 gm (98%) of a brown oil.

Preparation 7

1,3-Diethyl-2-oxo-2,3-dihydro-1H-benzoimidazole-5-carboxylic acid methyl ester

To a stirred solution of 4-amino-3-ethoxycarbonylaminobenzoic acid methyl ester (23.6 gm, 99 mmol) in DMF (330 mL, 0.3 M final concentration) was added cesium carbonate (114 gm, 350 mol, 3.5 eq.). The resulting green slurry was heated at 70 deg C overnight, after which time $^1$HNMR of an aliquot of the reaction mixture showed complete cyclization (as the reaction proceeds, the color changes from green to brown). The reaction was then cooled to room temperature and ethyl iodide (22.7 mL, 218 mmol) was added. The reaction was stirred at room temperature for 1 hour after which time $^1$HNMR of an aliquot showed complete reaction. The reaction mixture was then diluted with water (15 volumes) and the resulting aqueous layer was extracted with ethyl acetate (3×150 mL). The organics were combined, washed with 1 N HCl and water. The organic phase was dried over anhydrous sodium sulfate and concentrated in vacuo to give 19.4 gm of an orange solid which was used without further purification.

Preparation 8

We have previously demonstrated that the alkylation of the benzimidazolone nucleus can be carried out with cesium carbonate in place of sodium hydride. A represenative procedure is depicted below. Carbogen may have modified this procedure somewhat. See B. Shah for details about the Carbogen chemistry.

1-Cyclopentyl-3-methyl-5-m-tolylacetyl-1,3-dihydro-benzoimidazol-2-one

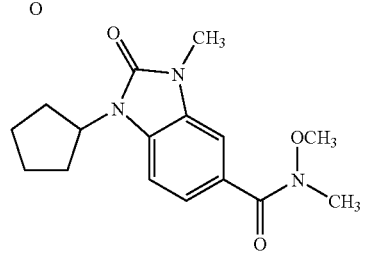

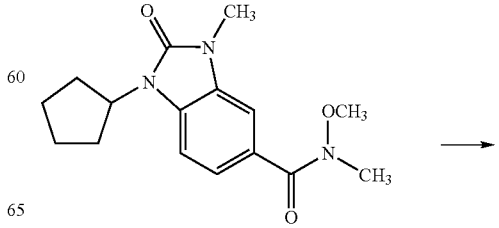

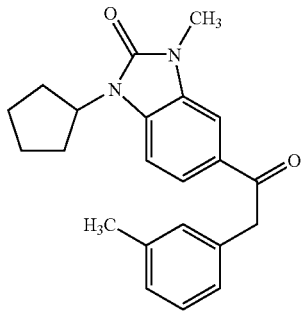

To a stirred solution of the Weinreb amide (17 gm, 56 mmol) in dry DME (700 mL) was added m-tolylmagnesium chloride (Rieke Metals, 0.5 M in THF, 200 mL, 100 mmol). The reaction mixture was allowed to stir overnight, after which time $^1$HNMR of an aliquot of the reaction indicated no starting material remained. The excess Grignard reagent in the reaction mixture was quenched with saturated aqueous sodium dihydrogen phosphate, and the DME was removed in vacuo. The remaining aqueous phase was extracted with ethyl acetate (3×200 mL) and the combined extracts were dried over anhydrous sodium sulfate and the solvent was concentrated in vacuo. Chromatography (Flash 75, gradient elution 25% ethyl acetate-hexanes to 50% ethyl acetate-hexanes) afforded 20 gm of a white solid.

What is claimed is:

1. A compound of the formula

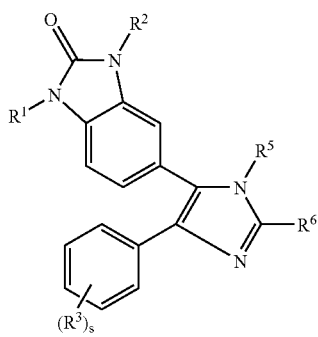

Ib wherein $R^1$ and $R^2$ are each independently selected from the group consisting of hydrogen, ($C_1$–$C_6$)alkyl, ($C_3$–$C_{10}$)cycloalkyl, phenyl, ($C_1$–$C_{10}$)heteroaryl and ($C_1$–$C_{10}$)heterocyclic; each of the aforesaid ($C_1$–$C_6$)alkyl, ($C_3$–$C_{10}$)cycloalkyl, phenyl, ($C_1$–$C_{10}$)heteroaryl and ($C_1$–$C_{10}$) heterocyclic substituents may optionally be independently substituted by one to four moieties independently selected from the group consisting of halo, ($C_1$–$C_6$)alkyl, ($C_2$–$C_6$) alkenyl, ($C_2$–$C_6$)alkynyl, perhalo($C_1$–$C_6$)alkyl, phenyl, ($C_3$–$C_{10}$)cycloalkyl, ($C_1$–$C_{10}$)heteroaryl, ($C_1$–$C_{10}$)heterocyclic, formyl, —CN, ($C_1$–$C_6$)alkyl-(C=O)—, phenyl-(C=O)—, HO—(C=O)—, ($C_1$–$C_6$)alkyl-O—(C=O)—, ($C_1$–$C_6$)alkyl-NH—(C=O)—, [($C_1$–$C_6$)alkyl]$_2$-N—(C=O)—, phenyl-NH—(C=O)—, phenyl-[(($C_1$–$C_6$)alkyl)-N]—(C=O)—, —NO$_2$, amino, ($C_1$–$C_6$)alkylamino, [($C_1$–$C_6$)alkyl]$_2$-amino, ($C_1$–$C_6$)alkyl-(C=O)—NH—, ($C_1$–$C_6$)alkyl-(C=O)—[(($C_1$–$C_6$)alkyl)-N]—, phenyl-(C=O)—NH—, phenyl-(C=O)—[(($C_1$–$C_6$)alkyl)-N]—, H$_2$N—(C=O)—NH—, ($C_1$–$C_6$)alkyl-HN—(C=O)—NH—, [($C_1$–$C_6$)alkyl-]$_2$N—(C=O)—NH—, ($C_1$–$C_6$)alkyl-HN—(C=O)—[(($C_1$–$C_6$)alkyl)-N]—, [($C_1$–$C_6$)alkyl-]$_2$N—(C=O)—[(($C_1$–$C_6$)alkyl)-N]—, phenyl-HN—(C=O)—NH—, (phenyl-)$_2$N—(C=O)—NH—, phenyl-HN—(C=O)—[(($C_1$–$C_6$)alkyl)-N]—, (phenyl-)$_2$N—(C=O)—[(($C_1$–$C_6$)alkyl)-N]—, ($C_1$–$C_6$)alkyl-O—(C=O)—NH—, ($C_1$–$C_6$)alkyl-O—(C=O)—[(($C_1$–$C_6$)alkyl)-N]—, phenyl-O—(C=O)—NH—, phenyl-O—(C=O)—[(($C_1$–$C_6$) alkyl)-N]—, ($C_1$–$C_6$)alkyl-SO$_2$NH—, phenyl-SO$_2$NH—, ($C_1$–$C_6$)alkyl-SO$_2$—, phenyl-SO$_2$—, hydroxy, ($C_1$–$C_6$) alkoxy, perhalo($C_1$–$C_6$)alkoxy, phenoxy, ($C_1$–$C_6$)alkyl-(C=O)—O—, phenyl-(C=O)—O—, H$_2$N—(C=O)—O—, ($C_1$–$C_6$)alkyl-HN—(C=O)—O—, [($C_1$–$C_6$)alkyl-]$_2$N—(C=O)—O—, phenyl-HN—(C=O)—O—, and (phenyl-)$_2$N—(C=O)—O—; wherein two adjacent substituents on said $R^1$ or $R^2$ ($C_3$–$C_{10}$)cycloalkyl, phenyl, ($C_1$–$C_{10}$)heteroaryl, or ($C_1$–$C_{10}$)heterocyclic may be taken together with the carbon or heteroatom to which they are attached to form a five to six membered carbocyclic or heterocyclic ring; wherein each of said moieties containing a phenyl alternative may optionally be substituted by one or two radicals independently selected from the group consisting of ($C_1$–$C_6$)alkyl, halo, ($C_1$–$C_6$)alkoxy, perhalo($C_1$–$C_6$)alkyl and perhalo($C_1$–$C_6$)alkoxy;

each $R^3$ is independently selected from the group consisting of halo, ($C_1$–$C_6$)alkyl, ($C_2$–$C_6$)alkenyl, ($C_2$–$C_6$) alkynyl, perhalo($C_1$–$C_6$)alkyl, phenyl, ($C_1$–$C_{10}$)heteroaryl, ($C_1$–$C_{10}$)heterocyclic, ($C_3$–$C_{10}$)cycloalkyl, hydroxy, ($C_1$–$C_6$)alkoxy, perhalo($C_1$–$C_6$)alkoxy, phenoxy, ($C_1$–$C_{10}$)heteroaryl-O—, ($C_1$–$C_{10}$)heterocyclic-O—, ($C_3$–$C_{10}$)cycloalkyl-O—, ($C_1$–$C_6$)alkyl-S—, ($C_1$–$C_6$)alkyl-SO$_2$—, ($C_1$–$C_6$)alkyl-NH—SO$_2$—, —NO$_2$, amino, ($C_1$–$C_6$)alkylamino, [($C_1$–$C_6$)alkyl]$_2$-amino, ($C_1$–$C_6$)alkyl-SO$_2$—NH—, ($C_1$–$C_6$)alkyl-(C=O)—NH—, ($C_1$–$C_6$)alkyl-(C=O)—[(($C_1$–$C_6$) alkyl)-N]—, phenyl-(C=O)—NH—, phenyl-(C=O)—[(($C_1$–$C_6$)alkyl)-N]—, —CN, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$) cycloalkyl-(C=O)—, HO—(C=O)—, ($C_1$–$C_6$)alkyl-O—(C=O)—, H$_2$N(C=O)—, ($C_1$–$C_6$)alkyl-NH—(C=O)—, [($C_1$–$C_6$)alkyl]$_2$-N—(C=O)—, phenyl-NH—(C=O)—, phenyl-[(($C_1$–$C_6$)alkyl)-N]—(C=O)—, ($C_1$–$C_{10}$)heteroaryl-NH—(C=O)—, ($C_1$–$C_{10}$)heterocyclic-NH—(C=O)—, ($C_3$–$C_{10}$)cycloalkyl-NH—(C=O)— and ($C_1$–$C_6$)alkyl-(C=O)—O—; wherein said phenyl, ($C_1$–$C_{10}$)heteroaryl, ($C_1$–$C_{10}$)heterocyclic and ($C_3$–$C_{10}$)cycloalkyl moieties of said phenyl, ($C_1$–$C_{10}$)heteroaryl, ($C_1$–$C_{10}$)heterocyclic, ($C_3$–$C_{10}$)cycloalkyl, phenoxy, ($C_1$–$C_{10}$)heteroaryl-O—, ($C_1$–$C_{10}$)heterocyclic-O—, ($C_3$–$C_{10}$)cycloalkyl-O—, phenyl-(C=O)—NH—, phenyl-(C=O)—[(($C_1$–$C_6$)alkyl)-N]—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, phenyl-NH—(C=O)—, phenyl-[(($C_1$–$C_6$)alkyl)-N]—(C=O)—, ($C_1$–$C_{10}$)heteroaryl-NH—(C=O)—, ($C_1$–$C_{10}$)heterocyclic-NH—(C=O)—, and ($C_3$–$C_{10}$) cycloalkyl-NH—(C=O)— may optionally be substituted with 1 to 3 substituents independently selected from the group consisting of fluoro, chloro, trifluoromethyl, ($C_1$–$C_6$)alkcoxy, ($C_6$–$C_{10}$)aryloxy, trifluoromethoxy, difluoromethoxy and ($C_1$–$C_6$)alkyl; wherein two adjacent $R^3$ groups may be taken together with the carbon atoms to which they are attached to form a three to six membered carbocyclic or heterocyclic ring;

s is an integer from zero to five;

$R^6$ is selected from the group consisting of hydrogen, halo and $R^9$—B—$(CH_2)_n$—;

n is an integer from zero to six;

each B is independently a bond, —$(CHR^{10})$—, —O—, —S—, —$(SO_2)$—, —$(C=O)$—, —O—$(C=O)$—, —$(C=O)$—O—, —$(C=O)$—$NR^{10}$—, —$(R^{10}$—N)—, —$(R^{10}$—N)—$SO_2$—, —$(R^{10}$—N)—$(C=O)$—, —$SO_2$—$(NR^{10})$—, —$(R^{10}$—N)—$(C=O)$—$(NR^{11})$—, —O—$(C=O)$—$(NR^{10})$— or —$(R^{10}$—N)—$(C=O)$—O—;

$R^5$ is selected from the group consisting of hydrogen, $R^{14}$—$(CR^{15}H)_p$—, phenyl, $(C_1$–$C_{10})$heteroaryl, $(C_1$–$C_{10})$heterocyclic, $(C_3$–$C_{10})$cycloalkyl, $(C_1$–$C_6)$alkyl-$(SO_2)$—, phenyl-$(SO_2)$—, $H_2N$—$(SO_2)$—, $(C_1$–$C_6)$alkyl-NH—$(SO_2)$—, [$(C_1$–$C_6)$alkyl-$]_2$N—$(SO_2)$—, phenyl-NH—$(SO_2)$—, (phenyl-$)_2$N—$(SO_2)$—, $R^{16}$—$(C_1$–$C_6)$alkyl-$(C=O)$—, phenyl-$(C=O)$—, $(C_1$–$C_{10})$heteroaryl-$(C=O)$—, $(C_1$–$C_{10})$heterocyclic-$(C=O)$—, $(C_3$–$C_{10})$cycloalkyl-$(C=O)$—, $(C_1$–$C_6)$alkyl-O—$(C=O)$—, $(C_1$–$C_{10})$heterocyclic-O—$(C=O)$—, $(C_3$–$C_{10})$cycloalkyl-O—$(C=O)$—, $H_2N$—$(C=O)$—, $(C_1$–$C_6)$alkyl-NH—$(C=O)$—, phenyl-NH—$(C=O)$—, $(C_1$–$C_{10})$heteroaryl-NH—$(C=O)$—, $(C_1$–$C_{10})$heterocyclic-NH—$(C=O)$—, $(C_3$–$C_{10})$cycloalkyl-NH—$(C=O)$—, [$(C_1$–$C_6)$alkyl-$]_2$N—$(C=O)$—, (phenyl-$)_2$N—$(C=O)$—, phenyl-[$((C_1$–$C_6)$alkyl)-N]—$(C=O)$—, $(C_1$–$C_{10})$heteroaryl-[$((C_1$–$C_6)$alkyl)-N]—$(C=O)$—, $(C_1$–$C_{10})$heterocyclic-[$((C_1$–$C_6)$alkyl)-N]—$(C=O)$—, and $(C_3$–$C_{10})$cycloalkyl-[$((C_1$–$C_6)$alkyl)-N]—$(C=O)$—, wherein each of the aforesaid phenyl, heterocyclic, heteroaryl or cycloalkyl $R^5$ alternatives may optionally be independently substituted by one to four moieties independently selected from the group consisting of halo, $R^{16}$ $(C_1$–$C_6)$alkyl, $(C_2$–$C_6)$alkenyl, $(C_2$–$C_6)$alkynyl, perhalo$(C_1$–$C_6)$alkyl, $(C_3$–$C_{10})$cycloalkyl, phenyl, benzyl, $(C_1$–$C_{10})$heterocyclic, $(C_1$–$C_{10})$heteroaryl, $(C_1$–$C_6)$alkyl-$SO_2$—, formyl, —CN, $(C_1$–$C_6)$alkyl-$(C=O)$—, $(C_3$–$C_{10})$cycloalkyl-$(C=O)$—, phenyl-$(C=O)$—, $(C_1$–$C_{10})$heterocyclic-$(C=O)$—, $(C_1$–$C_{10})$heteroaryl-$(C=O)$—, HO—$(C=O)$—, $(C_1$–$C_6)$alkyl-O—$(C=O)$—, $(C_3$–$C_{10})$cycloalkyl-O—$(C=O)$—, $(C_1$–$C_{10})$heterocyclic-O—$(C=O)$—, $(C_1$–$C_6)$alkyl-NH—$(C=O)$—, $(C_3$–$C_{10})$cycloalkyl-NH—$(C=O)$—, phenyl-NH—$(C=O)$—, $(C_1$–$C_{10})$heterocyclic-NH—$(C=O)$—, $(C_1$–$C_{10})$heteroaryl-NH—$(C=O)$—, [$(C_1$–$C_6)$alkyl$]_2$-N—$(C=O)$—, phenyl-[$((C_1$–$C_6)$alkyl)-N]—$(C=O)$—, hydroxy, $(C_1$–$C_6)$alkoxy, perhalo$(C_1$–$C_6)$alkoxy, $(C_3$–$C_{10})$cycloalkyl-O—, phenoxy, $(C_1$–$C_{10})$heterocyclic-O—, $(C_1$–$C_{10})$heteroaryl-O—, $(C_1$–$C_6)$alkyl-$(C=O)$—O—, $(C_3$–$C_{10})$cycloalkyl-$(C=O)$—O—, phenyl-$(C=O)$—O—, $(C_1$–$C_{10})$heterocyclic-$(C=O)$—O—, $(C_1$–$C_{10})$heteroaryl-$(C=O)$—O—, —$NO_2$, amino, $(C_1$–$C_6)$alkylamino, [$(C_1$–$C_6)$alkyl$]_2$-amino, formamidyl, $(C_1$–$C_6)$alkyl-$(C=O)$—NH—, $(C_3$–$C_{10})$cycloalkyl-$(C=O)$—NH—, phenyl-$(C=O)$—NH—, $(C_1$–$C_{10})$heterocyclic-$(C=O)$—NH—, $(C_1$–$C_{10})$heteroaryl-$(C=O)$—NH—, $(C_1$–$C_6)$alkyl-$(C=O)$—[$((C_1$–$C_6)$alkyl)-N]—, phenyl-$(C=O)$-[$(C_1$–$C_6)$alkyl-N]—, $(C_1$–$C_6)$alkyl-$SO_2NH$—, $(C_3$–$C_{10})$cycloalkyl-$SO_2NH$—, phenyl-$SO_2NH$—, $(C_1$–$C_{10})$heterocyclic-$SO_2NH$— and $(C_1$–$C_{10})$heteroaryl-$SO_2NH$—; wherein each of said phenyl and heteroaryl moiety alternatives may optionally be substituted by one or two radicals independently selected from halo, $(C_1$–$C_6)$alkyl, $(C_1$–$C_6)$alkoxy, perfluoro$(C_1$–$C_6)$alkyl and perfluoro$(C_1$–$C_6)$alkoxy;

p is an integer from one to six;

$R^9$ is selected from the group consisting of hydrogen, —$CF_3$, —C≡N, $R^{13}$—$(R^{12}CH)_m$—, phenyl, $(C_1$–$C_{10})$heteroaryl, $(C_1$–$C_{10})$heterocyclic and $(C_3$–$C_{10})$cycloalkyl; wherein each of the aforesaid $R^9$ phenyl, $(C_1$–$C_{10})$heteroaryl, $(C_1$–$C_{10})$heterocyclic and $(C_3$–$C_{10})$ cycloalkyl substituents may optionally be substituted by one to four moieties independently selected from the group consisting of $(C_2$–$C_6)$alkenyl, $(C_2$–$C_6)$alkynyl, perhalo$(C_1$–$C_6)$alkyl, phenyl, $(C_1$–$C_{10})$heteroaryl, $(C_1$–$C_{10})$heterocyclic, $(C_3$–$C_{10})$cycloalkyl, hydroxy, perhalo$(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, amino, $(C_1$–$C_6)$alkylamino, $(C_1$–$C_6)$alkyl-$SO_2$—NH—, $(C_1$–$C_6)$alkyl-$(C=O)$—NH—, $(C_1$–$C_6)$alkyl-$(C=O)$-[$((C_1$–$C_6)$alkyl)-N]—, phenyl-$(C=O)$—NH—, phenyl-$(C=O)$—[$((C_1$–$C_6)$alkyl)-N]—, —CN, $(C_1$–$C_6)$alkyl-$(C=O)$—, phenyl-$(C=O)$—, $(C_1$–$C_{10})$heteroaryl-$(C=O)$—, $(C_1$–$C_{10})$heterocyclic-$(C=O)$—, $(C_3$–$C_{10})$cycloalkyl-$(C=O)$—, HO—$(C=O)$—, $(C_1$–$C_6)$alkyl-O—$(C=O)$—, $H_2N$—$(C=O)$—, $(C_1$–$C_6)$alkyl-NH—$(C=O)$—, [$(C_1$–$C_6)$alkyl$]_2$-N—$(C=O)$—, phenyl-NH—$(C=O)$—, phenyl-[$((C_1$–$C_6)$alkyl)-N]—$(C=O)$—, $(C_1$–$C_{10})$heteroaryl-NH—$(C=O)$—, $(C_1$–$C_{10})$heterocyclic-NH—$(C=O)$—, $(C_3$–$C_{10})$cycloalkyl-NH—$(C=O)$—, $(C_1$–$C_6)$alkyl-$(C=O)$—O— and phenyl-$(C=O)$—O—; wherein two adjacent substituents on said $R^9$ $(C_1$–$C_{10})$heterocyclic or $(C_3$–$C_{10})$cycloalkyl may be taken together with the carbon or heteroatoms to which they are attached to form a five to six membered heterocyclic or carbocyclic ring;

m is an integer from one to six;

$R^{10}$ is hydrogen, $(C_1$–$C_6)$alkyl-$SO_2$— or $(C_1$–$C_6)$alkyl;

$R^{11}$ is hydrogen or $(C_1$–$C_6)$alkyl;

each $R^{12}$ is independently selected from the group consisting of hydrogen, amino, $(C_1$–$C_6)$alkoxy and $(C_1$–$C_6)$alkyl;

$R^{13}$ is selected from the group consisting of hydrogen, $(C_1$–$C_6)$alkyl, $(C_2$–$C_6)$alkenyl, $(C_2$–$C_6)$alkynyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo$(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$alkyl$]_2$-amino, $(C_1$–$C_6)$alkyl-$SO_2$—NH—, phenyl-$SO_2$—NH—, $(C_1$–$C_6)$alkyl-$SO_2$—[$((C_1$–$C_6)$alkyl)-N]—, phenyl-$SO_2$—[$((C_1$–$C_6)$alkyl)-N]—, $(C_1$–$C_6)$alkyl-$(C=O)$—NH—, $(C_1$–$C_6)$alkyl-$(C=O)$—[$((C_1$–$C_6)$alkyl)-N]—, phenyl-$(C=O)$—NH—, phenyl-$(C=O)$—[$((C_1$–$C_6)$alkyl)-N]—, —CN, $(C_1$–$C_6)$alkyl-$(C=O)$—, phenyl-$(C=O)$—, $(C_1$–$C_{10})$heteroaryl-$(C=O)$—, $(C_1$–$C_{10})$heterocyclic-$(C=O)$—, $(C_3$–$C_{10})$cycloalkyl-$(C=O)$—, HO—$(C=O)$—, $(C_1$–$C_6)$alkyl-O—$(C=O)$—, $H_2N$—$(C=O)$—, $(C_1$–$C_6)$alkyl-NH—$(C=O)$—, [$(C_1$–$C_6)$alkyl$]_2$-N—$(C=O)$—, phenyl-NH—$(C=O)$—, phenyl-[$((C_1$–$C_6)$alkyl)-N]—$(C=O)$—, $(C_1$–$C_{10})$heteroaryl-NH—$(C=O)$—, $(C_1$–$C_{10})$heterocyclic-NH—$(C=O)$—, $(C_3$–$C_{10})$cycloalkyl-NH—$(C=O)$—, $(C_1$–$C_6)$alkyl-$(C=O)$—O— and phenyl-$(C=O)$—O—;

$R^{14}$ is selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, $(C_1-C_{10})$heterocyclic, $(C_1-C_{10})$heteroaryl, $(C_1-C_6)$alkyl-(S=O)—, phenyl-(S=O)—, $(C_1-C_6)$alkyl-SO$_2$—, phenyl-SO$_2$—, H$_2$N—SO$_2$—, $(C_1-C_6)$alkyl-NH—SO$_2$—, phenyl-NH—SO$_2$—, [(C$_1$–C$_6$)alkyl-]$_2$N—SO$_2$—, (phenyl-)$_2$N—SO$_2$—, formyl, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $R^{16}$—$(C_1-C_6)$alkyl-O—(C=O)—, $(C_3-C_{10})$cycloalkyl-O—(C=O)—, $(C_1-C_{10})$heterocyclic-O—(C=O)—, H$_2$N—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, [(C$_1$–C$_6$)alkyl]$_2$-N—(C=O)—, phenyl-[((C$_1$–C$_6$)alkyl)-N]—(C=O)—, $(C_1-C_{10})$heteroaryl-[((C$_1$–C$_6$)alkyl)-N]—(C=O)—, $(C_1-C_{10})$heterocyclic-[((C$_1$–C$_6$)alkyl)-N]—(C=O)—, $(C_3-C_{10})$cycloalkyl[((C$_1$–C$_6$)alkyl)-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —NO$_2$, amino, $R^{16}$—$(C_1-C_6)$alkylamino, [(C$_1$–C$_6$)alkyl]$_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—[((C$_1$–C$_6$)alkyl)-N]—, phenyl-(C=O)—[((C$_1$–C$_6$)alkyl)-N]—, $R^{16}$—$(C_1-C_6)$alkyl-SO$_2$NH—, $(C_3-C_{10})$cycloalkyl-SO$_2$NH—, phenyl-SO$_2$NH—, $(C_1-C_{10})$heterocyclic-SO$_2$NH— and $(C_1-C_{10})$heteroaryl-SO$_2$NH—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-(S=O)—, $(C_1-C_6)$alkyl-SO$_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, H$_2$N—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, [(C$_1$–C$_6$)alkyl]$_2$-N—(C=O)—, phenyl-[((C$_1$–C$_6$)alkyl)-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —NO$_2$, amino, $R^{16}$—$(C_1-C_6)$alkylamino, [(C$_1$–C$_6$)alkyl]$_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—[((C$_1$–C$_6$)alkyl)-N]—, phenyl-(C=O)—[((C$_1$–C$_6$)alkyl)-N]—, $R^{16}$—$(C_1-C_6)$alkyl-SO$_2$NH—, $(C_3-C_{10})$cycloalkyl-SO$_2$NH—, phenyl-SO$_2$NH—, $(C_1-C_{10})$heterocyclic-SO$_2$NH— and $(C_1-C_{10})$heteroaryl-SO$_2$NH—; wherein each of said phenyl and heteroaryl moiety alternatives may optionally be substituted by one or two radicals independently selected from the group consisting of halo, $(C_1-C_6)$alkyl, $(C_1-C_6)$alkoxy, perfluoro$(C_1-C_6)$alkyl and perfluoro$(C_1-C_6)$alkoxy;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, H$_2$N—(C=O)—, $(C_1-C_6)$alkyl-NH—(C=O)—, [(C$_1$–C$_6$)alkyl]$_2$-N—(C=O)—, hydroxy, $(C_1-C_6)$alkoxy, $(C_1-C_6)$alkyl-(C=O)—O—, amino, $(C_1-C_6)$alkylamino, [(C$_1$–C$_6$)alkyl]$_2$-amino, formamidyl and $(C_1-C_6)$alkyl-(C=O)—NH—;

each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_1-C_{10})$heterocyclic, HO—(C=O)—, $(C_1-C_6)$alkyl-O—(C=O)—, H$_2$N—(C=O)—, $(C_1-C_6)$alkyl-NH—(C=O)—, [(C$_1$–C$_6$)alkyl]$_2$-N—(C=O)—, hydroxy, $(C_1-C_6)$alkoxy, perhalo$(C_1-C_6)$alkoxy, $(C_1-C_6)$alkyl-(C=O)—O—, —NO$_2$, amino, $(C_1-C_6)$alkylamino, [(C$_1$–C$_6$)alkyl]$_2$-amino, formamidyl and $(C_1-C_6)$alkyl-(C=O)—NH—; wherein said $(C_1-C_{10})$heterocyclic may optionally be substituted by one to three substitutents independently selected from the group consisting of halo, $(C_1-C_6)$alkyl, $(C_1-C_6)$alkoxy, benzyl, amino, $(C_1-C_6)$alkylamino and [(C$_1$–C$_6$)alkyl]$_2$-amino;

or $R^5$ and $R^6$ or may be taken together with the atoms to which they are attached to form an optionally substituted five to ten membered saturated, unsaturated or aromatic ring optionally containing two to three heteroatoms independently selected from NH, N, O, S, SO or SO$_2$; wherein said ring may be optionally substituted by one to three substituents independently selected from the group consisting of oxo, halo, $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-(S=O)—, $(C_1-C_6)$alkyl-SO$_2$—, phenyl-S—, phenyl-(S=O)—, phenyl-SO$_2$—, $(C_1-C_6)$alkyl-NH—SO$_2$—[(C$_1$–C$_6$)alkyl]$_2$- N—SO$_2$—, phenyl-NH— SO$_2$—, (phenyl-)$_2$N—SO$_2$—, phenyl-[N (C$_1$–C$_6$)alkyl]-SO$_2$—, formyl, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $(C_1-C_{10})$heterocyclic-O—(C=O)—, $(C_3-C_{10})$cycloalkyl-O—(C=O)—, H$_2$N—(C=O)—, $(C_1-C_6)$alkyl-NH—(C=O)—, [(C$_1$–C$_6$)alkyl]$_2$-N—(C=O)—, phenyl-NH—(C=O)—, phenyl-[((C$_1$–C$_6$)alkyl)-N]—(C=O)—, $(C_1-C_{10})$heteroaryl-NH—(C=O)—, $(C_1-C_{10})$heteroaryl-[((C$_1$–C$_6$)alkyl)-N]—(C=O)—, $(C_1-C_{10})$heterocyclic-NH—(C=O)—, $(C_1-C_{10})$heterocyclic-[((C$_1$–C$_6$)alkyl)-N]—(C=O)—, $(C_3-C_{10})$cycloalkyl-NH—(C=O)—, $(C_3-C_{10})$cycloalkyl-[((C$_1$–C$_6$)alkyl)-N]—(C=O)—, amino, $(C_1-C_6)$alkylamino, [(C$_1$–C$_6$)alkyl]$_2$amino, $(C_1-C_6)$alkyl-SO$_2$—NH—, phenyl-SO$_2$—NH—, $(C_1-C_6)$alkyl-SO$_2$—[((C$_1$–C$_6$)alkyl)-N]—, phenyl-SO$_2$—

[((C$_1$–C$_6$)alkyl)-N]—, formamidyl, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$)alkyl)-N]—, (C$_1$–C$_{10}$)heteroaryl-(C=O)—NH—, (C$_1$–C$_{10}$)heteroaryl-(C=O)—[((C$_1$–C$_6$)alkyl)-N]—, (C$_1$–C$_{10}$)heterocyclic-(C=O)—NH—, (C$_1$–C$_{10}$)heterocyclic-(C=O)—[((C$_1$–C$_6$)alkyl)-N]—, (C$_3$–C$_{10}$)cycloalkyl-(C=O)—NH—, (C$_3$–C$_{10}$)cycloalkyl-(C=O)—[((C$_1$–C$_6$)alkyl)-N]—, H$_2$N(C=O)—NH—, (C$_1$–C$_6$)alkyl-HN—(C=O)—NH—, (C$_1$–C$_6$)alkyl-HN—(C=O)—[((C$_1$–C$_6$)alkyl)-N]—, [(C$_1$–C$_6$)alkyl]$_2$-N—(C=O)—NH—, [(C$_1$–C$_6$)alkyl]$_2$-N—(C=O)—[((C$_{1-6}$)alkyl)-N]—, phenyl-HN—(C=O)—NH—, phenyl-HN—(C=O)—[((C$_1$–C$_6$)alkyl)-N]—, (phenyl)$_2$-N—(C=O)—NH—, (phenyl)$_2$-N—(C=O)—[((C$_1$–C$_6$)alkyl)-N]—, (C$_1$–C$_{10}$)heteroaryl-HN—(C=O)—NH—, (C$_1$–C$_{10}$)heteroaryl-HN—(C=O)—[((C$_1$–C$_6$)alkyl)-N]—, [(C$_1$–C$_{10}$)heteroaryl]$_2$-N—(C=O)—[((C$_1$–C$_6$)alkyl)-N]—, [(C$_1$–C$_{10}$)heteroaryl]$_2$-N—(C=O)—NH—, (C$_1$–C$_{10}$)heterocyclic-HN—(C=O)—NH—, (C$_1$–C$_{10}$)heterocyclic-HN—(C=O)—[((C$_1$–C$_6$)alkyl)-N]—, [(C$_1$–C$_{10}$)heterocyclic]$_2$-N—(C=O)—[((C$_1$–C$_6$)alkyl)-N]—, [(C$_1$–C$_{10}$)heterocyclic]$_2$-N—(C=O)—NH—, (C$_3$–C$_{10}$)cycloalkyl-HN—(C=O)—NH—, (C$_3$–C$_{10}$)cycloalkyl-HN—(C=O)—[((C$_1$–C$_6$)alkyl)-N]—, [(C$_3$–C$_{10}$)cycloalkyl]$_2$-N—(C=O)—[((C$_1$–C$_6$)alkyl)-N]—, [(C$_3$–C$_{10}$)cycloalkyl]$_2$-N—(C=O)—NH—, (C$_1$–C$_6$)alkyl-(C=O)—O—, phenyl-(C=O)—O—, (C$_1$–C$_{10}$)heteroaryl-(C=O)—O—, (C$_1$–C$_{10}$)heterocyclic-(C=O)—O—, (C$_3$–C$_{10}$)cycloalkyl-(C=O)—O—, (C$_1$–C$_6$)alkyl-NH—(C=O)—O—, [(C$_1$–C$_6$)alkyl]$_2$-N—(C=O)—O—, phenyl-NH—(C=O)—O—, (C$_1$–C$_{10}$)heteroaryl-NH—(C=O)—O—, (C$_1$–C$_{10}$)heterocyclic-NH—(C=O)—O— and (C$_3$–C$_{10}$)cycloalkyl-NH—(C=O)—O—;

with the proviso that when R$^6$ is R$^9$—B—(CH$_2$)$_n$—; n is zero and B is a bond; then R$^9$ must be other than phenyl;

or a pharmaceutically acceptable salt thereof.

2. A compound according to claim 1, wherein R$^1$ or R$^2$ are independently optionally substituted (C$_1$–C$_6$)alkyl, phenyl, (C$_3$–C$_{10}$)cycloalkyl, (C$_1$–C$_{10}$)heteroaryl or (C$_1$–C$_{10}$)heterocyclic.

3. A compound according to claim 1, wherein R$^1$ or R$^2$ are each independently (C$_1$–C$_6$)alkyl, optionally substituted with one to four groups independently selected from halo, (C$_1$–C$_6$)alkyl, (C$_2$–C$_6$)alkenyl, (C$_2$–C$_6$)alkynyl, (C$_1$–C$_6$)alkoxy, perhalo(C$_1$–C$_6$)alkyl, perhalo(C$_1$–C$_6$)alkoxy, —CN, —NO$_2$, amino, (C$_1$–C$_6$)alkylamino, [(C$_1$–C$_6$)alkyl]$_2$-amino, HO—(C=O)—, (C$_1$–C$_6$)alkyl-(C=O)—, (C$_1$–C$_6$)alkyl-O—(C=O)—, (C$_1$–C$_6$)alkyl-CO$_2$—, (C$_1$–C$_6$)alkyl-(C=O)—NH—, (C$_1$–C$_6$)alkyl-NH—(C=O)—, (C$_1$–C$_6$)alkyl-(C=O)—[((C$_1$–C$_6$)alkyl)-N]—, (C$_1$–C$_6$)alkyl-[((C$_1$–C$_6$)alkyl)-N]—(C=O)—, (C$_1$–C$_6$)alkyl-SO$_2$NH—, (C$_1$–C$_6$)alkyl-SO$_2$—, optionally substituted phenyl-(C=O)—, optionally substituted phenyl-(C=O)—O—, optionally substituted phenoxy, optionally substituted phenyl-NH—(C=O)—, optionally substituted phenyl-[((C$_1$–C$_6$)alkyl)-N]—(C=O)—, optionally substituted phenyl-(C=O)—NH— and optionally substituted phenyl-(C=O)—[((C$_1$–C$_6$)alkyl)-N]—.

4. A compound according to claim 1, wherein R$^2$ is (C$_1$–C$_4$)alkyl.

5. A compound according to claim 4, wherein R$^1$ is (C$_1$–C$_5$)alkyl or (C$_3$–C$_6$)cycloalkyl.

6. A compound according to claim 1, wherein R$^1$ is optionally substituted (C$_3$–C$_6$)cycloalkyl and R$^2$ is (C$_1$–C$_6$)alkyl.

7. A compound according to claim 1, wherein R$^1$ and R$^2$ are each independently (C$_1$–C$_6$)alkyl.

8. A compound according to claim 1, wherein R$^1$ is optionally substituted phenyl and R$^2$ is (C$_1$–C$_6$)alkyl.

9. A compound according to claim 1, wherein R$^1$ is optionally substituted (C$_1$–C$_{10}$)heterocyclic and R$^2$ is (C$_1$–C$_6$)alkyl.

10. A compound according to claim 1, wherein R$^1$ is optionally substituted (C$_1$–C$_{10}$)heteroaryl and R$^2$ is (C$_1$–C$_6$)alkyl.

11. A compound according to claim 1, wherein R$^1$ or R$^2$ is hydrogen.

12. A compound according to claim 1, wherein R$^5$ is hydrogen.

13. A compound according to claim 1, wherein R$^5$ is (C$_1$–C$_{10}$)heterocyclic or (C$_1$–C$_{10}$)heteroaryl; wherein each of the aforesaid heterocyclic and heteroaryl substituents may optionally be independently substituted by one to four moieties independently selected from the group consisting of halo, (C$_1$–C$_6$)alkyl, (C$_1$–C$_6$)alkoxy, HO—(C=O)—, (C$_1$–C$_6$)alkyl-O—(C=O)—, H$_2$N—(C=O)—, (C$_1$–C$_6$)alkyl-NH—(C=O)— and [(C$_1$–C$_6$)alkyl]$_2$-N—(C=O)—.

14. A compound according to claim 1, wherein R$^5$ is R$^{14}$—(CHR$^{15}$)$_p$—, p is 1–6; and R$^{14}$ is selected from the group consisting of hydrogen, (C$_1$–C$_6$)alkyl, (C$_2$–C$_6$)alkenyl, perhalo(C$_1$–C$_6$)alkyl, (C$_3$–C$_{10}$)cycloalkyl, phenyl, (C$_1$–C$_{10}$)heterocyclic, (C$_1$–C$_{10}$)heteroaryl, phenyl-(S=O)—, (C$_1$–C$_6$)alkyl-SO$_2$—, phenyl-SO$_2$—, H$_2$N—SO$_2$—, (C$_1$–C$_6$)alkyl-NH—SO$_2$—, phenyl-NH—SO$_2$—, [(C$_1$–C$_6$)alkyl-]$_2$N—SO$_2$—, (C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, HO—(C=O)—, R$^{16}$—(C$_1$–C$_6$)alkyl-O—(C=O)—, (C$_3$–C$_{10}$)cycloalkyl-O—(C=O)—, (C$_1$–C$_{10}$)heterocyclic-O—(C=O)—, (C$_1$–C$_{10}$)heteroaryl-O—(C=O)—, H$_2$N—(C=O)—, (C$_1$–C$_6$)alkyl-NH—(C=O)—, (C$_3$–C$_{10}$)cycloalkyl-NH—(C=O)—, phenyl-NH—(C=O)—, (C$_1$–C$_{10}$)heterocyclic-NH—(C=O)—, (C$_1$–C$_{10}$)heteroaryl-NH—(C=O)—, [(C$_1$–C$_6$)alkyl]$_2$-N—(C=O)—, phenyl-[((C$_1$–C$_6$)alkyl)-N]—(C=O)—, (C$_1$–C$_{10}$)heteroaryl-[N—(C$_1$–C$_6$)alkyl]-(C=O)—, (C$_1$–C$_{10}$)heterocyclic-[((C$_1$–C$_6$)alkyl)-N]—(C=O)—, (C$_3$–C$_{10}$)cycloalkyl[((C$_1$–C$_6$)alkyl)-N]—(C=O)—, hydroxy, R$^{16}$—(C$_1$–C$_6$)alkoxy, perhalo (C$_1$–C$_6$)alkoxy, (C$_3$–C$_{10}$)cycloalkyl-O—, phenoxy, (C$_1$–C$_{10}$)heterocyclic-O—, (C$_1$–C$_{10}$)heteroaryl-O—, R$^{16}$—(C$_1$–C$_6$)alkyl-(C=O)—O—, (C$_3$–C$_{10}$)cycloalkyl-(C=O)—O—, phenyl-(C=O)—O—, (C$_1$–C$_{10}$)heterocyclic-(C=O)—O—, (C$_1$–C$_{10}$)heteroaryl-(C=O)—O—, —NO$_2$, amino, R$^{16}$—(C$_1$–C$_6$)alkylamino, [(C$_1$–C$_6$)alkyl]$_2$-amino, formamidyl, R$^{16}$—(C$_1$–C$_6$)alkyl-(C=O)—NH—, (C$_3$–C$_{10}$)cycloalkyl-(C=O)—NH—, phenyl-(C=O)—NH—, R$^{16}$—(C$_1$–C$_6$)alkyl-SO$_2$NH—, (C$_3$–C$_{10}$)cycloalkyl-SO$_2$NH—, phenyl-SO$_2$NH—, (C$_1$–C$_{10}$)heterocyclic-SO$_2$NH— and (C$_1$–C$_{10}$)heteroaryl-SO$_2$NH—; wherein each of the aforesaid phenyl, heterocyclic, heteroaryl or cycloalkyl R$^{14}$ alternatives may optionally be independently substituted by one to four moieties independently selected from the group consisting of halo, R$^{16}$—(C$_1$–C$_6$)alkyl, (C$_2$–C$_6$)alkenyl, (C$_2$–C$_6$)alkynyl, perhalo(C$_1$–C$_6$)alkyl, (C$_3$–C$_{10}$)cycloalkyl, phenyl, benzyl, (C$_1$–C$_{10}$)heterocyclic, (C$_1$–C$_{10}$)heteroaryl, (C$_1$–C$_6$)alkyl-(S=O)—, (C$_1$–C$_6$)alkyl-SO$_2$—, formyl, —CN, R$^{16}$—(C$_1$–C$_6$)alkyl-(C=O)—, (C$_3$–C$_{10}$)cycloalkyl-(C=O)—, phenyl-(C=O)—, (C$_1$–C$_{10}$)heterocyclic-(C=O)—, (C$_1$–C$_{10}$)heteroaryl-(C=O)—, HO—(C=O)—, $(C_1–C_6)$alkyl-O—(C=O)—, $(C_3–C_{10})$cycloalkyl-O—(C=O)—, $(C_1–C_{10})$heterocyclic-O—(C=O)—, $(C_1–C_{10})$heteroaryl-O—(C=O)—, $H_2N$—(C=O)—, $R^{16}$—$(C_1–C_6)$alkyl-NH—(C=O)—, $(C_3–C_{10})$cycloalkyl-NH—(C=O)—, phenyl-NH—(C=O)—, $(C_1–C_{10})$heterocyclic-NH—(C=O)—, $(C_1–C_{10})$heteroaryl-NH—(C=O)—, $[(C_1–C_6)$alkyl$]_2$-N—(C=O)—, phenyl-$[((C_1–C_6)$alkyl)-N]$—(C=O)—, hydroxy, $R^{16}$—$(C_1–C_6)$alkoxy, perhalo$(C_1–C_6)$alkoxy, $(C_3–C_{10})$cycloalkyl-O—, phenoxy, $(C_1–C_{10})$heterocyclic-O—, $(C_1–C_{10})$heteroaryl-O—, $R^{16}$—$(C_1–C_6)$alkyl-(C=O)—O—, $(C_3–C_{10})$cycloalkyl-(C=O)—O—, phenyl-(C=O)—O—, $(C_1–C_{10})$heterocyclic-(C=O)—O—, $(C_1–C_{10})$heteroaryl-(C=O)—O—, —$NO_2$, amino, $R^{16}$—$(C_1–C_6)$alkylamino, $[(C_1–C_6)$alkyl$]_2$-amino, formamidyl, $R^{16}$—$(C_1–C_6)$alkyl-(C=O)—NH—, $(C_3–C_{10})$cycloalkyl-(C=O)—NH—, phenyl-(C=O)—NH—, $(C_1–C_{10})$heterocyclic-(C=O)—NH—, $(C_1–C_{10})$heteroaryl-(C=O)—NH—, $R^{16}$—$(C_1–C_6)$alkyl-(C=O)—$[((C_1–C_6)$alkyl)-N]$—, phenyl-(C=O)—$[(C_1–C_6)$alkyl-N]$—, $R^{16}$—$(C_1–C_6)$alkyl-$SO_2NH$—, $(C_3–C_{10})$cycloalkyl-$SO_2NH$—, phenyl-$SO_2NH$—, $(C_1–C_{10})$heterocyclic-$SO_2NH$— and $(C_1–C_{10})$heteroaryl-$SO_2NH$—; and wherein each of said phenyl and heteroaryl moiety alternatives may optionally be substituted by one or two radicals independently selected from halo, $(C_1–C_6)$alkyl, $(C_1–C_6)$alkoxy, amino, $(C_1–C_6)$alkylamino and $[(C_1–C_6)$alkyl$]_2$-amino.

15. A compound according to claim 1, wherein $R^5$ is $R^{14}$—$(CHR^{15})_p$—, p is 1–6; and $R^{14}$ is selected from the group consisting of hydrogen, $(C_1–C_6)$alkyl, $(C_2–C_6)$alkenyl, $(C_3–C_{10})$cycloalkyl, phenyl, $(C_1–C_{10})$heterocyclic, $(C_1–C_{10})$heteroaryl, HO—(C=O)—, $R^{16}$—$(C_1–C_6)$alkyl-O—(C=O)—, $H_2N$—(C=O)—, $R^{16}$—$(C_1–C_6)$alkyl-NH—(C=O)—, phenyl-NH—(C=O)—, $(C_1–C_{10})$heterocyclic-NH—(C=O), $[(C_1–C_6)$alkyl$]_2$-N—(C=O)—, phenyl-$[((C_1–C_6)$alkyl)-N]$—(C=O)—, hydroxy, $R^{16}$—$(C_1–C_6)$alkoxy, phenoxy, amino, $R^{16}$—$(C_1–C_6)$alkylamino, $[(C_1–C_6)$alkyl$]_2$-amino, and $R^{16}$—$(C_1–C_6)$alkyl-(C=O)—NH—; wherein each of the aforesaid phenyl, heterocyclic, heteroaryl or cycloalkyl $R^{14}$ alternatives may optionally be independently substituted by one to four moieties independently selected from the group consisting of halo, $R^{16}$—$(C_1–C_6)$alkyl, $(C_2–C_6)$alkenyl, $(C_2–C_6)$alkynyl, perhalo$(C_1–C_6)$alkyl, $(C_1–C_6)$alkyl-$SO_2$—, formyl, —CN, $R^{16}$—$(C_1–C_6)$alkyl-(C=O)—, HO—(C=O)—, $(C_1–C_6)$alkyl-O—(C=O)—, $H_2N$—(C=O)—, $R^{16}$—$(C_1–C_6)$alkyl-NH—(C=O)—, $[(C_1–C_6)$alkyl$]_2N$—(C=O)—, hydroxy, $R^{16}$—$(C_1–C_6)$alkoxy, perhalo$(C_1–C_6)$alkoxy, $R^{16}$—$(C_1–C_6)$alkyl-(C=O)—O—, amino, $R^{16}$—$(C_1–C_6)$alkylamino, $[(C_1–C_6)$alkyl$]_2$-amino, formamidyl, $R^{16}$—$(C_1–C_6)$alkyl-(C=O)—NH—, $R^{16}$—$(C_1–C_6)$alkyl-(C=O)—$[((C_1–C_6)$alkyl)-N]$— and $R^{16}$—$(C_1–C_6)$alkyl-$SO_2NH$—;

each $R^{15}$ is independently selected from the group consisting of hydrogen, halo, $(C_1–C_6)$alkyl, $(C_2–C_6)$alkenyl, perhalo$(C_1–C_6)$alkyl, HO—(C=O)—, $(C_1–C_6)$alkyl-O—(C=O)—, $H_2N$—(C=O)—, $(C_1–C_6)$alkyl-NH—(C=O)—, $[(C_1–C_6)$alkyl$]_2$-N—(C=O)—, hydroxy, $(C_1–C_6)$alkoxy, perhalo$(C_1–C_6)$alkoxy, amino, $(C_1–C_6)$alkylamino, $[(C_1–C_6)$alkyl$]_2$-amino, formamidyl and $(C_1–C_6)$alkyl-(C=O)—NH—; wherein no more than two of said $R^{15}$ groups may be other than hydrogen; and each $R^{16}$ is independently selected from the group consisting of hydrogen, halo, $(C_1–C_6)$alkyl, $(C_2–C_6)$alkenyl, $(C_2–C_6)$alkynyl, perhalo$(C_1–C_6)$alkyl, HO—(C=O)—, $(C_1–C_6)$alkyl-O—(C=O)—, $H_2N$—(C=O)—, $(C_1–C_6)$alkyl-NH—(C=O)—, $[(C_1–C_6)$alkyl$]_2$-N—(C=O)—, hydroxy, $(C_1–C_6)$alkoxy, perhalo$(C_1–C_6)$alkoxy, $(C_1–C_6)$alkyl-(C=O)—O—, —$NO_2$, amino, $(C_1–C_6)$alkylamino, $[(C_1–C_6)$alkyl$]_2$-amino, formamidyl and $(C_1–C_6)$alkyl-(C=O)—NH—.

16. A compound according to claim 1, wherein $R^6$ is hydrogen.

17. A compound according to claim 1, wherein $R^6$ is $R^9$—B—$(CH_2)_n$— and n is zero.

18. A compound according to claim 1, wherein $R^6$ is $R^9$—B—$(CH_2)_n$— and n is an integer from one to five.

19. A compound according to claim 1, wherein $R^6$ is $R^9$—B—$(CH_2)_n$—; n is zero; B is a bond and $R^9$ is selected from the group consisting of hydrogen, —$CF_3$, —C≡N, $(C_1–C_{10})$heteroaryl, $(C_1–C_{10})$heterocyclic or $(C_3–C_{10})$cycloalkyl; wherein each of the aforesaid $(C_1–C_{10})$heteroaryl, $(C_1–C_{10})$heterocyclic and $(C_3–C_{10})$cycloalkyl may optionally be substituted by one to three moieties independently selected from the group consisting of halo, $(C_1–C_6)$alkyl, $(C_2–C_6)$alkenyl, $(C_1–C_6)$alkynyl, perhalo$(C_1–C_6)$alkyl, hydroxy, $(C_1–C_6)$alkoxy, perhalo$(C_1–C_6)$alkoxy, $(C_1–C_6)$alkyl-S—, $(C_1–C_6)$alkyl-$SO_2$—, $(C_1–C_6)$alkyl-NH—$SO_2$—, —$NO_2$, amino, $(C_1–C_6)$alkylamino, $[(C_1–C_6)$alkyl$]_2$-amino, $(C_1–C_6)$alkyl-$SO_2$—NH—, $(C_1–C_6)$alkyl-(C=O)—NH—, $(C_1–C_6)$alkyl-(C=O)—$[((C_1–C_6)$alkyl)-N]$—, —CN, $(C_1–C_6)$alkyl-(C=O)—, HO—(C=O)—, $(C_1–C_6)$alkyl-O—(C=O)—, $H_2N$(C=O)—, $(C_1–C_6)$alkyl-NH—(C=O)—, $[(C_1–C_6)$alkyl$]_2$N—(C=O)— and $(C_1–C_6)$alkyl-(C=O)—O—.

20. A compound according to claim 1, wherein $R^6$ is $R^9$—B—$(CH_2)_n$—; n is zero; B is —(C=O)—$NR^{10}$—, —$(R^{10}$—N)$—, —$(R^{10}$—N)$—$SO_2$—, —$(R^{10}$—N)$—(C=O)—, >C=O, —O—(C=O)—, —$SO_2$—$(NR^{10})$—, or —$(R^{10}$—N)$—(C=O)—$(NR^{11})$—; and $R^9$ is selected from the group consisting of hydrogen, $(C_3–C_{10})$cycloalkyl or phenyl; wherein the aforesaid phenyl and $(C_3–C_{10})$cycloalkyl may optionally be substituted by one to three moieties independently selected from the group consisting of halo, $(C_2–C_6)$alkenyl, $(C_2–C_6)$alkynyl, perhalo$(C_1–C_6)$alkyl, hydroxy, $(C_1–C_6)$alkoxy, perhalo$(C_1–C_6)$alkoxy, $(C_1–C_6)$alkyl-S—, $(C_1–C_6)$alkyl-$SO_2$—, $(C_1–C_6)$alkyl-NH—$SO_2$—, —$NO_2$, amino, $(C_1–C_6)$alkylamino, $[(C_1–C_6)$alkyl$]_2$-amino, $(C_1–C_6)$alkyl-$SO_2$—NH—, $(C_1–C_6)$alkyl-(C=O)—NH—, $(C_1–C_6)$alkyl-(C=O)—$[N(C_1–C_6)$alkyl]-, —CN, $(C_1–C_6)$alkyl-(C=O)—, HO—(C=O)—, $(C_1–C_6)$alkyl-O—(C=O)—, $H_2N$(C=O)—, $(C_1–C_6)$alkyl-NH—(C=O)—, $[(C_1–C_6)$alkyl$]_2$-N—(C=O)— and $(C_1–C_6)$alkyl-(C=O)—O—.

21. A compound according to claim 1, wherein $R^6$ is $R^9$—B—$(CH_2)_n$—; n is zero; B is —(C=O)—$NR^{10}$—, —$(R^{10}$—N)$—, >C=O, —O—(C=O)—, —$(R^{10}$—N)$—(C=O)— or —$(R^{10}$—N)$—(C=O)—$(NR^{11})$—; $R^9$ is $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1–C_6)$alkyl, $(C_1–C_6)$alkoxy, phenyl, $(C_1–C_{10})$heteroaryl, $(C_1–C_{10})$heterocyclic, $(C_3–C_{10})$cycloalkyl, amino, $(_1–C_6)$alkylamino, $[(C_1–C_6)$alkyl$]_2$amino, $(C_1–C_6)$alkyl-$SO_2$—NH—, phenyl-$SO_2$—NH—, $(C_1–C_6)$alkyl-$SO_2$—$[N$—$(C_1–C_6)$alkyl]-, phenyl-$SO_2$—$[N$—$(C_1–C_6)$alkyl]-, hydroxy, $(C_1–C_6)$alkoxy, perhalo$(C_1–C_6)$alkoxy, phenoxy, $(C_1–C_{10})$heteroaryl-O—, $(C_1–C_{10}O)$heterocyclic-O—, $(C_3–C_{10})$cycloalkyl-O—, $(C_1–C_6)$alkyl-S—, $(C_1–C_6)$alkyl-$SO_2$—, $(C_1–C_6)$alkyl-NH—$SO_2$—, —$NO_2$, amino, $(C_1–C_6)$alkylamino, $[(C_1–C_6)$alkyl$]_2$-amino, $(C_1–C_6)$alkyl-$SO_2$—NH—, $(C_1–C_6)$alkyl-(C=O)—NH—, $(C_1–C_6)$alkyl-(C=O)—$[N(C_1–C_6)$alkyl]-, phenyl- (C=O)—NH—, phenyl-(C=O)—[N—($C_1$–$C_6$)alkyl]-, —CN, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, ($C_1$–$C_{10}$)heteroaryl-NH—(C=O)—, ($C_1$–$C_{10}$)heterocyclic-NH—(C=O)—, ($C_3$–$C_{10}$)cycloalkyl-NH—(C=O)—, HO—(C=O)—, ($C_1$–$C_6$)alkyl-O—(C=O)—, $H_2$N(C=O)—, ($C_1$–$C_6$)alkyl-NH—(C=O)—, [($C_1$–$C_6$)alkyl]$_2$-N—(C=O)—, phenyl-NH—(C=O)—, phenyl-[N—(($C_1$–$C_6$)alkyl)]-(C=O)—, ($C_1$–$C_6$)alkyl-(C=O)—O— and phenyl-(C=O)—O—.

22. A compound according to claim 1, wherein $R^6$ is $R^9$—B—$(CH_2)_n$—; n is zero; B is —($R^{10}$—N)—; $R^9$ is hydrogen or $R^{13}$—($R^{12}$CH)$_m$—; m is 1–6; $R^{10}$ is hydrogen or methyl; $R^{12}$ is hydrogen or methyl; and $R^{13}$ is selected from the group consisting of hydrogen, ($C_1$–$C_6$)alkyl, hydroxy, ($C_1$–$C_6$)alkoxy, amino, ($C_1$–$C_6$)alkylamino, [($C_1$–$C_6$)alkyl]$_2$amino, ($C_2$–$C_6$)alkenyl, ($C_2$–$C_6$)alkynyl, phenyl, ($C_1$–$C_{10}$)heteroaryl, ($C_1$–$C_{10}$)heterocyclic and ($C_3$–$C_{10}$)cycloalkyl.

23. A compound according to claim 1, wherein $R^6$ is $R^9$—B—$(CH_2)_n$—; n is one to four; B is —(C=O)—$NR^{10}$—, —($R^{10}$—N)—, —($R^{10}$—N)—(C=O)— or —($R^{10}$—N)—(C=O)—($NR^{11}$)—; $R^9$ is $R^{13}$—($R^{12}$CH)$_m$—; m is 1–6; $R^{10}$ is hydrogen or methyl; $R^{12}$ is hydrogen or methyl; and $R^{13}$ is selected from the group consisting of hydrogen, ($C_1$–$C_6$)alkyl, ($C_1$–$C_6$)alkoxy, phenyl, ($C_1$–$C_{10}$)heteroaryl, ($C_1$–$C_{10}$)heterocyclic, ($C_3$–$C_{10}$)cycloalkyl, amino, ($C_1$–$C_6$)alkylamino, [($C_1$–$C_6$)alkyl]$_2$amino, ($C_1$–$C_6$)alkyl-$SO_2$—NH—, phenyl-$SO_2$—NH—, ($C_1$–$C_6$)alkyl-$SO_2$—[N—($C_1$–$C_6$)alkyl]-, phenyl-$SO_2$—[N—($C_1$–$C_6$)alkyl]-, hydroxy, ($C_1$–$C_6$)alkoxy, perhalo($C_1$–$C_6$)alkoxy, phenoxy, ($C_1$–$C_{10}$)heteroaryl-O—, ($C_1$–$C_{10}$)heterocyclic-O—, ($C_3$–$C_{10}$)cycloalkyl-O—, ($C_1$–$C_6$)alkyl-S—, ($C_1$–$C_6$)alkyl-$SO_2$—, ($C_1$–$C_6$)alkyl-NH—$SO_2$—, —$NO_2$, amino, ($C_1$–$C_6$)alkylamino, [($C_1$–$C_6$)alkyl]$_2$-amino, ($C_1$–$C_6$)alkyl-$SO_2$—NH—, ($C_1$–$C_6$)alkyl-(C=O)—NH—, ($C_1$–$C_6$)alkyl-(C=O)—[(($C_1$–$C_6$)alkyl)-N]—, phenyl-(C=O)—NH—, phenyl-(C=O)—[(($C_1$–$C_6$)alkyl)-N]—, —CN, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, ($C_1$–$C_{10}$)heteroaryl-NH—(C=O)—, ($C_1$–$C_{10}$)heterocyclic-NH—(C=O)—, ($C_3$–$C_{10}$)cycloalkyl-NH—(C=O)—, HO—(C=O)—, ($C_1$–$C_6$)alkyl-O—(C=O)—, $H_2$N(C=O)—, ($C_1$–$C_6$)alkyl-NH—(C=O)—, [($C_1$–$C_6$)alkyl]$_2$-N—(C=O)—, phenyl-NH—(C=O)—, phenyl-[(($C_1$–$C_6$)alkyl)-N]—(C=O)—, ($C_1$–$C_6$)alkyl-(C=O)—O— and phenyl-(C=O)—O—.

24. A compound according to claim 1, wherein s is an integer from zero to four and each $R^3$ is independently selected from the group consisting of halo, ($C_1$–$C_6$)alkyl, ($C_2$–$C_6$)alkenyl, ($C_2$–$C_6$)alkynyl, perhalo($C_1$–$C_6$)alkyl, phenyl, ($C_1$–$C_{10}$)heteroaryl, ($C_1$–$C_{10}$)heterocyclic, ($C_3$–$C_{10}$)cycloalkyl, hydroxy, ($C_1$–$C_6$)alkoxy, perhalo($C_1$–$C_6$)alkoxy, phenoxy, ($C_1$–$C_{10}$)heteroaryl-O—, ($C_1$–$C_{10}$)heterocyclic-O—, ($C_3$–$C_{10}$)cycloalkyl-O—, ($C_1$–$C_6$)alkyl-S—, ($C_1$–$C_6$)alkyl-$SO_2$—, ($C_1$–$C_6$)alkyl-NH—$SO_2$—, —$NO_2$, amino, ($C_1$–$C_6$)alkylamino, [($C_1$–$C_6$)alkyl]$_2$-amino, ($C_1$–$C_6$)alkyl-$SO_2$—NH—, ($C_1$–$C_6$)alkyl-(C=O)—NH—, ($C_1$–$C_6$)alkyl-(C=O)—[(($C_1$–$C_6$)alkyl)-N]—, phenyl-(C=O)—NH—, phenyl-(C=O)—[(($C_1$–$C_6$)alkyl)-N]—, —CN, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, HO—(C=O), ($C_1$–$C_6$)alkyl-O—(C=O)—, $H_2$N(C=O)—($C_1$–$C_6$)alkyl-NH—(C=O)—, [($C_1$–$C_6$)alkyl]$_2$-N—(C=O)—, phenyl-NH—(C=O)—, phenyl-[(($C_1$–$C_6$)alkyl)-N]—(C=O)—, ($C_1$–$C_{10}$)heteroaryl-NH—(C=O)—, ($C_1$–$C_{10}$)heterocyclic-NH—(C=O)—, ($C_3$–$C_{10}$)cycloalkyl-NH—(C=O)— and ($C_1$–$C_6$)alkyl-(C=O)—O—.

25. A compound according to claim 1, wherein s is an integer from zero to four and each $R^3$ is independently selected from the group consisting of halo, ($C_1$–$C_6$)alkyl, ($C_2$–$C_6$)alkenyl, ($C_2$–$C_6$)alkynyl, perhalo($C_1$–$C_6$)alkyl, phenyl, ($C_1$–$C_{10}$)heteroaryl, ($C_1$–$C_{10}$)heterocyclic, ($C_3$–$C_{10}$)cycloalkyl, hydroxy, ($C_1$–$C_6$)alkoxy, perhalo($C_1$–$C_6$)alkoxy, phenoxy, ($C_1$–$C_{10}$)heteroaryl-O—, ($C_1$–$C_{10}$)heterocyclic-O—, ($C_3$–$C_{10}$)cycloalkyl-O—, ($C_1$–$C_6$)alkyl-S—, ($C_1$–$C_6$)alkyl-$SO_2$—, ($C_1$–$C_6$)alkyl-NH—$SO_2$—, —$NO_2$, amino, ($C_1$–$C_6$)alkylamino, [($C_1$–$C_6$)alkyl]$_2$-amino, ($C_1$–$C_6$)alkyl-$SO_2$—NH—, ($C_1$–$C_6$)alkyl-(C=O)—NH—, ($C_1$–$C_6$)alkyl-(C=O)—[(($C_1$–$C_6$)alkyl)-N]—, phenyl-(C=O)—NH—, phenyl-(C=O)—[(($C_1$–$C_6$)alkyl)-N]—, —CN, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, HO—(C=O), ($C_1$–$C_6$)alkyl-O—(C=O)—, $H_2$N(C=O)—($C_1$–$C_6$)alkyl-NH—(C=O)—, [($C_1$–$C_6$)alkyl]$_2$-N—(C=O)—, phenyl-NH—(C=O)—, phenyl-[(($C_1$–$C_6$)alkyl)-N]—(C=O)—, ($C_1$–$C_{10}$)heteroaryl-NH—(C=O)—, ($C_1$–$C_{10}$)heterocyclic-NH—(C=O)—, ($C_3$–$C_{10}$)cycloalkyl-NH—(C=O)— and ($C_1$–$C_6$)alkyl-(C=O)—O—.

26. A compound according to claim 1, wherein s is an integer from zero to four and each $R^3$ is independently selected from the group consisting of halo, —CN, ($C_1$–$C_6$)alkyl, ($C_2$–$C_6$)alkenyl, ($C_2$–$C_6$)alkynyl and perhalo($C_1$–$C_6$)alkyl.

27. A compound according to claim 1, wherein s is an integer from zero to four and zero, one or two of $R^3$ are independently selected from the group consisting of halo, ($C_1$–$C_6$)alkyl, perhalo($C_1$–$C_6$)alkyl, hydroxy, ($C_1$–$C_6$)alkoxy, perhalo($C_1$–$C_6$)alkoxy, amino, ($C_1$–$C_6$)alkylamino, [($C_1$–$C_6$)alkyl]$_2$-amino, —CN, and $H_2$N(C=O)—.

28. A compound according to claim 1, wherein s is an integer from zero to four and one of $R^3$ is selected from the group consisting of optionally substituted phenyl, ($C_1$–$C_{10}$)heteroaryl, ($C_1$–$C_{10}$)heterocyclic and ($C_3$–$C_{10}$)cycloalkyl.

29. A compound according to claim 1, wherein s is an integer from zero to three and each $R^3$ is independently selected from the group consisting of halo, ($C_1$–$C_6$)alkyl, perhalo($C_1$–$C_6$)alkyl, hydroxy, ($C_1$–$C_6$)alkoxy, perhalo($C_1$–$C_6$)alkoxy, —$NO_2$, amino, ($C_1$–$C_6$)alkylamino, [($C_1$–$C_6$)alkyl]$_2$-amino, —CN, and $H_2$N(C=O)—.

30. A compound according to claim 1, wherein s is an integer from zero to two and each $R^3$ is independently selected from the group consisting of halo, ($C_1$–$C_6$)alkyl, perhalo($C_1$–$C_6$)alkyl, ($C_1$–$C_6$)alkoxy, perhalo($C_1$–$C_6$)alkoxy and —CN.

31. A compound according to claim 1, wherein s is an integer from zero to three and each $R^3$ is independently selected from the group consisting of fluoro, chloro and methyl.

32. A compound according to claim 1, wherein s is an integer from zero to three and each $R^3$ is independently selected from the group consisting of fluoro, chloro and methyl.

\* \* \* \* \*